US008962805B2

(12) United States Patent
Beirnaert et al.

(10) Patent No.: US 8,962,805 B2
(45) Date of Patent: *Feb. 24, 2015

(54) ANTI IL-6R POLYPEPTIDES AND COMPOSITIONS THEREOF

(71) Applicant: Ablynx N.V., Zwijnaarde (BE)

(72) Inventors: Els Anna Alice Beirnaert, Bellem (BE); Cedric Jozef Neotere Ververken, Merelbeke (BE); Joost Alexander Kolkman, Maarn (NL); Maarten Van Roy, Zwijnaarde (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/221,364

(22) Filed: Mar. 21, 2014

(65) Prior Publication Data
US 2014/0343257 A1 Nov. 20, 2014

Related U.S. Application Data

(63) Continuation of application No. 13/263,179, filed as application No. PCT/EP2010/054764 on Apr. 12, 2010, now Pat. No. 8,748,581.

(60) Provisional application No. 61/168,410, filed on Apr. 10, 2009.

(51) Int. Cl.
C07K 16/00 (2006.01)
A61K 39/395 (2006.01)
A61K 39/00 (2006.01)
C07K 16/46 (2006.01)
C07K 16/18 (2006.01)
C07K 16/28 (2006.01)
C07K 16/42 (2006.01)

(52) U.S. Cl.
CPC ......... *C07K 16/468* (2013.01); *A61K 2039/505* (2013.01); *C07K 16/18* (2013.01); *C07K 16/2866* (2013.01); *C07K 2317/22* (2013.01); *C07K 2317/31* (2013.01); *C07K 2317/33* (2013.01); *C07K 2317/569* (2013.01); *C07K 2317/76* (2013.01); *C07K 2317/92* (2013.01); *C07K 2317/94* (2013.01); *C07K 2317/64* (2013.01); *C07K 16/4283* (2013.01)
USPC .................. 530/387.1; 424/130.1; 424/135.1; 424/178.1; 424/179.1

(58) Field of Classification Search
None
See application file for complete search history.

(56) References Cited

U.S. PATENT DOCUMENTS

| | | | |
|---|---|---|---|
| 5,888,510 | A | 3/1999 | Kishimoto et al. |
| 8,629,244 | B2 | 1/2014 | Kolkman et al. |
| 8,748,581 | B2 | 6/2014 | Beirnaert et al. |
| 2007/0036785 | A1 | 2/2007 | Kishimoto et al. |
| 2007/0280945 | A1 | 12/2007 | Stevens et al. |
| 2010/0215664 | A1 | 8/2010 | Kolkman et al. |
| 2011/0243954 | A1 | 10/2011 | Revets et al. |
| 2012/0077731 | A1 | 3/2012 | Beirnaert et al. |
| 2012/0171209 | A1 | 7/2012 | Compernolle et al. |
| 2012/0244158 | A1 | 9/2012 | Brige et al. |
| 2014/0212417 | A1 | 7/2014 | Holz et al. |
| 2014/0221623 | A1 | 8/2014 | Kolkman et al. |
| 2014/0329278 | A1 | 11/2014 | Beirnaert et al. |

FOREIGN PATENT DOCUMENTS

| | | |
|---|---|---|
| CN | 1535728 A | 10/2004 |
| EP | 0 257 406 A2 | 3/1988 |
| EP | 0 312 996 A2 | 4/1989 |
| EP | 0 325 474 A2 | 7/1989 |
| EP | 0 409 607 A2 | 1/1991 |
| EP | 0 411 946 A2 | 2/1991 |
| EP | 0 527 809 A1 | 2/1993 |
| EP | 0 572 118 A1 | 12/1993 |
| EP | 0 628 639 B1 | 12/1994 |
| EP | 0 409 607 B1 | 10/1996 |

(Continued)

OTHER PUBLICATIONS

[No Author Listed], Ablynx Reports Positive Phase I Data for ALX-0061 in Rheumatoid Arthritis. Press release. Ablynx. Ghent, Belgium. Nov. 30, 2011.

Ali et al., Improvements in the cell-free production of functional antibodies using cell extract from protease-deficient *Escherichia coli* mutant. J Biosci Bioeng. Feb. 2005;99(2):181-6.

Decanniere et al., A single-domain antibody fragment in complex with RNase A: non-canonical loop structures and nanomolar affinity using two CDR loops. Structure. Apr. 15, 1999;7(4):361-70.

Desgeorges et al., Concentrations and origins of soluble interleukin 6 receptor-alpha in serum and synovial fluid. J Rheumatol. Aug. 1997;24(8):1510-6.

(Continued)

*Primary Examiner* — Robert Landsman
(74) *Attorney, Agent, or Firm* — Wolf, Greenfield & Sacks, P.C.

(57) ABSTRACT

The present invention relates to amino acid sequences that are directed against/and or that can specifically bind Interleukin-6 Receptor (IL-6R) with improved affinity and/or avidity, and/or that have an improved efficacy and/or potency, and which are capable of (partially, or preferably totally) blocking the IL-6/IL-6R interaction and/or inhibit signalization through IL-6, IL-6R and/or the IL-6/IL-6R complex. The invention further relates to compounds or constructs, and in particular proteins and polypeptides, that comprise or essentially consist of one or more such amino acid sequences. The invention also relates to nucleic acids encoding such amino acid sequences and polypeptides, to methods for preparing such amino acid sequences and polypeptides, to host cells expressing or capable of expressing such amino acid sequences or polypeptides, to compositions, and in particular to pharmaceutical compositions, that comprise such amino acid sequences, polypeptides, nucleic acids and/or host cells, and to uses of such amino acid sequences or polypeptides, nucleic acids, host cells and/or compositions, in particular for prophylactic, therapeutic or diagnostic purposes.

19 Claims, 90 Drawing Sheets

(56) References Cited

FOREIGN PATENT DOCUMENTS

| | | |
|---|---|---|
| JP | 2000/500644 | 1/2000 |
| WO | WO 97/13781 A2 | 4/1997 |
| WO | WO 2005/003345 A2 | 1/2005 |
| WO | WO 2006/023144 A2 | 3/2006 |
| WO | WO 2006/079372 A1 | 8/2006 |
| WO | WO 2007/042289 A2 | 4/2007 |
| WO | WO 2007/104529 A2 | 9/2007 |
| WO | WO 2008/020079 A1 | 2/2008 |
| WO | WO 2008/071685 A1 | 6/2008 |
| WO | WO 2008/074840 A2 | 6/2008 |
| WO | WO 2008/077945 A2 | 7/2008 |
| WO | WO 2009/004065 A2 | 1/2009 |
| WO | WO 2009/010539 A2 | 1/2009 |
| WO | WO 2010/115995 A2 | 10/2010 |
| WO | WO 2010/115998 A2 | 10/2010 |
| WO | WO 2011/026948 A1 | 3/2011 |

OTHER PUBLICATIONS

Desmyter et al., Crystal structure of a camel single-domain VH antibody fragment in complex with lysozyme. Nat Struct Biol. Sep. 1996;3(9):803-11.

Frey et al., Population pharmacokinetic analysis of tocilizumab in patients with rheumatoid arthritis. J Clin Pharmacol. Jul. 2010;50(7):754-66. doi: 10.1177/0091270009350623. Epub Jan. 23, 2010.

Hibi et al., Molecular cloning and expression of an IL-6 signal transducer, gp130. Cell. Dec. 21, 1990;63(6):1149-57.

Hinton et al., An engineered human IgG1 antibody with longer serum half-life. J Immunol. Jan. 1, 2006;176(1):346-56.

Houdebine, Production of pharmaceutical proteins by transgenic animals. Comp Immunol Microbiol Infect Dis. Mar. 2009;32(2):107-21. doi: 10.1016/j.cimid.2007.11.005. Epub Feb. 19, 2008.

Ko et al., Production of antibodies in plants: approaches and perspectives. Curr Top Microbiol Immunol. 2009;332:55-78. doi: 10.1007/978-3-540-70868-1_4.

Levi et al., Effect of tocilizumab exposure on IL-6 and IL-6 receptor levels in patients with rheumatoid arthritis: graphical analysis of pooled data from four phase 3 clinical trials. Presentation EULAR conference. Jun. 11-14, 2008.

Levi et al., Effect of tocilizumab exposure on IL-6 and IL-6 receptor levels in patients with rheumatoid arthritis: graphical analysis of pooled data from four phase 3 clinical trials. Ann Rheum Dis. 2008;67(Suppl II):192. Abstract THU0176.

Levi et al., Reduction in inflammatory biomarkers with increasing exposure to the IL-6 inhibitor, tocilizumab, in patients with rheumatoid arthritis: Graphical analysis of pooled data. Ann Rheum Dis. 2008;67(Suppl II):192. Abstract THU0177.

Merk et al., Cell-free expression of two single-chain monoclonal antibodies against lysozyme: effect of domain arrangement on the expression. J Biochem. Feb. 1999;125(2):328-33.

Nishimoto et al., Interleukin 6: from bench to bedside. Nat Clin Pract Rheumatol. Nov. 2006;2(11):619-26. Erratum in: Nat Clin Pract Rheumatol. Dec. 2006;2(12):691.

Nishimoto et al., Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease. Blood. Nov. 15, 2008;112(10):3959-64. doi: 10.1182/blood-2008-05-155846. Epub Sep. 10, 2008.

Nishimoto et al., Toxicity, pharmacokinetics, and dose-finding study of repetitive treatment with the humanized anti-interleukin 6 receptor antibody MRA in rheumatoid arthritis. Phase I/II clinical study. J Rheumatol. Jul. 2003;30(7):1426-35.

Nishimoto et al., Treatment of rheumatoid arthritis with humanized anti-interleukin-6 receptor antibody: a multicenter, double-blind, placebo-controlled trial. Arthritis Rheum. Jun. 2004;50(6):1761-9.

Riechmann, Rearrangement of the former VL interface in the solution structure of a camelised, single antibody VH domain. J Mol Biol. Jun. 28, 1996;259(5):957-69.

Rose-John et al., Interleukin-6 biology is coordinated by membrane-bound and soluble receptors: role in inflammation and cancer. J Leukoc Biol. Aug. 2006;80(2):227-36. Epub May 17, 2006.

Sato et al., Reshaping a human antibody to inhibit the interleukin 6-dependent tumor cell growth. Cancer Res. Feb. 15, 1993;53(4):851-6.

Schmitt et al., Disease-drug-drug interaction involving tocilizumab and simvastatin in patients with rheumatoid arthritis. Clin Pharmacol Ther. May 2011;89(5):735-40. doi: 10.1038/clpt.2011.35. Epub Mar. 23, 2011. Erratum in: Clin Pharmacol Ther. Sep. 2011;90(3):479.

Smolen et al., OPTION Investigators. Effect of interleukin-6 receptor inhibition with tocilizumab in patients with rheumatoid arthritis (OPTION study): a double-blind, placebo-controlled, randomised trial. Lancet. Mar. 22, 2008;371(9617):987-97. doi: 10.1016/S0140-6736(08)60453-5.

Spinelli et al., The crystal structure of a llama heavy chain variable domain. Nat Struct Biol. Sep. 1996;3(9):752-7.

Usón et al., Soluble interleukin 6 (IL-6) receptor and IL-6 levels in serum and synovial fluid of patients with different arthropathies. J Rheumatol. Nov. 1997;24(11):2069-75.

Yokota et al., Phase 2 trials of anti-IL6 receptor antibody (MRA) for systemic onset juvenile idiopathic arthritis. Autoimmune Rev. 2004;3:599-600.

Zhang et al., Clinical pharmacology of tocilizumab for the treatment of patients with rheumatoid arthritis. Expert Rev Clin Pharmacol. Sep. 2011;4(5):539-58. doi: 10.1586/ecp.11.33.

Atreya et al., Blockade of interleukin 6 trans signaling suppresses T-cell resistance against apoptosis in chronic intestinal inflammation: evidence in crohn disease and experimental colitis in vivo. Nat Med. May 2000;6(5):583-8. Erratum in: Nat Med. Nov. 2010;16(11):1341.

Bataille et al., Biologic effects of anti-interleukin-6 murine monoclonal antibody in advanced multiple myeloma. Blood. Jul. 15, 1995;86(2):685-91.

Beck et al., Brief report: alleviation of systemic manifestations of Castleman's disease by monoclonal anti-interleukin-6 antibody. N Engl J Med. Mar. 3, 1994;330(9):602-5.

Becker et al., TGF-beta suppresses tumor progression in colon cancer by inhibition of IL-6 trans-signaling. Immunity. Oct. 2004;21(4):491-501.

Boulanger et al., Hexameric structure and assembly of the interleukin-6/IL-6 alpha-receptor/gp130 complex. Science. Jun. 27, 2003;300(5628):2101-4. Erratum in: Science. Aug. 15, 2003;301(5635):918.

Campbell et al., Essential role for interferon-gamma and interleukin-6 in autoimmune insulin-dependent diabetes in NOD/Wehi mice. J Clin Invest. Feb. 1991;87(2):739-42.

Choy et al., Therapeutic benefit of blocking interleukin-6 activity with an anti-interleukin-6 receptor monoclonal antibody in rheumatoid arthritis: a randomized, double-blind, placebo-controlled, dose-escalation trial. Arthritis Rheum. Dec. 2002;46(12):3143-50.

Colman, Effects of amino acid sequence changes on antibody-antigen interactions. Res Immunol. Jan. 1994;145(1):33-6.

Desmyter et al., Antigen specificity and high affinity binding provided by one single loop of a camel single-domain antibody. J Biol Chem. Jul. 13, 2001;276(28):26285-90. Epub May 7, 2001.

Doganci et al., The IL-6R alpha chain controls lung CD4+CD25+ Treg development and function during allergic airway inflammation in vivo. J Clin Invest. Feb. 2005;115(2):313-25. Erratum in: J Clin Invest. May 2005;115(5):1388. Lehr, Hans A [added].

Emilie et al., Cytokines in HIV infection. Int J Immunopharmacol. May-Jun. 1994;16(5-6):391-6.

Emilie et al., Administration of an anti-interleukin-6 monoclonal antibody to patients with acquired immunodeficiency syndrome and lymphoma: effect on lymphoma growth and on B clinical symptoms. Blood. Oct. 15, 1994;84(8):2472-9.

Frankel et al., Characterization of diphtheria fusion proteins targeted to the human interleukin-3 receptor. Protein Eng. Aug. 2000;13(8):575-81.

Gaillard et al., Identification of a novel antigenic structure of the human receptor for interleukin-6 involved in the interaction with the glycoprotein 130 chain. Immunology. Sep. 1996;89(1):135-41.

(56) References Cited

OTHER PUBLICATIONS

Grau et al., Interleukin 6 production in experimental cerebral malaria: modulation by anticytokine antibodies and possible role in hypergammaglobulinemia. J Exp Med. Nov. 1, 1990;172(5):1505-8.
Grogg et al., HIV infection and lymphoma. J Clin Pathol. Dec. 2007;60(12):1365-72.
Hirano et al., Interleukin 6 and its receptor in the immune response and hematopoiesis. Int J Cell Cloning. Jan. 1990;8 Suppl 1:155-66; discussion 166-7.
Hirano et al., Biological and clinical aspects of interleukin 6. Immunol Today. Dec. 1990;11(12):443-9.
Hirano et al., Purification to homogeneity and characterization of human B-cell differentiation factor (BCDF or BSFp-2). Proc Natl Acad Sci U S A. Aug. 1985;82(16):5490-4.
Holliger et al., Engineered antibody fragments and the rise of single domains. Nat Biotechnol. Sep. 2005;23(9):1126-36.
Holt et al., Domain antibodies: proteins for therapy. Trends Biotechnol. Nov. 2003;21(11):484-90.
Ishihara et al., IL-6 in autoimmune disease and chronic inflammatory proliferative disease. Cytokine Growth Factor Rev. Aug.-Oct. 2002;13(4-5):357-68.
Ishihara et al., Molecular basis of the cell specificity of cytokine action. Biochim Biophys Acta. Nov. 11, 2002;1592(3):281-96.
Ito et al., A pilot randomized trial of a human anti-interleukin-6 receptor monoclonal antibody in active Crohn's disease. Gastroenterology. 2004;126:989-96.
Jang et al., Pharmacokinetic/pharmacodynamic (PK/PD) modeling and trial simulations to guide dose selection with CNTO 328, a chimeric anti-IL-6 monoclonal antibody (Mab), in patients with renal cell carcinoma (RCC). Journal of Clinical Oncology, 2004 ASCO Annual Meeting Proceedings (Post-Meeting Edition). 2004;22(14S, Jul. 15 Supplement):2608. Abstract.
Jilka et al., Increased osteoclast development after estrogen loss: mediation by interleukin-6. Science. Jul. 3, 1992;257(5066):88-91.
Jones et al., Replacing the complementarity-determining regions in a human antibody with those from a mouse. Nature. May 29-Jun. 4, 1986;321(6069):522-5.
Jones et al., Therapeutic strategies for the clinical blockade of IL 6/gp130 signaling. J Clin Invest. Sep. 2011;121(9):3375-83. doi: 10.1172/JCI57158. Epub Sep. 1, 2011.
Kalai et al., Participation of two Ser-Ser-Phe-Tyr repeats in interleukin-6 (IL-6)-binding sites of the human IL-6 receptor. Eur J Biochem. Jun. 15, 1996;238(3):714-23.
Kipriyanov, Generation of bispecific and tandem diabodies. Methods Mol Biol. 2009;562:177-93.
Klein et al., Murine anti-interleukin-6 monoclonal antibody therapy for a patient with plasma cell leukemia. Blood. Sep. 1, 1991;78(5):1198-204.
Lederman et al., A single amino acid substitution in a common African allele of the CD4 molecule ablates binding of the monoclonal antibody, OKT4. Mol Immunol. Nov. 1991;28(11):1171-81.
Li et al., beta-Endorphin omission analogs: dissociation of immunoreactivity from other biological activities. Proc Natl Acad Sci U S A. Jun. 1980;77(6):3211-4.
Muyldermans et al., Unique single-domain antigen binding fragments derived from naturally occurring camel heavy-chain antibodies. J Mol Recognit. Mar.-Apr. 1999;12(2):131-40.
Nishimoto et al., Humanized anti-interleukin-6 receptor antibody treatment of multicentric Castleman disease. Blood. Oct. 15, 2005;106(8):2627-32. Epub Jul. 5, 2005.
Nowell et al., Soluble IL-6 receptor governs IL-6 activity in experimental arthritis: blockade of arthritis severity by soluble glycoprotein 130. J Immunol. Sep. 15, 2003;171(6):3202-9.
Paul, Fundamental immunology, 3rd Edition, 1993:292-295, under the heading Fv structure and diversity in three dimensions.
Prabhakar et al., Correlation of serum CNTO 328-Anti IL-6 monoclonal antibody (Mab) concentrations and biomarker expression in renal cell carcinoma (RCC) patients. Journal of ClinicalOncology, 2004 ASCO Annual Meeting Proceedings (Post-Meeting Edition). 2004;22(14S, Jul. 15 Supplement):2560. Abstract.
Rajpal et al., A general method for greatly improving the affinity of antibodies by using combinatorial libraries. Proc Natl Acad Sci U S A. Jun. 14, 2005;102(24):8466-71. Epub Jun. 6, 2005
Revets et al., Nanobodies as novel agents for cancer therapy. Expert Opin Biol Ther. Jan. 2005;5(1):111-24.
Riechmann et al., Single domain antibodies: comparison of camel VH and camelised human VH domains. J Immunol Methods. Dec. 10, 1999;231(1-2):25-38.
Robert et al., Tumor targeting with newly designed biparatopic antibodies directed against two different epitopes of the carcinoembryonic antigen (CEA). Int J Cancer. Apr. 12, 1999;81(2):285-91.
Roitt et al., Immunology. 5th edition. 1998;80-81, 107. (translation of 110-111, 150 from Russian-language version of Roitt et al., Immunology).
Roodman et al., Interleukin 6. A potential autocrine/paracrine factor in Paget's disease of bone. J Clin Invest. Jan. 1992;89(1):46-52.
Roodman et al., Interleukin-6: an osteotropic factor? J Bone Miner Res. May 1992;7(5):475-8.
Rudikoff et al., Single amino acid substitution altering antigen-binding specificity. Proc Natl Acad Sci U S A. Mar. 1982;79(6):1979-83.
Saito et al., Preparation of monoclonal antibodies against the IL-6 signal transducer, gp130, that can inhibit IL-6-mediated functions. J Immunol Methods. Aug. 9, 1993;163(2):217-23.
Scheller et al., Interleukin-6 and its receptor: from bench to bedside. Med Microbiol Immunol. Dec. 2006;195(4):173-83. Epub May 31, 2006.
Shinkura et al., In vivo blocking effects of a humanized antibody to human interleukin-6 receptor on interleukin-6 function in primates. Anticancer Res. Mar.-Apr. 1998;18(2A):1217-21.
Starnes et al., Anti-IL-6 monoclonal antibodies protect against lethal *Escherichia coli* infection and lethal tumor necrosis factor-alpha challenge in mice [retraction of Starnes HF Jr, Pearce MK, Tewari A, Yim JH, Zou JC, Abrams JS. In: J Immunol Dec. 15, 1990;145(12):4185-91]. J Immunol. Mar. 15, 1992;148(6):1968.
Strassman et al., Evidence for the involvement of interleukin 6 in experimental cancer cachexia. J Clin Invest. May 1992;89:1681-1684.
Taga et al., Interleukin-6 triggers the association of its receptor with a possible signal transducer, gp130. Cell. Aug. 11, 1989;58(3):573-81.
Tanaka et al., Targeting interleukin-6: all the way to treat autoimmune and inflammatory diseases. Int J Biol Sci. 2012;8(9):1227-36. doi: 10.7150/ijbs.4666. Epub Oct. 24, 2012.
Tijink et al., Improved tumor targeting of anti-epidermal growth factor receptor Nanobodies through albumin binding: taking advantage of modular Nanobody technology. Mol Cancer Ther. Aug. 2008;7(8):2288-97. doi: 10.1158/1535-7163.MCT-07-2384.
Vierboom et al., Preclinical evaluation of anti-rheumatic drugs in a non-human primate model of arthritic disease. Drug Discovery Today: Disease Models. 2008; 30(20):e1-7. doi.10.1016/j.ddmod.2008.06.003.
Wendling et al., Treatment of severe rheumatoid arthritis by anti-interleukin 6 monoclonal antibody. J Rheumatol. Feb. 1993;20(2):259-62.
Wesolowski et al., Single domain antibodies: promising experimental and therapeutic tools in infection and immunity. Med Microbiol Immunol. Aug. 2009;198(3):157-74. doi: 10.1007/s00430-009-0116-7. Epub Jun. 16, 2009.
Woo et al., Open label phase II trial of single, ascending doses of MRA in Caucasian children with severe systemic juvenile idiopathic arthritis: proof of principle of the efficacy of IL-6 receptor blockade in this type of arthritis and demonstration of prolonged clinical improvement. Arthritis Res Ther. 2005;7(6):R1281-8. Epub Sep. 15, 2005.
Yamasaki et al., Cloning and expression of the human interleukin-6 (BSF-2/IFN beta 2) receptor. Science. Aug. 12, 1988;241(4867):825-8.
Zaki et al., CNTO 328, a monoclonal antibody to IL-6, inhibits human tumor-induced cachexia in nude mice. Int J Cancer. Sep. 10, 2004;111(4):592-5.

Inhibitors

```
              ---------------FR1---------------  --CDR1--  ------FR2-------  --------CDR2---------
PMP40H5       EVQLVESGGGLVQPGGSLRLSCAASGFSLD    YYAIG     WFRQAPGKEREGVS    CMDSSSGTTSTYYSDSVKG
              ---------------FR3---------------           -----------CDR3-----------  -----FR4-----
              RFTISRDDAKNTVYLQMNSLKPEDTAVYYCAA            DGHLNWGQRYVPCSQISWRGWNDY    WGQGTQVTVSS

---------------FR1---------------  --CDR1--  ------FR2-------  --------CDR2---------
PMP35E11      EVQLVESGGGLVQAGGSLRLSCAASGFTFD    DYAIG     WFRQAPGKEHEGVS    CISSSDGSTYYADSVKG
              ---------------FR3---------------           -----------CDR3-----------  -----FR4-----
              RFTISSDNAKNTVYLQMNSLKPEDTAVYYCAA            ERDVPARSLCGSYYWYDY          RGQGTQVTVSS

---------------FR1---------------  --CDR1--  ------FR2-------  --------CDR2---------
PMP32C9       EVQLVESGGGLVQAGGSLRLSCAASGFTFD    DYDIG     WFRQAPGKEREGVS    GISSSDGNTYYADSVKG
              ---------------FR3---------------           -----------CDR3-----------  -----FR4-----
              RFTISSDNAKNTVYLQMNSLKPEDTAVYYCAA            EPPDSSWYLDGSPEFFKY          WGQGTQVTVSS

---------------FR1---------------  --CDR1--  ------FR2-------  --------CDR2---------
PMP35H4       EVQLVESGGGLVQPGGSLRLSCAASGFTFD    DYGMS     WVRQAPGRATEWVS    AISWNGNNTYYTESMKG
              ---------------FR3---------------           -----------CDR3-----------  -----FR4-----
              RFTISRDNAKNTVYLQMNSLKPEDTAVYYCVK            GSTAIVGVPPTYPDEYDY          WGQGTQVTVSS

---------------FR1---------------  --CDR1--  ------FR2-------  --------CDR2---------
PMP32E10      EVQLVESGGGLVQPGGSLRLSCAASGFTFG    SYDMS     WVRQAPGKGPEWVS    AINSGGGSTYYADSVKG
              ---------------FR3---------------           -----------CDR3-----------  -----FR4-----
              RFTISRDNAKNTLYLQMNSLKPEDTAVYYCAT            DWRYSDYDLPLPPPGDY           WGQGTQVTVSS

---------------FR1---------------  --CDR1--  ------FR2-------  --------CDR2---------
PMP30C11      EVQLVESGGGLVQAGGSLRLSCAASGRTFS    SYDMG     WYRQAPGKEREFVA    VISRSGSSTYYADSVKG
              ---------------FR3---------------           -----------CDR3-----------  -----FR4-----
              RFTISRDNAKNTVYLQMNSLKPEDTAIYYCKA            EVVAGDYDY                   WGQGTQVTVSS

---------------FR1---------------  --CDR1--  ------FR2-------  --------CDR2---------
PMP35C10      EVQLVESGGGLVQAGGSLRLSCAASGRTFS    SYDMG     WYRQAPGKEREFVA    VIHWSSGSTYYADPVKG
              ---------------FR3---------------           -----------CDR3-----------  -----FR4-----
              RFTISRDNAKNTVYLQMNSLKPEDTAIYYCNA            FLPGPEGFHDY                 WGQGTQVTVSS

---------------FR1---------------  --CDR1--  ------FR2-------  --------CDR2---------
PMP34G9       EVQLVESGGGLVQAGGSLRLSCAASGRTSS    SYDMT     WYRQVPGKEREFVA    VISWSGGSTYYADSVKG
              ---------------FR3---------------           -----------CDR3-----------  -----FR4-----
              RFTISRDNAKNTVYLQMNSLKPEDTAIYYCNA            YTGGGDDY                    WGQGTQVTVSS

---------------FR1---------------  --CDR1--  ------FR2-------  --------CDR2---------
PMP31A4       EVQLVESGGGLVQAGGSLRLSCAASGSIFK    VNAMG     WYRQAPGKQRELVA    GIISGGSTNYADSVKG
              ---------------FR3---------------           -----------CDR3-----------  -----FR4-----
              RLTISRDNAKNTVYLQMNSLKPEDTAVYYCSF            VTTNSDYDLGRDY               WGQGTQVTVSS

---------------FR1---------------  --CDR1--  ------FR2-------  --------CDR2---------
PMP32E2       EVQLVESGGGLVQAGGSLRLSCAASGNIFD    DNTMGWT   WNRQPPGKQRELVA    IIATDGSTNYADSVKG
              ---------------FR3---------------           -----------CDR3-----------  -----FR4-----
              RFTISRDNAKNTVYLQMNSLKPEDTAVYYCNL            FSLRLGRDY                   WGQGTQVTVSS

---------------FR1---------------  --CDR1--  ------FR2-------  --------CDR2---------
PMP33A3       EVQLVESGGGLVQPGGSLRLSCAASGFTLD    YGAIG     WFRQAPGKEREGVS    CISSTGSTYYADSVKG
              ---------------FR3---------------           -----------CDR3-----------  -----FR4-----
              RFTISRDNGKNTVYLQMNSLKPEDTAVYYCAA            DKMWSPCLVAANEEALFEYDY       WGQGTQVTVSS

---------------FR1---------------  --CDR1--  ------FR2-------  --------CDR2---------
PMP34A12      EVQLVESGGGLVQPGGSLRLSCVASGFSLD    YYVIG     WFRQAPGKEREGVS    CISSSDGSTYYADSVKG
              ---------------FR3---------------           -----------CDR3-----------  -----FR4-----
              RFTISRDNAKNTVYLQMNSLKPEDTAVYYCAA            DLLRTPEFCVDSAPYDY           WGQGTQVTVSS

---------------FR1---------------  --CDR1--  ------FR2-------  --------CDR2---------
PMP28E11      EVQLVESGGGLVQPGGSLRLSCAASGFPLD    YYAIG     WFRQAPGKEREGVS    CISSSDGSTYYADSVKG
              ---------------FR3---------------           -----------CDR3-----------  -----FR4-----
              RFTISRDNAKNTVYLQMNSLKPEDTAVYYCAL            VHTTAQATGVPQREYEYEW         WGQGTQVTVSS

---------------FR1---------------  --CDR1--  ------FR2-------  --------CDR2---------
PMP35F4       EVQLVESGGGLVQAGGSLRLSCAASGRTFS    SYDMG     WYRQAPGKEREFVA    IITWNSSTYYADSVKG
              ---------------FR3---------------           -----------CDR3-----------  -----FR4-----
              RFTISRDNAKNTVYLQMNSLKPEDTAIYYCNA            QYGLGYAEDY                  WGQGTQVTVSS
```

Fig. 4

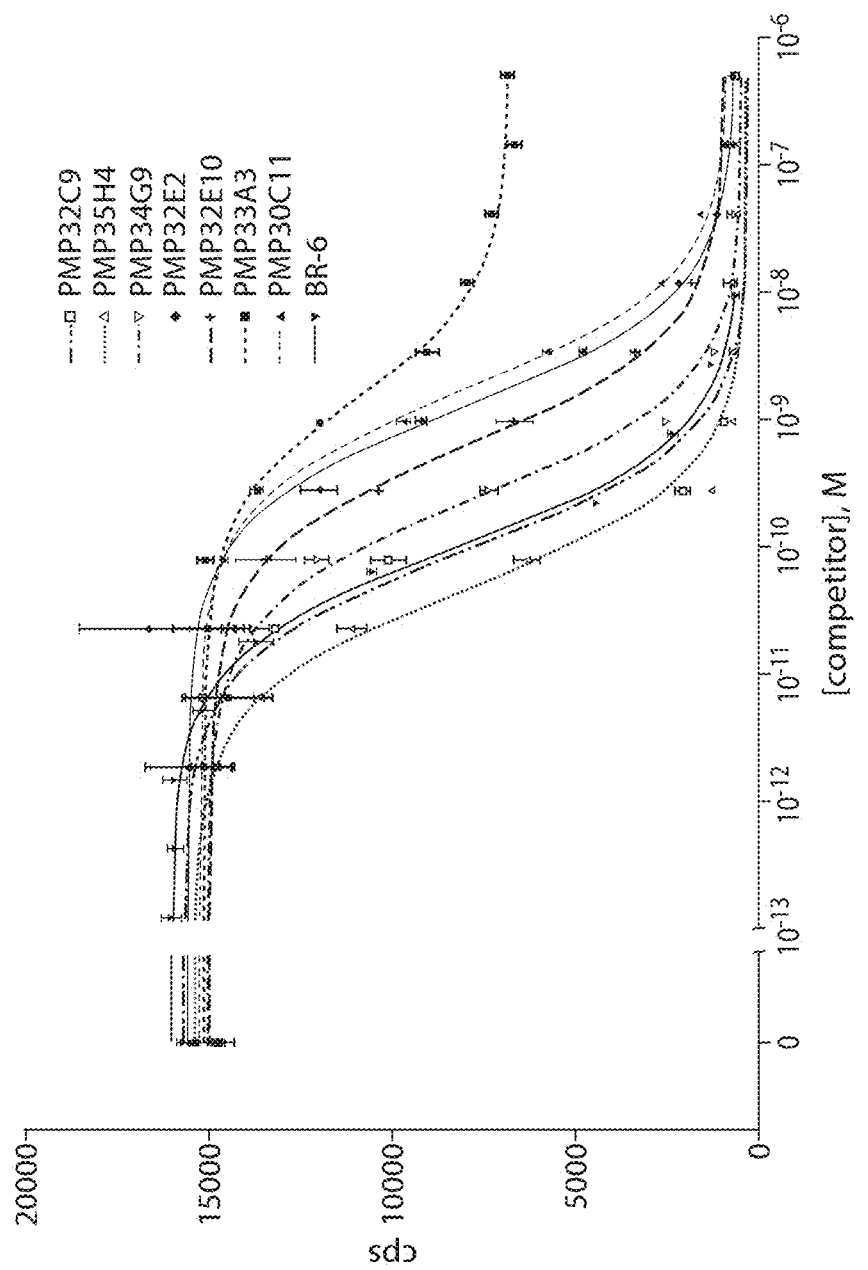

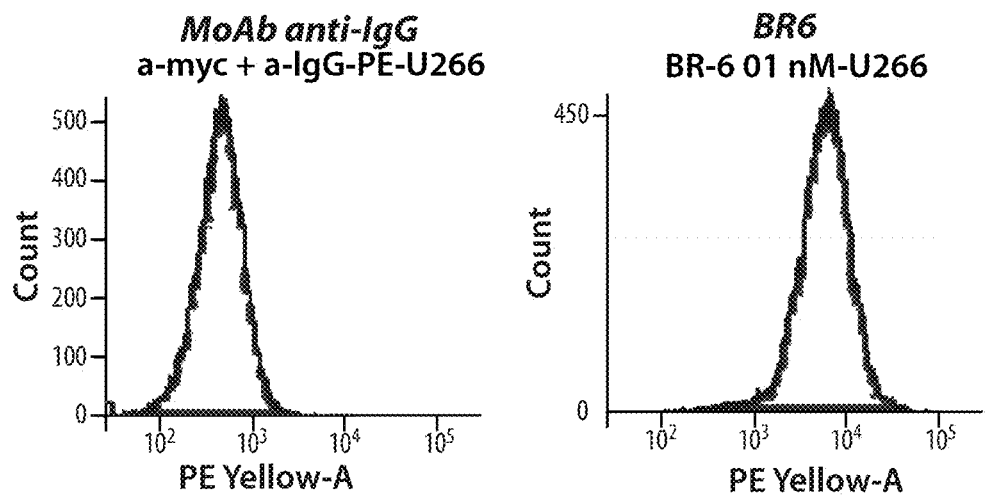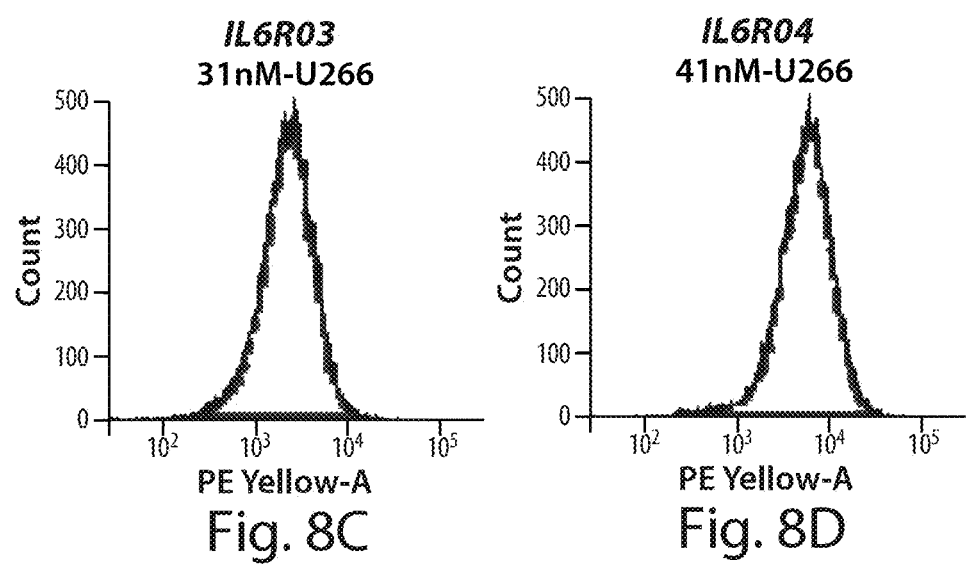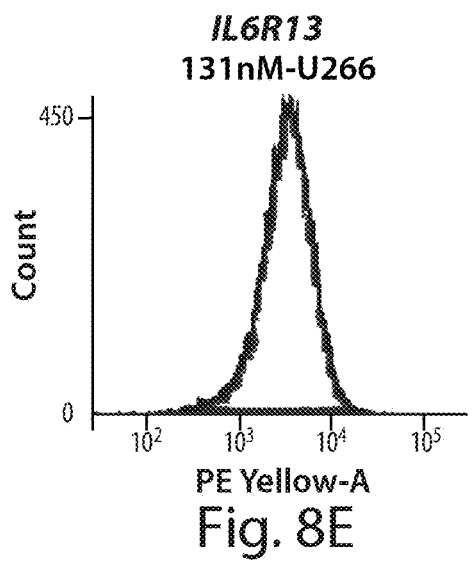

```
IL6R03      EVQLVESGGGLVQ[AG]GSLRLSCAASG[SIHA][WYA]NAMGM[R]QAPGK[GLE][WVA]GIISGG---SSNYADSVKG[R]F[TIS]ISRDNAKNT[V]LQMNSL[R]EDTAVYYCAR[ ]NAGLISGG---SSNYADSVKG[R]F[TIS]ISRDNAKNT[V]LQMNSL[R]EDTAVYYCAR[ ]TTNSDYDLGRDYWGQG[N]VTVSS
DP47        EVQLLESGGGLVQPGGSLRLSCAASGFTFSSYAMSWVRQAPGKGLEWVSAISGSGG--SSTYADSVKGRFTISRDNSKNTLYLQMNSLRAEDTAVYYCAR--------------------------WGQGTLVTVSS
(SEQ ID NO: 35)
DP51        EVQLVESGGGLVQPGGSLRLSCAASGFTFSSYSMNWVRQAPGKGLEWVSYISSSSS--STIYYADSVKGRFTISRDNAKNSLYLQMNSLRAEDTAVYYCAR--------------------------WGQGTLVTVSS
(SEQ ID NO: 36)
DP53        EVQLVESGGGLVQPGGSLRLSCAASGFTFSSYWMHWVRQAPGKGLEWVSRINSDGS--SSTSYADSVKGRFTISRDNAKNTLYLQMNSLRAEDTAVYYCAR--------------------------WGQGTLVTVSS
(SEQ ID NO: 37)
DP29        EVQLVESGGGLVQPGGSLRLSCAASGFTFSDHYMDWVRQAPGKGLEWVGRTRNKANSYTTEYAASVKGRFTISRDDSKNSLYLQMNSLKTEDTAVYYCAR--------------------------WGQGTLVTVSS
DP54        EVQLVESGGGLVQPGGSLRLSCAASGFTFSSYAMSWVRQAPGKGLEWVSAISGSGG--STIYADSVKGRFTISRDNAKNSLYLQMNSLRAEDTAVYYCAR--------------------------WGQGTLVTVSS
(SEQ ID NO: 38)
DP47        EVQLVESGGGLVQPGGSLRLSCAASGFTFSSYWMSWVRQAPGKGLEWVANIKQDGS--ERKYYVDSVKGRFTISRDNAKNSLYLQMNSLRAEDTAVYYCAR--------------------------WGQGTLVTVSS
(SEQ ID NO: 39)

IL6R04      EVQLVESGGGLVQ[AG]GSLRLSCAASGFTF[D]YDIGM[E]RQAPGK[GLE][WVA]SGISSSDG---NTVYADSVKGRFTIS[S]DNAKNT[V]LQMNSL[R]EDTAVYYCA[K][A]PPDSSWYLDGSPEFFKYWGGTLVTVSS
DP51        EVQLVESGGGLVQPGGSLRLSCAASGFTFSSYSMNWVRQAPGKGLEWVSYISSSSS--STIYYADSVKGRFTISRDNAKNSLYLQMNSLRAEDTAVYYCAR--------------------------WGQGTLVTVSS
DP53        EVQLVESGGGLVQPGGSLRLSCAASGFTFSSYWMHWVRQAPGKGLEWVSRINSDGS--SSTSYADSVKGRFTISRDNAKNTLYLQMNSLRAEDTAVYYCAR--------------------------WGQGTLVTVSS
DP29        EVQLVESGGGLVQPGGSLRLSCAASGFTFSDHYMDWVRQAPGKGLEWVGRTRNKANSYTTEYAASVKGRFTISRDDSKNSLYLQMNSLKTEDTAVYYCAR--------------------------WGQGTLVTVSS
DP47        EVQLLESGGGLVQPGGSLRLSCAASGFTFSSYAMSWVRQAPGKGLEWVSAISGSGG--STIYADSVKGRFTISRDNAKNSLYLQMNSLRAEDTAVYYCAR--------------------------WGQGTLVTVSS
DP54        EVQLVESGGGLVQPGGSLRLSCAASGFTFSSYWMSWVRQAPGKGLEWVANIKQDGS--ERKYYVDSVKGRFTISRDNAKNSLYLQMNSLRAEDTAVYYCAR--------------------------WGQGTLVTVSS

IL6R13      EVQLVESGGGLVQPGGSLRLSCAASGFTF[D]YGMSWVRQAPG[R]A[T]EWVSAISWNGN--NTVYTESMKGRFTISRDDSKNSLYLQMNSL[R]EDTAVYYCAR--------------------------WGQGTLVTVSS
DP29        EVQLVESGGGLVQPGGSLRLSCAASGFTFSDHYMDWVRQAPGKGLEWVGRTRNKANSYTTEYAASVKGRFTISRDDSKNSLYLQMNSLKTEDTAVYYCAR--------------------------WGQGTLVTVSS
DP47        EVQLLESGGGLVQPGGSLRLSCAASGFTFSSYAMSWVRQAPGKGLEWVSAISGSGG--STIYADSVKGRFTISRDNAKNSLYLQMNSLRAEDTAVYYCAR--------------------------WGQGTLVTVSS
DP51        EVQLVESGGGLVQPGGSLRLSCAASGFTFSSYSMNWVRQAPGKGLEWVSYISSSSS--STIYYADSVKGRFTISRDNAKNSLYLQMNSLRAEDTAVYYCAR--------------------------WGQGTLVTVSS
DP53        EVQLVESGGGLVQPGGSLRLSCAASGFTFSSYWMHWVRQAPGKGLEWVSRINSDGS--SSTSYADSVKGRFTISRDNAKNTLYLQMNSLRAEDTAVYYCAR--------------------------WGQGTLVTVSS
DP54        EVQLVESGGGLVQPGGSLRLSCAASGFTFSSYWMSWVRQAPGKGLEWVANIKQDGS--ERKYYVDSVKGRFTISRDNAKNSLYLQMNSLRAEDTAVYYCAR--------------------------WGQGTLVTVSS
```

Fig. 15

```
IL6R03  EVQLVESGGGLVQPGGSLRLSCAASGE..EF..VNAMGWFRQAPGK....AGIISGGSTNYADSVKGRFTISRDNAKNTVLQMNSL..PEDTAVYYC........VTTNSDYDLGRDYWGQGTQVTVSS
IL6R61  EVQLVESGGGLVQPGGSLRLSCAASGSIFKVNAMGWYRQAPGKGRELVAGIISGGSTNYADSVKGRLTISRDNAKNTVYLQMNSLRPEDTAVYYCSFVTTNSDYDLGRDYWGQGTQVTVSS
IL6R62  EVQLVESGGGLVQPGGSLRLSCAASGSIFKVNAMGWYRQAPGKGRELVAGIISGGSTNYADSVKGRLTISRDNAKNTVYLQMNSLRPEDTAVYYCSFVTTNSDYDLGRDYWGQGTQVTVSS
IL6R63  EVQLVESGGGLVQPGGSLRLSCAASGSIFKVNAMGWYRQAPGKGRELVAGIISGGSTNYADSVKGRLTISRDNAKNTLYLQMNSLRPEDTAVYYCSFVTTNSDYDLGRDYWGQGTQVTVSS
IL6R64  EVQLVESGGGLVQPGGSLRLSCAASGSIFKVNAMGWYRQAPGKGRELVAGIISGGSTNYADSVKGRLTISRDNAKNTVYLQMNSLRPEDTAVYYCAFVTTNSDYDLGRDYWGQGTQVTVSS
IL6R65  EVQLVESGGGLVQPEGSLRLSCAASGSIFKVNAMGWYRQAPGKGRELVAGIISGGSTNYADSVKGRFTISRDNAKNTVYLQMNSLRPEDTAVYYCAFVTTNSDYDLGRDYWGQGTQVTVSS
*************************************************************************************************

IL6R04  EVQLVESGGGLVQPG.NGSLRLSCAASGFTFDDYDIGWFRQAPGK....VSGISSSDGNTYYADSVKGRFTISSDNAKNTVLQMNSL..EDTAVYYCAA.EPPDSSWYLDGSPEFFKYWGQGTQVTVSS
IL6R71  EVQLVESGGGLVQPGGSLRLSCAASGFTFDDYDIGWFRQAPGKEREQVSGISSSDGNTYYADSVKGRFTISSDNAKNTVYLQMNSLRPEDTAVYYCAAEPPDSSWYLDGSPEFFKYWGQGTQVTVSS
IL6R72  EVQLVESGGGLVQPGGSLRLSCAASGFTFDDYDIGWFRQAPGKEREQVSGISSSDGNTYYADSVKGRFTISSDNAKNTVYLQMNSLRPEDTAVYYCAAEPPDSSWYLDGSPEFFKYWGQGTQVTVSS
IL6R73  EVQLVESGGGLVQPGGSLRLSCAASGFTFDDYDIGWFRQAPGKEREQVSGISSSDGNTYYADSVKGRFTISSDNAKNTVYLQMNSLRPEDTAVYYCAAEPPDSSWYLDGSPEFFKYWGQGTQVTVSS
IL6R74  EVQLVESGGGLVQPGGSLRLSCAASGFTFDDYDIGWFRQAPGKEREQVSGISSSDGNTYYADSVKGRFTISSDNAKNTFLQMNSLYLQMNSLRPEDTAVYYCAAEPPDSSWYLDGSPEFFKYWGQGTQVTVSS
IL6R75  EVQLVESGGGLVQPEGSLRLSCAASGFTFSDYDIGWFRQAPGKEREQVSGISSSDGNTYYADSVKGRFTISSDNAKNTFYLQMNSLRPEDTAVYYCAAEPPDSSWYLDGSPEFFKYWGQGTQVTVSS
```

Fig. 16A

| | |
|---|---|
| IL6R13 | EVQLVESGGGLVQPGGSLRLSCAASGFTFDDYGMSWVRQAPGKRATEWVSAISWNGNNTYYTESMKGRFTISRDNAKNTVYLQMNSLKPEDTAVYYCVKWKGSTAIVGVPPTYPDEYDYWGQGTQVTVSS |
| IL6R81 | EVQLVESGGGLVQPGGSLRLSCAASGFTFDDYGMSWVRQAPGRATEWVSAISWNGNNTYYTESMKGRFTISRDNAKNTVYLQMNSLRPEDTAVYYCVKGSTAIVGVPPTYPDEYDYWGQGTLVTVSS |
| IL6R82 | EVQLVESGGGLVQPGGSLRLSCAASGFTFDDYGMSWVRQAPGKGLEWVSAISWNGNNTYYTESMKGRFTISRDNAKNTVYLQMNSIRPEDTAVYYCVKGSTAIVGVPPTYPDEYDYWGQGTLVTVSS |
| IL6R83 | EVQLVESGGGLVQPGGSLRLSCAASGFTFDDYGMSWVRQAPGRATEWVSAISWNGNNTYYTESMKGRFTISRDNAKNTVYLQMNSIRPEDTAVYYCVKGSTAIVGVPPTYPDEYDYWGQGTLVTVSS |
| IL6R84 | EVQLVESGGGLVQPGGSLRLSCAASGFTFDDYGMSWVRQAPGKGLEWVSAISWNGNNTYYTESMKGRFTISRDNAKNTVYLQMNSIRPEDTAVYYCVKGSTAIVGVPPTYPDEYDYWGQGTLVTVSS |
| IL6R85 | EVQLVESGGGLVQPGGSLRLSCAASGFTFDDYGMSWVRQAPGRGLEWVSAISWNGNNTYYTESMKGRFTISRDNAKNTIYLQMNSLRPEDTAVYYCVKGSTAIVGVPPTYPDEYDYWGQGTLVTVSS |
| IL6R86 | EVQLVESGGGLVQPGGSLRLSCAASGFTFDDYGMSWVRQAPGRALEWVSAISWNGNNTYYTESMKGRFTISRDNAKNTIYLQMNSLRPEDTAVYYCVKGSTAIVGVPPTYPDEYDYWGQGTLVTVSS |
| IL6R87 | EVQLVESGGGLVQPGGSLRLSCAASGFTFDDYGMSWVRQAPGKATEWVSAISWNGNNTYYTESMKGRFTISRDNAKNTIYLQMNSLRPEDTAVYYCVKGSTAIVGVPPTYPDEYDYWGQGTLVTVSS |
| IL6R88 | EVQLVESGGGLVQPGGSLRLSCAASGFTFDDYGMSWVRQAPGKGTEWVSAISWNGNNTYYTESMKGRFTISRDNAKNTIYLQMNSLRPEDTAVYYCVKGSTAIVGVPPTYPDEYDYWGQGTLVTVSS |
| IL6R89 | EVQLVESGGGLVQPGGSLRLSCAASGFTFDDYGMSWVRQAPGRGLEWVSAISWNGNNTYYTESMKGRFTISRDNAKNTIYLQMNSLRPEDTAVYYCVKGSTAIVGVPPTYPDEYDYWGQGTLVTVSS |
| IL6R90 | EVQLVESGGGLVQPGGSLRLSCAASGFTFDDYGMSWVRQAPGKALEWVSAISWNGNNTYYTESMKGRFTISRDNAKNTIYLQMNSLRPEDTAVYYCVKGSTAIVGVPPTYPDEYDYWGQGTLVTVSS |

Fig. 16B

```
                    10         20         30         40         50         60
            ----|----|----|----|----|----|----|----|----|----|----|----|
IL6R65   EVQLVESGGGLVQPGGSLRLSCAASGSIFKVNAMGWYRQAPGKGRELVAGIISGGSTNYA
PMP7F4   ..........................TT...V.A.....................N...T..
PMP7C4   ..........................TT.RI.V.A..................TN...S..
PMP7D6   ...........................R..V.A....................AV.N..T.T..
PMP7G7   ..........................TT..I.I.A....................V.T..N.T..
PMP7G8   ...........................T.RI.V.A....................V.ND...T..

70         80         90         100        110        120
            ----|----|----|----|----|----|----|----|----|----|----|----|
IL6R65   DSVKGRFTISRDNAKNTLYLQMNSLRPEDTAVYYCAFVTTNSDYDLGRDYWGQGTLVTVSS
PMP7F4   ............................................................
PMP7C4   ............................................................
PMP7D6   ............................................................
PMP7G7   ............................................................
PMP7G8   ............................................................
```

Fig. 26

```
IL6R65      EVQLVESGGGLVQPGGSLRLSCAASGSIFKVNAMGWYRQAPGKGRELVAGIISGGSTNY-
            ADSVKG
PMP20F6     ................V..I.V.A.........................V......S.
            ......
PMP20A11    ................V..I.V.A.........................V......S.
            ......
PMP20E10    ................V..I.V.A.........................V......S.
            ......
PMP21A10    ...................I.V.A........................VT.....S.
            ......
PMP21D11    ................V..I.V.A........................VT.....S.
            ......

IL6R65      RFTISRDNAKNTLYLQMNSLRPEDTAVYYCAFVTTNSDYDLGRDYWGQGTLVTVSS
PMP20F6     ..........................I...................R.......
PMP20A11    ..........................I..E.................R.......
PMP20E10    ..........................I..E.................R.......
PMP21A10    ..........................I..E.................R.......
PMP21D11    ..........................I..E.................R.......
```

Fig. 31

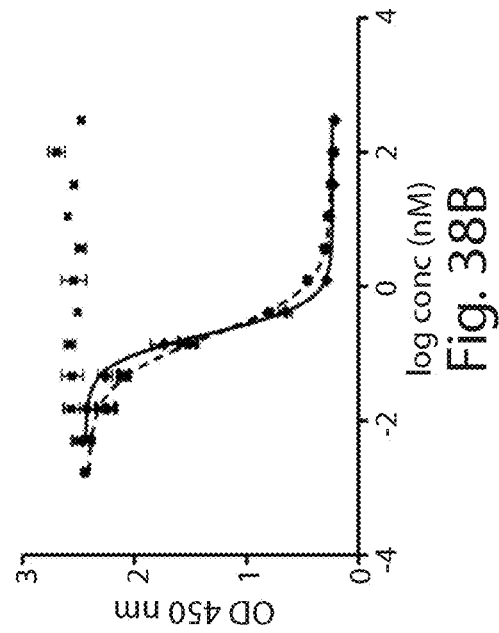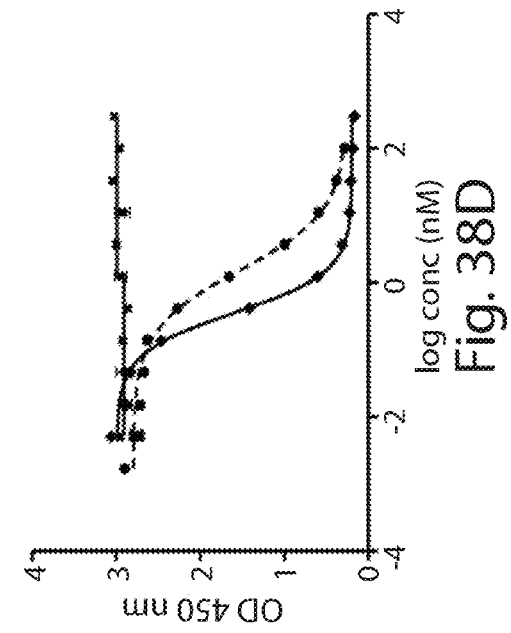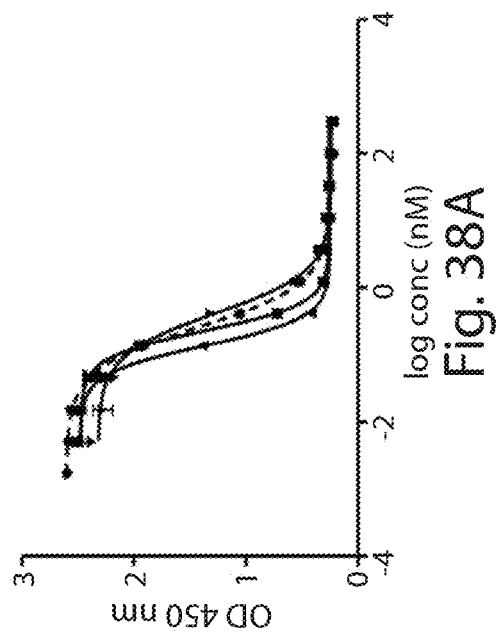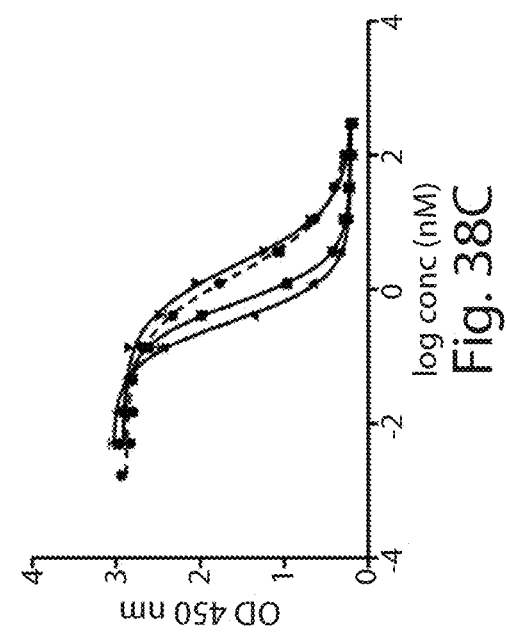

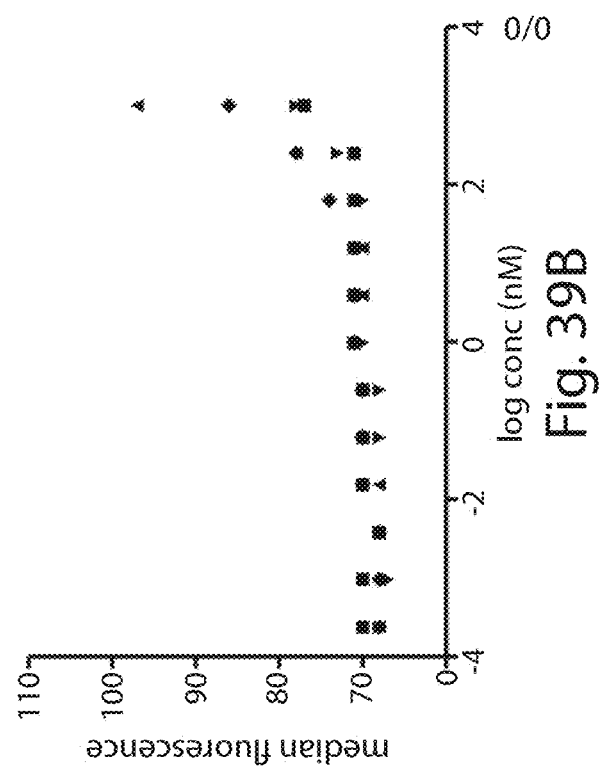
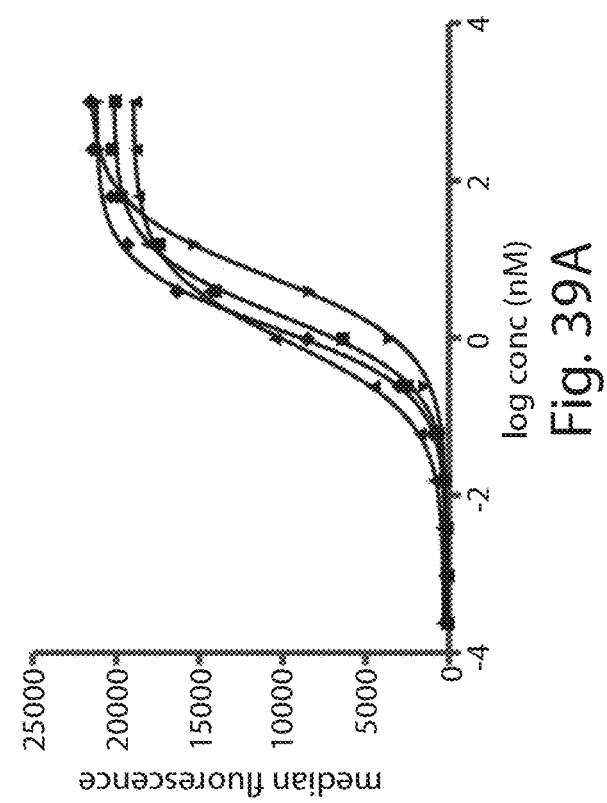

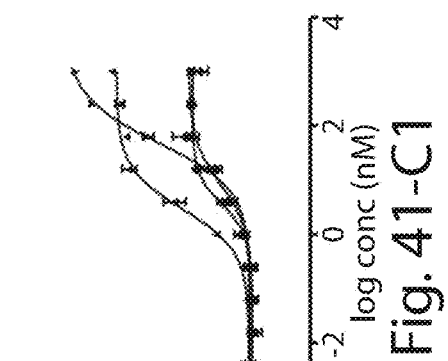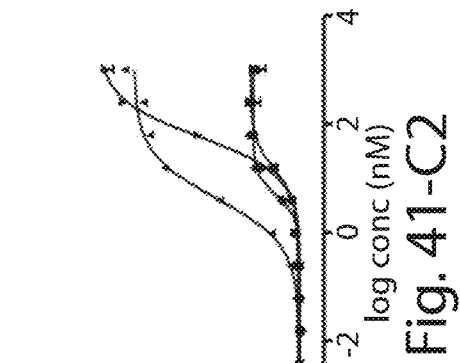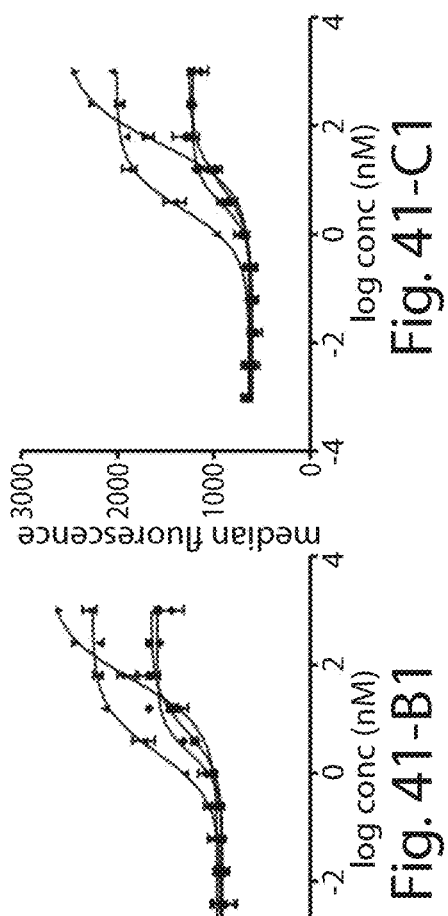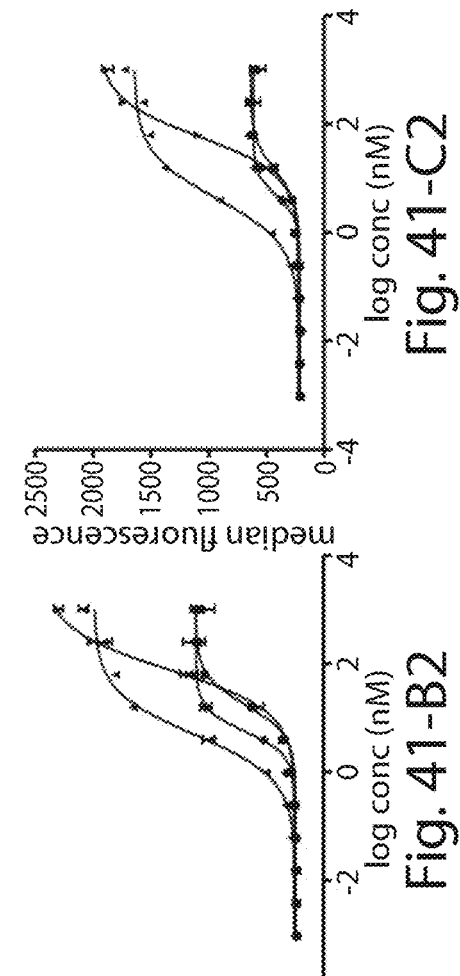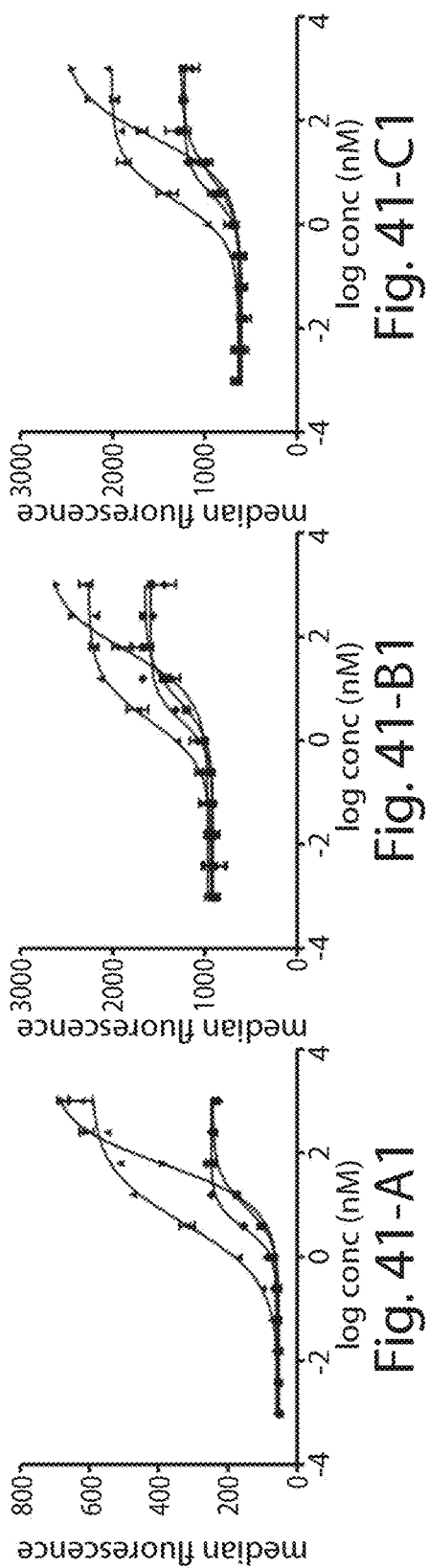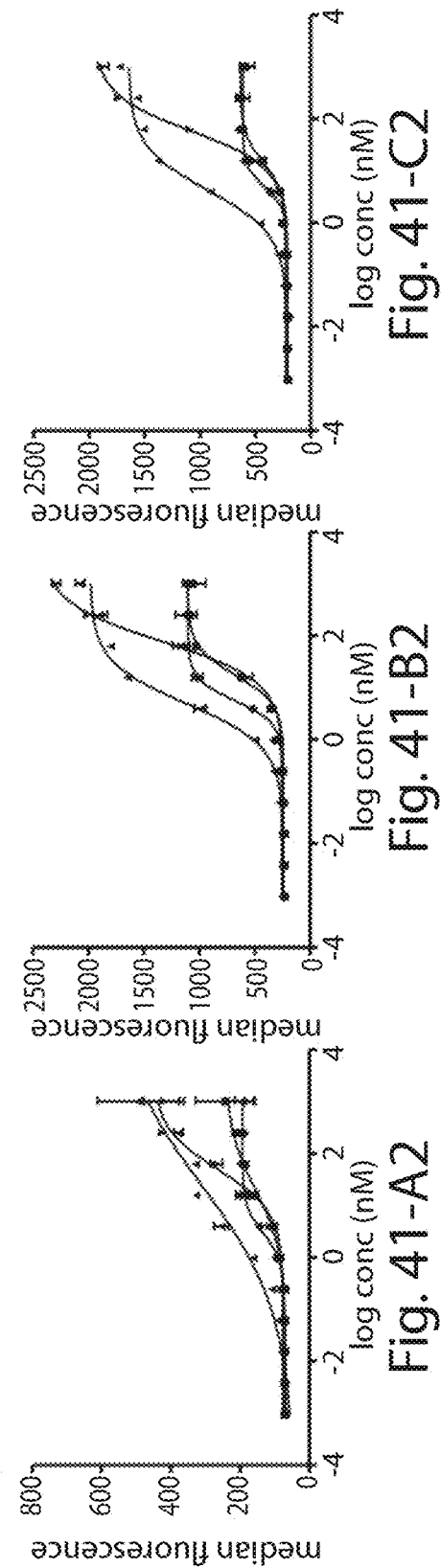
Fig. 41-A1  Fig. 41-B1  Fig. 41-C1
Fig. 41-A2  Fig. 41-B2  Fig. 41-C2

```
                        SEQUENCE LISTING

<160> NUMBER OF SEQ ID NOS: 105

<210> SEQ ID NO 1
<211> LENGTH: 449
<212> TYPE: PRT
<213> ORGANISM: Artificial Sequence
<220> FEATURE:
<223> OTHER INFORMATION: Recombinant antibody

<400> SEQUENCE: 1

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 2
<211> LENGTH: 214
<212> TYPE: PRT
<213> ORGANISM: Artificial Sequence
<220> FEATURE:
<223> OTHER INFORMATION: Recombinant antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 222
<212> TYPE: PRT
<213> ORGANISM: Artificial Sequence
<220> FEATURE:
<223> OTHER INFORMATION: Recombinant Fab

<400> SEQUENCE: 3

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220
```

<210> SEQ ID NO 4
<211> LENGTH: 214
<212> TYPE: PRT
<213> ORGANISM: Artificial Sequence
<220> FEATURE:
<223> OTHER INFORMATION: Recombinant Fab

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 135
<212> TYPE: PRT
<213> ORGANISM: Artificial Sequence
<220> FEATURE:
<223> OTHER INFORMATION: Nanobody

<400> SEQUENCE: 5

Glu Val Gln Leu Val Glu Ser Gly Gly Gly Leu Val Gln Pro Gly Gly
 1                5                  10                  15

Ser Leu Arg Leu Ser Cys Ala Ala Ser Gly Phe Ser Leu Asp Tyr Tyr
                20                  25                  30

Ala Ile Gly Trp Phe Arg Gln Ala Pro Gly Lys Glu Arg Glu Gly Val
            35                  40                  45

Ser Cys Met Asp Ser Ser Gly Thr Thr Thr Tyr Tyr Ser Asp
 50                  55                  60

Ser Val Lys Gly Arg Phe Thr Ile Ser Arg Asp Asp Ala Lys Asn Thr
 65                  70                  75                  80

Val Tyr Leu Gln Met Asn Ser Leu Lys Pro Glu Asp Thr Ala Val Tyr
                 85                  90                  95

Tyr Cys Ala Ala Asp Gly His Leu Asn Trp Gly Gln Arg Tyr Val Pro
            100                 105                 110

Cys Ser Gln Ile Ser Trp Arg Gly Trp Asn Asp Tyr Trp Gly Gln Gly
        115                 120                 125

Thr Gln Val Thr Val Ser Ser
    130                 135

<210> SEQ ID NO 6
<211> LENGTH: 127
<212> TYPE: PRT
<213> ORGANISM: Artificial Sequence
<220> FEATURE:
<223> OTHER INFORMATION: Nanobody

<400> SEQUENCE: 6
```

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu His Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Arg Asp Val Pro Ala Arg Ser Leu Cys Gly Ser Tyr Tyr
            100                 105                 110

Trp Tyr Asp Tyr Arg Gly Gln Gly Thr Gln Val Thr Val Ser Ser
            115                 120                 125
```

```
<210> SEQ ID NO 7
<211> LENGTH: 127
<212> TYPE: PRT
<213> ORGANISM: Artificial Sequence
<220> FEATURE:
<223> OTHER INFORMATION: Nanobody

<400> SEQUENCE: 7

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser
            115                 120                 125
```

```
<210> SEQ ID NO 8
<211> LENGTH: 127
<212> TYPE: PRT
<213> ORGANISM: Artificial Sequence
<220> FEATURE:
<223> OTHER INFORMATION: Nanobody

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Arg Ala Thr Glu Trp Val
        35                  40                  45

Ser Ala Ile Ser Trp Asn Gly Asn Asn Thr Tyr Tyr Thr Glu Ser Met
    50                  55                  60
```

```
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Gln Val Thr Val Ser Ser
        115                 120                 125

<210> SEQ ID NO 9
<211> LENGTH: 126
<212> TYPE: PRT
<213> ORGANISM: Artificial Sequence
<220> FEATURE:
<223> OTHER INFORMATION: Nanobody

<400> SEQUENCE: 9

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Gly Ser Tyr
             20                  25                  30

Asp Met Ser Trp Val Arg Gln Ala Pro Gly Lys Gly Pro Glu Trp Val
             35                  40                  45

Ser Ala Ile Asn Ser Gly Gly Gly Ser Thr Tyr Tyr Ala Asp Ser Val
         50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Thr Asp Trp Arg Tyr Ser Asp Tyr Asp Leu Pro Leu Pro Pro Pro
            100                 105                 110

Gly Asp Tyr Trp Gly Gln Gly Thr Gln Val Thr Val Ser Ser
        115                 120                 125

<210> SEQ ID NO 10
<211> LENGTH: 118
<212> TYPE: PRT
<213> ORGANISM: Artificial Sequence
<220> FEATURE:
<223> OTHER INFORMATION: Nanobody

<400> SEQUENCE: 10

Glu Val Gln Leu Val Glu Ser Gly Gly Gly Leu Val Gln Ala Gly Gly
 1               5                   10                  15

Ser Leu Arg Leu Ser Cys Ala Ala Ser Gly Arg Thr Phe Ser Ser Tyr
             20                  25                  30

Asp Met Gly Trp Tyr Arg Gln Ala Pro Gly Lys Glu Arg Glu Phe Val
             35                  40                  45

Ala Val Ile Ser Arg Ser Gly Ser Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Ile Tyr Tyr Cys
                 85                  90                  95

Lys Ala Glu Val Val Ala Gly Asp Tyr Asp Tyr Trp Gly Gln Gly Thr
            100                 105                 110

Gln Val Thr Val Ser Ser
```

<210> SEQ ID NO 11
<211> LENGTH: 120
<212> TYPE: PRT
<213> ORGANISM: Artificial Sequence
<220> FEATURE:
<223> OTHER INFORMATION: Nanobody

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asp Met Gly Trp Tyr Arg Gln Ala Pro Gly Lys Glu Arg Glu Phe Val
        35                  40                  45

Ala Val Ile His Trp Ser Ser Gly Ser Thr Tyr Tyr Ala Asp Pro Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Asn Ala Phe Leu Pro Gly Pro Glu Gly Phe His Asp Tyr Trp Gly Gln
            100                 105                 110

Gly Thr Gln Val Thr Val Ser Ser
        115                 120

<210> SEQ ID NO 12
<211> LENGTH: 117
<212> TYPE: PRT
<213> ORGANISM: Artificial Sequence
<220> FEATURE:
<223> OTHER INFORMATION: Nanobody

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Ser Tyr
            20                  25                  30

Asp Met Thr Trp Tyr Arg Gln Val Pro Gly Lys Glu Arg Glu Phe Val
        35                  40                  45

Ala Val Ile Ser Trp Ser Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Asn Ala Tyr Thr Gly Gly Gly Asp Asp Tyr Trp Gly Gln Gly Thr Gln
            100                 105                 110

Val Thr Val Ser Ser
        115

<210> SEQ ID NO 13
<211> LENGTH: 121
<212> TYPE: PRT
<213> ORGANISM: Artificial Sequence
<220> FEATURE:
<223> OTHER INFORMATION: Nanobody

<400> SEQUENCE: 13

-continued

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gln Arg Glu Leu Val
        35                  40                  45

Ala Gly Ile Ile Ser Gly Gly Ser Thr Asn Tyr Ala Asp Ser Val Lys
    50                  55                  60

Gly Arg Leu Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Phe Val Thr Thr Asn Ser Asp Tyr Asp Leu Gly Arg Asp Tyr Trp Gly
            100                 105                 110

Gln Gly Thr Gln Val Thr Val Ser Ser
        115                 120

<210> SEQ ID NO 14
<211> LENGTH: 119
<212> TYPE: PRT
<213> ORGANISM: Artificial Sequence
<220> FEATURE:
<223> OTHER INFORMATION: Nanobody

<400> SEQUENCE: 14

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Asp Asp Asn
            20                  25                  30

Thr Met Gly Trp Thr Trp Asn Arg Gln Pro Pro Gly Lys Gln Arg Glu
        35                  40                  45

Leu Val Ala Ile Ile Ala Thr Asp Gly Ser Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Asn Leu Phe Ser Leu Arg Leu Gly Arg Asp Tyr Trp Gly Gln Gly
            100                 105                 110

Thr Gln Val Thr Val Ser Ser
        115

<210> SEQ ID NO 15
<211> LENGTH: 130
<212> TYPE: PRT
<213> ORGANISM: Artificial Sequence
<220> FEATURE:
<223> OTHER INFORMATION: Nanobody

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Gly
            20                  25                  30

Ala Ile Gly Trp Phe Arg Gln Ala Pro Gly Lys Glu Arg Glu Gly Val
        35                  40                  45

Ser Cys Ile Ser Ser Ser Thr Gly Ser Thr Tyr Tyr Ala Asp Ser Val

```
                50                  55                  60
Lys Gly Arg Phe Thr Ile Ser Arg Asp Asn Gly Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Asp Lys Met Trp Ser Pro Cys Leu Val Ala Ala Asn Glu Glu
                100                 105                 110

Ala Leu Phe Glu Tyr Asp Tyr Trp Gly Gln Gly Thr Gln Val Thr Val
            115                 120                 125

Ser Ser
    130

<210> SEQ ID NO 16
<211> LENGTH: 126
<212> TYPE: PRT
<213> ORGANISM: Artificial Sequence
<220> FEATURE:
<223> OTHER INFORMATION: Nanobody

<400> SEQUENCE: 16

Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Ser Leu Asp Tyr Tyr
                 20                  25                  30

Val Ile Gly Trp Phe Arg Gln Ala Pro Gly Lys Glu Arg Glu Gly Val
             35                  40                  45

Ser Cys Ile Ser Ser Ser Asp Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Asp Leu Leu Arg Thr Pro Glu Phe Cys Val Asp Ser Ala Pro
                100                 105                 110

Tyr Asp Tyr Trp Gly Gln Gly Thr Gln Val Thr Val Ser Ser
            115                 120                 125

<210> SEQ ID NO 17
<211> LENGTH: 128
<212> TYPE: PRT
<213> ORGANISM: Artificial Sequence
<220> FEATURE:
<223> OTHER INFORMATION: Nanobody

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Pro Leu Asp Tyr Tyr
                 20                  25                  30

Ala Ile Gly Trp Phe Arg Gln Ala Pro Gly Lys Glu Arg Glu Gly Val
             35                  40                  45

Ser Cys Ile Ser Ser Ser Asp Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95
```

```
Ala Leu Val His Thr Thr Ala Gln Ala Thr Gly Val Pro Gln Arg Glu
            100                 105                 110

Tyr Glu Tyr Glu Trp Trp Gly Gln Gly Thr Gln Val Thr Val Ser Ser
            115                 120                 125

<210> SEQ ID NO 18
<211> LENGTH: 118
<212> TYPE: PRT
<213> ORGANISM: Artificial Sequence
<220> FEATURE:
<223> OTHER INFORMATION: Nanobody

<400> SEQUENCE: 18

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asp Met Gly Trp Tyr Arg Gln Ala Pro Gly Lys Glu Arg Glu Phe Val
            35                  40                  45

Ala Ile Ile Thr Trp Asn Ser Ser Thr Tyr Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Ile Tyr Tyr Cys Asn
                85                  90                  95

Ala Gln Tyr Gly Leu Gly Tyr Ala Glu Asp Tyr Trp Gly Gln Gly Thr
            100                 105                 110

Gln Val Thr Val Ser Ser
            115

<210> SEQ ID NO 19
<211> LENGTH: 242
<212> TYPE: PRT
<213> ORGANISM: Artificial Sequence
<220> FEATURE:
<223> OTHER INFORMATION: Nanobody

<400> SEQUENCE: 19

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asp Met Gly Trp Tyr Arg Gln Ala Pro Gly Lys Glu Arg Glu Phe Val
            35                  40                  45

Ala Val Ile Ser Arg Ser Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Lys Ala Glu Val Val Ala Gly Asp Tyr Asp Tyr Trp Gly Gln Gly Thr
            100                 105                 110

Gln Val Thr Val Ser Ser Gly Gly Gly Ser Gly Gly Ser Ala
            115                 120                 125

Val Gln Leu Val Glu Ser Gly Gly Gly Leu Val Gln Pro Gly Asn Ser
            130                 135                 140

Leu Arg Leu Ser Cys Ala Ala Ser Gly Phe Thr Phe Arg Ser Phe Gly
145                 150                 155                 160
```

```
Met Ser Trp Val Arg Gln Ala Pro Gly Lys Glu Pro Glu Trp Val Ser
            165                 170                 175

Ser Ile Ser Gly Ser Gly Ser Asp Thr Leu Tyr Ala Asp Ser Val Lys
            180                 185                 190

Gly Arg Phe Thr Ile Ser Arg Asp Asn Ala Lys Thr Thr Leu Tyr Leu
            195                 200                 205

Gln Met Asn Ser Leu Lys Pro Glu Asp Thr Ala Val Tyr Tyr Cys Thr
            210                 215                 220

Ile Gly Gly Ser Leu Ser Arg Ser Ser Gln Gly Thr Gln Val Thr Val
225                 230                 235                 240

Ser Ser
```

<210> SEQ ID NO 20
<211> LENGTH: 245
<212> TYPE: PRT
<213> ORGANISM: Artificial Sequence
<220> FEATURE:
<223> OTHER INFORMATION: Nanobody

<400> SEQUENCE: 20

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gln Arg Glu Leu Val
            35                  40                  45

Ala Gly Ile Ile Ser Gly Gly Ser Thr Asn Tyr Ala Asp Ser Val Lys
        50                  55                  60

Gly Arg Leu Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Phe Val Thr Thr Asn Ser Asp Tyr Asp Leu Gly Arg Asp Tyr Trp Gly
            100                 105                 110

Gln Gly Thr Gln Val Thr Val Ser Ser Gly Gly Gly Ser Gly Gly
            115                 120                 125

Gly Ser Ala Val Gln Leu Val Glu Ser Gly Gly Gly Leu Val Gln Pro
        130                 135                 140

Gly Asn Ser Leu Arg Leu Ser Cys Ala Ala Ser Gly Phe Thr Phe Arg
145                 150                 155                 160

Ser Phe Gly Met Ser Trp Val Arg Gln Ala Pro Gly Lys Glu Pro Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Lys Pro Glu Asp Thr Ala Val Tyr
        210                 215                 220

Tyr Cys Thr Ile Gly Gly Ser Leu Ser Arg Ser Ser Gln Gly Thr Gln
225                 230                 235                 240

Val Thr Val Ser Ser
            245
```

<210> SEQ ID NO 21
<211> LENGTH: 251

```
<212> TYPE: PRT
<213> ORGANISM: Artificial Sequence
<220> FEATURE:
<223> OTHER INFORMATION: Nanobody

<400> SEQUENCE: 21

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser Gly
        115                 120                 125

Gly Gly Gly Ser Gly Gly Gly Ser Ala Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Arg Ser Phe Gly Met Ser Trp Val Arg Gln Ala
                165                 170                 175

Pro Gly Lys Glu Pro Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Lys Pro
    210                 215                 220

Glu Asp Thr Ala Val Tyr Tyr Cys Thr Ile Gly Gly Ser Leu Ser Arg
225                 230                 235                 240

Ser Ser Gln Gly Thr Gln Val Thr Val Ser Ser
                245                 250

<210> SEQ ID NO 22
<211> LENGTH: 250
<212> TYPE: PRT
<213> ORGANISM: Artificial Sequence
<220> FEATURE:
<223> OTHER INFORMATION: Nanobody

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Asp Met Ser Trp Val Arg Gln Ala Pro Gly Lys Gly Pro Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Lys Pro Glu Asp Thr Ala Val Tyr Tyr Cys
                85                  90                  95

Ala Thr Asp Trp Arg Tyr Ser Asp Tyr Asp Leu Pro Leu Pro Pro Pro
            100                 105                 110

Gly Asp Tyr Trp Gly Gln Gly Thr Gln Val Thr Val Ser Ser Gly Gly
            115                 120                 125

Gly Gly Ser Gly Gly Ser Ala Val Gln Leu Val Glu Ser Gly Gly
            130                 135                 140

Gly Leu Val Gln Pro Gly Asn Ser Leu Arg Leu Ser Cys Ala Ala Ser
145                 150                 155                 160

Gly Phe Thr Phe Arg Ser Phe Gly Met Ser Trp Val Arg Gln Ala Pro
            165                 170                 175

Gly Lys Glu Pro Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
            195                 200                 205

Asn Ala Lys Thr Thr Leu Tyr Leu Gln Met Asn Ser Leu Lys Pro Glu
            210                 215                 220

Asp Thr Ala Val Tyr Tyr Cys Thr Ile Gly Gly Ser Leu Ser Arg Ser
225                 230                 235                 240

Ser Gln Gly Thr Gln Val Thr Val Ser Ser
            245                 250

<210> SEQ ID NO 23
<211> LENGTH: 243
<212> TYPE: PRT
<213> ORGANISM: Artificial Sequence
<220> FEATURE:
<223> OTHER INFORMATION: Nanobody

<400> SEQUENCE: 23

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Asp Asp Asn
            20                  25                  30

Thr Met Gly Trp Thr Trp Asn Arg Gln Pro Pro Gly Lys Gln Arg Glu
        35                  40                  45

Leu Val Ala Ile Ile Ala Thr Asp Gly Ser Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Asn Leu Phe Ser Leu Arg Leu Gly Arg Asp Tyr Trp Gly Gln Gly
            100                 105                 110

Thr Gln Val Thr Val Ser Ser Gly Gly Gly Ser Gly Gly Gly Ser
            115                 120                 125

Ala Val Gln Leu Val Glu Ser Gly Gly Gly Leu Val Gln Pro Gly Asn
            130                 135                 140

Ser Leu Arg Leu Ser Cys Ala Ala Ser Gly Phe Thr Phe Arg Ser Phe
145                 150                 155                 160

Gly Met Ser Trp Val Arg Gln Ala Pro Gly Lys Glu Pro Glu Trp Val
            165                 170                 175

Ser Ser Ile Ser Gly Ser Gly Ser Asp Thr Leu Tyr Ala Asp Ser Val
            180                 185                 190
```

```
Lys Gly Arg Phe Thr Ile Ser Arg Asp Asn Ala Lys Thr Thr Leu Tyr
        195                 200                 205

Leu Gln Met Asn Ser Leu Lys Pro Glu Asp Thr Ala Val Tyr Tyr Cys
210                 215                 220

Thr Ile Gly Gly Ser Leu Ser Arg Ser Ser Gln Gly Thr Gln Val Thr
225                 230                 235                 240

Val Ser Ser

<210> SEQ ID NO 24
<211> LENGTH: 250
<212> TYPE: PRT
<213> ORGANISM: Artificial Sequence
<220> FEATURE:
<223> OTHER INFORMATION: Nanobody

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Ser Leu Asp Tyr Tyr
            20                  25                  30

Val Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Leu Arg Thr Pro Glu Phe Cys Val Ser Ala Ser Pro
            100                 105                 110

Tyr Asp Tyr Trp Gly Gln Gly Thr Gln Val Thr Val Ser Ser Gly Gly
        115                 120                 125

Gly Gly Ser Gly Gly Gly Ser Ala Val Gln Leu Val Glu Ser Gly Gly
130                 135                 140

Gly Leu Val Gln Pro Gly Asn Ser Leu Arg Leu Ser Cys Ala Ala Ser
145                 150                 155                 160

Gly Phe Thr Phe Arg Ser Phe Gly Met Ser Trp Val Arg Gln Ala Pro
                165                 170                 175

Gly Lys Glu Pro Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
        195                 200                 205

Asn Ala Lys Thr Thr Leu Tyr Leu Gln Met Asn Ser Leu Lys Pro Glu
210                 215                 220

Asp Thr Ala Val Tyr Tyr Cys Thr Ile Gly Gly Ser Leu Ser Arg Ser
225                 230                 235                 240

Ser Gln Gly Thr Gln Val Thr Val Ser Ser
                245                 250

<210> SEQ ID NO 25
<211> LENGTH: 241
<212> TYPE: PRT
<213> ORGANISM: Artificial Sequence
<220> FEATURE:
<223> OTHER INFORMATION: Nanobody

<400> SEQUENCE: 25
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Ser Tyr
            20                  25                  30

Asp Met Thr Trp Tyr Arg Gln Val Pro Gly Lys Glu Arg Glu Phe Val
        35                  40                  45

Ala Val Ile Ser Trp Ser Gly Gly Ser Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Asn Ala Tyr Thr Gly Gly Gly Asp Asp Tyr Trp Gly Gln Gly Thr Gln
            100                 105                 110

Val Thr Val Ser Ser Gly Gly Gly Ser Gly Gly Ser Ala Val
        115                 120                 125

Gln Leu Val Glu Ser Gly Gly Gly Leu Val Gln Pro Gly Asn Ser Leu
130                 135                 140

Arg Leu Ser Cys Ala Ala Ser Gly Phe Thr Phe Arg Ser Phe Gly Met
145                 150                 155                 160

Ser Trp Val Arg Gln Ala Pro Gly Lys Glu Pro Glu Trp Val Ser Ser
            165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
            195                 200                 205

Met Asn Ser Leu Lys Pro Glu Asp Thr Ala Val Tyr Tyr Cys Thr Ile
        210                 215                 220

Gly Gly Ser Leu Ser Arg Ser Ser Gln Gly Thr Gln Val Thr Val Ser
225                 230                 235                 240

Ser

<210> SEQ ID NO 26
<211> LENGTH: 244
<212> TYPE: PRT
<213> ORGANISM: Artificial Sequence
<220> FEATURE:
<223> OTHER INFORMATION: Nanobody

<400> SEQUENCE: 26

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asp Met Gly Trp Tyr Arg Gln Ala Pro Gly Lys Glu Arg Glu Phe Val
        35                  40                  45

Ala Val Ile His Trp Ser Ser Gly Ser Thr Tyr Tyr Ala Asp Pro Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Asn Ala Phe Leu Pro Gly Pro Glu Gly Phe His Asp Tyr Trp Gly Gln
            100                 105                 110

```
Gly Thr Gln Val Thr Val Ser Gly Gly Gly Ser Gly Gly
            115                 120                 125

Ser Ala Val Gln Leu Val Glu Ser Gly Gly Leu Val Gln Pro Gly
        130                 135                 140

Asn Ser Leu Arg Leu Ser Cys Ala Ala Ser Gly Phe Thr Phe Arg Ser
145                 150                 155                 160

Phe Gly Met Ser Trp Val Arg Gln Ala Pro Gly Lys Glu Pro Glu Trp
                165                 170                 175

Val Ser Ser Ile Ser Gly Ser Gly Ser Asp Thr Leu Tyr Ala Asp Ser
                180                 185                 190

Val Lys Gly Arg Phe Thr Ile Ser Arg Asp Asn Ala Lys Thr Thr Leu
        195                 200                 205

Tyr Leu Gln Met Asn Ser Leu Lys Pro Glu Asp Thr Ala Val Tyr Tyr
    210                 215                 220

Cys Thr Ile Gly Gly Ser Leu Ser Arg Ser Ser Gln Gly Thr Gln Val
225                 230                 235                 240

Thr Val Ser Ser
```

<210> SEQ ID NO 27
<211> LENGTH: 251
<212> TYPE: PRT
<213> ORGANISM: Artificial Sequence
<220> FEATURE:
<223> OTHER INFORMATION: Nanobody

<400> SEQUENCE: 27

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu His Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Arg Asp Val Pro Ala Arg Ser Leu Cys Gly Ser Tyr Tyr
                100                 105                 110

Trp Tyr Asp Tyr Arg Gly Gln Gly Thr Gln Val Thr Val Ser Ser Gly
            115                 120                 125

Gly Gly Ser Gly Gly Gly Ser Ala Val Gln Leu Val Glu Ser Gly
        130                 135                 140

Gly Gly Leu Val Gln Pro Gly Asn Ser Leu Arg Leu Ser Cys Ala Ala
145                 150                 155                 160

Ser Gly Phe Thr Phe Arg Ser Phe Gly Met Ser Trp Val Arg Gln Ala
                165                 170                 175

Pro Gly Lys Glu Pro Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Lys Pro
    210                 215                 220

Glu Asp Thr Ala Val Tyr Tyr Cys Thr Ile Gly Gly Ser Leu Ser Arg
```

```
                225                 230                 235                 240

Ser Ser Gln Gly Thr Gln Val Thr Val Ser Ser
                        245                 250

<210> SEQ ID NO 28
<211> LENGTH: 242
<212> TYPE: PRT
<213> ORGANISM: Artificial Sequence
<220> FEATURE:
<223> OTHER INFORMATION: Nanobody

<400> SEQUENCE: 28

Glu Val Gln Leu Val Glu Ser Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asp Met Gly Trp Tyr Arg Gln Ala Pro Gly Lys Glu Arg Glu Phe Val
        35                  40                  45

Ala Ile Ile Thr Trp Asn Ser Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Ile Tyr Tyr Cys Asn
                85                  90                  95

Ala Gln Tyr Gly Leu Gly Tyr Ala Glu Asp Tyr Trp Gly Gln Gly Thr
            100                 105                 110

Gln Val Thr Val Ser Ser Gly Gly Gly Ser Gly Gly Gly Ser Ala
        115                 120                 125

Val Gln Leu Val Glu Ser Gly Gly Leu Val Gln Pro Gly Asn Ser
    130                 135                 140

Leu Arg Leu Ser Cys Ala Ala Ser Gly Phe Thr Phe Arg Ser Phe Gly
145                 150                 155                 160

Met Ser Trp Val Arg Gln Ala Pro Gly Lys Glu Pro Glu Trp Val Ser
                165                 170                 175

Ser Ile Ser Gly Ser Gly Ser Asp Thr Leu Tyr Ala Asp Ser Val Lys
            180                 185                 190

Gly Arg Phe Thr Ile Ser Arg Asp Asn Ala Lys Thr Thr Leu Tyr Leu
        195                 200                 205

Gln Met Asn Ser Leu Lys Pro Glu Asp Thr Ala Val Tyr Tyr Cys Thr
    210                 215                 220

Ile Gly Gly Ser Leu Ser Arg Ser Ser Gln Gly Thr Gln Val Thr Val
225                 230                 235                 240

Ser Ser

<210> SEQ ID NO 29
<211> LENGTH: 251
<212> TYPE: PRT
<213> ORGANISM: Artificial Sequence
<220> FEATURE:
<223> OTHER INFORMATION: Nanobody

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Arg Ala Thr Glu Trp Val
```

```
            35                  40                  45
Ser Ala Ile Ser Trp Asn Gly Asn Asn Thr Tyr Tyr Thr Glu Ser Met
 50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Glu Asp Thr Ala Val Tyr Tyr Cys
                 85                  90                  95
Val Lys Gly Ser Thr Ala Ile Val Gly Val Pro Pro Thr Tyr Pro Asp
            100                 105                 110
Glu Tyr Asp Tyr Trp Gly Gln Gly Thr Gln Val Thr Val Ser Ser Gly
            115                 120                 125
Gly Gly Gly Ser Gly Gly Gly Ser Ala Val Gln Leu Val Glu Ser Gly
            130                 135                 140
Gly Gly Leu Val Gln Pro Gly Asn Ser Leu Arg Leu Ser Cys Ala Ala
145                 150                 155                 160
Ser Gly Phe Thr Phe Arg Ser Phe Gly Met Ser Trp Val Arg Gln Ala
                165                 170                 175
Pro Gly Lys Glu Pro Glu Trp Val Ser Ser Ile Ser Gly Ser Gly Ser
            180                 185                 190
Asp Thr Leu Tyr Ala Asp Ser Val Lys Gly Arg Phe Thr Ile Ser Arg
            195                 200                 205
Asp Asn Ala Lys Thr Thr Leu Tyr Leu Gln Met Asn Ser Leu Lys Pro
210                 215                 220
Glu Asp Thr Ala Val Tyr Tyr Cys Thr Ile Gly Gly Ser Leu Ser Arg
225                 230                 235                 240
Ser Ser Gln Gly Thr Gln Val Thr Val Ser Ser
                245                 250

<210> SEQ ID NO 30
<211> LENGTH: 259
<212> TYPE: PRT
<213> ORGANISM: Artificial Sequence
<220> FEATURE:
<223> OTHER INFORMATION: Nanobody

<400> SEQUENCE: 30

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Ser Leu Asp Tyr Tyr
                 20                  25                  30
Ala Ile Gly Trp Phe Arg Gln Ala Pro Gly Lys Glu Arg Glu Gly Val
             35                  40                  45
Ser Cys Met Asp Ser Ser Gly Thr Thr Ser Thr Tyr Tyr Ser Asp Ser
 50                  55                  60
Ser Val Lys Gly Arg Phe Thr Ile Ser Arg Asp Asp Ala Lys Asn Thr
 65                  70                  75                  80
Val Tyr Leu Gln Met Asn Ser Leu Lys Pro Glu Asp Thr Ala Val Tyr
                 85                  90                  95
Tyr Cys Ala Ala Asp Gly His Leu Asn Trp Gly Gln Arg Tyr Val Pro
            100                 105                 110
Cys Ser Gln Ile Ser Trp Arg Gly Trp Asn Asp Tyr Trp Gly Gln Gly
            115                 120                 125
Thr Gln Val Thr Val Ser Ser Gly Gly Gly Ser Gly Gly Gly Ser
            130                 135                 140
Ala Val Gln Leu Val Glu Ser Gly Gly Gly Leu Val Gln Pro Gly Asn
```

```
145                 150                 155                 160
Ser Leu Arg Leu Ser Cys Ala Ala Ser Gly Phe Thr Phe Arg Ser Phe
                165                 170                 175

Gly Met Ser Trp Val Arg Gln Ala Pro Gly Lys Glu Pro Glu Trp Val
            180                 185                 190

Ser Ser Ile Ser Gly Ser Gly Ser Asp Thr Leu Tyr Ala Asp Ser Val
        195                 200                 205

Lys Gly Arg Phe Thr Ile Ser Arg Asp Asn Ala Lys Thr Thr Leu Tyr
    210                 215                 220

Leu Gln Met Asn Ser Leu Lys Pro Glu Asp Thr Ala Val Tyr Tyr Cys
225                 230                 235                 240

Thr Ile Gly Gly Ser Leu Ser Arg Ser Ser Gln Gly Thr Gln Val Thr
                245                 250                 255

Val Ser Ser

<210> SEQ ID NO 31
<211> LENGTH: 366
<212> TYPE: PRT
<213> ORGANISM: Artificial Sequence
<220> FEATURE:
<223> OTHER INFORMATION: Nanobody

<400> SEQUENCE: 31

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gln Arg Glu Leu Val
        35                  40                  45

Ala Gly Ile Ile Ser Gly Gly Ser Thr Asn Tyr Ala Asp Ser Val Lys
    50                  55                  60

Gly Arg Leu Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ser
                85                  90                  95

Phe Val Thr Thr Asn Ser Asp Tyr Asp Leu Gly Arg Asp Tyr Trp Gly
                100                 105                 110

Gln Gly Thr Gln Val Thr Val Ser Ser Gly Gly Gly Ser Gly Gly Gly
            115                 120                 125

Gly Ser Ala Val Gln Leu Val Glu Ser Gly Gly Gly Leu Val Gln Pro
        130                 135                 140

Gly Asn Ser Leu Arg Leu Ser Cys Ala Ala Ser Gly Phe Thr Phe Arg
145                 150                 155                 160

Ser Phe Gly Met Ser Trp Val Arg Gln Ala Pro Gly Lys Glu Pro Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Lys Pro Glu Asp Thr Ala Val Tyr
    210                 215                 220

Tyr Cys Thr Ile Gly Gly Ser Leu Ser Arg Ser Ser Gln Gly Thr Gln
225                 230                 235                 240

Val Thr Val Ser Ser Glu Val Gln Leu Val Glu Ser Gly Gly Gly Leu
                245                 250                 255
```

```
Val Gln Ala Gly Gly Ser Leu Arg Leu Ser Cys Ala Ala Ser Gly Ser
            260                 265                 270

Ile Phe Lys Val Asn Ala Met Gly Trp Tyr Arg Gln Ala Pro Gly Lys
        275                 280                 285

Gln Arg Glu Leu Val Ala Gly Ile Ile Ser Gly Ser Thr Asn Tyr
    290                 295                 300

Ala Asp Ser Val Lys Gly Arg Leu Thr Ile Ser Arg Asp Asn Ala Lys
305                 310                 315                 320

Asn Thr Val Tyr Leu Gln Met Asn Ser Leu Lys Pro Glu Asp Thr Ala
                325                 330                 335

Val Tyr Tyr Cys Ser Phe Val Thr Thr Asn Ser Asp Tyr Asp Leu Gly
            340                 345                 350

Arg Asp Tyr Trp Gly Gln Gly Thr Gln Val Thr Val Ser Ser
            355                 360                 365

<210> SEQ ID NO 32
<211> LENGTH: 387
<212> TYPE: PRT
<213> ORGANISM: Artificial Sequence
<220> FEATURE:
<223> OTHER INFORMATION: Nanobody

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Glu Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Gln Val Thr Val Ser Ser Gly
        115                 120                 125

Gly Gly Gly Ser Gly Gly Gly Ser Ala Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Arg Ser Phe Gly Met Ser Trp Val Arg Gln Ala
                165                 170                 175

Pro Gly Lys Glu Pro Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Lys Pro
    210                 215                 220

Glu Asp Thr Ala Val Tyr Tyr Cys Thr Ile Gly Gly Ser Leu Ser Arg
225                 230                 235                 240

Ser Ser Gln Gly Thr Gln Val Thr Val Ser Ser Gly Gly Gly Gly Ser
                245                 250                 255
```

Gly Gly Gly Ser Glu Val Gln Leu Val Glu Ser Gly Gly Gly Leu Val
                260                 265                 270

Gln Ala Gly Gly Ser Leu Arg Leu Ser Cys Ala Ala Ser Gly Phe Thr
            275                 280                 285

Phe Asp Asp Tyr Asp Ile Gly Trp Phe Arg Gln Ala Pro Gly Lys Glu
290                 295                 300

Arg Glu Gly Val Ser Gly Ile Ser Ser Ser Asp Gly Asn Thr Tyr Tyr
305                 310                 315                 320

Ala Asp Ser Val Lys Gly Arg Phe Thr Ile Ser Ser Asp Asn Ala Lys
                325                 330                 335

Asn Thr Val Tyr Leu Gln Met Asn Ser Leu Lys Pro Glu Asp Thr Ala
            340                 345                 350

Val Tyr Tyr Cys Ala Ala Glu Pro Pro Asp Ser Ser Trp Tyr Leu Asp
        355                 360                 365

Gly Ser Pro Glu Phe Phe Lys Tyr Trp Gly Gln Gly Thr Gln Val Thr
    370                 375                 380

Val Ser Ser
385

<210> SEQ ID NO 33
<211> LENGTH: 367
<212> TYPE: PRT
<213> ORGANISM: Artificial Sequence
<220> FEATURE:
<223> OTHER INFORMATION: Nanobody

<400> SEQUENCE: 33

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Ser Tyr
            20                  25                  30

Asp Met Thr Trp Tyr Arg Gln Val Pro Gly Lys Glu Arg Glu Phe Val
        35                  40                  45

Ala Val Ile Ser Trp Ser Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Asn Ala Tyr Thr Gly Gly Gly Asp Asp Tyr Trp Gly Gln Gly Thr Gln
            100                 105                 110

Val Thr Val Ser Ser Gly Gly Gly Ser Gly Gly Ser Ala Val
        115                 120                 125

Gln Leu Val Glu Ser Gly Gly Gly Leu Val Gln Pro Gly Asn Ser Leu
    130                 135                 140

Arg Leu Ser Cys Ala Ala Ser Gly Phe Thr Phe Arg Ser Phe Gly Met
145                 150                 155                 160

Ser Trp Val Arg Gln Ala Pro Gly Lys Glu Pro Glu Trp Val Ser Ser
                165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
        195                 200                 205

Met Asn Ser Leu Lys Pro Glu Asp Thr Ala Val Tyr Tyr Cys Thr Ile
    210                 215                 220

```
Gly Gly Ser Leu Ser Arg Ser Ser Gln Gly Thr Gln Val Thr Val Ser
225                 230                 235                 240

Ser Gly Gly Gly Ser Gly Gly Gly Ser Glu Val Gln Leu Val Glu
                245                 250                 255

Ser Gly Gly Gly Leu Val Gln Ala Gly Gly Ser Leu Arg Leu Ser Cys
                260                 265                 270

Ala Ala Ser Gly Arg Thr Ser Ser Tyr Asp Met Thr Trp Tyr Arg
            275                 280                 285

Gln Val Pro Gly Lys Glu Arg Glu Phe Val Ala Val Ile Ser Trp Ser
            290                 295                 300

Gly Gly Ser Thr Tyr Tyr Ala Asp Ser Val Lys Gly Arg Phe Thr Ile
305                 310                 315                 320

Ser Arg Asp Asn Ala Lys Asn Thr Val Tyr Leu Gln Met Asn Ser Leu
                325                 330                 335

Lys Pro Glu Asp Thr Ala Ile Tyr Tyr Cys Asn Ala Tyr Thr Gly Gly
                340                 345                 350

Gly Asp Asp Tyr Trp Gly Gln Gly Thr Gln Val Thr Val Ser Ser
            355                 360                 365

<210> SEQ ID NO 34
<211> LENGTH: 387
<212> TYPE: PRT
<213> ORGANISM: Artificial Sequence
<220> FEATURE:
<223> OTHER INFORMATION: Nanobody

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Arg Ala Thr Glu Trp Val
        35                  40                  45

Ser Ala Ile Ser Trp Asn Gly Asn Asn Thr Tyr Tyr Thr Glu Ser Met
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Val Lys Gly Ser Thr Ala Ile Val Gly Val Pro Pro Thr Tyr Pro Asp
        100                 105                 110

Glu Tyr Asp Tyr Trp Gly Gln Gly Thr Gln Val Thr Val Ser Ser Gly
    115                 120                 125

Gly Gly Gly Ser Gly Gly Gly Ser Ala Val Gln Leu Val Glu Ser Gly
130                 135                 140

Gly Gly Leu Val Gln Pro Gly Asn Ser Leu Arg Leu Ser Cys Ala Ala
145                 150                 155                 160

Ser Gly Phe Thr Phe Arg Ser Phe Gly Met Ser Trp Val Arg Gln Ala
            165                 170                 175

Pro Gly Lys Glu Pro Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Lys Pro
210                 215                 220
```

```
Glu Asp Thr Ala Val Tyr Tyr Cys Thr Ile Gly Gly Ser Leu Ser Arg
225                 230                 235                 240

Ser Ser Gln Gly Thr Gln Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Arg Leu Ser Cys Ala Ala Ser Gly Phe Thr
            275                 280                 285

Phe Asp Asp Tyr Gly Met Ser Trp Val Arg Gln Ala Pro Gly Arg Ala
            290                 295                 300

Thr Glu Trp Val Ser Ala Ile Ser Trp Asn Gly Asn Asn Thr Tyr Tyr
305                 310                 315                 320

Thr Glu Ser Met Lys Gly Arg Phe Thr Ile Ser Arg Asp Asn Ala Lys
                325                 330                 335

Asn Thr Val Tyr Leu Gln Met Asn Ser Leu Lys Pro Glu Asp Thr Ala
                340                 345                 350

Val Tyr Tyr Cys Val Lys Gly Ser Thr Ala Ile Val Gly Val Pro Pro
                355                 360                 365

Thr Tyr Pro Asp Glu Tyr Asp Tyr Trp Gly Gln Gly Thr Gln Val Thr
            370                 375                 380

Val Ser Ser
385

<210> SEQ ID NO 35
<211> LENGTH: 124
<212> TYPE: PRT
<213> ORGANISM: Artificial Sequence
<220> FEATURE:
<223> OTHER INFORMATION: VH sequence
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (101)..(113)
<223> OTHER INFORMATION: Xaa can be any naturally occurring amino acid

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Xaa Xaa Ser Thr Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Xaa Xaa Xaa Xaa Xaa Xaa Xaa Xaa Xaa Xaa Xaa Xaa
                100                 105                 110

Xaa Trp Gly Gln Gly Thr Leu Val Thr Val Ser Ser
            115                 120

<210> SEQ ID NO 36
<211> LENGTH: 123
```

<212> TYPE: PRT
<213> ORGANISM: Artificial Sequence
<220> FEATURE:
<223> OTHER INFORMATION: VH sequence
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (101)..(112)
<223> OTHER INFORMATION: Xaa can be any naturally occurring amino acid

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Xaa Xaa Thr Ile Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Asp Glu Asp Thr Ala Val Tyr
                85                  90                  95

Tyr Cys Ala Arg Xaa Xaa Xaa Xaa Xaa Xaa Xaa Xaa Xaa Xaa Xaa Xaa
            100                 105                 110

Trp Gly Gln Gly Thr Leu Val Thr Val Ser Ser
        115                 120

<210> SEQ ID NO 37
<211> LENGTH: 123
<212> TYPE: PRT
<213> ORGANISM: Artificial Sequence
<220> FEATURE:
<223> OTHER INFORMATION: VH sequence
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (101)..(112)
<223> OTHER INFORMATION: Xaa can be any naturally occurring amino acid

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Xaa Xaa Ser Thr Ser Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Xaa Xaa Xaa Xaa Xaa Xaa Xaa Xaa Xaa Xaa Xaa Xaa
            100                 105                 110

Trp Gly Gln Gly Thr Leu Val Thr Val Ser Ser

<210> SEQ ID NO 38
<211> LENGTH: 124
<212> TYPE: PRT
<213> ORGANISM: Artificial Sequence
<220> FEATURE:
<223> OTHER INFORMATION: VH sequence
<220> FEATURE:
<221> NAME/KEY: misc_feature
<222> LOCATION: (101)..(113)
<223> OTHER INFORMATION: Xaa can be any naturally occurring amino acid

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Xaa Xaa Xaa Xaa Xaa Xaa Xaa Xaa Xaa Xaa Xaa
            100                 105                 110

Xaa Trp Gly Gln Gly Thr Leu Val Thr Val Ser Ser
        115                 120
```

<210> SEQ ID NO 39
<211> LENGTH: 124
<212> TYPE: PRT
<213> ORGANISM: Artificial Sequence
<220> FEATURE:
<223> OTHER INFORMATION: VH sequence
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (101)..(113)
<223> OTHER INFORMATION: Xaa can be any naturally occurring amino acid

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Xaa Xaa Glu Lys Tyr Tyr Val Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Xaa Xaa Xaa Xaa Xaa Xaa Xaa Xaa Xaa Xaa Xaa
            100                 105                 110
```

```
Xaa Trp Gly Gln Gly Thr Leu Val Thr Val Ser Ser
        115                 120
```

<210> SEQ ID NO 40
<211> LENGTH: 121
<212> TYPE: PRT
<213> ORGANISM: Artificial Sequence
<220> FEATURE:
<223> OTHER INFORMATION: Nanobody

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Leu Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Ser
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120
```

<210> SEQ ID NO 41
<211> LENGTH: 121
<212> TYPE: PRT
<213> ORGANISM: Artificial Sequence
<220> FEATURE:
<223> OTHER INFORMATION: Nanobody

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Ser
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120
```

<210> SEQ ID NO 42
<211> LENGTH: 121
<212> TYPE: PRT
<213> ORGANISM: Artificial Sequence
<220> FEATURE:
<223> OTHER INFORMATION: Nanobody

```
<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Leu Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ser
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
            115                 120

<210> SEQ ID NO 43
<211> LENGTH: 121
<212> TYPE: PRT
<213> ORGANISM: Artificial Sequence
<220> FEATURE:
<223> OTHER INFORMATION: Nanobody

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45

Ala Gly Ile Ile Ser Gly Gly Ser Thr Asn Tyr Ala Asp Ser Val Lys
    50                  55                  60

Gly Arg Leu Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
            115                 120

<210> SEQ ID NO 44
<211> LENGTH: 121
<212> TYPE: PRT
<213> ORGANISM: Artificial Sequence
<220> FEATURE:
<223> OTHER INFORMATION: Nanobody

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Val Asn
            20                  25                  30

Ala Met Gly Trp Tyr Arg Gln Ala Pro Gly Lys Gly Arg Glu Leu Val
        35                  40                  45
```

-continued

```
Ala Gly Ile Ile Ser Gly Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
            115                 120

<210> SEQ ID NO 45
<211> LENGTH: 127
<212> TYPE: PRT
<213> ORGANISM: Artificial Sequence
<220> FEATURE:
<223> OTHER INFORMATION: Nanobody

<400> SEQUENCE: 45

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Ser Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 46
<211> LENGTH: 127
<212> TYPE: PRT
<213> ORGANISM: Artificial Sequence
<220> FEATURE:
<223> OTHER INFORMATION: Nanobody

<400> SEQUENCE: 46

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Asp Asn Ala Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Glu Pro Pro Asp Ser Ser Trp Tyr Leu Asp Gly Ser Pro Glu
            100                 105                 110
```

Phe Phe Lys Tyr Trp Gly Gln Gly Thr Leu Val Thr Val Ser Ser
            115                 120                 125

<210> SEQ ID NO 47
<211> LENGTH: 127
<212> TYPE: PRT
<213> ORGANISM: Artificial Sequence
<220> FEATURE:
<223> OTHER INFORMATION: Nanobody

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 48
<211> LENGTH: 127
<212> TYPE: PRT
<213> ORGANISM: Artificial Sequence
<220> FEATURE:
<223> OTHER INFORMATION: Nanobody

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
            115                 120                 125

<210> SEQ ID NO 49
<211> LENGTH: 127
<212> TYPE: PRT
<213> ORGANISM: Artificial Sequence
<220> FEATURE:
<223> OTHER INFORMATION: Nanobody

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile Gly Trp Phe Arg Gln Ala Pro Gly Lys Gly Arg Glu Gly Val
        35                  40                  45

Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser
        115                 120                 125

<210> SEQ ID NO 50
<211> LENGTH: 127
<212> TYPE: PRT
<213> ORGANISM: Artificial Sequence
<220> FEATURE:
<223> OTHER INFORMATION: Nanobody

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Arg Ala Thr Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser
        115                 120                 125

<210> SEQ ID NO 51
<211> LENGTH: 127
<212> TYPE: PRT
<213> ORGANISM: Artificial Sequence
<220> FEATURE:
<223> OTHER INFORMATION: Nanobody

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

```
Ser Ala Ile Ser Trp Asn Gly Asn Asn Thr Tyr Tyr Thr Glu Ser Met
    50                  55                  60
Lys Gly Arg Phe Thr Ile Ser Arg Asp Asn Ala Lys Asn Thr Val Tyr
 65                  70                  75                  80
Leu Gln Met Asn Ser Leu Arg Pro Glu Asp Thr Ala Val Tyr Tyr Cys
                85                  90                  95
Val Lys Gly Ser Thr Ala Ile Val Gly Val Pro Pro Thr Tyr Pro Asp
               100                 105                 110
Glu Tyr Asp Tyr Trp Gly Gln Gly Thr Leu Val Thr Val Ser Ser
            115                 120                 125
```

<210> SEQ ID NO 52
<211> LENGTH: 127
<212> TYPE: PRT
<213> ORGANISM: Artificial Sequence
<220> FEATURE:
<223> OTHER INFORMATION: Nanobody

<400> SEQUENCE: 52

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Asp Asp Tyr
                20                  25                  30
Gly Met Ser Trp Val Arg Gln Ala Pro Gly Arg Ala Thr Glu Trp Val
             35                  40                  45
Ser Ala Ile Ser Trp Asn Gly Asn Asn Thr Tyr Tyr Thr Glu Ser Met
    50                  55                  60
Lys Gly Arg Phe Thr Ile Ser Arg Asp Asn Ala Lys Asn Thr Leu Tyr
 65                  70                  75                  80
Leu Gln Met Asn Ser Leu Arg Pro Glu Asp Thr Ala Val Tyr Tyr Cys
                85                  90                  95
Val Lys Gly Ser Thr Ala Ile Val Gly Val Pro Pro Thr Tyr Pro Asp
               100                 105                 110
Glu Tyr Asp Tyr Trp Gly Gln Gly Thr Leu Val Thr Val Ser Ser
            115                 120                 125
```

<210> SEQ ID NO 53
<211> LENGTH: 127
<212> TYPE: PRT
<213> ORGANISM: Artificial Sequence
<220> FEATURE:
<223> OTHER INFORMATION: Nanobody

<400> SEQUENCE: 53

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Asp Asp Tyr
                20                  25                  30
Gly Met Ser Trp Val Arg Gln Ala Pro Gly Lys Gly Leu Glu Trp Val
             35                  40                  45
Ser Ala Ile Ser Trp Asn Gly Asn Asn Thr Tyr Tyr Thr Glu Ser Met
    50                  55                  60
Lys Gly Arg Phe Thr Ile Ser Arg Asp Asn Ala Lys Asn Thr Leu Tyr
 65                  70                  75                  80
Leu Gln Met Asn Ser Leu Arg Pro Glu Asp Thr Ala Val Tyr Tyr Cys
                85                  90                  95
Val Lys Gly Ser Thr Ala Ile Val Gly Val Pro Pro Thr Tyr Pro Asp
```

```
                100             105                 110
Glu Tyr Asp Tyr Trp Gly Gln Gly Thr Leu Val Thr Val Ser Ser
            115                 120             125

<210> SEQ ID NO 54
<211> LENGTH: 127
<212> TYPE: PRT
<213> ORGANISM: Artificial Sequence
<220> FEATURE:
<223> OTHER INFORMATION: Nanobody

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Arg Gly Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser
            115                 120             125

<210> SEQ ID NO 55
<211> LENGTH: 127
<212> TYPE: PRT
<213> ORGANISM: Artificial Sequence
<220> FEATURE:
<223> OTHER INFORMATION: Nanobody

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Arg Ala Leu Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser
            115                 120             125

<210> SEQ ID NO 56
<211> LENGTH: 127
<212> TYPE: PRT
<213> ORGANISM: Artificial Sequence
<220> FEATURE:
```

<223> OTHER INFORMATION: Nanobody

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Ala Thr Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser
        115                 120                 125

<210> SEQ ID NO 57
<211> LENGTH: 127
<212> TYPE: PRT
<213> ORGANISM: Artificial Sequence
<220> FEATURE:
<223> OTHER INFORMATION: Nanobody

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Thr Glu Trp Val
        35                  40                  45

Ser Ala Ile Ser Trp Asn Gly Asn Asn Thr Tyr Tyr Thr Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Val Lys Gly Ser Thr Ala Ile Val Gly Val Pro Pro Thr Tyr Pro Asp
            100                 105                 110

Glu Tyr Asp Tyr Trp Gly Gln Gly Thr Leu Val Thr Val Ser Ser
        115                 120                 125

<210> SEQ ID NO 58
<211> LENGTH: 127
<212> TYPE: PRT
<213> ORGANISM: Artificial Sequence
<220> FEATURE:
<223> OTHER INFORMATION: Nanobody

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Arg Gly Thr Glu Trp Val

```
                35                  40                  45

Ser Ala Ile Ser Trp Asn Gly Asn Asn Thr Tyr Tyr Thr Glu Ser Met
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Val Lys Gly Ser Thr Ala Ile Val Gly Val Pro Pro Thr Tyr Pro Asp
                100                 105                 110

Glu Tyr Asp Tyr Trp Gly Gln Gly Thr Leu Val Thr Val Ser Ser
            115                 120                 125

<210> SEQ ID NO 59
<211> LENGTH: 127
<212> TYPE: PRT
<213> ORGANISM: Artificial Sequence
<220> FEATURE:
<223> OTHER INFORMATION: Nanobody

<400> SEQUENCE: 59

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Ala Leu Glu Trp Val
                35                  40                  45

Ser Ala Ile Ser Trp Asn Gly Asn Asn Thr Tyr Tyr Thr Glu Ser Met
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Val Lys Gly Ser Thr Ala Ile Val Gly Val Pro Pro Thr Tyr Pro Asp
                100                 105                 110

Glu Tyr Asp Tyr Trp Gly Gln Gly Thr Leu Val Thr Val Ser Ser
            115                 120                 125

<210> SEQ ID NO 60
<211> LENGTH: 121
<212> TYPE: PRT
<213> ORGANISM: Artificial Sequence
<220> FEATURE:
<223> OTHER INFORMATION: Nanobody

<400> SEQUENCE: 60

Glu Val Gln Leu Val Glu Ser Gly Gly Gly Leu Val Gln Pro Gly Gly
 1               5                  10                  15

Ser Leu Arg Leu Ser Cys Ala Ala Ser Gly Thr Thr Phe Lys Val Asn
                20                  25                  30

Val Met Ala Trp Tyr Arg Gln Ala Pro Gly Lys Gly Arg Glu Leu Val
                35                  40                  45

Ala Gly Ile Ile Asn Gly Gly Ser Thr Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95
```

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 61
<211> LENGTH: 121
<212> TYPE: PRT
<213> ORGANISM: Artificial Sequence
<220> FEATURE:
<223> OTHER INFORMATION: Nanobody

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg Ile Asn
            20                  25                  30

Val Met Ala Trp Tyr Arg Gln Ala Pro Gly Lys Gly Arg Glu Leu Val
        35                  40                  45

Ala Gly Ile Ile Thr Asn Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 62
<211> LENGTH: 121
<212> TYPE: PRT
<213> ORGANISM: Artificial Sequence
<220> FEATURE:
<223> OTHER INFORMATION: Nanobody

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Val Asn
            20                  25                  30

Val Met Ala Trp Tyr Arg Gln Ala Pro Gly Lys Gly Arg Glu Leu Val
        35                  40                  45

Ala Ala Val Ile Asn Gly Gly Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 63
<211> LENGTH: 121
<212> TYPE: PRT
<213> ORGANISM: Artificial Sequence
<220> FEATURE:
<223> OTHER INFORMATION: Nanobody

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys Ile Asn
            20                  25                  30

Ile Met Ala Trp Tyr Arg Gln Ala Pro Gly Lys Gly Arg Glu Leu Val
        35                  40                  45

Ala Gly Val Ile Thr Gly Gly Asn Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: Nanobody

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg Ile Asn
            20                  25                  30

Val Met Ala Trp Tyr Arg Gln Ala Pro Gly Lys Gly Arg Glu Leu Val
        35                  40                  45

Ala Gly Val Ile Asn Asp Gly Ser Thr Thr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Val Thr Thr Asn Ser Asp Tyr Asp Leu Gly Arg Asp Tyr Trp Gly
            100                 105                 110

Gln Gly Thr Leu Val Thr Val Ser Ser
        115                 120

<210> SEQ ID NO 65
<211> LENGTH: 121
<212> TYPE: PRT
<213> ORGANISM: Artificial Sequence
<220> FEATURE:
<223> OTHER INFORMATION: Nanobody

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
            35                  40                  45

Ala Gly Ile Val Ser Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Asn Ser Asp Tyr Asp Leu Gly Arg Arg Tyr Trp Gly
            100                 105                 110

Gln Gly Thr Leu Val Thr Val Ser Ser
        115                 120

<210> SEQ ID NO 66
<211> LENGTH: 121
<212> TYPE: PRT
<213> ORGANISM: Artificial Sequence
<220> FEATURE:
<223> OTHER INFORMATION: Nanobody

<400> SEQUENCE: 66

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
            35                  40                  45

Ala Gly Ile Ile Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser
        115                 120

<210> SEQ ID NO 67
<211> LENGTH: 121
<212> TYPE: PRT
<213> ORGANISM: Artificial Sequence
<220> FEATURE:
<223> OTHER INFORMATION: Nanobody

<400> SEQUENCE: 67

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
            35                  40                  45

Ala Gly Ile Val Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: Nanobody

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys Ile Asn
            20                  25                  30

Val Met Ala Trp Tyr Arg Gln Ala Pro Gly Lys Gly Arg Glu Leu Val
        35                  40                  45

Ala Gly Ile Val Thr Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser
        115                 120

<210> SEQ ID NO 69
<211> LENGTH: 121
<212> TYPE: PRT
<213> ORGANISM: Artificial Sequence
<220> FEATURE:
<223> OTHER INFORMATION: Nanobody

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Val Thr Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
                100                 105                 110

Gln Gly Thr Leu Val Thr Val Ser Ser
        115                 120

<210> SEQ ID NO 70
<211> LENGTH: 245
<212> TYPE: PRT

<213> ORGANISM: Artificial Sequence
<220> FEATURE:
<223> OTHER INFORMATION: Nanobody

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser
                245
```

<210> SEQ ID NO 71
<211> LENGTH: 375
<212> TYPE: PRT
<213> ORGANISM: Artificial Sequence
<220> FEATURE:
<223> OTHER INFORMATION: Nanobody

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
        35                  40                  45

Ala Gly Ile Ile Ser Gly Gly Ser Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80
```

```
Gln Met Asn Ser Leu Arg Pro Glu Asp Thr Ala Val Tyr Tyr Cys Ala
             85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
            115                 120                 125

Gly Ser Glu Val Gln Leu Val Glu Ser Gly Gly Leu Val Gln Pro
130                 135                 140

Gly Gly Ser Leu Arg Leu Ser Cys Ala Ala Ser Gly Ser Val Phe Lys
145                 150                 155                 160

Ile Asn Val Met Ala Trp Tyr Arg Gln Ala Pro Gly Lys Gly Arg Glu
            165                 170                 175

Leu Val Ala Gly Ile Ile Ser Gly Gly Ser Thr Ser Tyr Ala Asp Ser
            180                 185                 190

Val Lys Gly Arg Phe Thr Ile Ser Arg Asp Asn Ala Lys Asn Thr Leu
            195                 200                 205

Tyr Leu Gln Met Asn Ser Leu Arg Pro Glu Asp Thr Ala Val Tyr Tyr
            210                 215                 220

Cys Ala Phe Ile Thr Thr Glu Ser Asp Tyr Asp Leu Gly Arg Arg Tyr
225                 230                 235                 240

Trp Gly Gln Gly Thr Leu Val Thr Val Ser Ser Gly Gly Gly Ser
            245                 250                 255

Gly Gly Gly Ser Glu Val Gln Leu Val Glu Ser Gly Gly Leu Val
            260                 265                 270

Gln Pro Gly Asn Ser Leu Arg Leu Ser Cys Ala Ala Ser Gly Phe Thr
            275                 280                 285

Phe Ser Ser Phe Gly Met Ser Trp Val Arg Gln Ala Pro Gly Lys Gly
290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
            325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
            355                 360                 365

Thr Leu Val Thr Val Ser Ser
            370                 375

<210> SEQ ID NO 72
<211> LENGTH: 375
<212> TYPE: PRT
<213> ORGANISM: Artificial Sequence
<220> FEATURE:
<223> OTHER INFORMATION: Nanobody

<400> SEQUENCE: 72

Glu Val Gln Leu Val Glu Ser Gly Gly Leu Val Gln Pro Gly Gly
1               5                   10                  15

Ser Leu Arg Leu Ser Cys Ala Ala Ser Gly Ser Val Phe Lys Ile Asn
            20                  25                  30

Val Met Ala Trp Tyr Arg Gln Ala Pro Gly Lys Gly Arg Glu Leu Val
            35                  40                  45

Ala Gly Ile Ile Ser Gly Gly Ser Thr Ser Tyr Ala Asp Ser Val Lys
50                  55                  60
```

```
Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
             85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser Gly Gly Gly Ser Gly Gly
            115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
            165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Ser Gly Gly Gly Ser Glu Val
            245                 250                 255

Gln Leu Val Glu Ser Gly Gly Leu Val Gln Pro Gly Gly Ser Leu
    260                 265                 270

Arg Leu Ser Cys Ala Ala Ser Gly Ser Val Phe Lys Ile Asn Val Met
    275                 280                 285

Ala Trp Tyr Arg Gln Ala Pro Gly Lys Gly Arg Glu Leu Val Ala Gly
    290                 295                 300

Ile Ile Ser Gly Gly Ser Thr Ser Tyr Ala Asp Ser Val Lys Gly Arg
305                 310                 315                 320

Phe Thr Ile Ser Arg Asp Asn Ala Lys Asn Thr Leu Tyr Leu Gln Met
            325                 330                 335

Asn Ser Leu Arg Pro Glu Asp Thr Ala Val Tyr Tyr Cys Ala Phe Ile
            340                 345                 350

Thr Thr Glu Ser Asp Tyr Asp Leu Gly Arg Arg Tyr Trp Gly Gln Gly
            355                 360                 365

Thr Leu Val Thr Val Ser Ser
    370                 375

<210> SEQ ID NO 73
<211> LENGTH: 251
<212> TYPE: PRT
<213> ORGANISM: Artificial Sequence
<220> FEATURE:
<223> OTHER INFORMATION: Nanobody

<400> SEQUENCE: 73

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Asp Ile Gly Trp Phe Arg Gln Ala Pro Gly Lys Gly Arg Glu Gly Val
         35                  40                  45
```

```
Ser Gly Ile Ser Ser Ser Asp Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Glu Pro Pro Asp Ser Ser Trp Tyr Leu Asp Gly Ser Pro Glu
            100                 105                 110

Phe Phe Lys Tyr Trp Gly Gln Gly Thr Leu Val Thr Val Ser Ser Gly
            115                 120                 125

Gly Gly Gly Ser Gly Gly Gly Ser Glu Val Gln Leu Val Glu Ser Gly
130                 135                 140

Gly Gly Leu Val Gln Pro Gly Asn Ser Leu Arg Leu Ser Cys Ala Ala
145                 150                 155                 160

Ser Gly Phe Thr Phe Ser Ser Phe Gly Met Ser Trp Val Arg Gln Ala
                165                 170                 175

Pro Gly Lys Gly Leu Glu Trp Val Ser Ser Ile Ser Gly Ser Gly Ser
            180                 185                 190

Asp Thr Leu Tyr Ala Asp Ser Val Lys Gly Arg Phe Thr Ile Ser Arg
            195                 200                 205

Asp Asn Ala Lys Thr Thr Leu Tyr Leu Gln Met Asn Ser Leu Arg Pro
210                 215                 220

Glu Asp Thr Ala Val Tyr Tyr Cys Thr Ile Gly Gly Ser Leu Ser Arg
225                 230                 235                 240

Ser Ser Gln Gly Thr Leu Val Thr Val Ser Ser
                245                 250

<210> SEQ ID NO 74
<211> LENGTH: 30
<212> TYPE: PRT
<213> ORGANISM: Artificial Sequence
<220> FEATURE:
<223> OTHER INFORMATION: Framework sequence

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Lys
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Framework sequence

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: Framework sequence
```

```
<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg
            20                  25                  30

<210> SEQ ID NO 77
<211> LENGTH: 30
<212> TYPE: PRT
<213> ORGANISM: Artificial Sequence
<220> FEATURE:
<223> OTHER INFORMATION: Framework sequence

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Arg
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: Framework sequence

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: Framework sequence

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Lys
            20                  25                  30

<210> SEQ ID NO 80
<211> LENGTH: 5
<212> TYPE: PRT
<213> ORGANISM: Artificial Sequence
<220> FEATURE:
<223> OTHER INFORMATION: CDR1 sequence

<400> SEQUENCE: 80

Ile Asn Val Met Ala
1               5

<210> SEQ ID NO 81
<211> LENGTH: 5
<212> TYPE: PRT
<213> ORGANISM: Artificial Sequence
<220> FEATURE:
<223> OTHER INFORMATION: CDR1 sequence

<400> SEQUENCE: 81
```

```
Val Asn Val Met Ala
1               5

<210> SEQ ID NO 82
<211> LENGTH: 5
<212> TYPE: PRT
<213> ORGANISM: Artificial Sequence
<220> FEATURE:
<223> OTHER INFORMATION: CDR1 sequence

<400> SEQUENCE: 82

Ile Asn Ile Met Ala
1               5

<210> SEQ ID NO 83
<211> LENGTH: 14
<212> TYPE: PRT
<213> ORGANISM: Artificial Sequence
<220> FEATURE:
<223> OTHER INFORMATION: Framework sequence

<400> SEQUENCE: 83

Trp Tyr Arg Gln Ala Pro Gly Lys Gly Arg Glu Leu Val Ala
1               5                   10

<210> SEQ ID NO 84
<211> LENGTH: 16
<212> TYPE: PRT
<213> ORGANISM: Artificial Sequence
<220> FEATURE:
<223> OTHER INFORMATION: CDR2 sequence

<400> SEQUENCE: 84

Gly Ile Ile Ser Gly Gly Ser Thr Ser Tyr Ala Asp Ser Val Lys Gly
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: CDR2 sequence

<400> SEQUENCE: 85

Gly Ile Ile Thr Asn Gly Ser Thr Ser Tyr Ala Asp Ser Val Lys Gly
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: CDR2 sequence

<400> SEQUENCE: 86

Ala Val Ile Asn Gly Gly Thr Thr Thr Tyr Ala Asp Ser Val Lys Gly
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: CDR2 sequence

<400> SEQUENCE: 87

Gly Val Ile Thr Gly Gly Asn Thr Thr Tyr Ala Asp Ser Val Lys Gly
```

-continued

```
1               5                   10                  15
```

<210> SEQ ID NO 88
<211> LENGTH: 16
<212> TYPE: PRT
<213> ORGANISM: Artificial Sequence
<220> FEATURE:
<223> OTHER INFORMATION: CDR2 sequence

<400> SEQUENCE: 88

```
Gly Val Ile Asn Asp Gly Ser Thr Thr Tyr Ala Asp Ser Val Lys Gly
1               5                   10                  15
```

<210> SEQ ID NO 89
<211> LENGTH: 16
<212> TYPE: PRT
<213> ORGANISM: Artificial Sequence
<220> FEATURE:
<223> OTHER INFORMATION: CDR2 sequence

<400> SEQUENCE: 89

```
Gly Ile Val Ser Gly Gly Ser Thr Ser Tyr Ala Asp Ser Val Lys Gly
1               5                   10                  15
```

<210> SEQ ID NO 90
<211> LENGTH: 16
<212> TYPE: PRT
<213> ORGANISM: Artificial Sequence
<220> FEATURE:
<223> OTHER INFORMATION: CDR2 sequence

<400> SEQUENCE: 90

```
Gly Ile Ile Asn Gly Gly Ser Thr Thr Tyr Ala Asp Ser Val Lys Gly
1               5                   10                  15
```

<210> SEQ ID NO 91
<211> LENGTH: 16
<212> TYPE: PRT
<213> ORGANISM: Artificial Sequence
<220> FEATURE:
<223> OTHER INFORMATION: CDR2 sequence

<400> SEQUENCE: 91

```
Gly Ile Val Thr Gly Gly Ser Thr Ser Tyr Ala Asp Ser Val Lys Gly
1               5                   10                  15
```

<210> SEQ ID NO 92
<211> LENGTH: 32
<212> TYPE: PRT
<213> ORGANISM: Artificial Sequence
<220> FEATURE:
<223> OTHER INFORMATION: Framework sequence

<400> SEQUENCE: 92

```
Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Phe
                20                  25                  30
```

<210> SEQ ID NO 93
<211> LENGTH: 13
<212> TYPE: PRT
<213> ORGANISM: Artificial Sequence
<220> FEATURE:
<223> OTHER INFORMATION: CDR3 sequence

<400> SEQUENCE: 93

```
Ile Thr Thr Glu Ser Asp Tyr Asp Leu Gly Arg Arg Tyr
1               5                   10

<210> SEQ ID NO 94
<211> LENGTH: 13
<212> TYPE: PRT
<213> ORGANISM: Artificial Sequence
<220> FEATURE:
<223> OTHER INFORMATION: CDR3 sequence

<400> SEQUENCE: 94

Ile Thr Thr Asn Ser Asp Tyr Asp Leu Gly Arg Arg Tyr
1               5                   10

<210> SEQ ID NO 95
<211> LENGTH: 13
<212> TYPE: PRT
<213> ORGANISM: Artificial Sequence
<220> FEATURE:
<223> OTHER INFORMATION: CDR3 sequence

<400> SEQUENCE: 95

Val Thr Thr Asn Ser Asp Tyr Asp Leu Gly Arg Asp Tyr
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Framework sequence

<400> SEQUENCE: 96

Trp Gly Gln Gly Thr Leu Val Thr Val Ser Ser
1               5                   10

<210> SEQ ID NO 97
<211> LENGTH: 115
<212> TYPE: PRT
<213> ORGANISM: Artificial Sequence
<220> FEATURE:
<223> OTHER INFORMATION: Nanobody

<400> SEQUENCE: 97

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 98
```

```
<211> LENGTH: 115
<212> TYPE: PRT
<213> ORGANISM: Artificial Sequence
<220> FEATURE:
<223> OTHER INFORMATION: Nanobody

<400> SEQUENCE: 98

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 99
<211> LENGTH: 117
<212> TYPE: PRT
<213> ORGANISM: Artificial Sequence
<220> FEATURE:
<223> OTHER INFORMATION: Nanobody

<400> SEQUENCE: 99

Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Leu Asn
            20                  25                  30

Leu Met Gly Trp Tyr Arg Gln Gly Pro Gly Asn Glu Arg Glu Leu Val
        35                  40                  45

Ala Thr Cys Ile Thr Val Gly Asp Ser Thr Asn Tyr Ala Asp Ser Val
    50                  55                  60

Lys Gly Arg Phe Thr Ile Ser Met Asp Tyr Thr Lys Gln Thr Val Tyr
65                  70                  75                  80

Leu His Met Asn Ser Leu Arg Pro Glu Asp Thr Gly Leu Tyr Tyr Cys
                85                  90                  95

Lys Ile Arg Arg Thr Trp His Ser Glu Leu Trp Gly Gln Gly Thr Gln
            100                 105                 110

Val Thr Val Ser Ser
        115

<210> SEQ ID NO 100
<211> LENGTH: 17
<212> TYPE: PRT
<213> ORGANISM: Artificial Sequence
<220> FEATURE:
<223> OTHER INFORMATION: Myc tag
```

<400> SEQUENCE: 100

Ala Ala Ala Glu Gln Lys Leu Ile Ser Glu Glu Asp Leu Asn Gly Ala
1               5                   10                  15

Ala

<210> SEQ ID NO 101
<211> LENGTH: 30
<212> TYPE: PRT
<213> ORGANISM: Artificial Sequence
<220> FEATURE:
<223> OTHER INFORMATION: Linker sequence

<400> SEQUENCE: 101

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser
                20                  25                  30

<210> SEQ ID NO 102
<211> LENGTH: 15
<212> TYPE: PRT
<213> ORGANISM: Artificial Sequence
<220> FEATURE:
<223> OTHER INFORMATION: Linker sequence

<400> SEQUENCE: 102

Gly Gly Gly Gly Ser Gly Gly Gly Gly Ser Gly Gly Gly Gly Ser
1               5                   10                  15

<210> SEQ ID NO 103
<211> LENGTH: 9
<212> TYPE: PRT
<213> ORGANISM: Artificial Sequence
<220> FEATURE:
<223> OTHER INFORMATION: Linker sequence

<400> SEQUENCE: 103

Gly Gly Gly Gly Ser Gly Gly Gly Ser
1               5

<210> SEQ ID NO 104
<211> LENGTH: 7
<212> TYPE: PRT
<213> ORGANISM: Artificial Sequence
<220> FEATURE:
<223> OTHER INFORMATION: Linker sequence

<400> SEQUENCE: 104

Ser Gly Gly Ser Gly Gly Ser
1               5

<210> SEQ ID NO 105
<211> LENGTH: 12
<212> TYPE: PRT
<213> ORGANISM: Artificial Sequence
<220> FEATURE:
<223> OTHER INFORMATION: Linker sequence

<400> SEQUENCE: 105

Glu Pro Lys Thr Pro Lys Pro Gln Pro Ala Ala Ala
1               5                   10

ANTI IL-6R POLYPEPTIDES AND COMPOSITIONS THEREOF

This application is a continuation of Ser. No. 13/263,179, filed Dec. 8, 2011, now issued as U.S. Pat. No. 8,748,581, which is a national stage filing under 35 U.S.C. §371 of international application PCT/EP2010/054764, filed Apr. 12, 2010, which was published under PCT Article 21(2) in English, and claims the benefit under 35 U.S.C. §119(e) of U.S. provisional application Ser. No. 61/168,410, filed Apr. 10, 2009, the disclosures of which are incorporated by reference herein in their entireties.

FIELD OF THE INVENTION

The present invention relates to amino acid sequences that are directed against/and or that can specifically bind (as defined herein) Interleukin-6 Receptor (IL-6R), as well as to compounds or constructs, and in particular proteins and polypeptides, that comprise or essentially consist of one or more such amino acid sequences (also referred to herein as "amino acid sequences of the invention", "compounds of the invention", "constructs of the invention" and "polypeptides of the invention", respectively).

The invention also relates to nucleic acids encoding such amino acid sequences and polypeptides (also referred to herein as "nucleic acids of the invention" or "nucleotide sequences of the invention"); to methods for preparing such amino acid sequences and polypeptides; to host cells expressing or capable of expressing such amino acid sequences or polypeptides; to compositions, and in particular to pharmaceutical compositions, that comprise such amino acid sequences, polypeptides, nucleic acids and/or host cells; and to uses of such amino acid sequences or polypeptides, nucleic acids, host cells and/or compositions, in particular for prophylactic, therapeutic or diagnostic purposes, such as the prophylactic, therapeutic or diagnostic purposes mentioned herein.

Other aspects, embodiments, advantages and applications of the invention will become clear from the further description herein.

BACKGROUND ART

The interaction of IL-6, a protein originally identified as a B cell differentiation factor (Hirano et al., 1985, Proc. Natl. Acad. Sci. USA, 82: 5490-4; EP 0257406), with IL-6R (Yamasaki et al., 1988, Science, 241: 825-8; EP 0325474) results in the formation of the IL-6/IL-6R complex. This complex binds to gp130 (Taga et al., 1989, Cell, 58: 573-81; EP 0411946), a membrane protein on a target cell, which transmits various physiological actions of IL-6. IL-6 is currently known to be involved in—amongst others—the regulation of the immune response, hematopoiesis, the acute phase response, bone metabolism, angiogenesis, and inflammation. Deregulation of IL-6 production is implicated in the pathology of several autoimmune and chronic inflammatory proliferative disease processes (Ishihara and Hirano, 2002, Biochim. Biophys. Acta, 1592: 281-96). As a consequence, inhibitors of IL-6 induced signaling have attracted much attention in the past (Hirano et al., 1990, Immunol. Today, 11: 443-9). Polypeptides specifically binding to IL-6 (Klein et al., 1991, Blood, 78: 1198-204; EP 0312996), IL-6R (EP 0409607) or gp130 (Saito et al., 1993, J. Immunol. Methods, 163: 217-223; EP 0572118) proved to exhibit an efficient inhibitory effect on IL-6 functioning.

IL-6 overproduction and signalling (and in particular so-called trans-signalling) are involved in various diseases and disorders, such as sepsis (Starnes et al., 1999, J. Immunol., 148: 1968) and various forms of cancer such as multiple myeloma disease (MM), renal cell carcinoma (RCC), plasma cell leukaemia (Klein et al., 1991), lymphoma, B-lymphoproliferative disorder (BLPD) and prostate cancer. Non-limiting examples of other diseases caused by excessive IL-6 production or signalling include bone resorption (osteoporosis) (Roodman et al., 1992, J. Bone Miner. Res., 7: 475-8; Jilka et al., 1992, Science, 257: 88-91), cachexia (Strassman et al., 1992, J. Clin. Invest. 89: 1681-1684), psoriasis, mesangial proliferative glomerulonephritis, Kaposi's sarcoma, AIDS-related lymphoma (Emilie et al., 1994, Int. J. Immunopharmacol. 16: 391-6), inflammatory diseases and disorder such as rheumatoid arthritis, systemic onset juvenile idiopathic arthritis, hypergammaglobulinemia (Grau et al., 1990, J. Exp. Med. 172: 1505-8); Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus (Campbell et al., 1991, J. Clin. Invest. 87: 739-742). Other IL-6 related disorders will be clear to the skilled person.

As can for example be seen from the references above, the prior art describes antibodies and antibody fragments directed against human IL-6, against human IL-6R and against human gp130 protein for the prevention and treatment of IL-6 relates disorders. Examples are Tocilizumab (see Woo et al., 2005, Arthritis Res. Ther. 7: 1281-8; Nishimoto et al., 2005, Blood 106: 2627-32; Ito et al., 2004, Gastroenterology, 126: 989-96; Choy et al., 2002, Arthritis Rheum. 46: 3143-50), BE8 (see Bataille et al., 1995, Blood 86: 685-91; Emilie et al., 1994, Blood 84: 2472-9; Beck et al., 1994, N. Engl. J. Med. 330: 602-5; Wendling et al., 1993, J. Rheumatol. 20: 259-62) and CNTO-328 of Centocor (see Journal of Clinical Oncology, 2004, 22/14S: 2560; Journal of Clinical Oncology, 2004, 22/14S: 2608; Int. J. Cancer, 2004, 111:592-5). Another active principle known in the art for the prevention and treatment of IL-6 related disorders is an Fc fusion of soluble gp130 (see Becker et al. 2004, Immunity, 21: 491-501; Doganci et al., 2005, J. Clin. Invest. 115: 313-25; Nowell et al., 2003, J. Immunol. 171: 3202-9; Atreya et al., 2000, Nat. Med. 6: 583-8). Amino acid sequences and Nanobodies directed against IL-6R and polypeptides comprising the same are described in WO 08/020,079.

SUMMARY OF THE INVENTION

A specific, but non-limiting object of the present invention is to provide amino acid sequences, polypeptides and therapeutic compounds and compositions that have improved therapeutic and/or pharmacological properties, in addition to other advantageous properties (such as, for example, improved ease of preparation and/or reduced costs of goods), compared to the prior art amino acid sequences, antibodies and Nanobodies. These improved and advantageous properties will become clear from the further description herein. Without being limiting, the amino acid sequences, polypeptides and therapeutic compounds and compositions provided by the invention may have an improved binding and/or affinity, improved avidity, improved efficacy and/or potency, an increased selectivity and/or they may be capable of partially or preferably totally blocking the IL-6/IL-6R interaction, and/or inhibit signalization through IL-6, IL-6R and/or the IL-6/IL-6R complex.

Generally, it is an object of the invention to provide pharmacologically active agents, as well as compositions comprising the same, that can be used in the diagnosis, prevention and/or treatment of one or more IL-6R related disorders (as defined herein); and to provide methods for the diagnosis, prevention and/or treatment of such diseases and/or disorders that involve the administration and/or use of such agents and compositions.

The present invention relates to amino acid sequences (also referred to as "amino acid sequence(s) of the invention") that are directed against/and or that can specifically bind (as defined herein) Interleukin-6 Receptor (IL-6R) with improved affinity and/or avidity, and/or that have an improved efficacy and/or potency, and which are capable of (partially, or preferably totally) blocking the IL-6/IL-6R interaction and/or inhibit signalization through IL-6, IL-6R and/or the IL-6/IL-6R complex. More particularly, the present invention provides amino acid sequences that comprise one or more stretches of amino acid residues chosen from the following:

a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and/or c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and/or e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

For binding to its epitope on IL-6R, an amino acid sequence will usually contain within its amino acid sequence one or more amino acid residues or one or more stretches of amino acid residues (as further defined herein; i.e. with each "stretch" comprising two or more amino acid residues that are adjacent to each other or in close proximity to each other, i.e. in the primary or tertiary structure of the amino acid sequence) via which the amino acid sequence of the invention can bind to the epitope on IL-6R. These amino acid residues or stretches of amino acid residues thus form the "site" for binding to the epitope on IL-6R (also referred to herein as the "antigen binding site"; as further defined herein).

The present invention provides a number of stretches of amino acid residues (as defined herein) that are particularly suited for binding to a specific epitope on IL-6R. These stretches of amino acid residues may be present in, and/or may be incorporated into, an amino acid sequence of the invention, in particular in such a way that they form (part of) the antigen binding site of the amino acid sequence of the invention. As such, the resulting amino acid sequences, bind a specific epitope on IL-6R that lies in, forms part of, or overlaps with (i.e. in the primary or tertiary structure) or is in close proximity to (i.e. in the primary or tertiary structure) the IL-6 binding site on IL-6R (for example, competitively with IL-6); and as such, the resulting amino acid sequences are capable of partially or preferably totally blocking the IL-6/IL-6R interaction and/or inhibit signalization through IL-6, IL-6R and/or the IL-6/IL-6R complex. In this context, the amino acid sequences and polypeptides of the invention are preferably such that they can compete with IL-6 for binding to the IL-6 receptor. The amino acid sequences and polypeptides of the invention are preferably such that they can compete for binding to the IL-6 receptor with the commercially available human-mouse reconstituted chimeric monoclonal anti-IL-6R antibody Tocilizumab (MRA) (Chugai/Roche) or an antigen binding fragment thereof (see for example WO 92/19759 and corresponding European patent EP 0628639, as well as Shinkura et al., 1998, Anticancer Research 18, 1217-1222), for example in the assay described in Example 11; and/or such that they can bind to the same epitope or binding site on IL-6R as Tocilizumab, or to an epitope close to said binding site and/or overlapping with said binding site.

Also, the amino acid sequences of the invention are preferably such that they can compete for binding to the IL-6 receptor with the reference IgG as defined by SEQ ID NO's: 1 and 2 and/or the reference Fab as defined by SEQ ID NO's: 3 and 4 (see Example 1); and/or such that they can bind to the same epitope or binding site on IL-6R as said reference IgG or said reference Fab, or to an epitope close to said binding site and/or overlapping with said binding site. For the preparation and sequence of said reference IgG and reference Fab, reference is made to Example 1 below, as well as to SEQ ID NO's: 1 to 4.

It should be noted that the invention in its broadest sense is not limited to a specific structural role or function that these stretches of amino acid residues may have in the amino acid sequence of the invention, as long as these stretches of amino acid residues allow the amino acid sequence of the invention to bind to the specific epitope on IL-6R with a certain affinity and/or potency (as further defined herein). Thus, generally, the invention in its broadest sense comprises any amino acid sequence that is capable of binding to the specific epitope on IL-6R and that comprises one or more stretches of amino acid residues as described herein (and in particular a suitable combination of two or more such stretches of amino acid residues) that are suitably linked to each other via one or more further amino acid sequences, such that the entire amino acid sequence forms a binding domain and/or binding unit that is capable of binding to the specific epitope on IL-6R. It should however also be noted that the presence of only one such stretches of amino acid residues in an amino acid sequence of the invention may by itself already be sufficient to provide an amino acid sequence of the invention that is capable of binding to the specific epitope on IL-6R (reference is for example again made to the so-called "Expedite fragments" described in WO 03/050531).

Amino acid sequences comprising one or more of these specific stretches of amino acid residues show improved properties such as e.g. improved binding and/or affinity, improved avidity, improved efficacy and potency, and/or an increased selectivity, in addition to their capacity to partially or totally block the IL-6/IL-6R interaction, and/or inhibit signalization through IL-6, IL-6R and/or the IL-6/IL-6R complex.

More in particular, the amino acid sequences of the invention comprising one or more of these specific stretches of amino acid residues can bind to IL-6R with an affinity (suitably measured and/or expressed as a $K_D$-value (actual or apparent), a $K_A$-value (actual or apparent), a $k_{on}$-rate and/or a $k_{off}$-rate, or alternatively as an IC$_{50}$ value, as further described herein) preferably such that they:

bind to hIL-6R with a dissociation constant ($K_D$) of 1 nM to 1 pM or less, preferably 500 pM to 1 pM or less, more preferably 100 pM to 1 pM or less, or even more preferably about 50 pM to 1 pM or less;

and/or such that they:

bind to cyno IL-6R with a dissociation constant ($K_D$) of 1 nM to 1 pM or less, preferably 500 pM to 1 pM or less, more preferably 100 pM to 1 pM or less, or even more preferably about 50 pM to 1 pM or less;

and/or such that they:

bind to hIL-6R with a $k_{on}$-rate of between $10^4$ M$^{-1}$ s$^{-1}$ to about $10^7$ M$^{-1}$ s$^{-1}$, preferably between $10^5$ M$^{-1}$ s$^{-1}$ and $10^7$ M$^{-1}$ s$^{-1}$, more preferably about $10^6$ M$^{-1}$ s$^{-1}$ or more;

and/or such that they:

bind to cyno IL-6R with a $k_{on}$-rate of between $10^4$ M$^{-1}$ s$^{-1}$ to about $10^7$ M$^{-1}$ s$^{-1}$, preferably between $10^5$ M$^{-1}$ s$^{-1}$ and $10^7$ M$^{-1}$ s$^{-1}$, more preferably about $10^6$ M$^{-1}$ s$^{-1}$ or more;

and/or such that they:

bind to hIL-6R with a $k_{off}$ rate between $10^{-3}$ s$^{-1}$ ($t_{1/2}$=0.69 s) and $10^{-6}$ s$^{-1}$ (providing a near irreversible complex with a $t_{1/2}$ of multiple days), preferably between $10^{-4}$ s$^{-1}$ and $10^{-6}$ s$^{-1}$, more preferably between $10^{-5}$ s$^{-1}$ and $10^{-6}$ s$^{-1}$, such as about $10^{-5}$ s$^{-1}$ or lower;

and/or such that they:

bind to cyno IL-6R with a $k_{off}$ rate between $10^{-3}$ s$^{-1}$ ($t_{1/2}$=0.69 s) and $10^{-6}$ s$^{-1}$ (providing a near irreversible complex with a $t_{1/2}$ of multiple days), preferably between $10^{-4}$ s$^{-1}$ and $10^{-6}$ s$^{-1}$, more preferably between $10^{-5}$ s$^{-1}$ and $10^{-6}$ s$^{-1}$, such as about $10^{-5}$ s$^{-1}$ or lower.

Some preferred IC50 values for binding of the amino acid sequences of the invention to IL-6R will become clear from the further description and examples herein.

For example, in the TF-1 assay as described by Kitamura et al. (1989, J. Cell Physiol., 140: 323), the amino acid sequences of the invention may have IC50 values (at 100 IU/mL IL-6) between 10 nM and 50 pM, preferably between 5 nM and 50 pM, more preferably between 1 nM and 50 pM or less, such as about 750 or 500 pM or less. In this TF-1 assay the amino acid sequences of the invention may have IC50 values (at 5000 IU/mL IL-6) between 50 nM and 1 nM, preferably between 25 nM and 1 nM, more preferably between 10 nM and 1 nM or less, such as about 8 nM or less. In this TF-1 assay, the amino acid sequences of the invention may have IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4 (see Example 1). In this TF-1 assay, the amino acid sequences of the invention may have IC50 values that are at least the same and preferably better, at least two times, preferably three times, more preferably four times, even more preferably 5 times, 7 times or more than 7 times better compared to the IC50 value obtained for Tocilizumab (MRA).

In a plasma potency assay at EC50 values of IL-6 (e.g. in the presence of 27.29 ng/mL IL-6 as described in Example 45), the amino acid sequences of the invention may have IC50 values between 500 pM and 50 pM, preferably between 250 pM and 50 pM, more preferably between 200 pM and 50 pM or less, such as 150 pM or less. In a plasma potency assay at EC95 values of IL-6 (e.g. in the presence of 885 ng/mL IL-6 as described in Example 45) the amino acid sequences of the invention may have IC50 values between 1000 pM and 100 pM, preferably between 750 pM and 100 pM, more preferably between 500 pM and 100 pM or less, such as 400 pM or less. In this plasma potency assay, the amino acid sequences of the invention may have IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4 (see Example 1). In this plasma potency assay, the amino acid sequences of the invention may have IC50 values that are at least the same and preferably better, at least two times, preferably three times, more preferably four times, even more preferably 5 times, 7 times or more than 7 times better compared to the IC50 value obtained for Tocilizumab (MRA).

In an assay for defining binding to membrane IL-6R on CHO cells, the amino acid sequences of the invention may have IC50 values between 10 nM and 100 pM, preferably between 5 nM and 100 pM, more preferably between 2 nM and 10 pM or less, such as 2 nM or less.

In a preferred aspect, the amino acid sequences of the invention may comprises two or more stretches of amino acid residues chosen from the following:

a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and/or c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and/or e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

such that (i) when the first stretch of amino acid residues corresponds to one of the amino acid sequences according to a), or b), the second stretch of amino acid residues corresponds to one of the amino acid sequences according to c), d), e) or f); (ii) when the first stretch of amino acid residues corresponds to one of the amino acid sequences according to c) or d), the second stretch of amino acid residues corresponds to one of the amino acid sequences according to a), b), e) or f); or (iii) when the first stretch of amino acid residues corresponds to one of the amino acid sequences according to e) or f), the second stretch of amino acid residues corresponds to one of the amino acid sequences according to a), b), c) or d).

Even more preferably, the amino acid sequences of the invention comprise three or more stretches of amino acid residues, in which the first stretch of amino acid residues is chosen from the group consisting of:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;
the second stretch of amino acid residues is chosen from the group consisting of:
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;
and the third stretch of amino acid residues is chosen from the group consisting of:
e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

It should be noted that the invention is not limited as to the origin of the amino acid sequence of the invention (or of the nucleotide sequence of the invention used to express it), nor as to the way that the amino acid sequence or nucleotide sequence of the invention is (or has been) generated or obtained. Thus, the amino acid sequences of the invention may be naturally occurring amino acid sequences (from any suitable species) or synthetic or semi-synthetic amino acid sequences.

In one specific, but non-limiting aspect, the amino acid sequence of the invention may be an amino acid sequence that comprises an immunoglobulin fold or an amino acid sequence that, under suitable conditions (such as physiological conditions) is capable of forming an immunoglobulin fold (i.e. by folding). Reference is inter alia made to the review by Halaby et al. (1999, J. Protein Eng. 12: 563-71). Preferably, when properly folded so as to form an immunoglobulin fold, the stretches of amino acid residues may be capable of properly forming the antigen binding site for binding the specific epitope on IL-6R; and more preferably capable of binding to their epitope on IL-6R with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In another specific, but non-limiting aspect, the amino acid sequences of the invention are immunoglobulin sequences. In particular, but without limitation, the amino acid sequences of the invention may be amino acid sequences that essentially consist of 4 framework regions (FR1 to FR4 respectively) and 3 complementarity determining regions (CDR1 to CDR3 respectively); or any suitable fragment of such an amino acid sequence that still binds the specific epitope on IL-6R.

In such an amino acid sequence of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from a light chain variable domain (e.g. a $V_L$-sequence) and/or from a heavy chain variable domain (e.g. a $V_H$-sequence). When the amino acid sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

For a general description of heavy chain antibodies and the variable domains thereof, reference is inter alia made to the prior art cited herein, as well as to the prior art mentioned on page 59 of WO 08/020,079 and to the list of references mentioned on pages 41-43 of the International application WO 06/040153, which prior art and references are incorporated herein by reference.

The amino acid sequence of the invention may in particular be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody (as defined herein, and including but not limited to a $V_{HH}$ sequence); other single variable domains, or any suitable fragment of any one thereof.

In particular, the amino acid sequence of the invention may be a Nanobody® (as defined herein) or a suitable fragment thereof. [Note: Nanobody®, Nanobodies® and Nanoclone® are registered trademarks of Ablynx N.V.] Such Nanobodies directed against IL-6R will also be referred to herein as "Nanobodies of the invention".

In general, a Nanobody can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as defined in WO 08/020,079 (Tables A-3 to A-8).

Generally, Nanobodies (in particular $V_{HH}$ sequences and partially humanized Nanobodies) can in particular be characterized by the presence of one or more "Hallmark residues" in one or more of the framework sequences (as e.g. further described in WO 08/020,079, page 61, line 24 to page 98, line 3).

In this respect, the amino acid sequences of the invention may essentially consist of 4 framework regions (FR1 to FR4, respectively) and 3 complementarity determining regions (CDR1 to CDR3, respectively), in which:

CDR1 is chosen from the group consisting of:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and/or

CDR2 is chosen from the group consisting of:
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and/or

CDR3 is chosen from the group consisting of:
e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

These preferred complementarity determining regions (CDR1 to CDR3, respectively) are also referred to as "CDR(s) of the invention".

Preferably, the amino acid sequences of the invention essentially consist of 4 framework regions (FR1 to FR4, respectively) and 3 complementarity determining regions (CDR1 to CDR3, respectively), in which:

CDR1 is chosen from the group consisting of:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and

CDR2 is chosen from the group consisting of:
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and

CDR3 is chosen from the group consisting of:
e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

Such Nanobodies may be derived in any suitable manner and from any suitable source, and may for example be naturally occurring $V_{HH}$ sequences (i.e. from a suitable species of Camelid) or synthetic or semi-synthetic amino acid sequences.

In a specific aspect, the amino acid sequences or Nanobody of the invention comprises at least SEQ ID NO: 80; or a stretch of amino acid residues that has no more than 2, preferably no more than 1 amino acid difference with SEQ ID NO: 80, provided that the amino acid sequence or Nanobody comprising said stretch of amino acid residues binds IL-6R with the same, about the same, or a higher affinity compared to the amino acid sequence or Nanobody comprising said stretch of amino acid residues without the 2 or 1 amino acid difference, said affinity as measured by surface plasmon resonance.

In another specific aspect, the amino acid sequence or Nanobody of the invention comprises at least a stretch of amino acid residues chosen from SEQ ID NO's: 84, 89 or 91; or a stretch of amino acid residues that has no more than 2, preferably no more than 1 amino acid difference with one of SEQ ID NO's: 84, 89 or 91, provided that the amino acid sequence or Nanobody comprising said stretch of amino acid residues binds IL-6R with the same, about the same, or a higher affinity compared to the amino acid sequence or Nanobody comprising said stretch of amino acid residues without the 2 or 1 amino acid difference, said affinity as measured by surface plasmon resonance.

In yet another specific aspect, the amino acid sequence or Nanobody of the invention comprises at least SEQ ID NO: 84; or a stretch of amino acid residues that has no more than 2, preferably no more than 1 amino acid difference with SEQ ID NO: 84, provided that the amino acid sequence or Nanobody comprising said stretch of amino acid residues binds IL-6R with the same, about the same, or a higher affinity compared to the amino acid sequence or Nanobody comprising said stretch of amino acid residues without the 2 or 1 amino acid difference, said affinity as measured by surface plasmon resonance.

In yet another specific aspect, the amino acid sequence or Nanobody of the invention comprises at least a stretch of amino acid residues chosen from SEQ ID NO's: 93-94; or a stretch of amino acid residues that has no more than 2, preferably no more than 1 amino acid difference with one of SEQ ID NO's: 93-94, provided that the amino acid sequence or Nanobody comprising said stretch of amino acid residues binds IL-6R with the same, about the same, or a higher affinity compared to the amino acid sequence or Nanobody comprising said stretch of amino acid residues without the 2 or 1 amino acid difference, said affinity as measured by surface plasmon resonance.

In yet another specific aspect, the amino acid sequence or Nanobody of the invention comprises at least SEQ ID NO: 93; or a stretch of amino acid residues that has no more than 2, preferably no more than 1 amino acid difference with SEQ ID NO: 93, provided that the amino acid sequence or Nanobody comprising said stretch of amino acid residues binds IL-6R with the same, about the same, or a higher affinity compared to the amino acid sequence or Nanobody comprising said stretch of amino acid residues without the 2 or 1 amino acid difference, said affinity as measured by surface plasmon resonance.

In yet another specific aspect, the amino acid sequence or Nanobody of the invention comprises at least SEQ ID NO: 80 and SEQ ID NO: 84.

In yet another specific aspect, the amino acid sequence or Nanobody of the invention comprises at least SEQ ID NO: 80 and SEQ ID NO: 93.

In yet another specific aspect, the amino acid sequence or Nanobody of the invention comprises at least SEQ ID NO: 84 and SEQ ID NO: 93.

In yet another specific aspect, the amino acid sequence or Nanobody of the invention comprises at least SEQ ID NO: 80, SEQ ID NO: 84 and SEQ ID NO: 93.

Other preferred combinations of CDR1, CDR2, and CDR3 sequences are also shown in Table A-1.

Preferred amino acid sequences of the invention may be selected from the group consisting of SEQ ID NO's: 60-69; a sequence that has no more than 2, preferably no more than 1 amino acid difference in one, two or all of its CDRs with one of SEQ ID NO's: 60-69, provided that the amino acid sequence with no more than 2, preferably no more than 1 amino acid difference in one, two or all of its CDRs binds IL-6R with the same, about the same, or a higher affinity compared to the binding by the one of SEQ ID NO's: 60-69, said affinity as measured by surface plasmon resonance; and a sequence that has no more than 2, preferably no more than 1 amino acid difference with one of SEQ ID NO's: 60-69, provided that the amino acid sequence with no more than 2, preferably no more than 1 amino acid difference with one of SEQ ID NO's: 60-69 binds IL-6R with the same, about the same, or a higher affinity compared to the binding by the one of SEQ ID NO's: 60-69, said affinity as measured by surface plasmon resonance.

Such amino acid sequences of the invention should preferably be capable of specifically binding to the specific epitope on IL-6R, and even more preferably capable of binding to the specific epitope on IL-6R with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Such amino acid sequences of the invention should preferably also have a cell based potency and a plasma potency as defined herein.

The amino acid sequences and Nanobodies provided by the invention are preferably in essentially isolated form (as defined herein), or form part of a protein or polypeptide of the invention (also referred to as "polypeptide of the invention" or "protein of the invention"), which may comprise or essentially consist of one or more amino acid sequences or Nanobodies of the invention and which may optionally further comprise one or more further amino acid sequences or Nanobodies (all optionally linked via one or more suitable linkers).

Accordingly, in another aspect, the invention relates to a compound or construct, and in particular a protein or polypeptide (also referred to herein as a "compound of the invention" or "polypeptide of the invention", respectively) that comprises or essentially consists of one or more amino acid sequences or Nanobodies of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence of the invention (and/or to the compound, construct or polypeptide in which it is present) and may or may not modify the properties of the amino acid sequence or Nanobody of the invention.

For example, such further groups, residues, moieties or binding units may be one or more additional amino acid sequences, such that the compound, construct or polypeptide is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more amino acid sequences or Nanobodies of the invention so as to provide a "derivative" of an amino acid sequence or polypeptide of the invention, as further described herein.

Also within the scope of the present invention are compounds, constructs or polypeptides, that comprise or essentially consist of one or more derivates as described herein, and optionally further comprise one or more other groups, residues, moieties or binding units, optionally linked via one or more linkers. Preferably, said one or more other groups, residues, moieties or binding units are amino acid sequences.

In the compounds, constructs or polypeptides described above, the one or more amino acid sequences or Nanobodies of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound, construct or polypeptide is a fusion (protein) or fusion (polypeptide).

The process of designing/selecting and/or preparing a compound or polypeptide of the invention, starting from an amino acid sequence or Nanobody of the invention, is also referred to herein as "formatting" said amino acid sequence or Nanobody of the invention; and an amino acid sequence or Nanobody of the invention that is made part of a compound or polypeptide of the invention is said to be "formatted" or to be "in the format of" said compound or polypeptide of the invention. Examples of ways in which an amino acid sequence or Nanobody of the invention can be formatted and examples of such formats will be clear to the skilled person based on the disclosure herein; and such formatted amino acid sequences or Nanobodies form a further aspect of the invention.

For example, and without limitation, the one or more amino acid sequences or Nanobodies of the invention may be used as a binding unit in such a protein or polypeptide, which may optionally contain one or more further amino acid sequences that can serve as a binding unit (i.e. against another epitope on IL-6R and/or against one or more other antigens, proteins or targets than IL-6R), so as to provide a monovalent, multivalent, multiparatopic or multispecific polypeptide of the invention, respectively, all as described herein. The present invention thus also relates to a compound, construct or polypeptide which is a monovalent construct comprising or essentially consisting of an amino acid sequence or Nanobody of the invention. The present invention thus also relates to a compound, construct or polypeptide which is a multivalent construct, such as e.g. a bivalent or trivalent construct. The present invention also relates to a compound, construct or polypeptide which is a multispecific construct, such as e.g. a bispecific or trispecific construct. The present invention also relates to a compound, construct or polypeptide which is a multiparatopic construct, such as e.g. a bisparatopic or triparatopic construct.

In one specific aspect of the invention, a compound of the invention or a polypeptide of the invention may have an increased half-life, compared to the corresponding amino acid sequence or Nanobody of the invention. Some preferred, but non-limiting examples of such compounds and polypeptides will become clear to the skilled person based on the further disclosure herein, and for example comprise amino acid sequences, Nanobodies or polypeptides of the invention that have been chemically modified to increase the half-life thereof (for example, by means of pegylation); amino acid sequences or Nanobodies of the invention that comprise at least one additional binding site for binding to a serum protein (such as serum albumin); or polypeptides of the invention that comprise at least one amino acid sequence or Nanobody of the invention that is linked to at least one moiety (and in particular at least one amino acid sequence) that increases the half-life of the amino acid sequence or Nanobody of the invention. Examples of polypeptides, amino acid sequences or Nanobodies of the invention that comprise such half-life extending moieties will become clear to the skilled person based on the further disclosure herein; and for example include, without limitation, polypeptides in which the one or more amino acid sequences or Nanobodies of the invention are suitable linked to one or more serum proteins or fragments thereof (such as (human) serum albumin or suitable fragments thereof) or to one or more binding units that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies can bind to serum proteins such as serum albumin (such as human serum albumin), serum immunoglobulins such as IgG, or transferrine; reference is made to the further description and references mentioned herein); polypeptides in which an amino acid sequence or Nanobody of the invention is linked to an Fc portion (such as a human Fc) or a suitable part or fragment thereof; or polypeptides in which the one or more amino acid sequences or Nanobodies of the invention are suitable linked to one or more small proteins or peptides that can bind to serum proteins (such as, without limitation, the proteins and peptides described in WO 91/01743, WO 01/45746, WO 02/076489).

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence or Nanobody of the invention per se.

In a preferred, but non-limiting aspect, such compounds or polypeptides of the invention have a serum half-life that is increased with more than 1 hour, preferably more than 2 hours, more preferably more than 6 hours, such as more than 12 hours, or even more than 24, 48 or 72 hours, compared to the corresponding amino acid sequence or Nanobody of the invention per se.

In another preferred, but non-limiting aspect, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Such a protein, polypeptide, compound or construct may also be in essentially isolated form (as defined herein).

Some preferred compounds, constructs or polypeptides of the invention include the following polypeptide sequences:
  a) SEQ ID NO's: 70-72;
  b) a polypeptide sequence that has no more than 2, preferably no more than 1 amino acid difference in one, two or all of its CDRs of the invention with one of SEQ ID NO's: 70-72, provided that the polypeptide sequence with no more than 2, preferably no more than 1 amino acid difference in one, two or all of its CDRs of the invention binds IL-6R with the same, about the same, or a higher affinity compared to the binding by the one of SEQ ID NO's: 70-72, said affinity as measured by surface plasmon resonance;
  c) a polypeptide sequence that has no more than 2, preferably no more than 1 amino acid difference with one of SEQ ID NO's: 70-72, provided that the polypeptide sequence with no more than 2, preferably no more than 1 amino acid difference with one of SEQ ID NO's: 70-72 binds IL-6R with the same, about the same, or a higher affinity compared to the binding by the one of SEQ ID NO's: 70-72, said affinity as measured by surface plasmon resonance.

Polypeptides with these sequences show advantageous properties for use as pharmacologically active agents such as e.g. good binding characteristics (high affinity and/or avidity), high efficacy and/or potency, in addition to their capacity to (partially or totally) block the IL-6/IL-6R interaction and/or inhibit signalization through, IL-6, IL-6R and/or the IL-6/IL-6R complex.

More in particular, these polypeptides and compounds of the invention can bind to IL-6R with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:

bind to hIL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;

and/or such that they:

bind to cyno IL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;

and/or such that they:

bind to hIL-6R with a $k_{on}$-rate of between $10^4 \, M^{-1} \, s^{-1}$ to about $10^7 \, M^{-1} \, s^{-1}$, preferably between $10^5 \, M^{-1} \, s^{-1}$ and $10^7 \, M^{-1} \, s^{-1}$, more preferably about $10^6 \, M^{-1} \, s^{-1}$ or more;

and/or such that they:

bind to cyno IL-6R with a $k_{off}$-rate of between $10^4 \, M^{-1} \, s^{-1}$, to about $10^7 \, M^{-1} \, s^{-1}$, preferably between $10^5 \, M^{-1} \, s^{-1}$ and $10^7 \, M^{-1} \, s^{-1}$, more preferably about $10^6 \, M^{-1} \, s^{-1}$ or more;

and/or such that they:

bind to hIL-6R with a $k_{off}$ rate between $10^{-3} \, s^{-1}$ ($t_{1/2}$=0.69 s) and $10^{-6} \, s^{-1}$ (providing a near irreversible complex with a $t_{1/2}$ of multiple days), preferably between $10^{-4} \, s^{-1}$ and $10^{-6} \, s^{-1}$, more preferably between $10^{-5} \, s^{-1}$ and $10^{-6} \, s^{-1}$, such as about $10^{-5} \, s^{-1}$ or lower;

and/or such that they:

bind to cyno IL-6R with a $k_{off}$ rate between $10^{-3} \, s^{-1}$ ($t_{1/2}$=0.69 s) and $10^{-6} \, s^{-1}$ (providing a near irreversible complex with a $t_{1/2}$ of multiple days), preferably between $10^{-4} \, s^{-1}$ and $10^{-6} \, s^{-1}$, more preferably between $10^{-5} \, s^{-1}$ and $10^{-6} \, s^{-1}$, such as about $10^{-5} \, s^{-1}$ or lower.

Some preferred IC50 values for binding of the polypeptides and compounds of the invention to IL-6R will become clear from the further description and examples herein.

For example, in the TF-1 assay as described by Kitamura et al. (J. Cell Physiol. 1989; 140: 323), the polypeptides and compounds of the invention may have IC50 values (at 100 IU/mL IL-6) between 10 nM and 50 pM, preferably between 5 nM and 50 pM, more preferably between 1 nM and 50 pM or less, such as about 750 or 500 pM or less. In this TF-1 assay the polypeptides and compounds of the invention may have IC50 values (at 5000 IU/mL IL-6) between 50 nM and 1 nM, preferably between 25 nM and 1 nM, more preferably between 10 nM and 1 nM or less, such as about 8 nM or less. In this TF-1 assay, the polypeptides and compounds of the invention may have IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4 (see Example 1). In this TF-1 assay, the amino acid sequences of the invention may have IC50 values that are at least the same and preferably better, at least two times, preferably three times, more preferably four times, even more preferably 5 times, 7 times or more than 7 times better compared to the IC50 value obtained for Tocilizumab (MRA).

In a plasma potency assay at EC50 values of IL-6 (e.g. in the presence of 27.29 ng/mL IL-6 as described in Example 45) the polypeptides and compounds of the invention may have IC50 values between 500 pM and 50 pM, preferably between 250 pM and 50 pM, more preferably between 200 pM and 50 pM or less, such as 150 pM or less. In a plasma potency assay at EC95 values of IL-6 (e.g. in the presence of 885 ng/mL IL-6 as described in Example 45) the polypeptides and compounds of the invention may have IC50 values between 1000 pM and 100 pM, preferably between 750 pM and 100 pM, more preferably between 500 pM and 100 pM or less, such as 400 pM or less. In this plasma potency assay, the polypeptides and compounds of the invention may have IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4 (see Example 1). In this plasma potency assay, the amino acid sequences of the invention may have IC50 values that are at least the same and preferably better, at least two times, preferably three times, more preferably four times, even more preferably 5 times, 7 times or more than 7 times better compared to the IC50 value obtained for Tocilizumab (MRA).

In an assay for defining binding to membrane IL-6R on CHO cells, the polypeptides and compounds of the invention may have IC50 values between 10 nM and 100 pM, preferably between 5 nM and 100 pM, more preferably between 2 nM and 10 pM or less, such as 2 nM or less.

In another specific aspect, the polypeptide, compound or construct of the invention essentially consists of the amino acid sequence of SEQ ID NO: 70.

In another specific aspect, the polypeptide, compound or construct of the invention essentially consists of the amino acid sequence of SEQ ID NO: 71

The compounds or polypeptides of the invention can generally be prepared by a method which comprises at least the step of suitably linking the one or more amino acid sequence, Nanobody or monovalent construct of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

Accordingly, the present invention also relates to the use of an amino acid sequence, a Nanobody or a monovalent construct of the invention in preparing a multivalent compound, construct or polypeptide. The method for the preparation of a multivalent compound, construct or polypeptide will comprise the linking of an amino acid sequence, a Nanobody or a monovalent construct of the invention to at least one other group, residue, moiety or binding unit, optionally via one or more linkers.

Generally, when an amino acid sequence or Nanobody of the invention (or a compound, construct or polypeptide comprising the same) is intended for administration to a subject (for example for therapeutic and/or diagnostic purposes as described herein), it is preferably either an amino acid sequence or Nanobody that does not occur naturally in said subject; or, when it does occur naturally in said subject, in essentially isolated form (as defined herein).

The amino acid sequences, Nanobodies, polypeptides and compounds of the invention are directed against IL-6R from humans. However, they should preferably also be cross-reactivity with IL-6R from cynomolgus monkeys (*Macaca fascicularis*), by which is meant that these amino acid sequences, Nanobodies, polypeptides and compounds are also "directed against" (as defined herein) and/or are capable of specific binding to (as defined herein) IL-6R from cynomolgus monkeys (*Macaca fascicularis*). Such cross-reactivity, may have advantages from a drug development point of view, since it allows the amino acid sequences, Nanobodies, polypeptides and compounds against human IL-6R to be tested in a cynomolgus monkey disease model.

An amino acid sequence or Nanobody of the invention (as well as compounds, constructs and polypeptides comprising the same) is "cross-reactive" with IL-6R from humans and from cynomolgus monkey means that the amino acid sequence or Nanobody of the invention (as well as compounds, constructs and polypeptides comprising the same) binds to IL-6R from a cynomolgus monkey with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is the same or at least 70% of (preferably at least 80% of, more preferably at least 90% of, even more preferably at least 95% of) the affinity with which said amino acid sequence or Nanobody of the invention (as well as compounds, constructs and polypeptides comprising the same) binds to IL-6R from humans. For the IL-6R sequence and the corresponding cDNA sequence of cynomolgus monkey, reference is also made to WO 09/010,539 filed by Ablynx N.V. on Jul. 16, 2008 entitled "Receptor for interleukin-6 (IL-6) from *Macaca fascicularis*"; see SEQ ID NO: 3 and FIG. 1B for the cDNA sequence and SEQ ID NO: 4 and FIG. 3B for the amino acid sequence).

It is also within the scope of the invention to use parts, fragments, analogs, mutants, variants, alleles and/or derivatives of the amino acid sequences and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against the specific epitope on IL-6R; and more preferably will be capable of specific binding to the specific epitope on IL-6R, and even more preferably capable of binding to the specific epitope on IL-6R with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Such parts, fragments, analogs, mutants, variants, alleles and/or derivatives will usually also have a cell based potency and a plasma potency as defined herein. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

In another aspect, the invention also relates to a nucleic acid or a nucleotide sequence that encodes an amino acid sequence of the invention, a Nanobody of the invention or a polypeptide of the invention (or a suitable fragment thereof). Such a nucleic acid will also be referred to herein as a "nucleic acid of the invention" and may for example be in the form of a genetic construct, as further described herein. Accordingly, the present invention also relates to a nucleic acid or nucleotide sequence that is in the form of a genetic construct.

The nucleotide sequences of the invention may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

In another aspect, the invention relates to a host or host cell that expresses (or that under suitable circumstances is capable of expressing) an amino acid sequence of the invention, a Nanobody of the invention and/or a polypeptide of the invention; and/or that contains a nucleic acid of the invention. Some preferred but non-limiting examples of such hosts or host cells will become clear from the further description herein.

The invention further relates to a product or composition containing or comprising at least one amino acid sequence of the invention (or a suitable fragment thereof), at least one Nanobody of the invention, at least one polypeptide of the invention, at least one compound or construct of the invention, at least one monovalent construct of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention further relates to methods for preparing the amino acid sequences, Nanobodies, polypeptides, nucleic acids, host cells, products and compositions described herein. The method for producing an amino acid sequence of the invention, a Nanobody of the invention, a polypeptide of the invention, or a monovalent construct of the invention may comprise the following steps:

a) expressing, in a suitable host cell or host organism or in another suitable expression system, a nucleic acid or nucleotide sequence of the invention, or a genetic construct of the invention; optionally followed by:

b) isolating and/or purifying the amino acid sequence, the Nanobody, the polypeptide, or the monovalent construct of the invention thus obtained.

The method for producing an amino acid sequence, a Nanobody, a polypeptide, or a monovalent construct of the invention may comprise the steps of:

a) cultivating and/or maintaining a host or host cell of the invention under conditions that are such that said host or host cell expresses and/or produces at least one amino acid sequence, Nanobody, polypeptide, or a monovalent construct of the invention, optionally followed by:

b) isolating and/or purifying the amino acid sequence, the Nanobody, the polypeptide, or the monovalent construct of the invention thus obtained.

The invention further relates to applications and uses of the amino acid sequences, polypeptides, compounds, constructs, nucleic acids, host cells, products and compositions described herein, as well as to methods for the prevention and/or treatment for diseases and disorders associated with IL-6R. Some preferred but non-limiting applications and uses will become clear from the further description herein.

The amino acid sequences, Nanobodies, polypeptides, compounds, constructs and compositions of the present invention can generally be used to modulate, and in particular inhibit and/or prevent, binding of IL-6R to IL-6 and subsequent binding of the IL-6/IL-6R complex to gp130 and thus to modulate, and in particular inhibit and/or prevent, the signalling that is mediated by IL-6R, IL-6, IL-6/IL-6R complex and/or gp130, to modulate the biological pathways in which IL-6R, IL-6, the IL-6/IL-6R complex and/or gp130 are involved, and/or to modulate the biological mechanisms, responses and effects associated with such signalling or these pathways.

In one aspect, the invention provides amino acid sequences, Nanobodies, polypeptides, constructs and compounds that are, and/or that can be used as, an antagonist of IL-6R, of IL-6R-mediated signalling, and/or of the biological pathways mechanisms, responses and/or effects in which IL-6R and/or IL-6R mediated signalling are involved.

In this respect, the amino acid sequences, Nanobodies, polypeptides, compounds, constructs and compositions of the present invention are such that they (a) specifically bind (as defined herein) to the IL-6 receptor; and (b) are capable of downregulating the IL-6 receptor and/or are capable of inhibiting, decreasing or downregulating the signalling of the IL-6 receptor and/or the pathway(s), mechanism(s) or signalling in which IL-6 or IL-6R is involved. As will be clear to the skilled person, such an amino acid sequence, Nanobody, polypeptide, compound or construct can generally be used as an antagonist of IL-6, of the IL-6 receptor and/or of the biological pathways, mechanisms or effects in which IL-6, IL-6R and/or IL-6/IL-6R complex mediated signalling is involved. Any such decrease or downregulation (which can be at least 1%, such as at least 5%, as at least 10%, or more than 10%, or up to 50% or 100% or more in a relevant parameter, compared to the same parameter under conditions in which the amino acid sequence, Nanobody, polypeptide, compound or construct is not bound to the IL-6 receptor), may be measured in any suitable manner known per se, for example using one of the assays used described above and/or in the Experimental Part and/or mentioned herein.

More in particular, and in addition to (a) and (b) above, such antagonistic amino acid sequences, Nanobodies, polypeptides, compounds and constructs bind to IL-6R in such a way that (c) binding of IL-6 to IL-6R is blocked, inhibited or reduced; compared to the binding of IL-6 to its receptor without the presence of the amino acid sequence, Nanobody or polypeptide of the invention.

Without limitation, such antagonistic amino acid sequences, Nanobodies, polypeptides, compounds and constructs may bind to a specific epitope on IL-6R close to the IL-6 interaction side on IL-6R.

Also, in addition to (a) and (b) above, and in addition to (c) above, such antagonistic amino acid sequences and polypeptides may bind to IL-6R (i.e. as such or as present in the IL-6/IL-6R complex) in such a way that (d) the formation of the IL-6/IL-6R complex is inhibited or affected (e.g. fully or partially disrupted) in such a way that the binding of the complex to—e.g. its affinity for—gp130 is reduced (or reversely, that the binding of gp 130 to—e.g. its affinity for—the complex is reduced), so that the signaling induced/mediated by the binding of the complex to gp130 is modulated (e.g. reduced); compared to the formation of the complex and its binding to gp130 without the presence of the amino acid sequence, Nanobody, polypeptide, compound or construct of the invention.

The amino acid sequences, Nanobodies, polypeptides, compounds, constructs and compositions of the invention are also preferably (but without limitation) such that they effect a decrease (i.e. by at least 1 percent such as by at least 10 percent, preferably by at least 30 percent, more preferably by at least 50 percent, even more preferably by at least 75 percent or more) or a total inhibition of the induction of C-reactive protein (CRP) in a mammal (such as in a human subject or in a suitable animal model for inflammation such as the a cynomolgus monkey) when they are administered to said mammal in a therapeutically relevant amount compared to a mammal not receiving the amino acid sequence, Nanobody, polypeptide, compound, construct or compositions of the invention.

The amino acid sequences, Nanobodies, polypeptides, compounds, constructs and compositions of the invention are also preferably (but without limitation) such that they effect a decrease (i.e. by at least 1 percent such as by at least 10 percent, preferably by at least 30 percent, more preferably by at least 50 percent, even more preferably by at least 75 percent or more) or a total inhibition of the induction of the platelet count in a mammal (such as in a human subject or in a suitable animal model for inflammation such as the a cynomolgus monkey) when they are administered to said mammal in a therapeutically relevant amount compared to a mammal not receiving the amino acid sequence, Nanobody, polypeptide, compound, construct or compositions of the invention.

The amino acid sequences, Nanobodies, polypeptides, compounds, constructs and compositions of the invention are also preferably (but without limitation) such that they effect a decrease (i.e. by at least 1 percent such as by at least 10 percent, preferably by at least 30 percent, more preferably by at least 50 percent, even more preferably by at least 75 percent or more) or a total inhibition of the induction of fibrinogen in a mammal (such as in a human subject or in a suitable animal model for inflammation such as the cynomolgus monkey) when they are administered to said mammal in a therapeutically relevant amount compared to a mammal not receiving the amino acid sequence, Nanobody, polypeptide, compound, construct or compositions of the invention.

As such, the amino acid sequences, polypeptides, compounds, constructs and compositions of the present invention can be used for the prevention and/or treatment of diseases and disorders associated with IL-6R, with IL-6, with the IL-6/IL-6R complex (optionally in further complex with gp130), and/or with the signaling pathway(s) and/or the biological functions and responses in which IL-6, IL-6R and/or the IL-6/IL-6R complex (optionally in further complex with gp130) are involved, and in particular for the prevention and/or treatment of diseases and disorders associated with IL-6R, IL-6, with the IL-6/IL-6R complex (optionally in further complex with gp130), and/or with the signaling pathway(s) and/or the biological functions and responses in which IL-6R, IL-6 and/or the IL-6/IL-6R complex (optionally in further complex with gp130) are involved, which are characterized by excessive and/or unwanted signalling mediated by IL-6R or by the pathway(s) in which IL-6R is involved. Examples of such diseases and disorders associated with IL-6R, with IL-6, with the IL-6/IL-6R complex, and/or with the signaling pathway(s) and/or the biological functions and responses in which IL-6, IL-6R and/or the IL-6/IL-6R complex are involved, will be clear to the skilled person based on the disclosure herein, and for example include the following diseases and disorders: sepsis (Starnes et al., 1999, J. Immunol., 148: 1968) and various forms of cancer such as multiple myeloma disease (MM), renal cell carcinoma (RCC), plasma cell leukaemia (Klein et al., 1991, Blood, 78: 1198-1204), lymphoma, B-lymphoproliferative disorder (BLPD) and prostate cancer. Non-limiting examples of other diseases caused by excessive IL-6 production or signalling include bone resorption (osteoporosis) (Roodman et al., 1992, J. Clin. Invest. 89: 45-52; Jilka et al., 1992, Science, 257: 88-91), cachexia (Strassman et al., 1992, J. Clin. Invest., 89: 1681-1684), psoriasis, mesangial proliferative glomerulonephritis, Kaposi's sarcoma, AIDS-related lymphoma (Emilie et al., 1994, Blood, 84: 2472-2479), inflammatory diseases and disorder such as rheumatoid arthritis, systemic onset juvenile idiopathic arthritis, hypergammaglobulinemia (Grau et al., 1990, J. Exp. Med., 172: 1505-1508); Crohn's disease, ulcerative colitis, systemic lupus erythematosus (SLE), multiple sclerosis, Castleman's disease, IgM gammopathy, cardiac myxoma, asthma (in particular allergic asthma) and autoimmune insulin-dependent diabetes mellitus (Campbell et al., 1991, J. Clin. Invest. 87: 739-742). Other IL-6R, IL-6 and/or IL-6/IL-6R complex related disorders will be clear to the skilled person. Such diseases and disorders are also generally referred to herein as "IL-6R related diseases and disorders".

Thus, without being limited thereto, the amino acid sequences, Nanobodies, polypeptides, compounds, constructs and compositions of the invention can for example be used to prevent and/or to treat all diseases and disorders that are currently being prevented or treated with active principles that can modulate IL-6R-mediated signalling, such as those mentioned in the prior art cited above. It is also envisaged that the amino acid sequences, Nanobodies, polypeptides, compounds, constructs and compositions of the invention can be used to prevent and/or to treat all diseases and disorders for which treatment with such active principles is currently being developed, has been proposed, or will be proposed or developed in future. In addition, it is envisaged that, because of their favourable properties as further described herein, the amino acid sequences, Nanobodies, polypeptides, compounds, constructs and compositions of the present invention may be used for the prevention and treatment of other diseases and disorders than those for which these known active principles are being used or will be proposed or developed; and/or that the amino acid sequences, Nanobodies, polypeptides, compounds, constructs and compositions of the present invention may provide new methods and regimens for treating the diseases and disorders described herein.

Accordingly, the present invention also relates to a method for the prevention and/or treatment of at least one disease or disorder that can be prevented and/or treated by administering, to a subject in need thereof, an amino acid sequence of the invention, a Nanobody of the invention, a polypeptide of the invention, or a monovalent construct of the invention, said method comprising administering, to a subject in need thereof, a pharmaceutically active amount of at least one amino acid sequence of the invention, Nanobody of the invention, polypeptide of the invention, compound of the invention, or (monovalent) construct of the invention, or a composition of the invention.

The invention also relates to the use of an amino acid sequence of the invention, a Nanobody of the invention, a polypeptide of the invention, compound of the invention, or (monovalent) construct of the invention in the preparation of a pharmaceutical composition for prevention and/or treatment of at least one of the diseases and disorders associated with IL-6, with IL-6R, with the IL-6/IL-6R complex and/or with the signalling pathways and/or the biological functions and responses in which IL-6, IL-6R and/or the IL-6/IL-6R complex are involved; and/or for use in one or more of the methods described herein.

The invention further relates to an amino acid sequence of the invention, a Nanobody of the invention, a polypeptide of the invention, compound of the invention, or (monovalent) construct of the invention for use in the prevention and/or treatment of at least one of the diseases and disorders associated with IL-6, with IL-6R, with the IL-6/IL-6R complex and/or with the signalling pathways and/or the biological functions and responses in which IL-6, IL-6R and/or the IL-6/IL-6R complex are involved; and/or for use in one or more of the methods described herein.

In particular, the present invention provides amino acid sequences, Nanobodies, proteins, polypeptides, compounds and/or constructs that are suitable for prophylactic, therapeutic and/or diagnostic use in a warm-blooded animal, and in particular in a mammal, and more in particular in a human being.

More in particular, the present invention provides such amino acid sequences, Nanobodies, proteins, polypeptides, compounds and/or constructs that can be used for the prevention, treatment, alleviation and/or diagnosis of one or more IL-6R related disorders (as defined herein) in a warm-blooded animal, in particular in a mammal, and more in particular in a human being.

Other applications and uses of the amino acid sequences, Nanobodies, polypeptides and compounds of the invention will become clear to the skilled person from the further disclosure herein.

BRIEF DESCRIPTION OF THE DRAWINGS

FIG. 4: Amino acid sequences of anti-IL-6R Nanobodies.

FIG. 6A-6C: Inhibition of the IL-6/IL-6R interaction by selected Nanobodies as measured in alphascreen. MAb BR-6 and the reference Fab fragment (described in Example 1) were used as a control.

FIG. 8A-J: Binding of the anti-IL-6R Nanobodies to U266 cells in the absence (top) and presence (bottom) of human plasma. (A) MoAb anti-IgG; (B) BR6; (C) IL6R03; (D) IL6R04; (E) IL6R13; (F) MOAb anti-IgG; (G) BR6; (H) IL6R03; (I) IL6R04; (J) IL6R13.

FIG. 15: Alignment of IL6R03, IL6R04 and IL6R13 sequences with 5 most homologous human germlines. For further explanation see Example 23.

FIGS. 16A and B: Amino acid sequences of sequence optimized variants of IL6R03, IL6R04 and IL6R13. For further explanation see Example 23.

FIG. 26: Amino acid sequences of affinity matured IL6R65 variants.

FIGS. 27-1 and 27-2: Binding curves of Nanobody IL6R65 (referred to as parent Nanobody) and its affinity matured variants.

FIG. 31: Sequences of IL-6R binding Nanobodies after 2nd round of affinity maturation (combinatorial libraries CDR1/2+CDR3).

FIG. 38: Plasma potency ELISA in human plasma. Neutralization of binding of human IL-6 to plasma sIL-6R by the reference IgG (•), IL6R20A11 (♦), IL6R304 (■), IL6R305 (▲), IL6R306 (▼) or an irrelevant NB (x). The mean±s.e. of duplicate measurements is shown. A, B: competition with 25 ng/mL of IL-6 (EC50). C,D: competition with 885 ng/mL of IL-6 (EC95).

FIG. 39: Binding of IL6R20A11 and formatted variants to CHO cells. CHO cells expressing IL-6R (A) or negative CHO cells (B) were incubated with IL6R20A11 (♦), IL6R304 (■), IL6R305 (▲) or IL6R306 (▼). Bound Nanobody was detected using MAb c1.5.3.1 and anti-mouse-PE.

FIG. 41A1-C2: Binding of IL-6R Nanobodies to human PBL. EDTA-treated blood from 2 donors was incubated with IL6R20A11 (♦), IL6R304 (■), IL6R305 (▲) or IL6R306 (▼). Bound Nanobody was detected using MAb c1.5.3.1 and anti-mouse-PE. A: lymphocytes; B: monocytes; C: granulocytes.

FIGS. 42-1 and 42-2: Binding curves of formatted affinity matured Nanobodies on human and cyno serum albumin.

DETAILED DESCRIPTION

Figure 1:
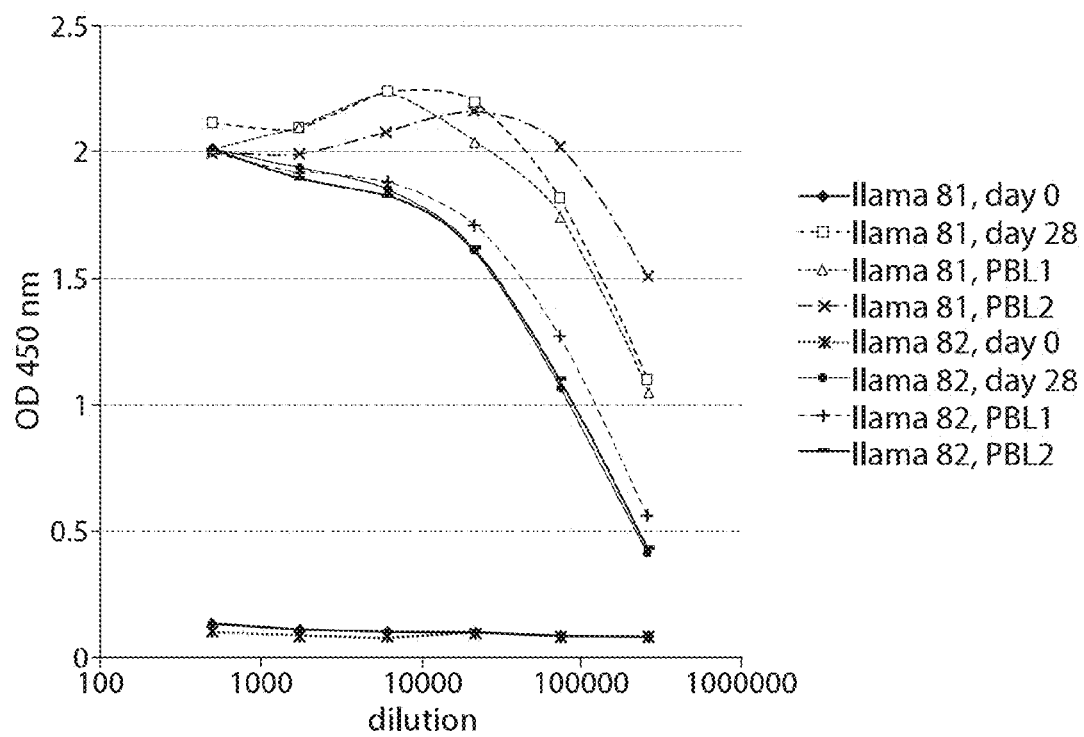
FIG. 1: Analysis of the immune response in llamas 81 and 82 by ELISA as described in Example 2.
Figure 2A:
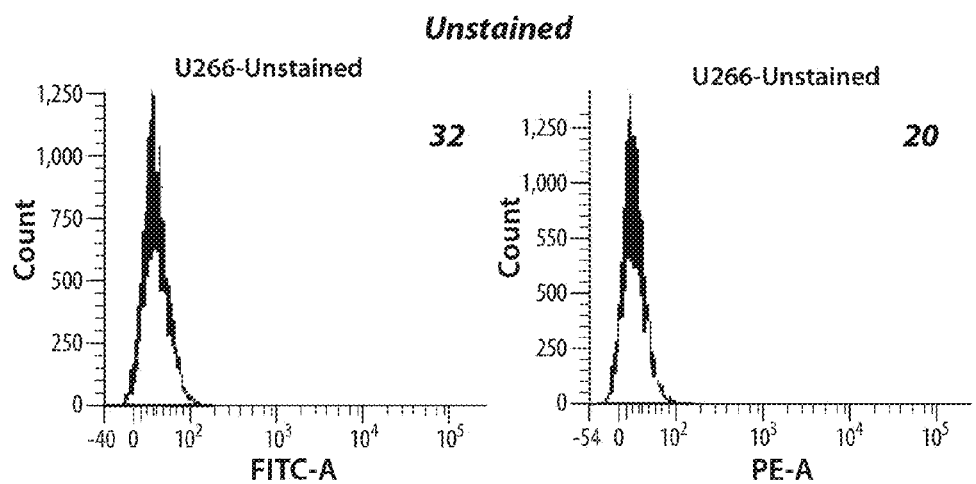
FIG. 2A-J: Analysis of the immune response in llamas 81 and 82 by FACS as described in Example 2. Legend: LI81 pre: pre-immune serum from llama 81; LI81 PBL1: serum collected at day 28 from llama 81; LI82 pre: pre-immune serum from llama 82; LI82 PBL2: serum collected at day 43 from llama 82. (A) FITC-A, (B) PE-A, (C) A-mouse-IgG-PE, PE-A, (D) a-Llama-IgG-FITC, FITC-A; (E) BN-12, PE-A; (F) BR-6, PE-A; (G) M182, PE-A; (H) LI81 pre 1/100 FITC-A; (I) LI81 pre 1/500, FITC-A; (J) LI81 pre 1/2500, FITC-A; (K) LI81 pre 1/2500, FITC-1; (L) LI81 PBL 1/100, FITC-A; (M) LI81 PBL 1/500, FITC-A; (N) LI81 PBL 1/2500, FITC-A; (O) LI81 PBL 1/2500, FITC-A; (P) LI82 pre 1/100, FITC-A; (O) LI82 pre 1/500, FITC-A; (R) LI82 pre 1/2500, FITC-A; (S) LI82 pre 1/2500, FITC-A; (T) LI82 PBL2 1/100, FITC-A; (U) LI82 PBL2 1/500, FITC-A; (V) LI82 PBL2 1/2500, FITC-A; (W) LI82 PBL2 1/2500, FITC-A.
Figures 2B, 2C:
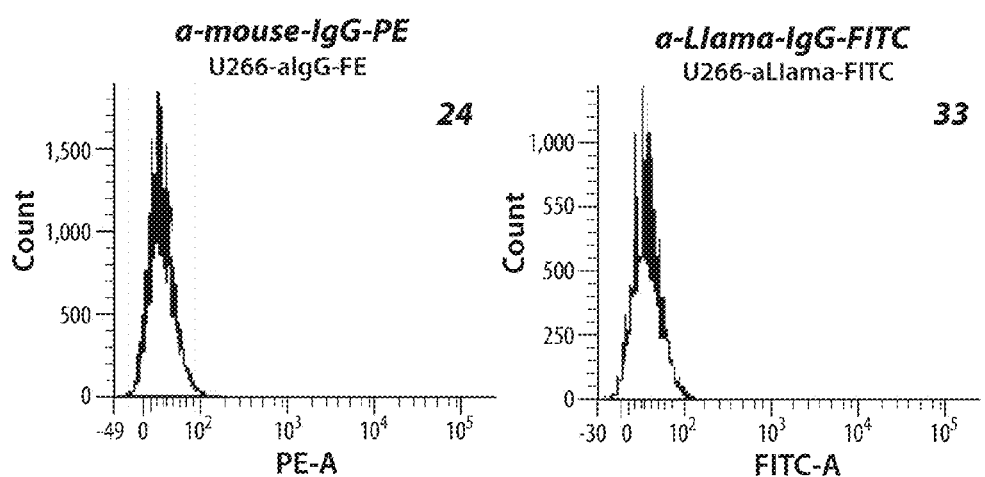
Figure 2D:
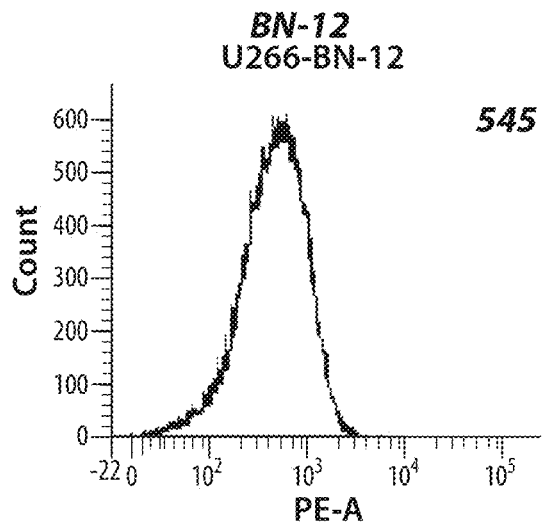
Figure 2E:
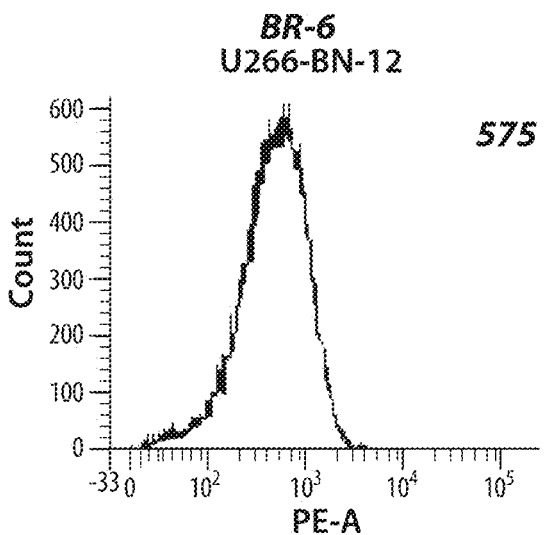
Figure 2F:
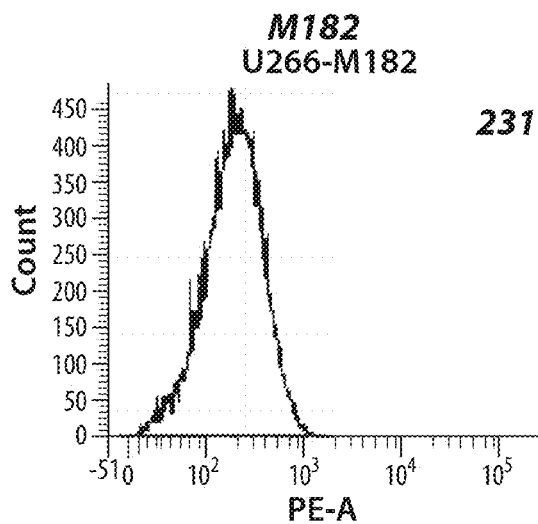
Figure 2G:
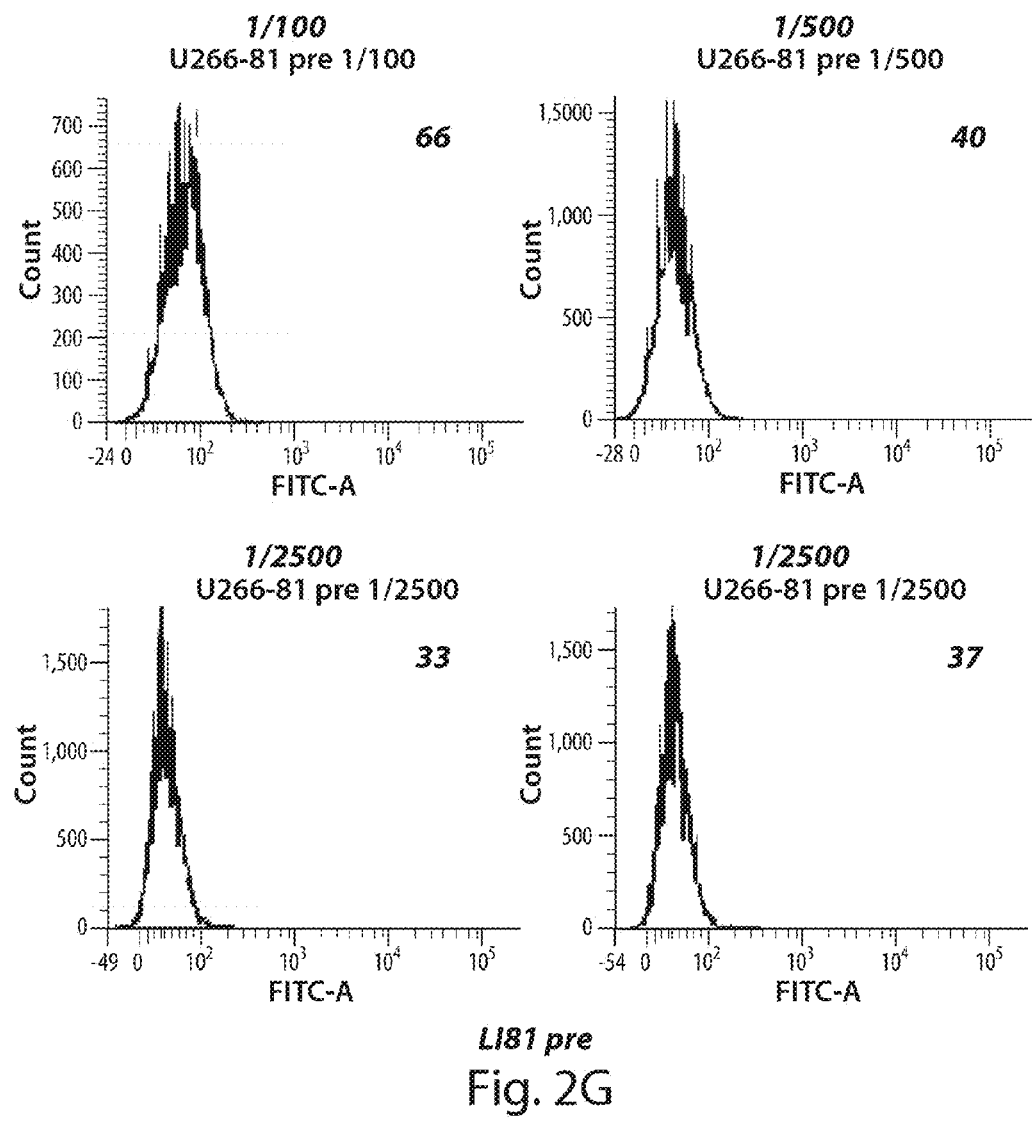
Figure 2H:
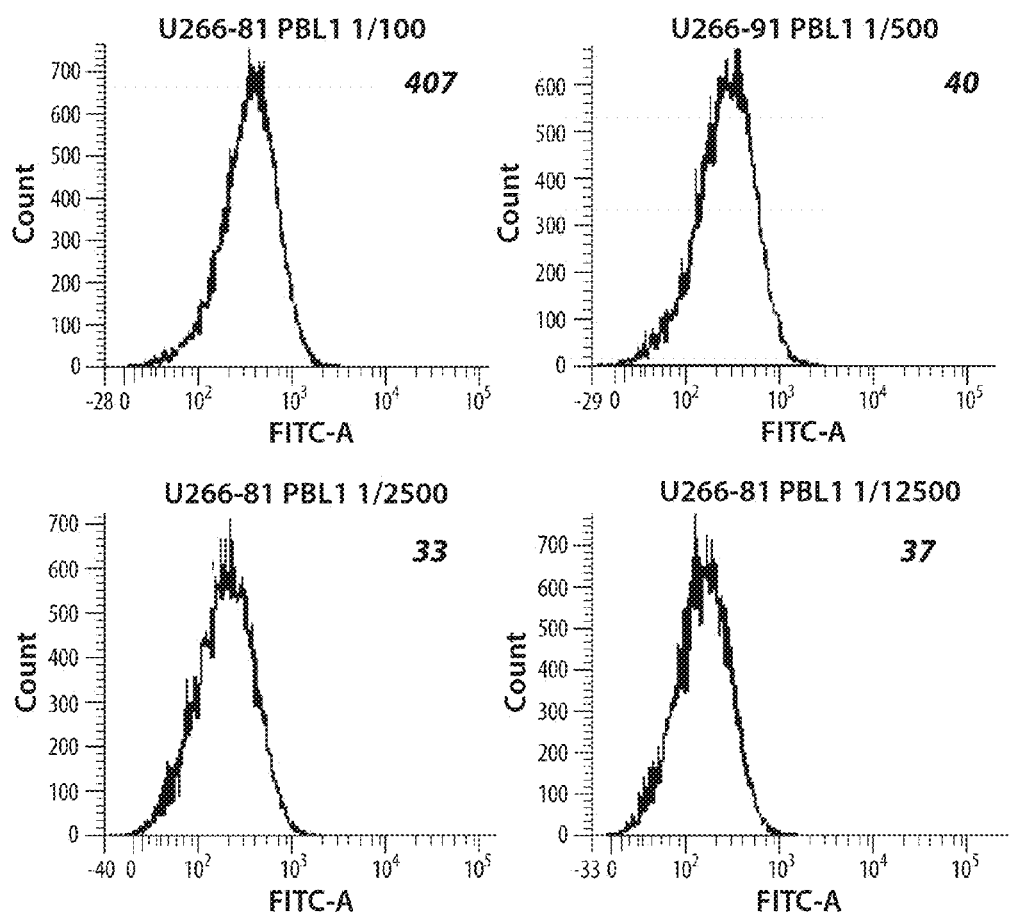
Figure 2I:
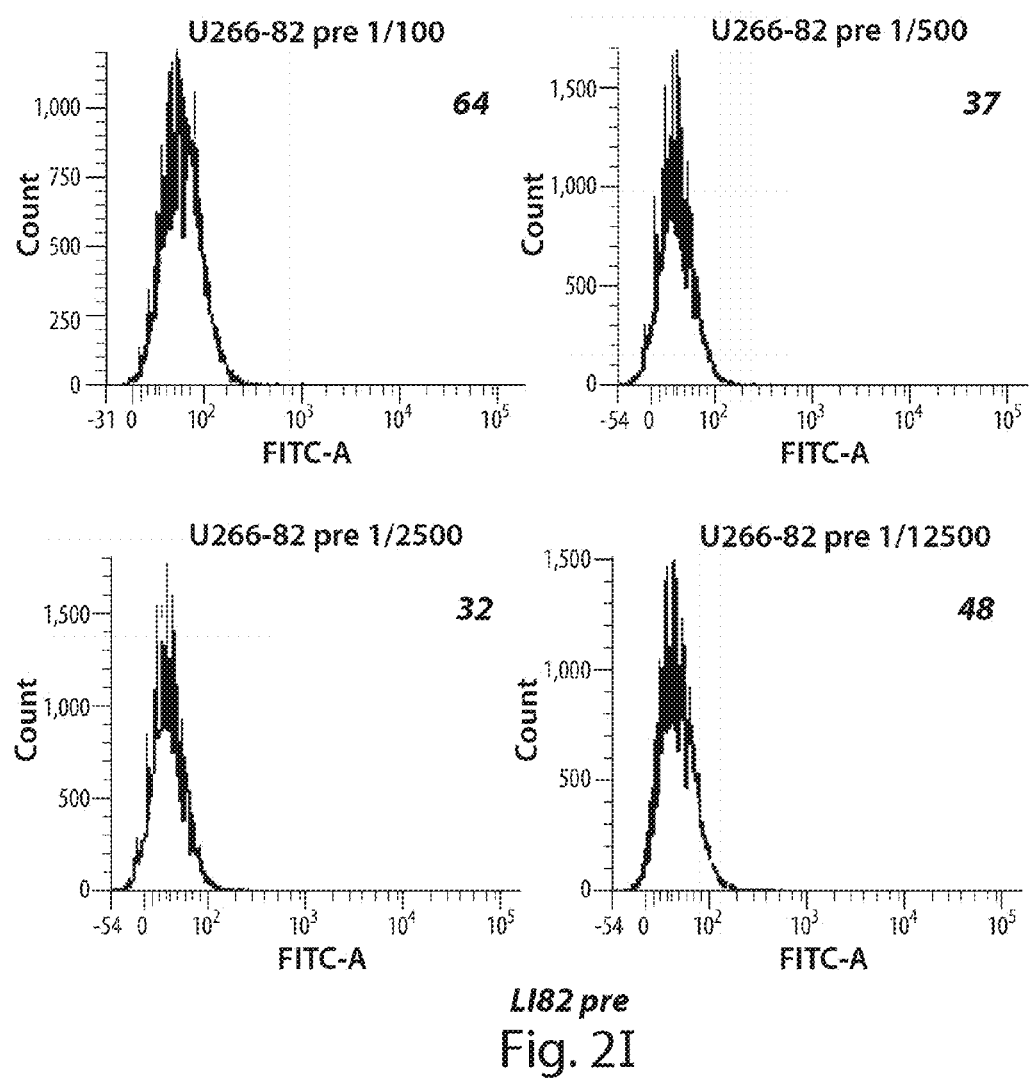
Figure 2J:
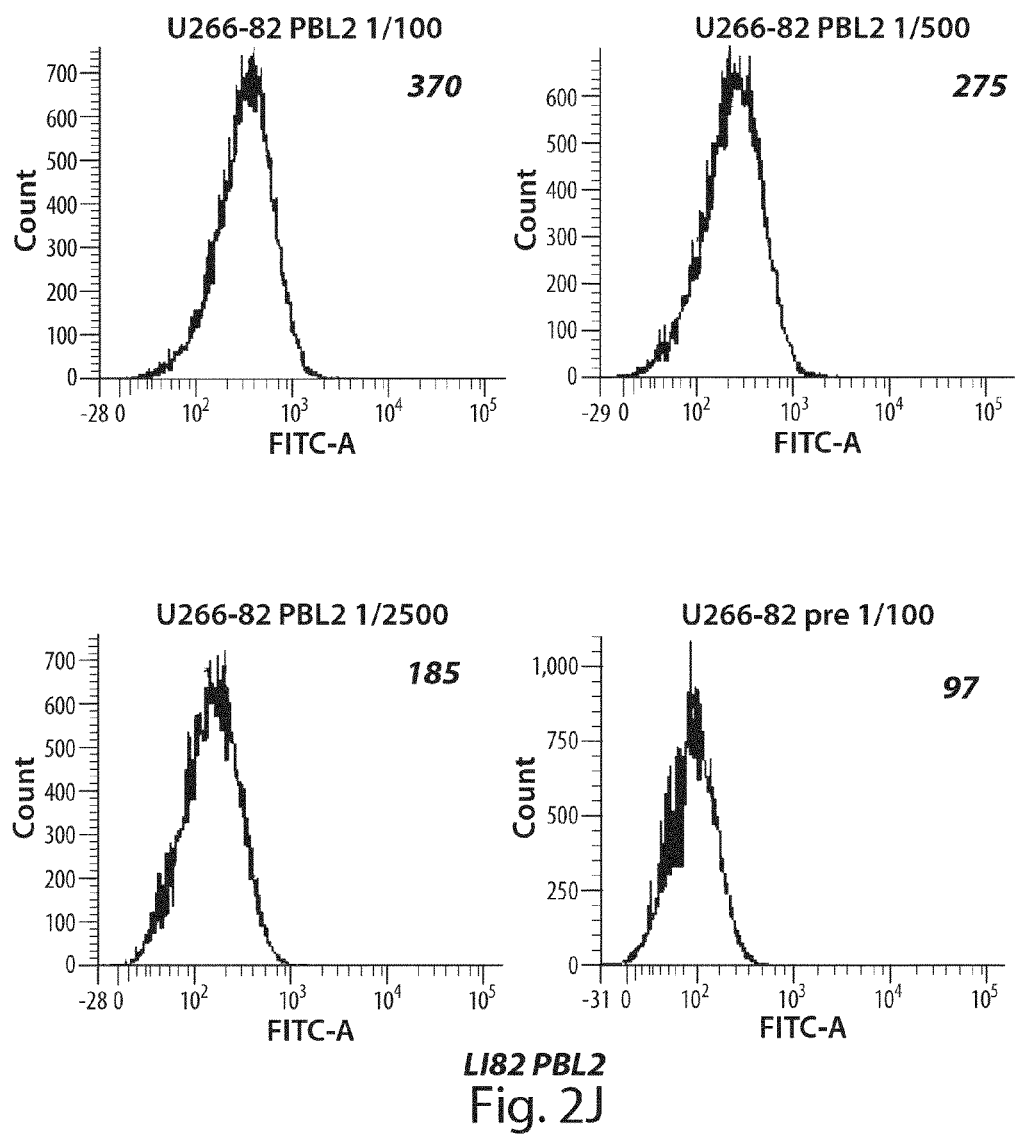

In the present description, examples and claims:
a) Unless indicated or defined otherwise, all terms used have their usual meaning in the art, which will be clear to the skilled person. Reference is for example made to the standard handbooks, such as Sambrook et al., "Molecular Cloning: A Laboratory Manual" ($2^{nd}$ Ed.), Vols. 1-3, Cold Spring Harbor Laboratory Press (1989); F. Ausubel et al., eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, $10^{th}$ Ed. Blackwell Publishing, UK (2001); and Janeway et al., "Immunobiology" (6th Ed.), Garland Science Publishing/Churchill Livingstone, New York (2005), as well as to the general background art cited herein;
b) Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation. Also, the term "nucleotide sequence" as used herein also encompasses a nucleic acid molecule with said nucleotide sequence, so that the terms "nucleotide sequence" and "nucleic acid" should be considered equivalent and are used interchangeably herein;
c) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, 2006, Adv. Drug Deliv. Rev., 58 (5-6): 640-56; Levin and Weiss, 2006, Mol. Biosyst., 2(1): 49-57; Irving et al., 2001, J. Immunol. Methods, 248(1-2): 31-45; Schmitz et al., 2000, Placenta, 21 Suppl. A, S106-12; Gonzales et al., 2005, Tumour Biol., 26(1): 31-43, which describe techniques for protein engineering, such as affinity maturation and other techniques for improving the specificity and other desired properties of proteins such as immunoglobulins.
d) Amino acid residues will be indicated according to the standard three-letter or one-letter amino acid code, as mentioned in Table A-2;

TABLE A-2 one-letter and three-letter amino acid code

| | | | |
|---|---|---|---|
| Nonpolar, uncharged (at pH 6.0-7.0)[3] | Alanine | Ala | A |
| | Valine | Val | V |
| | Leucine | Leu | L |
| | Isoleucine | Ile | I |
| | Phenylalanine | Phe | F |
| | Methionine[1] | Met | M |
| | Tryptophan | Trp | W |
| | Proline | Pro | P |
| Polar, uncharged (at pH 6.0-7.0) | Glycine[2] | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar, charged (at pH 6.0-7.0) | Lysine | Lys | K |
| | Arginine | Arg | R |
| | Histidine[4] | His | H |
| | Aspartate | Asp | D |
| | Glutamate | Glu | E |

Notes:
[1]Sometimes also considered to be a polar uncharged amino acid.
[2]Sometimes also considered to be a nonpolar uncharged amino acid.
[3]As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4]As is known in the art, the charge of a His residue is greatly dependant upon even small shifts in pH, but a His residue can generally be considered essentially uncharged at a pH of about 6.5.

e) For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position).
Alternatively, the degree of sequence identity between two or more nucleotide sequences may be calculated using a known computer algorithm for sequence alignment such as NCBI Blast v2.0, using standard settings.
Some other techniques, computer algorithms and settings for determining the degree of sequence identity are for example described in WO 04/037999, EP 0967284, EP 1085089, WO 00/55318, WO 00/78972, WO 98/49185 and GB 2357768-A.
Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence;
f) For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335 768-A, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Any amino acid substitutions applied to the polypeptides described herein may also be based on the analysis of the frequencies of amino acid variations between homologous proteins of different species developed by Schulz et al. (1978, "Principles of Protein Structure", Springer-Verlag), on the analyses of structure forming potentials developed by Chou and Fasman (1974, Biochemistry 13: 211, and 1978, Adv. Enzymol., 47: 45-149), and on the analysis of hydrophobicity patterns in proteins developed by Eisenberg et al. (1984, Proc. Natl. Acad. Sci. USA 81: 140-144), Kyte and Doolittle (1981, J. Molec. Biol. 157: 105-132), and Goldman et al. 1986, Ann. Rev. Biophys. Chem. 15: 321-353), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (1996, Nature Structural Biology, 3 (9): 803), Spinelli et al. (1996, Natural Structural Biology, 3: 752-757) and Decanniere et al. (1999, Structure, 7 (4): 361). Further information about some of the amino acid residues that in conventional $V_H$ domains form the $V_H/V_L$ interface and potential camelizing substitutions on these positions can be found in the prior art cited above.

g) Amino acid sequences and nucleic acid sequences are said to be "exactly the same" if they have 100% sequence identity (as defined herein) over their entire length;

h) When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;

i) When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the firstmentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when an amino acid sequence of the invention is said to comprise a stretch of amino acid residues, this may mean that said stretch of amino acid residues has been incorporated into the amino acid sequence of the invention, but more usually this generally means that the amino acid sequence of the invention contains within its sequence the stretch of amino acid residues irrespective of how said amino acid sequence of the invention has been generated or obtained. When a Nanobody of the invention is said to comprise a CDR sequence, this may mean that said CDR sequence has been incorporated into the Nanobody of the invention, but more usually this generally means that the Nanobody of the invention contains within its sequence a stretch of amino acid residues with the same amino acid sequence as said CDR sequence, irrespective of how said Nanobody of the invention has been generated or obtained. It should also be noted that when the latter amino acid sequence has a specific biological or structural function, it preferably has essentially the same, a similar or an equivalent biological or structural function in the firstmentioned amino acid sequence (in other words, the firstmentioned amino acid sequence is preferably such that the latter sequence is capable of performing essentially the same, a similar or an equivalent biological or structural function). For example, when a Nanobody of the invention is said to comprise a CDR sequence or framework sequence, respectively, the CDR sequence and framework are preferably capable, in said Nanobody, of functioning as a CDR sequence or framework sequence, respectively. Also, when a nucleotide sequence is said to comprise another nucleotide sequence, the first mentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the firstmentioned, larger nucleotide sequence).

j) A nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis;

k) The term "domain" as used herein generally refers to a globular region of an amino acid sequence (such as an antibody chain, and in particular to a globular region of a heavy chain antibody), or to a polypeptide that essentially consists of such a globular region. Usually, such a domain will comprise peptide loops (for example 3 or 4 peptide loops) stabilized, for example, as a sheet or by disulfide bonds. The term "binding domain" refers to such a domain that is directed against an antigenic determinant (as defined herein);

l) The term "antigenic determinant" refers to the epitope on the antigen recognized by the antigen-binding molecule (such as an amino acid sequence, a Nanobody or a polypeptide of the invention) and more in particular by the antigen-binding site of said molecule. The terms "antigenic determinant" and "epitope" may also be used interchangeably herein.

m) An amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

n) The term "specificity" refers to the number of different types of antigens or antigenic determinants to which a particular antigen-binding molecule or antigen-binding protein (such as an amino acid sequence, a Nanobody or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as an amino acid sequence, a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4 M^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D=1/K_A$]. The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or $M^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation DG=RT.ln($K_D$) (equivalently DG=−RT.ln($K_A$)), where R equals the gas constant, T equals the absolute temperature and ln denotes the natural logarithm.

The $K_D$ for biological interactions which are considered meaningful (e.g. specific) are typically in the range of $10^{-10}$ M (0.1 nM) to $10^{-5}$ M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$ s$^{-1}$. The on-rate may vary between $10^2$ M$^{-1}$ s$^{-1}$ to about $10^7$ M$^{-1}$ s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}$=0.69 s). The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (1985, J. Immunol. Methods, 77: 305-19). This method establishes a solution phase binding equilibrium measurement and avoids possible artefacts relating to adsorption of one of the molecules on a support such as plastic. However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an IC$_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D\ ref})$. Note that if $c_{ref}<<K_{D\ ref}$, $K_D \approx IC_{50}$. Provided the measurement of the IC$_{50}$ is performed in a consistent way (e.g. keeping $c_{ref}$ fixed) for the binders that are compared, the strength or stability of a molecular interaction can be assessed by the IC$_{50}$ and this measurement is judged as equivalent to $K_D$ or to apparent $K_D$ throughout this text.

o) The half-life of an amino acid sequence, Nanobody, compound or polypeptide of the invention can generally be defined as the time taken for the serum concentration of the amino acid sequence, Nanobody, compound or polypeptide to be reduced by 50%, in vivo, for example due to degradation of the sequence or compound and/or clearance or sequestration of the sequence or compound by natural mechanisms. The in vivo half-life of an amino acid sequence, Nanobody, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)) a suitable dose of the amino acid sequence, Nanobody, compound or polypeptide of the invention; collecting blood samples or other samples from said animal; determining the level or concentration of the amino acid sequence, Nanobody, compound or polypeptide of the invention in said blood sample; and calculating, from (a plot of) the data thus obtained, the time until the level or concentration of the amino acid sequence, Nanobody, compound or polypeptide of the invention has been reduced by 50% compared to the initial level upon dosing. Reference is for example made to the Experimental Part below, as well as to the standard handbooks, such as Kenneth A et al. (Chemical Stability of Pharmaceuticals: A Handbook for Pharmacists) and Peters et al. (1996, Pharmacokinete analysis: A Practical Approach). Reference is also made to Gibaldi M and Perron D (1982, "Pharmacokinetics", published by Marcel Dekker, 2nd Rev. edition).

As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both.

p) In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the amino acid sequence, Nanobody, polypeptide, compound or construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the amino acid sequence, Nanobody, polypeptide, compound or construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the amino acid sequence, Nanobody, polypeptide, compound or construct of the invention.

Modulating may for example also involve allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may for example also involve effecting a change in respect of the folding or confirmation of the target or antigen, or in respect of the ability of the target or antigen to fold, to change its confirmation (for example, upon binding of a ligand), to associate with other (sub)units, or to disassociate. Modulating may for example also involve effecting a change in the ability of the target or antigen to transport other compounds or to serve as a channel for other compounds (such as ions).

Modulating may be reversible or irreversible, but for pharmaceutical and pharmacological purposes will usually be in a reversible manner.

In the context of the present invention, "modulating" or "to modulate" generally means exercising an agonistic or antagonistic effect, respectively, with respect to IL-6, IL-6R and/or the biological pathways, responses, signalling, mechanisms or effects in which IL-6 and/or IL-6R is involved. In particular, "modulating" or "to modulate" may mean either an agonistic or antagonistic effect (i.e. a full or partial agonistic or antagonistic effect, respectively), as measured using a suitable in vitro, cellular or in vivo assay (such as those mentioned herein), that leads to a change in a relevant parameter by at least 1%, preferably at least 5%, such as at least 10% or at least 25%, for example by at least 50%, at least 60%, at least 70%, at least 80%, or 90% or more, compared to the same parameter in the same assay under the same conditions but without the presence of the amino acid sequence, Nanobody, polypeptide, compound or construct of the invention.

In the context of the present invention "modulating, inhibiting and/or preventing binding of the IL-6/IL-6R complex to gp130" means that the amino acid sequences, Nanobodies, polypeptides, compounds or constructs of the present invention bind to the specific epitope on IL-6R (i.e. as such or as present in the IL-6/IL-6R complex) in such a way that the formation of the IL-6/IL-6R complex is affected, inhibited and/or prevented (e.g. fully or partially disrupted) in such a way that the binding of the complex to—e.g. its affinity for—gp130 is reduced, inhibited and/or prevented (or reversely, that the binding of gp 130 to—e.g. its affinity for—the complex is reduced, inhibited and/or prevented), so that the signaling induced/mediated by the binding of the complex to gp130 is modulated (e.g. reduced, inhibited and/or prevented) compared to the formation of the complex and its binding to gp130 without the presence of the amino acid sequence, Nanobodies, polypeptide, compound or construct of the invention.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence, Nanobody, polypeptide, compound or construct of the invention can bind such that the target or antigen (and/or any pathway, interaction, signalling, biological mechanism or biological effect in which the target or antigen is involved) is modulated (as defined herein).

r) A "stretch of amino acid residues" means two or more amino acid residues that are adjacent to each other or in close proximity to each other, i.e. in the primary or tertiary structure of the amino acid sequence. In the context of the present invention, the "stretch of amino acid residues" will be (at least partially) responsible for the binding of the amino acid sequence, Nanobody, polypeptide, compound or construct of the invention to its specific epitope on IL-6R.

s) An amino acid sequence, Nanobody, polypeptide, compound or construct is said to be "specific for" a first target or antigen compared to a second target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10.000 times or more better than the affinity with which said amino acid sequence, Nanobody, polypeptide, compound or construct binds to the second target or polypeptide. For example, the first amino acid sequence, Nanobody, polypeptide, compound or construct may bind to the target or antigen with a $K_D$ value that is at least 10 times less, such as at least 100 times less, and preferably at least 1000 times less, such as 10.000 times less or even less than that, than the $K_D$ with which said amino acid sequence, Nanobody, polypeptide, compound or construct binds to the second target or polypeptide. Preferably, when an amino acid sequence, Nanobody, polypeptide, compound or construct is "specific for" a first target or antigen compared to a second target or antigen, it is directed against (as defined herein) said first target or antigen, but not directed against said second target or antigen.

t) An amino acid sequence or Nanobody of the invention (as well as compounds, constructs and polypeptides comprising the same) is "cross-reactive" with IL-6R from two different species (i.e. a first species and a second species) means that the amino acid sequence or Nanobody of the invention (as well as compounds, constructs and polypeptides comprising the same) binds to IL-6R from a second species with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is the same or at least 70% (preferably at least 80%, more preferably at least 90%, or even more preferably at least 95%) of the affinity with which said amino acid sequence or Nanobody of the invention (as well as compounds, constructs and polypeptides comprising the same) binds to IL-6R from a first species.

u) As further described herein, the total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein;

v) The amino acid residues of a Nanobody are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans (2000, J. Immunol. Methods 240 (1-2): 185-195; see for example FIG. 2 of this publication); or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of $V_H$ domains, which methods can also be applied in an analogous manner to $V_{HH}$ domains from Camelids and to Nanobodies, are the method described by Chothia et al. (1989, Nature 342: 877-883), the so-called "AbM definition" and the so-called "contact definition". However, in the present description, claims and figures, the numbering according to Kabat as applied to $V_{HH}$ domains by Riechmann and Muyldermans will be followed, unless indicated otherwise; and w) The Figures, Sequence Listing and the Experimental Part/Examples are only given to further illustrate the invention and should not be interpreted or construed as limiting the scope of the invention and/or of the appended claims in any way, unless explicitly indicated otherwise herein.

The present invention provides stretches of amino acid residues (SEQ ID NO's: 80-82, SEQ ID NO's: 84-91 and SEQ ID NO's: 93-95) that are particularly suited for binding to IL-6R. These stretches of amino acid residues may be present in, and/or may be incorporated into, an amino acid sequence of the invention, in particular in such a way that they form (part of) the antigen binding site of the amino acid sequence of the invention. These stretches of amino acid residues have been generated as CDR sequences of heavy chain antibodies or $V_{HH}$ sequences that were raised against the IL-6R and that were further affinity matured (see Example section) to further increase their affinity for binding to IL-6R as well as other properties such as their efficacy and/or potency, and/or their selectivity, in addition to their capacity to partially or totally block the IL-6/IL-6R interaction, and/or inhibit signalization through, IL-6, IL-6R and/or the IL-6/IL-6R complex. These stretches of amino acid residues are also referred to herein as "CDR sequences of the invention" (i.e. as "CDR1 sequences of the invention", "CDR2 sequences of the invention" and "CDR3 sequences of the invention", respectively).

It should however be noted that the invention in its broadest sense is not limited to a specific structural role or function that these stretches of amino acid residues may have in an amino acid sequence of the invention, as long as these stretches of amino acid residues allow the amino acid sequence of the invention to bind to IL-6R. Thus, generally, the invention in its broadest sense provides amino acid sequences that are capable of binding to IL-6R with a certain specified affinity, avidity, efficacy and/or potency in addition to their capacity to partially or totally block the IL-6/IL-6R interaction, and/or inhibit signalization through, IL-6, IL-6R and/or the IL-6/IL-6R complex and that comprises one or more CDR sequences as described herein and, in particular a suitable combination of two or more such CDR sequences, that are suitably linked to each other via one or more further amino acid sequences, such that the entire amino acid sequence forms a binding domain and/or binding unit that is capable of binding to IL-6R. It should however also be noted that the presence of only one such CDR sequence in an amino acid sequence of the invention may by itself already be sufficient to provide the amino acid sequence of the invention the capacity of binding to IL-6R; reference is for example again made to the so-called "Expedite fragments" described in WO 03/050531.

Thus, in a specific, but non-limiting aspect, the amino acid sequence of the invention may comprises at least one stretch of amino acid residues that is chosen from the group consisting of:
the CDR1 sequences:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;
and/or
the CDR2 sequences:
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;
and/or
the CDR3 sequences:
e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same or a higher affinity compared to the amino acid sequence comprising said stretch of amino acid residues without the 2 or 1 amino acid difference, said affinity as measured by surface plasmon resonance.

In particular, an amino acid sequence of the invention may be an amino acid sequence that comprises at least one antigen binding site, wherein said antigen binding site comprises at least one stretch of amino acid residues that is chosen from the group consisting of the CDR1 sequences, CDR2 sequences and CDR3 sequences as described above (or any suitable combination thereof). In a preferred aspect, however, the amino acid sequence of the invention comprises more than one, such as two or more stretches of amino acid residues chosen from the group consisting of the CDR1 sequences of the invention, the CDR2 sequences of the invention and/or the CDR3 sequences of the invention.

Accordingly the present invention also relates to amino acid sequences that comprises two or more stretches of amino acid residues chosen from the following:
the CDR1 sequences
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same or a higher affinity compared to the amino acid sequence comprising said stretch of amino acid residues without the 2 or 1 amino acid difference, said affinity as measured by surface plasmon resonance;
and/or
the CDR2 sequences
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;
and/or
the CDR3 sequences
e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.
such that (i) when the first stretch of amino acid residues corresponds to one of the amino acid sequences according to a), or b), the second stretch of amino acid residues corresponds to one of the amino acid sequences according to c), d), e) or f); (ii) when the first stretch of amino acid residues corresponds to one of the amino acid sequences according to c) or d), the second stretch of amino acid residues corresponds to one of the amino acid sequences according to a), b), e) or f); or (iii) when the first stretch of amino acid residues corresponds to one of the amino acid sequences according to e) or f), the second stretch of amino acid residues corresponds to one of the amino acid sequences according to a), b), c) or d).

In a specific aspect, the present invention also relates to amino acid sequences that comprises three or more stretches of amino acid residues, in which the first stretch of amino acid residues is chosen from the following CDR1 sequences:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

the second stretch of amino acid residues is chosen from the following CDR2 sequences:

c) SEQ ID NO's: 84-91; or d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and the third stretch of amino acid residues is chosen from the following CDR3 sequences:

e) SEQ ID NO's: 93-95; or f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

As described herein, the present invention also encompasses amino acid sequences that comprise one or more stretches of amino acid residues that have no more than 2, preferably no more than 1 amino acid difference with one of the stretches of amino acid residues specified in a), c) and/or e), i.e. with one of the specified CDR1 sequences (i.e. with one of SEQ ID NO's: 80-82), with one of the specified CDR2 sequences (i.e. with one of SEQ ID NO's: 84-91) and/or with one of the specified CDR3 sequences (i.e. with one of SEQ ID NO's: 93-95).

The term "amino acid difference" refers to an insertion, deletion or substitution of a single amino acid residue on a position of the stretch of amino acid residues (or CDR sequence) specified in b), d) or f), compared to the stretch of amino acid residues (or CDR sequence) of respectively a), c) or e); it being understood that the stretch of amino acid residues (or CDR sequence) of b), d) and f) can contain one or maximal two such amino acid differences compared to the stretch of amino acid residues of respectively a), c) or e).

The "amino acid difference" can be any one or maximal two substitutions, deletions or insertions, or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind IL-6R with the same, about the same, or a higher affinity compared to the amino acid sequence comprising the one or more stretches of amino acid residues without the one or maximal two substitutions, deletions or insertions, said affinity as measured by surface plasmon resonance.

For example, and depending on the host organism used to express the amino acid sequence of the invention, such deletions and/or substitutions may be designed in such a way that one or more sites for post-translational modification (such as one or more glycosylation sites) are removed, as will be within the ability of the person skilled in the art.

In a preferred aspect of the invention, the "amino acid difference" is an amino acid substitution. The amino acid substitution may be any one or maximal two substitutions that either improve the properties of the amino acid sequence of the invention or that at least do not detract too much from the desired properties or from the balance or combination of desired properties of the amino acid sequence of the invention. In this respect, the resulting amino acid sequence of the invention should at least bind IL-6R with the same, about the same, or a higher affinity compared to the amino acid sequence comprising the one or more stretches of amino acid residues without the one or maximal two substitutions, said affinity as measured by surface plasmon resonance.

The amino acid substitution in the one or more stretches of amino acid residues may be a conservative amino acid substitution. "Conservative" amino acid substitutions are generally amino acid substitutions in which an amino acid residue is replaced with another amino acid residue of similar chemical structure and which has little or essentially no influence on the function, activity or other biological properties of the resulting amino acid sequence. Such conservative amino acid substitutions are well known in the art, for example from WO 04/037999, GB 3357768-A, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In another aspect of the invention, the amino acid substitutions in the one or more stretches of amino acid residues may provides the amino acid sequence with increased affinity for binding to IL-6R. This may be done by techniques such as random or site-directed mutagenesis and/or other techniques for affinity maturation known per se, such as e.g. described in WO 09/004,065, WO 2009/004066, WO 05/003345, WO 06/023144, EP 527809, EP 397834.

Without being limiting, rules (partly or fully followed) for substitutions of amino acid residues in the CDRs may be as follows (i.e. substitution with amino acids with similar side chain chemistries):

K is substituted by R;
R is substituted by K;
A is substituted by S or T;
S is substituted by A or T;
T is substituted by A or S;
I is substituted by L or V;
L is substituted by I or V;
V is substituted by I or L;
F is substituted by Y;
Y is substituted by F;
N is substituted by D;
D is substituted by N;
Q is substituted by E;
E is substituted by Q;

G is substituted by A;

M is substituted by L;

H, C, W and P are kept constant.

Furthermore, and also without being limiting, the rules (partly or fully followed) for substitutions of amino acid residues in the CDRs may be alternatively as follows for substitutions at positions 27 to 35 and positions 50 to 58 (using Kabat numbering system), wherein for positions 27 to 35:

Original amino acid residue in position 27 (Kabat numbering used) is substituted by F; G; R; S; 2 out of F, G, R, S; 3 out of F, G, R, S; or all of them, preferably all of them;

Original amino acid residue in position 28 (Kabat numbering used) is substituted by A; I; S; T; 2 out of A, I, S, T; 3 out of A, I, S, T; or all of them, preferably all of them;

Original amino acid residue in position 29 (Kabat numbering used) is substituted by F; G; L; S; 2 out of F, G, L, S; 3 out of F, G, L, S; or all of them, preferably all of them;

Original amino acid residue in position 30 (Kabat numbering used) is substituted by D; G; S; T; 2 out of D, G, S, T; 3 out of D, G, S, T; or all of them, preferably all of them;

Original amino acid residue in position 31 (Kabat numbering used) is substituted by D; I; N; S; T; 2 out of D, I, N, S, T; 3 out of D, I, N, S, T; or all of them, preferably all of them;

Original amino acid residue in position 32 (Kabat numbering used) is substituted by D; N; Y; 2 out of D, n, Y; or all of them, preferably all of them;

Original amino acid residue in position 33 (Kabat numbering used) is substituted by A; G; T; V; 2 out of A, G, T, V; 3 out of A, G, T, V; or all of them, preferably all of them;

Original amino acid residue in position 34 (Kabat numbering used) is substituted by I; M; or all of them, preferably all of them;

Original amino acid residue in position 35 (Kabat numbering used) is substituted by A; G; S; 2 out of A, G, S; or all of them, preferably all of them;

and positions 50 to 58 if original amino acid sequence has an amino acid sequence in position 52a (Kabat numbering used), Original amino acid residue in position 50 (Kabat numbering used) is substituted by A; C; G; S; T; 2 out of A, C, G, S, T; 3 out of A, C, G, S, T; 4 out of A, C, G, S, T; or all of them, preferably all of them;

Original amino acid residue in position 51 (Kabat numbering used) is substituted by I;

Original amino acid residue in position 52 (Kabat numbering used) is substituted by N; R; S; T; 2 out of N, R, S, T; 3 out of N, R, S, T; or all of them, preferably all of them;

Original amino acid residue in position 52a (Kabat numbering used) is substituted by R; S; T; W; 2 out of R, S, T, W; 3 out of R, S, T, W; or all of them, preferably all of them;

Original amino acid residue in position 53 (Kabat numbering used) is substituted by D; G; N; S; T; 2 out of D, G, N, S, T; 3 out of D, G, N, S, T; 4 out of D, G, N, S, T; or all of them, preferably all of them;

Original amino acid residue in position 54 (Kabat numbering used) is substituted by D; G; or all of them, preferably all of them;

Original amino acid residue in position 55 (Kabat numbering used) is substituted by D; G; S; 2 out of D, G, S; or all of them, preferably all of them;

Original amino acid residue in position 56 (Kabat numbering used) is substituted by I; N; R; S; T; 2 out of I, N, R, S, T; 3 out of I, N, R, S, T; 4 out of I, N, R, S, T; or all of them, preferably all of them;

Original amino acid residue in position 57 (Kabat numbering used) is substituted by T;

Original amino acid residue in position 58 (Kabat numbering used) is substituted by D; H; N; S; Y; 2 out of D, H, N, S, Y; 3 out of D, H, N, S, Y; 4 out of D, H, N, S, Y; or all of them, preferably all of them;

and wherein for positions 50 to 58 if original amino acid sequence has not an amino acid sequence in position 52a (Kabat numbering used), Original amino acid residue in position 50 (Kabat numbering used) is substituted by A; G; R; S; T; 2 out of A, G, R, S, T; 3 out of A, G, R, S, T; 4 out of A, G, R, S, T; or all of them, preferably all of them;

Original amino acid residue in position 51 (Kabat numbering used) is substituted by I;

Original amino acid residue in position 52 (Kabat numbering used) is substituted by N; S; T; 2 out of N, S, T; or all of them, preferably all of them;

Original amino acid residue in position 53 (Kabat numbering used) is substituted by N; R; S; T; Y; 2 out of N, R, S, T, Y; 3 out of N, R, S, T, Y; 4 out of N, R, S, T, Y; or all of them, preferably all of them;

Original amino acid residue in position 54 (Kabat numbering used) is substituted by D; G; R; S; 2 out of D, G, R, S; 3 out of D, G, R, S; or all of them, preferably all of them;

Original amino acid residue in position 55 (Kabat numbering used) is substituted by G;

Original amino acid residue in position 56 (Kabat numbering used) is substituted by G; N; R; S; T; 2 out of D, N, R, S, T; 3 out of D, N, R, S, T; 4 out of D, N, R, S, T; or all of them, preferably all of them;

Original amino acid residue in position 57 (Kabat numbering used) is substituted by T;

Original amino acid residue in position 58 (Kabat numbering used) is substituted by D; N; T; Y; 2 out of D, N, T, Y; 3 out of D, N, T, Y; or all of them, preferably all of them.

after which one or more of the potentially useful substitutions (or combinations thereof) thus determined can be introduced into said CDR sequence (in any manner known per se, as further described herein) and the resulting amino acid sequence(s) can be tested for affinity for IL-6R, and/or for other desired properties such as the capacity to (partially or preferably totally) block the IL-6/IL-6R interaction and/or inhibit signalization through, IL-6, IL-6R and/or the IL-6/IL-6R complex. In this way, by means of a limited degree of trial and error, other suitable substitutions in the CDRs (or suitable combinations thereof) can be determined by the skilled person based on the disclosure herein.

The amino acid sequence of the invention may be any amino acid sequence that comprises at least one stretch of amino acid residues, in which said stretch of amino acid residues has an amino acid sequence that corresponds to the sequence of at least one of the CDR sequences defined herein. Such an amino acid sequence may or may not comprise an immunoglobulin fold. For example, and without limitation, such an amino acid sequence may be a suitable fragment of an immunoglobulin sequence that comprises at least one such CDR sequence (as defined above), but that is not large enough to form a (complete) immunoglobulin fold (reference is for example again made to the "Expedite fragments" described in WO 03/050531). Alternatively, such an amino acid sequence may be a suitable "protein scaffold" that comprises at least one stretch of amino acid residues that corresponds to a CDR sequence as defined herein for the amino acid sequences of the invention (i.e. as part of its antigen binding site). Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al., 2005, Nat. Biotech., 23: 1257), and binding moieties based on DNA or RNA including but not limited to DNA or RNA aptamers (Ulrich et al., 2006, Comb. Chem. High Throughput Screen 9(8): 619-32).

Again, any amino acid sequence of the invention that comprises one or more of the CDR sequences as defined herein for the amino acid sequences of the invention (i.e. "CDR of the invention") is preferably such that it can specifically bind (as defined herein) to IL-6R, and more in particular such that it can bind to IL-6R with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), that is as defined herein. Any amino acid sequence of the invention that comprises one or more of the CDR sequences as defined herein for the amino acid sequences of the invention is preferably such that it has a cell based potency and a plasma potency as defined herein.

Furthermore, it will also be clear to the skilled person that it may be possible to "graft" one or more of the CDR's defined herein for the amino acid sequences of the invention (i.e. "CDR of the invention") onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054, 297, Nicaise et al. (2004, Protein Science, 13: 1882-1891), Ewert et al. (2004, Methods, 34(2): 184-199), Kettleborough et al. (1991, Protein Eng. 4(7): 773-783), O'Brien and Jones (2003, Methods Mol. Biol. 207: 81-100), Skerra (2000, J. Mol. Recognit. 13: 167-187), and Saerens et al. (2005, J. Mol. Biol. 352(3): 597-607), and the further references cited therein. For example, techniques known per se for grafting mouse or rat CDR's onto human frameworks and scaffolds can be used in an analogous manner to provide chimeric proteins comprising one or more of the CDR sequences defined herein for the amino acid sequences of the invention and one or more human framework regions or sequences.

Thus, in a specific aspect, the invention also encompasses chimeric amino acid sequences comprising at least one CDR sequence chosen from the group consisting of CDR1 sequences of the invention, CDR2 sequences of the invention and CDR3 sequences of the invention (defined herein for the amino acid sequences of the invention). Preferably, such a chimeric amino acid sequences comprise at least one CDR sequence chosen from the group consisting of the CDR1 sequences of the invention (defined herein for the amino acid sequences of the invention), and also at least one CDR sequence chosen from the group consisting of the CDR2 sequences of the invention (defined herein for the amino acid sequences of the invention); or at least one CDR sequence chosen from the group consisting of the CDR1 sequences of the invention (defined herein for the amino acid sequences of the invention) and at least one CDR sequence chosen from the group consisting of the CDR3 sequences of the invention (defined herein for the amino acid sequences of the invention); or such a chimeric polypeptide may comprises at least one CDR sequence chosen from the group consisting of the CDR2 sequences of the invention (defined herein for the amino acid sequences of the invention) and also at least one CDR sequence chosen from the group consisting of the CDR3 sequences of the invention (defined herein for the amino acid sequences of the invention). For example, such a chimeric polypeptide may comprise one CDR sequence chosen from the group consisting of the CDR3 sequences of the invention (defined herein for the amino acid sequences of the invention), one CDR sequence chosen from the group consisting of the CDR1 sequences of the invention (defined herein for the amino acid sequences of the invention) and one CDR sequence chosen from the group consisting of the CDR2 sequences of the invention (defined herein for the amino acid sequences of the invention). The combinations of CDR's that are mentioned herein as being preferred for the amino acid sequences of the invention (see Table A-1) will usually also be preferred for these chimeric polypeptides.

In said chimeric polypeptides, the CDR's may be linked to further amino acid sequences sequences and/or may be linked to each other via amino acid sequences, in which said amino acid sequences are preferably framework sequences or are amino acid sequences that act as framework sequences, or together form a scaffold for presenting the CDR's.

According to one non-limiting embodiment, the chimeric amino acid sequences comprises at least two CDR sequences (defined herein for the amino acid sequences of the invention) linked via at least one framework sequence, in which preferably at least one of the two CDR sequences is a CDR3 sequence, with the other CDR sequence being a CDR1 or CDR2 sequence. According to a preferred, but non-limiting embodiment, the chimeric amino acid sequences comprise at least three CDR sequences of the invention (defined herein for the amino acid sequences of the invention) linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the chimeric amino acid sequences have the structure FR1'-CDR1-FR2'-CDR2-FR3'-CDR3-FR4', in which CDR1, CDR2 and CDR3 are as defined herein for the amino acid sequences of the invention, and FR1', FR2', FR3' and FR4' are framework sequences. FR1', FR2', FR3' and FR4' may in particular be Framework 1, Framework 2, Framework 3 and Framework 4 sequences, respectively, of a human antibody (such as $V_H3$ sequences) and/or parts or fragments of such Framework sequences. It is also possible to use parts or fragments of a chimeric polypeptide with the structure FR1'-CDR1-FR2'-CDR2-FR3'-CDR3-FR4'. Preferably, such parts or fragments are such that they meet the criteria set out for the amino acid sequences of the invention.

In such an amino acid sequence of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from a light chain variable domain (e.g. a $V_L$-sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional V$_H$ sequences that have been camelized (as defined herein).

The framework sequences may preferably be such that the amino acid sequence of the invention is a domain antibody (or an amino acid sequence that is suitable for use as a domain antibody); is a single domain antibody (or an amino acid sequence that is suitable for use as a single domain antibody); is a "dAb" (or an amino acid sequence that is suitable for use as a dAb); or is a Nanobody (including but not limited to V$_{HH}$ sequence). Again, suitable framework sequences will be clear to the skilled person, for example on the basis the standard handbooks and the further disclosure and prior art mentioned herein.

In particular, the framework sequences present in the amino acid sequences of the invention may contain one or more of Hallmark residues (as defined in WO 08/020,079 (Tables A-3 to A-8)), such that the amino acid sequence of the invention is a Nanobody. Some preferred, but non-limiting examples of (suitable combinations of) such framework sequences will become clear from the further disclosure herein (see e.g. Table A-1). Generally, Nanobodies (in particular V$_{HH}$ sequences and (partially) humanized VHH sequences) can in particular be characterized by the presence of one or more "Hallmark residues" in one or more of the framework sequences (as e.g. further described in WO 08/020,079, page 61, line 24 to page 98, line 3).

In a preferred aspect, the amino acid sequence of the invention comprises an immunoglobulin fold or is capable, under suitable conditions to form an immunoglobulin fold. Preferably the amino acid sequence of the invention is an immunoglobulin sequence; and even more preferably the amino acid sequence of the invention has the structure of

FR1-CDR1-FR2-CDR2-FR3-CDR3-FR4

Accordingly, the present invention also relates to an amino acid sequence which essentially consists of 4 framework regions (FR1 to FR4, respectively) and 3 complementarity determining regions (CDR1 to CDR3, respectively), in which:
CDR1 is chosen from the group consisting of:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;
and/or
CDR2 is chosen from the group consisting of:
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;
and/or
CDR3 is chosen from the group consisting of:
e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

In this embodiment, the amino acid sequences comprise at least one CDR sequence chosen from the group consisting of the CDR1 sequences of the invention (defined herein for the amino acid sequences of the invention), the CDR2 sequences of the invention (defined herein for the amino acid sequences of the invention), or the CDR3 sequences of the invention (defined herein for the amino acid sequences of the invention). Preferably the amino acid sequences comprise at least two CDR sequence chosen from the group consisting of the CDR1 sequences of the invention (defined herein for the amino acid sequences of the invention), the CDR2 sequences of the invention (defined herein for the amino acid sequences of the invention), or the CDR3 sequences of the invention (defined herein for the amino acid sequences of the invention), such as at least one CDR sequence chosen from the group consisting of the CDR1 sequences of the invention (defined herein for the amino acid sequences of the invention) and at least one CDR sequence chosen from the group consisting of the CDR2 sequences of the invention (defined herein for the amino acid sequences of the invention); or at least one CDR sequence chosen from the group consisting of the CDR1 sequences of the invention (defined herein for the amino acid sequences of the invention) and at least one CDR sequence chosen from the group consisting of the CDR3 sequences of the invention (defined herein for the amino acid sequences of the invention); or at least one CDR sequence chosen from the group consisting of the CDR2 sequences of the invention (defined herein for the amino acid sequences of the invention) and at least one CDR sequence chosen from the group consisting of the CDR3 sequences of the invention (defined herein for the amino acid sequences of the invention); or such a amino acid sequence may comprises three CDR sequence chosen from the group consisting of the CDR1 sequences of the invention (defined herein for the amino acid sequences of the invention), CDR2 sequences of the invention (defined herein for the amino acid sequences of the invention) and the CDR3 sequences of the invention (defined herein for the amino acid sequences of the invention). The invention thus also relates to an amino acid sequence which essentially consists of 4 framework regions (FR1 to FR4, respectively) and 3 complementarity determining regions (CDR1 to CDR3, respectively), in which:
CDR1 is chosen from the group consisting of:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;
and
CDR2 is chosen from the group consisting of:
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance;

and

CDR3 is chosen from the group consisting of:

e) SEQ ID NO's: 93-95; or f) a stretch of amino acid residues that has no more than 2, preferably no more than 1 amino acid difference with one of SEQ ID NO's: 93-95, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

Preferred combinations of CDR sequences for the amino acid sequences of the invention are shown in Table A-1.

The amino acid sequences of the invention may essentially consists of a heavy chain variable domain sequence that is derived from a conventional four-chain antibody or may essentially consist of a heavy chain variable domain sequence that is derived from heavy chain antibody. The amino acid sequences of the invention may essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody.

For a general description of (single) domain antibodies, reference is also made to the prior art cited above, as well as to EP 0368684. For the term "dAb's", reference is for example made to Ward et al. (1989, Nature 341: 544-6), to Holt et al. (2003, Trends Biotechnol. 21: 484-490); as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention essentially consists of or may be a Nanobody® (as defined herein) or a suitable fragment thereof. [Note: Nanobody®, Nanobodies® and Nanoclone® are registered trademarks of Ablynx N.V.] Such Nanobodies directed against IL-6R will also be referred to herein as "Nanobodies of the invention".

For a general description of Nanobodies, reference is made to the further description below, as well as to the prior art cited herein, such as e.g. described in WO 08/020,079 (page 16).

In a specific aspect, the amino acid sequence or Nanobody of the invention comprises at least SEQ ID NO: 80; or a stretch of amino acid residues that has no more than 2, preferably no more than 1 amino acid difference with SEQ ID NO: 80, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

In another specific aspect, the amino acid sequence or Nanobody of the invention comprises at least a stretch of amino acid residues chosen from SEQ ID NO's: 84, 89 or 91; or a stretch of amino acid residues that has no more than 2, preferably no more than 1 amino acid difference with one of SEQ ID NO's: 84, 89 or 91, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

In yet another specific aspect, the amino acid sequence or Nanobody of the invention comprises at least SEQ ID NO: 84; or a stretch of amino acid residues that has no more than 2, preferably no more than 1 amino acid difference with SEQ ID NO: 84, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

In yet another specific aspect, the amino acid sequence or Nanobody of the invention comprises at least a stretch of amino acid residues chosen from SEQ ID NO's: 93-94; or a stretch of amino acid residues that has no more than 2, preferably no more than 1 amino acid difference with one of SEQ ID NO's: 93-94, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

In yet another specific aspect, the amino acid sequence or Nanobody of the invention comprises at least SEQ ID NO: 93; or a stretch of amino acid residues that has no more than 2, preferably no more than 1 amino acid difference with SEQ ID NO: 93, provided that the amino acid sequence comprising said stretch of amino acid residues binds IL-6R with the same, about the same, or a higher affinity compared to the amino acid sequence comprising said stretch of amino acid residues without the 2 or 1 amino acid difference, said affinity as measured by surface plasmon resonance.

In yet another specific aspect, the amino acid sequence or Nanobody of the invention comprises at least SEQ ID NO: 80; or a stretch of amino acid residues that has no more than 2, preferably no more than 1 amino acid difference with SEQ ID NO: 80; and at least a stretch of amino acid residues chosen from SEQ ID NO's: 84, 89 or 91; or a stretch of amino acid residues that has no more than 2, preferably no more than 1 amino acid difference with one of SEQ ID NO's: 84, 89 or 91, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 80; or a stretch of amino acid residues that has no more than 2, preferably no more than 1 amino acid difference with SEQ ID NO: 80; and at least SEQ ID NO: 84; or a stretch of amino acid residues that has no more than 2, preferably no more than 1 amino acid difference with SEQ ID NO: 84, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 80; or a stretch of amino acid residues that has no more than 2, preferably no more than 1 amino acid difference with SEQ ID NO: 80; and at least a stretch of amino acid residues chosen from SEQ ID NO's: 93-94; or a stretch of amino acid residues that has no more than 2, preferably no more than 1 amino acid difference with one of SEQ ID NO's: 93-94, provided that the amino acid sequence comprising said stretches of amino acid residues binds IL-6R with the same, about the same, or a higher affinity compared to the amino acid sequence comprising said stretches of amino acid residues without the 1 or 2 amino acid difference, said affinity as measured by surface plasmon resonance.

In yet another specific aspect, the amino acid sequence or Nanobody of the invention comprises at least SEQ ID NO: 80; or a stretch of amino acid residues that has no more than 2, preferably no more than 1 amino acid difference with SEQ ID NO: 80; and at least SEQ ID NO: 93; or a stretch of amino acid residues that has no more than 2, preferably no more than 1 amino acid difference with SEQ ID NO: 93, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least a stretch of amino acid residues chosen from SEQ ID NO's: 84, 89, or 91; or a stretch of amino acid residues that has no more than 2, preferably no more than 1 amino acid difference with one of SEQ ID NO's: 84, 89, or 91; and at least a stretch of amino acid residues chosen from SEQ ID NO's: 93-94; or a stretch of amino acid residues that has no more than 2, preferably no more than 1 amino acid difference with one of SEQ ID NO's: 93-94, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least a stretch of amino acid residues chosen from SEQ ID NO's: 84, 89, or 91; or a stretch of amino acid residues that has no more than 2, preferably no more than 1 amino acid difference with one of SEQ ID NO's: 84, 89, or 91; and at least SEQ ID NO: 93; or a stretch of amino acid residues that has no more than 2, preferably no more than 1 amino acid difference with SEQ ID NO: 93, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 84; or a stretch of amino acid residues that has no more than 2, preferably no more than 1 amino acid difference with SEQ ID NO: 84; and at least a stretch of amino acid residues chosen from SEQ ID NO's: 93-94; or a stretch of amino acid residues that has no more than 2, preferably no more than 1 amino acid difference with one of SEQ ID NO's: 93-94, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 84; or a stretch of amino acid residues that has no more than 2, preferably no more than 1 amino acid difference with SEQ ID NO: 84; and at least SEQ ID NO: 93; or a stretch of amino acid residues that has no more than 2, preferably no more than 1 amino acid difference with SEQ ID NO: 93, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 80 and SEQ ID NO: 84.

In yet another specific aspect, the amino acid sequence or Nanobody of the invention comprises at least SEQ ID NO: 80 and SEQ ID NO: 93.

In yet another specific aspect, the amino acid sequence or Nanobody of the invention comprises at least SEQ ID NO: 84 and SEQ ID NO: 93.

In yet another specific aspect, the amino acid sequence or Nanobody of the invention comprises at least SEQ ID NO: 80; or a stretch of amino acid residues that has no more than 2, preferably no more than 1 amino acid difference with SEQ ID NO: 80; and at least a stretch of amino acid residues chosen from SEQ ID NO's: 84, 89, or 91; or a stretch of amino acid residues that has no more than 2, preferably no more than 1 amino acid difference with one of SEQ ID NO's: 84, 89, or 91; and at least a stretch of amino acid residues chosen from SEQ ID NO's: 93-94; or a stretch of amino acid residues that has no more than 2, preferably no more than 1 amino acid difference with one of SEQ ID NO's: 93-94, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 80; or a stretch of amino acid residues that has no more than 2, preferably no more than 1 amino acid difference with SEQ ID NO: 80; and at least a stretch of amino acid residues chosen from SEQ ID NO's: 84, 89, or 91; or a stretch of amino acid residues that has no more than 2, preferably no more than 1 amino acid difference with one of SEQ ID NO's: 84, 89, or 91; and at least SEQ ID NO: 93; or a stretch of amino acid residues that has no more than 2, preferably no more than 1 amino acid difference with SEQ ID NO: 93, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 80; or a stretch of amino acid residues that has no more than 2, preferably no more than 1 amino acid difference with SEQ ID NO: 80; and at least SEQ ID NO: 84; or a stretch of amino acid residues that has no more than 2, preferably no more than 1 amino acid difference with SEQ ID NO: 84; and at least a stretch of amino acid residues chosen from SEQ ID NO's: 93-94; or a stretch of amino acid residues that has no more than 2, preferably no more than 1 amino acid difference with one of SEQ ID NO's: 93-94, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 80; or a stretch of amino acid residues that has no more than 2, preferably no more than 1 amino acid difference with SEQ ID NO: 80; and at least SEQ ID NO: 84; or a stretch of amino acid residues that has no more than 2, preferably no more than 1 amino acid difference with SEQ ID NO: 84; and at least SEQ ID NO: 93; or a stretch of amino acid residues that has no more than 2, preferably no more than 1 amino acid difference with SEQ ID NO: 93, provided that the amino acid sequence comprising said stretches of amino acid residues binds IL-6R with the same, about the same, or a higher affinity compared to the amino acid sequence comprising said stretches of amino acid residues without the 2 or 1 amino acid difference, said affinity as measured by surface plasmon resonance.

In yet another specific aspect, the amino acid sequence or Nanobody of the invention comprises at least SEQ ID NO: 80, SEQ ID NO: 84 and SEQ ID NO: 93.

Preferred combinations of CDR1, CDR2, and CDR3 sequences defined herein for the amino acid sequences of the invention are also shown in Table A-1.

In a preferred aspect, amino acid sequences of the invention are selected from the group consisting of:
a) SEQ ID NO's: 60-69;
b) an amino acid sequence that has no more than 2, preferably no more than 1 amino acid difference in one, two or all of its CDR sequences with one of SEQ ID NO's: 60-69, provided that the amino acid sequence with no more than 2, preferably no more than 1 amino acid difference in one, two or all of its CDR sequences binds IL-6R with the same, about the same, or a higher affinity compared to the binding by the one of SEQ ID NO's: 60-69, said affinity as measured by surface plasmon resonance; and
c) a sequence that has no more than 2, preferably no more than 1 amino acid difference with one of SEQ ID NO's: 60-69, provided that the amino acid sequence with no more than 2, preferably no more than 1 amino acid difference with one of SEQ ID NO's: 60-69 binds IL-6R with the same, about the same, or a higher affinity compared to the binding by the one of SEQ ID NO's: 60-69, said affinity as measured by surface plasmon resonance.

In another preferred aspect, the amino acid sequences of the invention are selected from the group consisting of:
a) SEQ ID NO's: 65-69;
b) an amino acid sequence that has no more than 2, preferably no more than 1 amino acid difference in one, two or all of its CDR sequences with one of SEQ ID NO's: 65-69, provided that the amino acid sequence with no more than 2, preferably no more than 1 amino acid difference in one, two or all of its CDR sequences binds IL-6R with the same, about the same, or a higher affinity compared to the binding by the one of SEQ ID NO's: 65-69, said affinity as measured by surface plasmon resonance; and
c) a sequence that has no more than 2, preferably no more than 1 amino acid difference with one of SEQ ID NO's: 65-69, provided that the amino acid sequence with no more than 2, preferably no more than 1 amino acid difference with one of SEQ ID NO's: 65-69 binds IL-6R with the same, about the same, or a higher affinity compared to the binding by the one of SEQ ID NO's: 65-69, said affinity as measured by surface plasmon resonance.

In yet another preferred aspect, the amino acid sequences of the invention are selected from the group consisting of:
a) SEQ ID NO: 66;
b) an amino acid sequence that has no more than 2, preferably no more than 1 amino acid difference in one, two or all of its CDR sequences with SEQ ID NO: 66, provided that the amino acid sequence with no more than 2, preferably no more than 1 amino acid difference in one, two or all of its CDR sequences binds IL-6R with the same, about the same, or a higher affinity compared to the binding by SEQ ID NO: 66, said affinity as measured by surface plasmon resonance; and
c) a sequence that has no more than 2, preferably no more than 1 amino acid difference with SEQ ID NO: 66, provided that the amino acid sequence with no more than 2, preferably no more than 1 amino acid difference binds IL-6R with the same, about the same, or a higher affinity compared to the binding by SEQ ID NO: 66, said affinity as measured by surface plasmon resonance.

When comparing two stretches of amino acid residues (or two CDR sequences), the term "amino acid difference in one, two or all of its CDRs" refers to an insertion, deletion or substitution of a single amino acid residue on a position of a stretch of amino acid residues (or CDR sequence) comprised in the amino acid sequence of the invention specified in b), compared to the stretch of amino acid residues (or CDR sequence) comprised in the amino acid sequence of the invention specified in a); it being understood that two stretches of amino acid residues (or CDR sequences) can contain one or maximal two such amino acid differences.

By "amino acid difference in one, two or all of its CDRs" is meant that amino acid sequence of the invention may have no more than 2, preferably no more than 1 amino acid difference in its CDR1 and/or no more than 2, preferably no more than 1 amino acid difference in its CDR2, and/or no more than 2, preferably no more than 1 amino acid difference in its CDR3 compared to CDR1, CDR2 and/or CDR3 in one of the amino acid sequences of a) (i.e. one of SEQ ID NO's: 60-69); such as no more than 2, preferably no more than 1 amino acid difference in its CDR1 compared to the CDR1 in one of the amino acid sequences of a) (i.e. one of SEQ ID NO's: 60-69); or no more than 2, preferably no more than 1 amino acid difference in its CDR2 compared to the CDR2 in one of the amino acid sequences of a) (i.e. one of SEQ ID NO's: 60-69); or no more than 2, preferably no more than 1 amino acid difference in its CDR3 compared to the CDR3 in one of the amino acid sequences of a) (i.e. one of SEQ ID NO's: 60-69); or no more than 2, preferably no more than 1 amino acid difference in its CDR1 compared to the CDR1 in one of the amino acid sequences of a) (i.e. one of SEQ ID NO's: 60-69) and no more than 2, preferably no more than 1 amino acid difference in its CDR2 compared to the CDR2 in one of the amino acid sequences of a) (i.e. one of SEQ ID NO's: 60-69); or no more than 2, preferably no more than 1 amino acid difference in its CDR1 compared to the CDR1 in one of the amino acid sequences of a) (i.e. one of SEQ ID NO's: 60-69) and no more than 2, preferably no more than 1 amino acid difference in its CDR3 compared to the CDR3 in one of SEQ ID NO's: 60-69; or no more than 2, preferably no more than 1 amino acid difference in its CDR2 compared to the CDR2 in one of the amino acid sequences of a) (i.e. one of SEQ ID NO's: 60-69) and no more than 2, preferably no more than 1 amino acid difference in its CDR3 compared to the CDR3 in one of the amino acid sequences of a) (i.e. one of SEQ ID NO's: 60-69); or no more than 2, preferably no more than 1 amino acid difference in its CDR1 compared to the CDR1 in one of the amino acid sequences of a) (i.e. one of SEQ ID NO's: 60-69), no more than 2, preferably no more than 1 amino acid difference in its CDR2 compared to the CDR2 in one of the amino acid sequences of a) (i.e. one of SEQ ID NO's: 60-69) and no more than 2, preferably no more than 1 amino acid difference in its CDR3 compared to the CDR3 in one of the amino acid sequences of a) (i.e. one of SEQ ID NO's: 60-69).

The "amino acid difference in one, two or all of its CDRs" can be any one or maximal two substitutions, deletions or insertions in one or more of the CDRs, or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind IL-6R with the same, about the same or a higher affinity compared to the amino acid sequence comprising the one or more stretch of amino acid residues without the one or maximal two substitutions, deletions or insertions, said affinity as measured by surface plasmon resonance. The resulting amino acid sequences are preferably such that they can bind to the specific epitope on the IL-6 receptor, with affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. The resulting amino acid sequences also preferably have a cell based potency and a plasma potency as defined herein.

In one aspect of the invention, the "amino acid difference in one, two or all of its CDRs" is an amino acid substitution. The amino acid substitution may be any one or maximal two substitutions in one or more of the CDRs that either improve the properties of the amino acid sequence of the invention or that at least do not detract too much from the desired properties or from the balance or combination of desired properties of the amino acid sequence of the invention. In this respect, the resulting amino acid sequence of the invention should at least bind IL-6R with the same, about the same or a higher affinity compared to the amino acid sequence comprising the one or more stretches of amino acid residues without the one or maximal two substitutions, said affinity as measured by surface plasmon resonance. The resulting amino acid sequence are preferably such that they can bind to the specific epitope on the IL-6 receptor, with affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. The resulting amino acid sequences also preferably have a cell based potency and a plasma potency as defined herein.

As discussed above, the amino acid substitution in the CDRs may be any possible substitution such as a "conservative substitution" (as defined herein), it may be driven by certain rules (as defined herein), and/or it may induce improved properties to the resulting amino acid sequences.

The invention also relates to an amino acid sequence that has no more than 2, preferably no more than 1 amino acid difference with one of (the full sequence of) SEQ ID NO's: 60-69.

When comparing two amino acid sequences, the term "amino acid difference" refers to an insertion, deletion or substitution of a single amino acid residue on a position of the first amino acid sequence, compared to the second amino acid sequence; it being understood that two amino acid sequences can contain one or maximal two such amino acid differences.

The "amino acid difference" can be any one or maximal any two substitutions, deletions or insertions in the amino acid sequence, i.e. in one or more of the framework regions or in one or more of the CDRs, or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind IL-6R with the same, about the same, or a higher affinity compared to the amino acid sequence without the one or maximal two substitutions, deletions or insertions, said affinity as measured by surface plasmon resonance. The resulting amino acid sequences are preferably such that they can bind to the specific epitope on the IL-6 receptor, with affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. The resulting amino acid sequences also preferably have a cell based potency and a plasma potency as defined herein. The skilled person will generally be able to determine and select suitable substitutions, deletions or insertions, or suitable combinations thereof, and determining their influence on the properties of the amino acid sequence thus obtained.

In one aspect of the invention, the "amino acid difference" is an amino acid substitution. The amino acid substitution may be any one or maximal two substitutions in one or more of the framework regions or in one or more of the CDRs, or any combination thereof, that either improve the properties of the amino acid sequence of the invention or that at least do not detract too much from the desired properties or from the balance or combination of desired properties of the amino acid sequence of the invention. In this respect, the resulting amino acid sequence of the invention should at least bind IL-6R with the same, about the same, or a higher affinity compared to the amino acid sequence without the one or maximal two substitutions, said affinity as measured by surface plasmon resonance. The resulting amino acid sequences are preferably such that they can bind to the specific epitope on the IL-6 receptor, with affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. The resulting amino acid sequences also preferably have a cell based potency and a plasma potency as defined herein. The skilled person will generally be able to determine and select suitable substitutions, and determining their influence on the properties of the amino acid sequences thus obtained.

As indicated above, the substitutions, insertions or deletions can be in one or more of the framework regions and/or in one or more of the CDR's. As discussed above, the amino acid substitution in one or more of the CDRs can be any substitution such as a "conservative substitution" (as defined herein), it may be driven by certain rules (as defined herein), and/or it may induce improved properties to the resulting amino acid sequences.

When such substitutions, insertions or deletions are made in one or more of the framework regions, they may be made at one or more of the Hallmark residues (as e.g. defined in WO 08/020,079; Tables A-3 to A-8) and/or at one or more of the other positions in the framework residues, although substitutions, insertions or deletions at the Hallmark residues are generally less preferred (unless these are suitable humanizing substitutions as described herein). By means of non-limiting examples, a substitution may for example be a conservative substitution (as described herein) and/or an amino acid residue may be replaced by another amino acid residue that naturally occurs at the same position in another $V_{HH}$ domain (see WO 08/020,079, Tables A-5 to A-8), although the invention is generally not limited thereto.

Substitutions, insertions or deletions made (preferably) in one or more of the framework regions may be substitutions for sequence optimization of the framework regions such as e.g. humanizing substitution. Some preferred, but non-limiting humanizing substitutions (and suitable combinations thereof) will become clear to the skilled person based on the disclosure herein. Potentially useful humanizing substitutions can be ascertained by comparing the sequence of the framework regions of one of the amino acid sequence of the invention defined in a) with the corresponding framework sequence of one or more closely related human $V_H$ sequences, after which one or more of the potentially useful humanizing substitutions (or combinations thereof) thus determined can be introduced into said amino acid sequence of the invention defined in a) (in any manner known per se, as further described herein) and the resulting humanized amino acid sequence can be tested for affinity for IL-6R, for stability, for ease and level of expression, and/or for other desired properties defined herein. In this way, by means of a limited degree of trial and error, other suitable humanizing substitutions (or suitable combinations thereof) can be determined by the skilled person based on the disclosure herein.

Depending on the host organism used to express the amino acid sequence, Nanobody or polypeptide of the invention, such deletions and/or substitutions may also be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables A-5-A-8 of WO 08/020,079, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions.

The resulting amino acid sequences of the invention or Nanobodies of the invention should preferably bind to IL-6R with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:
  bind to hIL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;
and/or such that they:
  bind to cyno IL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;
and/or such that they:
  bind to hIL-6R with a $k_{on}$-rate of between $10^4$ $M^{-1}$ $s^{-1}$ to about $10^7$ $M^{-1}$ $s^{-1}$ preferably between $10^5$ $M^{-1}$ $s^{-1}$ and $10^7$ $M^{-1}$ $s^{-1}$, more preferably about $10^6$ $M^{-1}$ $s^{-1}$ or more;
and/or such that they:
  bind to cyno IL-6R with a $k_{on}$-rate of between $10^4$ $M^{-1}$ $s^{-1}$ to about $10^7$ $M^{-1}$ $s^{-1}$ preferably between $10^5$ $M^{-1}$ $s^{-1}$ and $10^7$ $M^{-1}$ $s^{-1}$, more preferably about $10^6$ $M^{-1}$ $s^{-1}$ or more;
and/or such that they:
  bind to hIL-6R with a $k_{off}$ rate between $10^{-3}$ $s^{-1}$ ($t_{1/2}$=0.69 s) and $10^{-6}$ $s^{-1}$ (providing a near irreversible complex with a $t_{1/2}$ of multiple days), preferably between $10^{-4}$ $s^{-1}$ and $10^{-6}$ $s^{-1}$, more preferably between $10^{-5}$ $s^{-1}$ and $10^{-6}$ $s^{-1}$, such as about $10^{-5}$ $s^{-1}$ or lower;
and/or such that they:
  bind to cyno IL-6R with a $k_{off}$ rate between $10^{-3}$ $s^{-1}$ ($t_{1/2}$=0.69 s) and $10^{-6}$ $s^{-1}$ (providing a near irreversible complex with a $t_{1/2}$ of multiple days), preferably between $10^{-4}$ $s^{-1}$ and $10^{-6}$ $s^{-1}$, more preferably between $10^{-5}$ $s^{-1}$ and $10^{-6}$ $s^{-1}$, such as about $10^{-5}$ $s^{-1}$ or lower.

Some preferred IC50 values for binding of the amino acid sequences of the invention to IL-6R will become clear from the further description and examples herein.

The potency and/or efficacy of the amino acid sequences and Nanobodies of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include proliferation assays using IL-6-dependent cell lines including TF-1, XG1 and 7TD1, collagen induced arthritis model, transplant model of synovial tissue in SCID mice, xenograft models of various human cancers, including lymphoma, myeloma, prostate cancer and renal cell carcinoma, IBD models including TNBS, primate models (such as e.g. described in Shinkura et al., 1998, Anticancer Research 18: 1217-1222), non-human primate models of arthritic disease (as e.g described in Vierboom et al., 2008, Drug Discov. Today: Dis Model doi:10.1016/j.ddmod. 2008.06.003) as well as the assays and animal models used in the experimental part below and in the prior art cited herein (Peake et al., 2006, Rheumatology 45: 1485-9; Wahid et al., 2000, Clin. Exp. Immunol., 122: 133-142; Matsuno et al., 1998, Arthritis and rheumatism 41: 2014-2021; WO 08/020,079).

For example, in the TF-1 assay as described by Kitamura et al. (1989, J. Cell Physiol. 140: 323), the amino acid sequences of the invention or Nanobodies of the invention may have IC50 values (at 100 IU/mL IL-6) between 10 nM and 50 pM, preferably between 5 nM and 50 pM, more preferably between 1 nM and 50 pM or less, such as about 750 or 500 pM or less. In this TF-1 assay the amino acid sequences of the invention or Nanobodies of the invention may have IC50 values (at 5000 IU/mL IL-6) between 50 nM and 1 nM, preferably between 25 nM and 1 nM, more preferably between 10 nM and 1 nM or less, such as about 8 nM or less. In this TF-1 assay, the amino acid sequences of the invention or Nanobodies of the invention may have IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4 (see Example 1). In this TF-1 assay, the amino acid sequences of the invention or Nanobodies of the invention may have IC50 values that are at least the same and preferably better, at least two times, preferably three times, more preferably four times, even more preferably 5 times, 7 times or more than 7 times better compared to the IC50 value obtained for Tocilizumab (MRA).

In a plasma potency assay at EC50 values of IL-6 (e.g. in the presence of 27.29 ng/mL IL-6 as described in Example 45), the amino acid sequences of the invention or Nanobodies of the invention may have IC50 values between 500 pM and 50 pM, preferably between 250 pM and 50 pM, more preferably between 200 pM and 50 pM or less, such as 150 pM or less. In a plasma potency assay at EC95 values of IL-6 (e.g. in the presence of 885 ng/mL IL-6 as described in Example 45) the amino acid sequences of the invention or Nanobodies of the invention may have IC50 values between 1000 pM and 100 pM, preferably between 750 pM and 100 pM, more preferably between 500 pM and 100 pM or less, such as 400 pM or less. In this plasma potency assay, the amino acid sequences of the invention or Nanobodies of the invention may have IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4 (see Example 1). In this plasma potency assay, the amino acid sequences of the invention or Nanobodies of the invention may have IC50 values that are at least the same and preferably better, at least two times, preferably three times, more preferably four times, even more preferably 5 times, 7 times or more than 7 times better compared to the IC50 value obtained for Tocilizumab (MRA).

In an assay for defining binding to membrane IL-6R on CHO cells, the amino acid sequences of the invention or Nanobodies of the invention may have IC50 values between 10 nM and 100 pM, preferably between 5 nM and 100 pM, more preferably between 2 nM and 10 pM or less, such as 2 nM or less.

As will also be clear from the disclosure herein, it is also within the scope of the invention to use parts or fragments, or combinations of two or more parts or fragments, of the amino acid sequences or Nanobodies of the invention as defined herein, and in particular parts or fragments of the amino acid sequences of SEQ ID NO's: 60-69. Thus, according to one embodiment of the invention, the term "amino acid sequence of the invention" or "Nanobody of the invention" in its broadest sense also covers such parts or fragments.

Generally, such parts or fragments of the amino acid sequences or Nanobodies of the invention (including analogs thereof) have amino acid sequences in which, compared to the amino acid sequence of the corresponding full length amino acid sequence or Nanobody of the invention, one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to the specific epitope on the IL-6 receptor, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In particular, amino acid sequences, Nanobodies, and parts or fragments are preferably such that they:
bind to hIL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;

and/or such that they:
bind to cyno IL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;

and/or such that they:
bind to hIL-6R with a $k_{on}$-rate of between $10^4$ M$^{-1}$ s$^{-1}$, to about $10^7$ M$^{-1}$ s$^{-1}$, preferably between $10^5$ M$^{-1}$ s$^{-1}$ and $10^7$ M$^{-1}$ s$^{-1}$, more preferably about $10^6$ M$^{-1}$ s$^{-1}$ or more;

and/or such that they:
bind to cyno IL-6R with a $k_{on}$-rate of between $10^4$ M$^{-1}$ s$^{-1}$ to about $10^7$ M$^{-1}$ s$^{-1}$, preferably between $10^5$ M$^{-1}$ s$^{-1}$ and $10^7$ M$^{-1}$ s$^{-1}$, more preferably about $10^6$ M$^{-1}$ s$^{-1}$ or more;

and/or such that they:
bind to hIL-6R with a $k_{off}$-rate between $10^{-3}$ s$^{-1}$ ($t_{1/2}$=0.69 s) and $10^{-6}$ s$^{-1}$ (providing a near irreversible complex with a $t_{1/2}$ of multiple days), preferably between $10^{-4}$ s$^{-1}$ and $10^{-6}$ s$^{-1}$, more preferably between $10^{-5}$ s$^{-1}$ and $10^{-6}$ s$^{-1}$, such as about $10^{-5}$ s$^{-1}$ or lower;

and/or such that they:
bind to cyno IL-6R with a $k_{off}$ rate between $10^{-3}$ s$^{-1}$ ($t_{1/2}$=0.69 s) and $10^{-6}$ s$^{-1}$ (providing a near irreversible complex with a $t_{1/2}$ of multiple days), preferably between $10^{-4}$ s$^{-1}$ and $10^{-6}$ s$^{-1}$, more preferably between $10^{-6}$ s$^{-1}$ and $10^{-6}$ s$^{-1}$, such as about $10^{-6}$ s$^{-1}$ or lower.

The affinity of the parts or fragments against the IL-6 receptor, can be determined in a manner known per se, for example using the assay described herein.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length amino acid sequence or Nanobody of the invention.

Also, any part or fragment is such preferably that it comprises at least one of CDR1, CDR2 and/or CDR3 or at least part thereof (and in particular at least CDR3 or at least part thereof). More preferably, any part or fragment is such that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting embodiment, such a part or fragment comprises at least CDR3, such as FR3, CDR3 and FR4 of the corresponding full length Nanobody of the invention, i.e. as for example described in the International application WO 03/050531 (Lasters et al.).

As already mentioned above, it is also possible to combine two or more of such parts or fragments (i.e. from the same or different amino acid sequences or Nanobodies of the invention), i.e. to provide further parts or fragments (as defined herein) of an amino acid sequence or a Nanobody of the invention. It is for example also possible to combine one or more parts or fragments of an amino acid sequence or a Nanobody of the invention with one or more parts or fragments of a human $V_H$ domain.

According to one preferred embodiment, the parts or fragments have a degree of sequence identity of at least 50%, preferably at least 60%, more preferably at least 70%, even more preferably at least 80%, such as at least 90%, 95% or 99% or more with one of the amino acid sequences or Nanobodies of SEQ ID NO's: 60-69.

The parts and fragments, and nucleic acid sequences encoding the same, can be provided and optionally combined in any manner known per se. For example, such parts or fragments can be obtained by inserting a stop codon in a nucleic acid that encodes a full-sized amino acid sequence or Nanobody of the invention, and then expressing the nucleic acid thus obtained in a manner known per se (e.g. as described herein). Alternatively, nucleic acids encoding such parts or fragments can be obtained by suitably restricting a nucleic acid that encodes a full-sized amino acid sequence or Nanobody of the invention or by synthesizing such a nucleic acid in a manner known per se. Parts or fragments may also be provided using techniques for peptide synthesis known per se.

The invention further relates to compounds or constructs, that comprise or essentially consist of one or more amino acid sequences or Nanobodies of the invention, and optionally further comprise one or more other groups, residues, moieties or binding units, optionally linked via one or more linkers. In a preferred aspect said one or more other groups, residues, moieties or binding units are amino acid sequences. In another preferred aspect, said one or more linkers are one or more amino acid sequences. Such compounds or constructs are also referred to as "polypeptides of the invention".

A polypeptide of the invention may comprise an amino acid sequence or Nanobody of the invention, which is fused at its amino terminal end, at its carboxy terminal end, or both at its amino terminal end and at its carboxy terminal end to at least one further amino acid sequence, i.e. so as to provide a fusion protein comprising said amino acid sequence or Nanobody of the invention and the one or more further amino acid sequence.

The one or more further amino acid sequence may be any suitable and/or desired amino acid sequence. The further amino acid sequence may or may not change, alter or otherwise influence the (biological) properties of the amino acid sequence or Nanobody of the invention, and may or may not add further functionality to the amino acid sequence, Nanobody or the polypeptide of the invention. Preferably, the further amino acid sequence is such that it confers one or more desired properties or functionalities to the amino acid sequence, Nanobody or the polypeptide of the invention.

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the amino acid sequence or Nanobody of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

The further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the amino acid sequence or Nanobody of the invention is directed, or a different protein, polypeptide, antigen, antigenic determinant or epitope). For example, the further amino acid sequence may provide a second binding site that is directed against a serum protein (such as, for example, human serum albumin or another serum protein such as IgG), so as to provide increased half-life in serum. Such amino acid sequences for example include Nanobodies, as well as the small peptides and binding proteins described in WO 91/01743, WO 01/45746 and WO 02/076489 and the dAb's described in WO 03/002609 and WO 04/003019. Reference is also made to Harmsen et al. (2005, Vaccine, 23 (41): 4926-42), as well as to EP 0368684, as well as to WO 08/028,977, WO 08/043,821, WO 08/043,822 and WO 08/068,280 of Ablynx N.V.

Preferred amino acid sequences that may provide the amino acid sequences or Nanobodies of the invention with increased half-life may be chosen from SEQ ID NO's: 97-99.

Such amino acid sequences may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see for example WO 06/0122787) and/or amino acid sequences that are capable of binding to amino acid residues on serum albumin that do not form part of domain III of serum albumin (see again for example WO 06/0122787); amino acid sequences that have or can provide an increased half-life (see for example WO 08/028,977); amino acid sequences against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*), reference is again made to WO 08/028,977); amino acid sequences that can bind to serum albumin in a pH independent manner (see for example WO 08/043,821) and/or amino acid sequences that are conditional binders (see for example WO 08/043, 822).

According to another embodiment, the one or more further amino acid sequences may comprise one or more parts, fragments or domains of conventional 4-chain antibodies (and in particular human antibodies) and/or of heavy chain antibodies. For example, although usually less preferred, an amino acid sequence or Nanobody of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

Accordingly, in the compound or construct of the invention, said one or more other groups, residues, moieties or binding units may be chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

In one specific aspect of the invention, the compound, construct or polypeptide of the invention comprising at least one amino acid sequence or Nanobody of the invention may have an increased half-life, compared to the corresponding amino acid sequence or Nanobody of the invention. Some preferred, but non-limiting examples of such compounds, constructs and polypeptides will become clear to the skilled person based on the further disclosure herein, and may be for example compounds, constructs and polypeptides that comprise amino acid sequences, Nanobodies or polypeptides of the invention that have been chemically modified to increase the half-life thereof (for example, by means of pegylation); or polypeptides of the invention that comprise at least one amino acid sequence or Nanobody of the invention that is linked to at least one moiety (and in particular at least one amino acid sequence) that increases the half-life of the Nanobody of the invention. Examples of compounds, constructs or polypeptides of the invention that comprise such half-life extending moieties or amino acid sequences will become clear to the skilled person based on the further disclosure herein; and for example include, without limitation, polypeptides in which the one or more amino acid sequences or Nanobodies of the invention are suitable linked to one or more serum proteins or fragments thereof (such as serum albumin or suitable fragments thereof) or to one or more binding units that can bind to serum proteins (such as, for example, Nanobodies or (single) domain antibodies that can bind to serum proteins such as serum albumin, serum immunoglobulins such as IgG, or transferrine); polypeptides in which an amino acid sequence or Nanobody of the invention is linked to an Fc portion (such as a human Fc) or a suitable part or fragment thereof; or polypeptides in which the one or more amino acid sequences or Nanobodies of the invention are suitable linked to one or more small proteins or peptides that can bind to serum proteins (such as, without limitation, the proteins and peptides described in WO 91/01743, WO 01/45746, WO 02/076489).

The at least one amino acid sequence or Nanobody may also be linked to one or more (preferably human) $C_H1$, $C_H2$ and/or $C_H3$ domains, optionally via a linker sequence. For instance, an amino acid sequence or Nanobody linked to a suitable $C_H1$ domain could for example be used—together with suitable light chains—to generate antibody fragments/structures analogous to conventional Fab fragments or F(ab')$_2$ fragments, but in which one or (in case of an F(ab')$_2$ fragment) both of the conventional $V_H$ domains have been replaced by an amino acid sequence or Nanobody of the invention. Also, two amino acid sequences or Nanobodies could be linked to a $C_H3$ domain (optionally via a linker) to provide a construct with increased half-life in vivo.

According to one specific aspect of a polypeptide of the invention, one or more amino acid sequences or Nanobodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the amino acid sequences or Nanobodies of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to WO 09/068,628). Coupling of an amino acid sequence or Nanobody of the invention to an Fc portion may also lead to an increased half-life, compared to the corresponding amino acid sequence or Nanobody of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more amino acid sequences or Nanobodies and one or more constant domains with increased half-life in vivo will be clear to the skilled person, and may for example comprise two amino acid sequences or Nanobodies linked to a $C_H3$ domain, optionally via a linker sequence. Generally, any fusion protein or derivatives with increased half-life will preferably have a molecular weight of more than 50 kD, the cut-off value for renal absorption.

In another specific, but non-limiting, aspect, in order to form a polypeptide of the invention, one or more amino acid sequences of the invention may be linked (optionally via a suitable linker or hinge region) to naturally occurring, synthetic or semisynthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al. (1996, J. Biol. Chem. 271: 7494), describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Generally, the amino acid sequences or Nanobodies of the invention (or compounds, constructs or polypeptides comprising the same) with increased half-life preferably have a half-life that is at least 1.5 times, preferably at least 2 times, such as at least 5 times, for example at least 10 times or more than 20 times, greater than the half-life of the corresponding amino acid sequence or Nanobody of the invention per se. For example, the amino acid sequences, Nanobodies, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence or Nanobody of the invention per se.

In a preferred, but non-limiting aspect of the invention, such amino acid sequences, Nanobodies, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), at preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

The further amino acid sequence may also form a signal sequence or leader sequence that directs secretion of the amino acid sequence, Nanobody or the polypeptide of the invention from a host cell upon synthesis (for example to provide a pre-, pro- or prepro-form of the polypeptide of the invention, depending on the host cell used to express the polypeptide of the invention).

The further amino acid sequence may also form a sequence or signal that allows the amino acid sequence, Nanobody or polypeptide of the invention to be directed towards and/or to penetrate or enter into specific organs, tissues, cells, or parts or compartments of cells, and/or that allows the amino acid sequence, Nanobody or polypeptide of the invention to penetrate or cross a biological barrier such as a cell membrane, a cell layer such as a layer of epithelial cells, a tumor including solid tumors, or the blood-brain-barrier. Suitable examples of such amino acid sequences will be clear to the skilled person, and for example include, but are not limited to, the "Peptrans" vectors mentioned above, the sequences described by Cardinale et al. and the amino acid sequences and antibody fragments known per se that can be used to express or produce the Nanobodies and polypeptides of the invention as so-called "intrabodies", for example as described in WO 94/02610, WO 95/22618, U.S. Pat. No. 7,004,940, WO 03/014960, WO 99/07414; WO 05/01690; EP 1512696; and in Cattaneo A. and Biocca S. (1997, Intracellular Antibodies: Development and Applications. Landes and Springer-Verlag) and in Kontermann, (2004, Methods 34: 163-170, and the further references described therein.

According to one preferred, but non-limiting embodiment, the amino acid sequence or Nanobody of the invention comprises at least one further amino acid sequence or Nanobody, so as to provide a polypeptide of the invention that comprises at least two, such as two, three, four, five or more amino acid sequences or Nanobodies, in which said amino acid sequences or Nanobodies may optionally be linked via one or more linker sequences (as defined herein). Polypeptides of the invention that comprise two or more amino acid sequences or Nanobodies, of which at least one is a amino acid sequence or Nanobody of the invention, will also be referred to herein as "multivalent" polypeptides of the invention, and the amino acid sequences or Nanobodies present in such polypeptides will also be referred to herein as being in a "multivalent format". For example a "bivalent" polypeptide of the invention comprises two amino acid sequences and/or Nanobodies, optionally linked via a linker sequence, whereas a "trivalent" polypeptide of the invention comprises three amino acid sequences and/or Nanobodies, optionally linked via two linker sequences; etc.; in which at least one of the amino acid sequences and/or Nanobodies present in the polypeptide, and up to all of the amino acid sequences and/or Nanobodies present in the polypeptide, is/are a amino acid sequence and/or Nanobody of the invention.

In a multivalent polypeptide of the invention, the two or more amino acid sequences or Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical amino acid sequences or Nanobodies; (b) a first amino acid sequence or Nanobody directed against a first antigenic determinant of a protein or antigen and a second amino acid sequence or Nanobody directed against the same antigenic determinant of said protein or antigen which is different from the first amino acid sequence or Nanobody; (c) a first amino acid sequence or Nanobody directed against a first antigenic determinant of a protein or antigen and a second amino acid sequence or Nanobody directed against another antigenic determinant of said protein or antigen; or (d) a first amino acid sequence or Nanobody directed against a first protein or antigen and a second amino acid sequence or Nanobody directed against a second protein or antigen (i.e. different from said first antigen). Similarly, a trivalent polypeptide of the invention may, for example and without being limited thereto. comprise (a) three identical amino acid sequences or Nanobodies; (b) two identical amino acid sequences or Nanobody against a first antigenic determinant of an antigen and a third amino acid sequence or Nanobody directed against a different antigenic determinant of the same antigen; (c) two identical amino acid sequences or Nanobodies against a first antigenic determinant of an antigen and a third amino acid sequence or Nanobody directed against a second antigen different from said first antigen; (d) a first amino acid sequence or Nanobody directed against a first antigenic determinant of a first antigen, a second amino acid sequence or Nanobody directed against a second antigenic determinant of said first antigen and a third amino acid sequence or Nanobody directed against a second antigen different from said first antigen; or (e) a first amino acid sequence or Nanobody directed against a first antigen, a second amino acid sequence or Nanobody directed against a second antigen different from said first antigen, and a third amino acid sequence or Nanobody directed against a third antigen different from said first and second antigen.

Polypeptides of the invention that contain at least two amino acid sequences and/or Nanobodies, in which at least one amino acid sequence or Nanobody is directed against a first antigen (i.e. against the IL-6 receptor) and at least one amino acid sequence or Nanobody is directed against a second antigen (i.e. different from the IL-6 receptor), will also be referred to as "multispecific" polypeptides of the invention, and the amino acid sequences or Nanobodies present in such polypeptides will also be referred to herein as being in a "multispecific format". Thus, for example, a "bispecific" polypeptide of the invention is a polypeptide that comprises at least one amino acid sequence or Nanobody directed against a first antigen (i.e. the IL-6 receptor) and at least one further amino acid sequence or Nanobody directed against a second antigen (i.e. different from the IL-6 receptor), whereas a "trispecific" polypeptide of the invention is a polypeptide that comprises at least one amino acid sequence or Nanobody directed against a first antigen (i.e. the IL-6 receptor), at least one further amino acid sequence or Nanobody directed against a second antigen (i.e. different from the IL-6 receptor) and at least one further amino acid sequence or Nanobody directed against a third antigen (i.e. different from both the IL-6 receptor, and the second antigen); etc.

Accordingly, in its simplest form, a bispecific polypeptide of the invention is a bivalent polypeptide of the invention (as defined herein), comprising a first amino acid sequence or Nanobody directed against the IL-6 receptor, and a second amino acid sequence or Nanobody directed against a second antigen, in which said first and second amino acid sequence or Nanobody may optionally be linked via a linker sequence (as defined herein); whereas a trispecific polypeptide of the invention in its simplest form is a trivalent polypeptide of the invention (as defined herein), comprising a first amino acid sequence or Nanobody directed against the IL-6 receptor, a second amino acid sequence or Nanobody directed against a second antigen and a third amino acid sequence or Nanobody directed against a third antigen, in which said first, second and third amino acid sequence or Nanobody may optionally be linked via one or more, and in particular one and more in particular two, linker sequences.

In a specific aspect, the polypeptide of the invention is a trivalent, bispecific polypeptide. A trivalent, bispecific polypeptide of the invention in its simplest form may be a trivalent polypeptide of the invention (as defined herein), comprising two identical amino acid sequences or Nanobodies against the IL-6 receptor and a third amino acid sequence or Nanobody directed against another antigen, in which said first, second and third amino acid sequence or Nanobody may optionally be linked via one or more, and in particular one and more in particular two, linker sequences.

In another specific aspect, the polypeptide of the invention is a bispecific polypeptide. A bispecific polypeptide of the invention in its simplest form may be a bivalent polypeptide of the invention (as defined herein), comprising a first amino acid sequence or Nanobody against the IL-6 receptor and a second amino acid sequence or Nanobody directed against another antigen, in which said first and second amino acid sequence or Nanobody may optionally be linked via a linker sequence.

In a preferred, but non-limiting, example, the multispecific polypeptide of the invention comprises at least one amino acid sequence or Nanobody of the invention and at least one Nanobody that provides for an increased half-life. Some preferred, but non-limiting examples of such Nanobodies include Nanobodies directed against serum proteins, such as human serum albumin, thyroxine-binding protein, (human) transferrin, fibrinogen, an immunoglobulin such as IgG, IgE or IgM, or one of the other serum proteins listed in WO 04/003019.

For example, for experiments in mice, Nanobodies against mouse serum albumin (MSA) can be used, whereas for pharmaceutical use, Nanobodies against human serum albumin can be used.

Another embodiment of the present invention is a polypeptide construct as described above wherein said at least one (human) serum protein is any of (human) serum albumin, (human) serum immunoglobulins, (human) thyroxine-binding protein, (human) transferrin, (human) fibrinogen, etc.

Accordingly, in a specific aspect, the polypeptide of the invention is a trivalent, bispecific polypeptide, comprising two identical amino acid sequences or Nanobodies against the IL-6 receptor and a third amino acid sequence or Nanobody directed against (human) serum albumin, in which said first, second and third amino acid sequence or Nanobody may optionally be linked via one or more, and in particular one and more, in particular two, linker sequences.

In another specific aspect, the polypeptide of the invention is a bispecific polypeptide comprising a first amino acid sequence or Nanobody against the IL-6 receptor and a second amino acid sequence or Nanobody directed against (human) serum albumin, in which said first and second amino acid sequence or Nanobody may optionally be linked via a linker sequence.

According to a specific, but non-limiting aspect of the invention, the polypeptides of the invention contain, besides the one or more amino acid sequences or Nanobodies of the invention, at least one Nanobody against human serum albumin. Although these Nanobodies against human serum albumin may be as generally described in the applications by Ablynx N.V. cited above (see for example WO4/062551), according to a particularly preferred, but non-limiting embodiment, said Nanobody against human serum albumin essentially consists of an amino acid sequence selected from SEQ ID NO's: 97-99.

Some preferred, but non-limiting examples of polypeptides of the invention that comprise at least one amino acid sequence or Nanobody against IL-6R and at least one amino acid sequence or Nanobody that provides for increased half-life are:
a) SEQ ID NO's: 70-72;
b) a polypeptide sequence that has no more than 2, preferably no more than 1 amino acid difference in one, two or all of its CDRs of the invention with one of SEQ ID NO's: 70-72, provided that the polypeptide sequence with no more than 2, preferably no more than 1 amino acid difference in one, two or all of its CDRs of the invention binds IL-6R with the same, about the same, or a higher affinity compared to the binding by the one of SEQ ID NO's: 70-72, said affinity as measured by surface plasmon resonance; and
c) a polypeptide sequence that has no more than 2, preferably no more than 1 amino acid difference with one of SEQ ID NO's: 70-72, provided that the amino acid sequence with no more than 2, preferably no more than 1 amino acid difference with one of SEQ ID NO's: 70-72 binds IL-6R with the same, about the same, or a higher affinity compared to the binding by the one of SEQ ID NO's: 70-72, said affinity as measured by surface plasmon resonance.

Some preferred, but non-limiting examples of trivalent bispecific polypeptides of the invention are:
a) SEQ ID NO's: 71-72;
b) a polypeptide sequence that has no more than 2, preferably no more than 1 amino acid difference in one, two or all of its CDRs of the invention with one of SEQ ID NO's: 71-72, provided that the polypeptide sequence with no more than 2, preferably no more than 1 amino acid difference in one, two or all of its CDRs of the invention binds IL-6R with the same, about the same, or a higher affinity compared to the binding by the one of SEQ ID NO's: 71-72, said affinity as measured by surface plasmon resonance; and
c) a polypeptide sequence that has no more than 2, preferably no more than 1 amino acid difference with one of SEQ ID NO's: 71-72, provided that the amino acid sequence with no more than 2, preferably no more than 1 amino acid difference with one of SEQ ID NO's: 71-72 binds IL-6R with the same, about the same, or a higher affinity compared to the binding by the one of SEQ ID NO's: 71-72, said affinity as measured by surface plasmon resonance.

Some preferred, but non-limiting examples of bispecific polypeptides of the invention that comprise an amino acid sequence or Nanobody against IL-6R and an amino acid sequence or Nanobody that provides for increased half-life are:

a) SEQ ID NO: 70;

b) a polypeptide sequence that has no more than 2, preferably no more than 1 amino acid difference in one, two or all of its CDRs of the invention with SEQ ID NO: 70, provided that the polypeptide sequence with no more than 2, preferably no more than 1 amino acid difference in one, two or all of its CDRs of the invention binds IL-6R with the same, about the same, or a higher affinity compared to the binding by SEQ ID NO: 70, said affinity as measured by surface plasmon resonance; and c) a polypeptide sequence that has no more than 2, preferably no more than 1 amino acid difference with SEQ ID NO: 70, provided that the amino acid sequence with no more than 2, preferably no more than 1 amino acid difference with SEQ ID NO: 70 binds IL-6R with the same, about the same, or a higher affinity compared to the binding by SEQ ID NO: 70, said affinity as measured by surface plasmon resonance.

When comparing two stretches of amino acid residues (or two CDR sequences), the term "amino acid difference in one, two or all of its CDRs of the invention" refers to an insertion, deletion or substitution of a single amino acid residue on a position of a stretch of amino acid residues (or CDR sequence) of the invention comprised in the polypeptide of the invention specified in b) compared to the stretch of amino acid residues (or CDR sequence) of the invention comprised in the polypeptide of the invention specified in a); it being understood that two stretches of amino acid residues (or CDR sequences) of the invention can contain one or maximal two such amino acid differences.

By "amino acid difference in one, two or all of its CDRs of the invention" is meant that the amino acid sequence or Nanobody of the invention comprised in the polypeptide of the invention may have no more than 2, preferably no more than 1 amino acid difference in its CDR1 and/or no more than 2, preferably no more than 1 amino acid difference in its CDR2, and/or no more than 2, preferably no more than 1 amino acid difference in its CDR3 (i.e. in CDR1, CDR2 and/or CDR3 that form the antigen binding site for binding by the compound or polypeptide of the invention to the specific eptiope on IL-6R) compared to CDR1, CDR2 and/or CDR3 in the amino acid sequence or Nanobody of the invention comprised in one of the polypeptides of a) (i.e. one of SEQ ID NO's: 60-69); such as no more than 2, preferably no more than 1 amino acid difference in its CDR1 (i.e. CDR1 that forms the antigen binding site for binding by the compound or polypeptide of the invention to the specific eptiope on IL-6R) compared to CDR1 in the amino acid sequence or Nanobody of the invention comprised in one of the polypeptides of a) (i.e. CDR1 in one of SEQ ID NO's: 60-69); or no more than 2, preferably no more than 1 amino acid difference in its CDR2 (i.e. CDR2 that form the antigen binding site for binding by the compound or polypeptide of the invention to the specific eptiope on IL-6R) compared to CDR2 in the amino acid sequence or Nanobody of the invention comprised in one of the polypeptides of a) (i.e. CDR2 in one of SEQ ID NO's: 60-69); or no more than 2, preferably no more than 1 amino acid difference in its CDR3 (i.e. CDR3 that form the antigen binding site for binding by the compound or polypeptide of the invention to the specific eptiope on IL-6R) compared to CDR3 in the amino acid sequence or Nanobody of the invention comprised in one of the polypeptides of a) (i.e. CDR3 in one of SEQ ID NO's: 60-69); no more than 2, preferably no more than 1 amino acid difference in its CDR1 (i.e. CDR1 that form the antigen binding site for binding by the compound or polypeptide of the invention to the specific eptiope on IL-6R) compared to CDR1 in the amino acid sequence or Nanobody of the invention comprised in one of the polypeptides of a) (i.e. CDR1 in one of SEQ ID NO's: 60-69) and no more than 2, preferably no more than 1 amino acid difference in its CDR2 (i.e. CDR2 that form the antigen binding site for binding by the compound or polypeptide of the invention to the specific eptiope on IL-6R) comprised compared to CDR2 in the amino acid sequence or Nanobody of the invention comprised in one of the polypeptides of a) (i.e. CDR2 in one of SEQ ID NO's: 60-69); or no more than 2, preferably no more than 1 amino acid difference in its CDR1 (i.e. CDR1 that form the antigen binding site for binding by the compound or polypeptide of the invention to the specific eptiope on IL-6R) compared to CDR1 in the amino acid sequence or Nanobody of the invention comprised in one of the polypeptides of a) (i.e. CDR1 in one of SEQ ID NO's: 60-69) and no more than 2, preferably no more than 1 amino acid difference in its CDR3 (i.e. CDR3 that form the antigen binding site for binding by the compound or polypeptide of the invention to the specific eptiope on IL-6R) compared to CDR3 in the amino acid sequence or Nanobody of the invention comprised in one of the polypeptides of a) (i.e. CDR3 in one of SEQ ID NO's: 60-69); or no more than 2, preferably no more than 1 amino acid difference in its CDR2 (i.e. CDR2 that form the antigen binding site for binding by the compound or polypeptide of the invention to the specific eptiope on IL-6R) compared to CDR2 in the amino acid sequence or Nanobody of the invention comprised in one of the polypeptides of a) (i.e. CDR2 in one of SEQ ID NO's: 60-69) and no more than 2, preferably no more than 1 amino acid difference in its CDR3 (i.e. CDR3 that form the antigen binding site for binding by the compound or polypeptide of the invention to the specific eptiope on IL-6R) compared to CDR3 in the amino acid sequence or Nanobody of the invention comprised in one of the polypeptides of a) (i.e. CDR3 in one of SEQ ID NO's: 60-69); no more than 2, preferably no more than 1 amino acid difference in its CDR1 (i.e. CDR1 that form the antigen binding site for binding by the compound or polypeptide of the invention to the specific eptiope on IL-6R) compared to CDR1 in the amino acid sequence or Nanobody of the invention comprised in one of the polypeptides of a) (i.e. CDR1 in one of SEQ ID NO's: 60-69) and no more than 2, preferably no more than 1 amino acid difference in its CDR2 (i.e. CDR2 that form the antigen binding site for binding by the compound or polypeptide of the invention to the specific eptiope on IL-6R) compared to CDR2 in the amino acid sequence or Nanobody of the invention comprised in one of the polypeptides of a) (i.e. CDR2 in one of SEQ ID NO's: 60-69) and no more than 2, preferably no more than 1 amino acid difference in its CDR3 (i.e. CDR3 that form the antigen binding site for binding by the compound or polypeptide of the invention to the specific eptiope on IL-6R) compared to CDR3 in the amino acid sequence or Nanobody of the invention comprised in one of the polypeptides of a) (i.e. CDR3 in one of SEQ ID NO's: 60-69).

The "amino acid difference in one, two or all of its CDRs" can be any one or maximal any two substitutions, deletions or insertions in one or more of the CDRs of the invention, or any combination thereof, that either improve the properties of the compound or polypeptide of the invention or that at least do not detract too much from the desired properties or from the balance or combination of desired properties of the compound or polypeptide of the invention. In this respect, the resulting compound or polypeptide of the invention should at least bind IL-6R with the same, about the same or a higher affinity compared to the compound or polypeptide comprising the one or more CDRs of the invention without the one or maximal two substitutions, deletions or insertions, said affinity as measured by surface plasmon resonance. The resulting compounds or polypeptides are preferably such that they can bind to the specific epitope on the IL-6 receptor, with affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. The resulting compounds or polypeptides also preferably have a cell based potency and a plasma potency as defined herein.

In one aspect of the invention, the "amino acid difference in one, two or all of its CDRs" is an amino acid substitution. The amino acid substitution may be any one or maximal any two substitutions in one or more CDRs of the invention that either improve the properties of the compound or polypeptide of the invention or that at least do not detract too much from the desired properties or from the balance or combination of desired properties of the compound or construct of the invention. In this respect, the resulting compound or polypeptide of the invention should at least bind IL-6R with the same, about the same or a higher affinity compared to the compound or construct comprising the one or more CDRs of the invention without the one or maximal two substitutions, said affinity as measured by surface plasmon resonance. The resulting compounds or polypeptides are preferably such that they can bind to the specific epitope on the IL-6 receptor, with affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. The resulting compounds or polypeptides also preferably have a cell based potency and a plasma potency as defined herein. The skilled person will generally be able to determine and select suitable substitutions, based on the disclosure herein and optionally after a limited degree of routine experimentation, which may for example involve introducing a limited number of possible substitutions and determining their influence on the properties of the compounds or polypeptides thus obtained.

The amino acid substitution in one or more of the CDRs of the invention may be any possible substitution such as a "conservative substitution" (as defined herein), it may be driven by certain rules (as defined herein), and/or it may induce improved properties to the resulting compounds or polypeptides (as is further defined herein).

The invention also relates to a compound or polypeptide that has no more than 2, preferably no more than 1 amino acid difference with one of (the full sequence of) SEQ ID NO's: 70-72.

When comparing two compounds or polypeptides, the term "amino acid difference" refers to an insertion, deletion or substitution of a single amino acid residue on a position of the first compound or polypeptide, compared to the second compound or polypeptide; it being understood that two compounds or polypeptides can contain one or maximal two such amino acid differences.

The "amino acid difference" can be any one or maximal two substitutions, deletions or insertions in the compound or polypeptide, i.e. in one or more of the framework regions or in one or more of the CDRs (which may be in a CDR of the invention (i.e. present in an amino acid sequence or Nanobody of the invention) or in another CDR (i.e. present in SEQ ID NO: 98)), in a linker sequence, or any combination thereof, that either improve the properties of the compound or polypeptide of the invention or that at least do not detract too much from the desired properties or from the balance or combination of desired properties of the compound or polypeptide of the invention. In this respect, the resulting compound or polypeptide of the invention should at least bind IL-6R with the same, about the same, or a higher affinity compared to the compound or polypeptide without the one or maximal two substitutions, deletions or insertions, said affinity as measured by surface plasmon resonance. The resulting compounds or polypeptides are preferably such that they can bind to the specific epitope on the IL-6 receptor, with affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. The resulting compounds or polypeptides also preferably have a cell based potency and a plasma potency as defined herein.

In one aspect of the invention, the "amino acid difference" is an amino acid substitution. The amino acid substitution may be any one or maximal any two substitutions in the framework regions, in one or more of the CDRs (which may be in a CDR of the invention (i.e. present in an amino acid sequence or Nanobody of the invention) or in another CDR (i.e. present in SEQ ID NO: 98)), in a linker sequence, or any combination thereof, that either improve the properties of the compound or polypeptide of the invention or that at least do not detract too much from the desired properties or from the balance or combination of desired properties of the compound or polypeptide of the invention. In this respect, the resulting compound or polypeptide of the invention should at least bind IL-6R with the same, about the same or a higher affinity compared to the compound or polypeptide without the one or maximal two substitutions, said affinity as measured by surface plasmon resonance. The resulting compounds or polypeptides are preferably such that they can bind to the specific epitope on the IL-6 receptor, with affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. The resulting compounds or polypeptides also preferably have a cell based potency and a plasma potency as defined herein.

As indicated above, the substitutions, insertions or deletions can be in one or more of the framework regions, in one or more of the CDR's, and/or in one or more of the linker sequences. The substitutions, insertions or deletions in the CDR's may be any possible substitutions, insertions or deletions such as "conservative substitution" (as defined herein), it may be driven by certain rules (as defined herein), and/or it may induce improved properties to the resulting compounds or polypeptides.

When such substitutions, insertions or deletions are made in one or more of the framework regions, they may be any possible substitutions, insertions or deletions. They can be made at one or more of the Hallmark residues (as e.g. defined in WO 08/020,079; Tables A-3 to A-8) and/or at one or more of the other positions in the framework residues, although substitutions, insertions or deletions at the Hallmark residues are generally less preferred (unless these are suitable humanizing substitutions as described herein). By means of non-limiting examples, a substitution may for example be a conservative substitution (as described herein) and/or an amino acid residue may be replaced by another amino acid residue that naturally occurs at the same position in another $V_{HH}$ domain (see WO 08/020,079, Tables A-5 to A-8), although the invention is generally not limited thereto.

Substitutions, insertions or deletions made (preferably) in one or more of the framework regions may be sequence optimizing substitutions such as e.g. humanizing substitution. Some preferred, but non-limiting humanizing substitutions (and suitable combinations thereof) will become clear to the skilled person based on the disclosure herein. Potentially useful humanizing substitutions can be ascertained by comparing the sequence of the framework regions of one of the amino acid sequence or Nanobodies comprised in one of the polypeptides of the invention defined in a) with the corresponding framework sequence of one or more closely related human $V_H$ sequences, after which one or more of the potentially useful humanizing substitutions (or combinations thereof) thus determined can be introduced into said amino acid sequence or Nanobody comprised in one of the polypeptides of the invention defined in a) (in any manner known per se, as further described herein) and the resulting humanized polypeptide can be tested for affinity for IL-6R, for stability, for ease and level of expression, and/or for other desired properties defined herein. In this way, by means of a limited degree of trial and error, other suitable humanizing substitutions (or suitable combinations thereof) can be determined by the skilled person based on the disclosure herein.

Depending on the host organism used to express the compound or polypeptide of the invention, deletions and/or substitutions may also be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables A-5-A-8 of WO 08/020,079, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions.

The resulting compounds of the invention or polypeptides of the invention should preferably bind to IL-6R with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:

bind to hIL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;

and/or such that they:
bind to cyno IL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less; and/or such that they:

bind to hIL-6R with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more; and/or such that they:

bind to cyno IL-6R with a $k_{on}$-rate of between $10^4$ $M^{-1}$ $s^{-1}$ to about $10^7$ $M^{-1}$ $s^{-1}$ preferably between $10^5$ $M^{-1}$ $s^{-1}$ and $10^7$ $M^{-1}$ $s^{-1}$, more preferably about $10^6$ $M^{-1}$ $s^{-1}$ or more; and/or such that they:

bind to hIL-6R with a $k_{off}$ rate between $10^{-3}$ $s^{-1}$ ($t_{1/2}$=0.69 s) and $10^{-6}$ $s^{-1}$ (providing a near irreversible complex with a $t_{1/2}$ of multiple days), preferably between $10^{-4}$ $s^{-1}$ and $10^{-6}$ $s^{-1}$, more preferably between $10^{-5}$ $s^{-1}$ and $10^{-6}$ $s^{-1}$, such as about $10^{-5}$ $s^{-1}$ or lower;

and/or such that they:
bind to cyno IL-6R with a $k_{off}$ rate between $10^{-3}$ $s^{-1}$ ($t_{1/2}$=0.69 s) and $10^{-6}$ $s^{-1}$ (providing a near irreversible complex with a $t_{1/2}$ of multiple days), preferably between $10^{-4}$ $s^{-1}$ and $10^{-6}$ $s^{-1}$, more preferably between $10^{-5}$ $s^{-1}$ and $10^{-6}$ $s^{-1}$, such as about $10^{-5}$ $s^{-1}$ or lower.

Some preferred IC50 values for binding of the compounds or polypeptides of the invention to IL-6R will become clear from the further description and examples herein.

The potency and/or efficacy of the polypeptides and compounds of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include proliferation assays using IL-6-dependent cell lines including TF-1, XG1 and 7TD1, collagen induced arthritis model, transplant model of synovial tissue in SCID mice, xenograft models of various human cancers, including lymphoma, myeloma, prostate cancer and renal cell carcinoma, IBD models including TNBS, primate models (such as e.g. described in Shinkura et al. 1998, Anticancer Research 18: 1217-1222), non-human primate models of arthritic disease (as e.g described in Vierboom et al., 2008, Drug Discov. Today: Dis Model doi:10.1016/j.ddmod. 2008.06.003) as well as the assays and animal models used in the experimental part below and in the prior art cited herein (Peake et al., 2006, Rheumatology 45: 1485-9; Wahid et al., 2000, Clin. Exp. Immunol., 122: 133-142; Matsuno et al., 1998, Arthritis and rheumatism 41: 2014-2021; WO 08/020,079).

For example, in the TF-1 assay as described by Kitamura et al. (1989, J. Cell Physiol. 140: 323), the compounds of the invention or polypeptides of the invention may have IC50 values (at 100 IU/mL IL-6) between 10 nM and 50 pM, preferably between 5 nM and 50 pM, more preferably between 1 nM and 50 pM or less, such as about 750 or 500 pM or less. In this TF-1 assay the compounds of the invention or polypeptides of the invention may have IC50 values (at 5000 IU/mL IL-6) between 50 nM and 1 nM, preferably between 25 nM and 1 nM, more preferably between 10 nM and 1 nM or less, such as about 8 nM or less. In this TF-1 assay, the compounds of the invention or polypeptides of the invention may have IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4 (see Example 1). In this TF-1 assay, the compounds of the invention or polypeptides of the invention may have IC50 values that are at least the same and preferably better, at least two times, preferably three times, more preferably four times, even more preferably 5 times, 7 times or more than 7 times better compared to the IC50 value obtained for Tocilizumab (MRA).

In a plasma potency assay at EC50 values of IL-6 (e.g. in the presence of 27.29 ng/mL IL-6 as described in Example 45), the compounds of the invention or polypeptides of the invention may have IC50 values between 500 pM and 50 pM, preferably between 250 pM and 50 pM, more preferably between 200 pM and 50 pM or less, such as 150 pM or less. In a plasma potency assay at EC95 values of IL-6 (e.g. in the presence of 885 ng/mL IL-6 as described in Example 45) the compounds of the invention or polypeptides of the invention may have IC50 values between 1000 pM and 100 pM, preferably between 750 pM and 100 pM, more preferably between 500 pM and 100 pM or less, such as 400 pM or less. In this plasma potency assay, the compounds of the invention or polypeptides of the invention may have IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4 (see Example 1). In this plasma potency assay, the compounds of the invention or polypeptides of the invention may have IC50 values that are the at least the same and preferably better, at least two times, preferably three times, more preferably four times, even more preferably 5 times, 7 times or more than 7 times better compared to the IC50 value obtained for Tocilizumab (MRA).

In an assay for defining binding to membrane IL-6R on CHO cells, the compounds of the invention or polypeptides of the invention may have IC50 values between 10 nM and 100 pM, preferably between 5 nM and 100 pM, more preferably between 2 nM and 10 pM or less, such as 2 nM or less.

In a preferred aspect, the compound or polypeptide of the invention has or essentially consists of the amino acid sequence of SEQ ID NO: 70. In another preferred aspect, the compound or polypeptide of the invention has or essentially consists the amino acid sequence of SEQ ID NO: 71. Polypeptides with these amino acid sequences show improved properties such as e.g. improved binding and/or affinity, improved avidity, improved efficacy and potency, and/or an increased selectivity, in addition to their capacity to partially or totally block the IL-6/IL-6R interaction, and/or inhibit signalization through, IL-6, IL-6R and/or the IL-6/IL-6R complex.

The invention also relates to a monovalent construct (also referred to as "monovalent construct of the invention"), comprising or essentially consisting of one amino acid sequence or Nanobody of the invention. Preferred monovalent constructs of the invention comprise or essentially consist of SEQ ID NO's: 60-69, such as SEQ ID NO's: 65-69, such as e.g. SEQ ID NO: 66. Such a monovalent constructs, as well as the amino acid sequences and Nanobodies of the invention can be used for the preparation of a compound or polypeptide of the invention, such as e.g. the multivalent and/or multispecific compounds or polypeptides of the invention.

Accordingly, the present invention also relates to the use of an amino acid sequence, Nanobody or monovalent construct of the invention for the preparation of a compound, construct or polypeptide of the invention. The invention further relates to a method for the preparation of a compound, construct or polypeptide of the invention, comprising the linking of an amino acid sequence, Nanobody or monovalent construct of the invention to one or more other groups, residues, moieties or binding units. Such a method may comprise the linking of an amino acid sequence, Nanobody or monovalent construct of the invention to one or more other groups, residues, moieties or binding units via one or more linkers.

In a preferred aspect the one or more other groups, residues, moieties or binding units are binding units, such as amino acid sequences or Nanobodies. Accordingly, the present invention also relates to the use of an amino acid sequence, Nanobody or monovalent construct of the invention for the preparation of a multivalent and/or multispecific compound, construct or polypeptide of the invention. The invention further relates to a method for the preparation of a multivalent and/or multispecific compound, construct or polypeptide of the invention, comprising the linking of an amino acid sequence, Nanobody or monovalent construct of the invention to one or more other binding units, such as amino acid sequences or Nanobodies. Such a method may comprise the linking of an amino acid sequence, Nanobody or monovalent construct of the invention to one or more binding units via one or more linkers.

In a specific aspect, the present invention also relates to the use of a monovalent construct comprising or essentially consisting of one of SEQ ID NO's: 60-69 (preferably SEQ ID NO's: 65-69, more preferably SEQ ID NO: 66) for the preparation of a multivalent and/or multispecific compound, construct or polypeptide of the invention. The invention further relates to a method for the preparation of a multivalent and/or multispecific compound, construct or polypeptide of the invention, comprising the linking of a monovalent construct comprising or essentially consisting of one of SEQ ID NO's: 60-69 (preferably SEQ ID NO's: 65-69, more preferably SEQ ID NO: 66) to one or more other binding units, such as amino acid sequences or Nanobodies. Such a method may comprise the linking of a monovalent construct comprising or essentially consisting of one of SEQ ID NO's: 60-69 (preferably SEQ ID NO's: 65-69, more preferably SEQ ID NO: 66) to one or more binding units via one or more linkers.

In another specific aspect, the present invention relates to the use of a monovalent construct comprising or essentially consisting of one of SEQ ID NO's: 60-69 (preferably SEQ ID NO's: 65-69, more preferably SEQ ID NO: 66) for the preparation of a multivalent and/or multispecific compound, construct or polypeptide comprising or essentially consisting of SEQ ID NO's: 70-72 (preferably SEQ ID NO's: 70-71, more preferably SEQ ID NO: 70 or SEQ ID NO: 71). The invention further relates to a method for the preparation of a multivalent and/or multispecific compound, construct or polypeptide comprising or essentially consisting of SEQ ID NO's: 70-72 (preferably SEQ ID NO's: 70-71, more preferably SEQ ID NO: 70 or SEQ ID NO: 71), comprising the linking of a monovalent construct comprising or essentially consisting of one of SEQ ID NO's: 60-69 (preferably SEQ ID NO's: 65-69, more preferably SEQ ID NO: 66) to an amino acid sequence comprising or essential consisting of SEQ ID NO: 98 via one or more linkers.

Suitable spacers or linkers for use in multivalent and/or multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each amino acid sequence or Nanobody by itself forms a complete antigen-binding site).

For example, a linker may be a suitable amino acid sequence, and in particular amino acid sequences of between 1 and 50, preferably between 1 and 30, such as between 1 and 20 or between 1 and 10 amino acid residues. Some preferred examples of such amino acid sequences include gly-ser linkers, for example of the type $(gly_x ser_y)_z$, such as (for example (gly$_4$ser)$_3$ or (gly$_3$ser$_2$)$_3$, as described in WO 99/42077, hinge-like regions such as the hinge regions of naturally occurring heavy chain antibodies or similar sequences (such as described in WO 94/04678).

Some other particularly preferred linkers are poly-alanine (such as AAA), as well as the linkers mentioned in Table B-8, of which AAA, GS-7 and GS-9 are particularly preferred.

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for the IL-6 receptor, or for one or more of the other antigens. Based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the amino acid sequences, Nanobodies, compounds and polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thererto. For example, when a polypeptide of the invention comprises three of more amino acid sequences or Nanobodies, it is possible to link them by use of a linker with three or more "arms", which each "arm" being linked to an amino acid sequence or Nanobody, so as to provide a "star-shaped" construct. It is also possible, although usually less preferred, to use circular constructs.

The invention in its broadest sense also comprises derivatives of the amino acid sequences, Nanobodies, compounds or polypeptides of the invention. Such derivatives can generally be obtained by modification, and in particular by chemical and/or biological (e.g enzymatical) modification, of the amino acid sequences, Nanobodies, compounds or polypeptides of the invention and/or of one or more of the amino acid residues that form the amino acid sequences, Nanobodies, compounds or polypeptides of the invention.

Examples of such modifications, as well as examples of amino acid residues within the amino acid sequence, Nanobody sequence, compound or polypeptide sequences that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the amino acid sequence, Nanobody, compound or polypeptide of the invention, and in particular of one or more functional groups, residues or moieties that confer one or more desired properties or functionalities to the amino acid sequence, Nanobody, compound or polypeptide of the invention. Example of such functional groups will be clear to the skilled person.

For example, such modification may comprise the introduction (e.g. by covalent binding or in any other suitable manner) of one or more functional groups that that increase the half-life, the solubility and/or the absorption of the amino acid sequence, Nanobody, compound or polypeptide of the invention, that reduce the immunogenicity and/or the toxicity of the amino acid sequence, Nanobody, compound or polypeptide of the invention, that eliminate or attenuate any undesirable side effects of the amino acid sequence, Nanobody, compound or polypeptide of the invention, and/or that confer other advantageous properties to and/or reduce the undesired properties of the amino acid sequence, Nanobody, compound or polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences (1980, 16th ed., Mack Publishing Co., Easton, Pa.). Such functional groups may for example be linked directly (for example covalently) to an amino acid sequence, Nanobody, compound or polypeptide of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman (2002, Nat. Biotechnol., 54: 531-545); by Veronese and Harris (2003, Adv. Drug Deliv. Rev. 54: 453-456), by Harris and Chess (2003, Nat. Rev. Drug. Discov., 2: 214-21) and in WO 04/060965. Various reagents for pegylation of proteins are also commercially available, for example from Nektar Therapeutics, USA.

Preferably, site-directed pegylation is used, in particular via a cysteine-residue (see for example Yang et al. (2003, Protein Engineering, 16 (10): 761-770). For example, for this purpose, PEG may be attached to a cysteine residue that naturally occurs in an amino acid sequence, Nanobody, compound or polypeptide of the invention, an amino acid sequence, Nanobody, compound or polypeptide of the invention may be modified so as to suitably introduce one or more cysteine residues for attachment of PEG, or an amino acid sequence comprising one or more cysteine residues for attachment of PEG may be fused to the N- and/or C-terminus of an amino acid sequence, Nanobody, compound or polypeptide of the invention, all using techniques of protein engineering known per se to the skilled person.

Preferably, for the amino acid sequences, Nanobodies, compounds or polypeptides of the invention of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the amino acid sequence, Nanobody, compound or polypeptide of the invention.

Yet another modification may comprise the introduction of one or more detectable labels or other signal-generating groups or moieties, depending on the intended use of the labelled amino acid sequence, Nanobody, compound or polypeptide of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^3$H, $^{125}$I, $^{32}$P, $^{35}$S, $^{14}$C, $^{51}$Cr, $^{36}$Cl, $^{57}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled amino acid sequences, Nanobodies, compounds or polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the amino acid sequence, Nanobody, compound or polypeptide of the invention to another protein, polypeptide or chemical compound that is bound to the other half of the binding pair, i.e. through formation of the binding pair. For example, an amino acid sequence, Nanobody, compound or polypeptide of the invention may be conjugated to biotin, and linked to another protein, polypeptide, compound or carrier conjugated to avidin or streptavidin. For example, such a conjugated amino acid sequence, Nanobody, compound or polypeptide of the invention may be used as a reporter, for example in a diagnostic system where a detectable signal-producing agent is conjugated to avidin or streptavidin. Such binding pairs may for example also be used to bind the amino acid sequence, Nanobody, compound or polypeptide of the invention to a carrier, including carriers suitable for pharmaceutical purposes. One non-limiting example are the liposomal formulations described by Cao and Suresh (2000, Journal of Drug Targetting, 8 (4): 257). Such binding pairs may also be used to link a therapeutically active agent to the amino acid sequence, Nanobody, compound or polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (1997, Biotechnol. Appl. Biochem., 26: 143-151).

Preferably, the derivatives are such that they bind to the specific eptiope on the IL-6 receptor, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In particular, such derivatives of the invention are preferably such that they:
bind to hIL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;
and/or such that they:
bind to cyno IL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less;
and/or such that they:
bind to hIL-6R with a $k_{on}$-rate of between $10^4$ M$^{-1}$ s$^{-1}$ to about $10^7$ M$^{-1}$ s$^{-1}$, preferably between $10^5$ M$^{-1}$ s$^{-1}$ and $10^7$ M$^{-1}$ s$^{-1}$, more preferably about $10^6$ M$^{-1}$ s$^{-1}$ or more;
and/or such that they:
bind to cyno IL-6R with a $k_{on}$-rate of between $10^4$ M$^{-1}$ s$^{-1}$ to about $10^7$ M$^{-1}$ s$^{-1}$, preferably between $10^5$ M$^{-1}$ s$^{-1}$ and $10^7$ M$^{-1}$ s$^{-1}$, more preferably about $10^6$ M$^{-1}$ s$^{-1}$ or more;
and/or such that they:
bind to hIL-6R with a $k_{off}$ rate between $10^{-3}$ s$^{-1}$ ($t_{1/2}$=0.69 s) and $10^{-6}$ s$^{-1}$ (providing a near irreversible complex with a $t_{1/2}$ of multiple days), preferably between $10^{-4}$ s$^{-1}$ and $10^{-6}$ s$^{-1}$, more preferably between $10^{-5}$ s$^{-1}$ and $10^{-6}$ s$^{-1}$, such as about $10^{-5}$ s$^{-1}$ or lower;
and/or such that they:
bind to cyno IL-6R with a $k_{off}$ rate between $10^{-3}$ s$^{-1}$ ($t_{1/2}$=0.69 s) and $10^{-6}$ s$^{-1}$ (providing a near irreversible complex with a $t_{1/2}$ of multiple days), preferably between $10^{-4}$ s$^{-1}$ and $10^{-6}$ s$^{-1}$, more preferably between $10^{-5}$ s$^{-1}$ and $10^{-6}$ s$^{-1}$, such as about $10^{-5}$ s$^{-1}$ or lower.

As mentioned above, the invention also relates to proteins or polypeptides that essentially consist of or comprise at least one amino acid sequence, Nanobody, compound or polypeptide of the invention. By "essentially consist of" is meant that the amino acid sequence of the protein or polypeptide of the invention either is exactly the same as the amino acid sequence, Nanobody, compound or polypeptide of the invention or corresponds to the amino acid sequence, Nanobody, compound or polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence, Nanobody, compound or polypeptide.

Said amino acid residues may or may not change, alter or otherwise influence the (biological) properties of the amino acid sequence, Nanobody, compound or polypeptide of the invention and may or may not add further functionality to the amino acid sequence, Nanobody, compound or polypeptide. For example, such amino acid residues:

a) can comprise an N-terminal Met residue, for example as result of expression in a heterologous host cell or host organism.
b) may form a signal sequence or leader sequence that directs secretion of the amino acid sequence, Nanobody, compound or polypeptide from a host cell upon synthesis. Suitable secretory leader peptides will be clear to the skilled person, and may be as further described herein. Usually, such a leader sequence will be linked to the N-terminus of the amino acid sequence, Nanobody, compound or polypeptide, although the invention in its broadest sense is not limited thereto;
c) may form a sequence or signal that allows the amino acid sequence, Nanobody, compound or polypeptide to be directed towards and/or to penetrate or enter into specific organs, tissues, cells, or parts or compartments of cells, and/or that allows the amino acid sequence, Nanobody, compound or polypeptide to penetrate or cross a biological barrier such as a cell membrane, a cell layer such as a layer of epithelial cells, a tumor including solid tumors, or the blood-brain-barrier. Examples of such amino acid sequences will be clear to the skilled person. Some non-limiting examples are the small peptide vectors ("Pep-trans vectors") described in WO 03/026700 and in Temsamani et al., Expert Opin. Biol. Ther., 1, 773 (2001); Temsamani and Vidal, Drug Discov. Today, 9, 1012 (004) and Rousselle, J. Pharmacol. Exp. Ther., 296, 124-131 (2001), and the membrane translocator sequence described by Zhao et al., Apoptosis, 8, 631-637 (2003). C-terminal and N-terminal amino acid sequences for intracellular targeting of antibody fragments are for example described by Cardinale et al., Methods, 34, 171 (2004). Other suitable techniques for intracellular targeting involve the expression and/or use of so-called "intrabodies" comprising a amino acid sequence, Nanobody, compound or polypeptide of the invention, as mentioned below;
d) may form a "tag", for example an amino acid sequence or residue that allows or facilitates the purification of the amino acid sequence, Nanobody, compound or polypeptide, for example using affinity techniques directed against said sequence or residue. Thereafter, said sequence or residue may be removed (e.g. by chemical or enzymatical cleavage) to provide the amino acid sequence, Nanobody, compound or polypeptide (for this purpose, the tag may optionally be linked to the amino acid sequence, Nanobody, compound or polypeptide sequence via a cleavable linker sequence or contain a cleavable motif). Some preferred, but non-limiting examples of such residues are multiple histidine residues, glutatione residues and a myc-tag such as AAAEQKLISEEDLNGAA (SEQ ID NO: 100);
e) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the amino acid sequences, Nanobodies, compounds or polypeptides of the invention.

The amino acid sequences, Nanobodies, polypeptides and nucleic acids of the invention can be prepared in a manner known per se, as will be clear to the skilled person from the further description herein. For example, the amino acid sequences, Nanobodies and polypetides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies, polypeptides and nucleic acids include the methods and techniques described herein.

As will be clear to the skilled person, one particularly useful method for preparing an amino acid sequence, Nanobody and/or a polypeptide of the invention generally comprises the steps of:
the expression, in a suitable host cell or host organism (also referred to herein as a "host of the invention") or in another suitable expression system of a nucleic acid that encodes said amino acid sequence, Nanobody or polypeptide of the invention (also referred to herein as a "nucleic acid of the invention"), optionally followed by:
isolating and/or purifying the amino acid sequence, Nanobody or polypeptide of the invention thus obtained.
In particular, such a method may comprise the steps of:
cultivating and/or maintaining a host of the invention under conditions that are such that said host of the invention expresses and/or produces at least one amino acid sequence, Nanobody and/or polypeptide of the invention; optionally followed by:
isolating and/or purifying the amino acid sequence, Nanobody or polypeptide of the invention thus obtained.

Accordingly, the present invention also relates to a nucleic acid or nucleotide sequence that encodes an amino acid sequence, a Nanobody, a polypeptide or a monovalent construct of the invention (also referred to as "nucleic acid of the invention" or "nucleotide sequence of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences, Nanobodies and/or polypeptides of the invention given herein, and/or can be isolated from a suitable natural source. Also, as will be clear to the skilled person, to prepare a nucleic acid of the invention, also several nucleotide sequences, such as at least one nucleotide sequence encoding an amino acid sequence or Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to
b) one or more regulatory elements, such as a promoter and optionally a suitable terminator; and optionally also
c) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e. under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence, Nanobody or polypeptide of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 7,207,410, U.S. Pat. No. 5,693,492 and EP 1085089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e. for expression and/or production of the amino acid sequence, Nanobody or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example:

- a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*;
- a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of Arxula, for example of *Arxula adeninivorans*; of *Yarrowia*, for example of *Yarrowia lipolytica*;
- an amphibian cell or cell line, such as *Xenopus* oocytes;
- an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (1998, Res. Immunol. 149(6): 589-99), Riechmann and Muyldermans (1999, J. Immunol. Methods, 231(1-2): 25-38), van der Linden (2000, J. Biotechnol. 80(3): 261-70), Joosten et al. (2003, Microb. Cell Fact. 2(1): 1), Joosten et al. (2005, Appl. Microbiol. Biotechnol. 66(4): 384-92.); and the further references cited herein.

The amino acid sequences, Nanobodies and polypeptides of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patient by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-) introduced into the body of the patient. All this can be performed using gene therapy vectors, techniques and delivery systems which are well known to the skilled person, and for example described in Culver K. W. (1994, "Gene Therapy", p. xii, Mary Ann Liebert, Inc., Publishers, New York, N.Y), Giordano (1996, Nature F Medicine 2: 534-539), Schaper (1996, Circ. Res. 79: 911-919), Anderson (1992, Science 256: 808-813), Verma (1994, Nature 389: 239); Isner (1996, Lancet 348: 370-374), Muhlhauser (1995, Circ. Res. 77: 1077-1086); Onodera (1998, Blood 91: 30-36); Verma (1998, Gene Ther. 5: 692-699); Nabel (1997, Ann. N.Y. Acad. Sci., 811: 289-292), Verzeletti (1998, Hum. Gene Ther. 9: 2243-51); Wang 1996, Nature Medicine 2: 714-716), WO 94/29469, WO 97/00957, U.S. Pat. No. 5,580,859, or Schaper (1996, Current Opinion in Biotechnology 7: 635-640). For example, in situ expression of ScFv fragments (Afanasieva et al. (2003, Gene Ther., 10: 1850-1859) and of dia bodies (Blanco et al., 2003, J. Immunol., 171: 1070-1077) has been described in the art.

For expression of the amino acid sequences, Nanobodies or polypeptides in a cell, they may also be expressed as so-called "intrabodies", as for example described in WO 94/02610, WO 95/22618, U.S. Pat. No. 7,004,940, WO 03/014960, in Cattaneo A. and Biocca S. (1997, Intracellular Antibodies: Development and Applications. Landes and Springer-Verlag) and in Kontermann (2004, Methods 34: 163-170).

The amino acid sequences, Nanobodies and polypeptides of the invention can for example also be produced in the milk of transgenic mammals, for example in the milk of rabbits, cows, goats or sheep (see for example U.S. Pat. No. 6,741, 957, U.S. Pat. No. 6,304,489 and U.S. Pat. No. 6,849,992 for general techniques for introducing transgenes into mammals), in plants or parts of plants including but not limited to their leaves, flowers, fruits, seed, roots or turbers (for example in tobacco, maize, soybean or alfalfa) or in for example pupae of the silkworm *Bombix mori*.

Furthermore, the amino acid sequences, Nanobodies and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of Nanobodies or Nanobody-containing protein therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, Nanobody or polypeptide to be obtained.

Thus, according to one non-limiting embodiment of the invention, the amino acid sequence, Nanobody or polypeptide of the invention is glycosylated. According to another non-limiting embodiment of the invention, the amino acid sequence, Nanobody or polypeptide of the invention is non-glycosylated.

According to one preferred, but non-limiting embodiment of the invention, the amino acid sequence, Nanobody or polypeptide of the invention is produced in a bacterial cell, in particular a bacterial cell suitable for large scale pharmaceutical production, such as cells of the strains mentioned above.

According to another preferred, but non-limiting embodiment of the invention, the amino acid sequence, Nanobody or polypeptide of the invention is produced in a yeast cell, in particular a yeast cell suitable for large scale pharmaceutical production, such as cells of the species mentioned above.

According to yet another preferred, but non-limiting embodiment of the invention, the amino acid sequence, Nanobody or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the amino acid sequences, Nanobodies and the polypeptides of the invention, the amino acid sequences, Nanobodies and polypeptides of the invention can be produced either intracellullarly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. When eukaryotic host cells are used, extracellular production is usually preferred since this considerably facilitates the further isolation and downstream processing of the amino acid sequences, Nanobodies, polypeptides and proteins obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies.

Alternatively, as will be clear to the skilled person, recombinant strains of bacteria that have been genetically modified so as to secrete a desired protein, and in particular a amino acid sequence, Nanobody or a polypeptide of the invention, can be used.

Thus, according to one non-limiting embodiment of the invention, the amino acid sequence, Nanobody or polypeptide of the invention is an amino acid sequence, Nanobody or polypeptide that has been produced intracellularly and that has been isolated from the host cell, and in particular from a bacterial cell or from an inclusion body in a bacterial cell. According to another non-limiting embodiment of the invention, the amino acid sequence, Nanobody or polypeptide of the invention is an amino acid sequence, Nanobody or polypeptide that has been produced extracellularly, and that has been isolated from the medium in which the host cell is cultivated.

Some preferred, but non-limiting promoters for use with these host cells include,
- for expression in *E. coli*: lac promoter (and derivatives thereof such as the lacUV5 promoter); arabinose promoter; left-(PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;
- for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1,10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);
- for expression in *Pichia pastoris*: the AOX1 promoter (alcohol oxidase I);
- for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:
- vectors for expression in mammalian cells: pMAMneo (Clontech), pcDNA3 (Invitrogen), pMClneo (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUC-Tag (ATCC 37460) and 1ZD35 (ATCC 37565), as well as viral-based expression systems, such as those based on adenovirus;
- vectors for expression in bacterial cells: pET vectors (Novagen) and pQE vectors (Qiagen);
- vectors for expression in yeast or other fungal cells: pYES2 (Invitrogen) and *Pichia* expression vectors (Invitrogen);
- vectors for expression in insect cells: pBlueBacII (Invitrogen) and other baculovirus vectors
- vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include:
- for use in bacterial cells such as *E. coli*: PelB, Bla, OmpA, OmpC, OmpF, OmpT, StII, PhoA, PhoE, MalE, Lpp, Lam B, and the like; TAT signal peptide, hemolysin C-terminal secretion signal;
- for use in yeast: α-mating factor prepro-sequence, phosphatase (phoI), invertase (Suc), etc.;
- for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence, Nanobody or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences of the invention, the transformed host cell or transformed host organism may generally be kept, maintained and/or cultured under conditions such that the (desired) amino acid sequence, Nanobody or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence, Nanobody or polypeptide of the invention may (first) be generated in an immature form (as mentioned above), which may then be subjected to post-translational modification, depending on the host cell/host organism used. Also, the amino acid sequence, Nanobody or polypeptide of the invention may be glycosylated, again depending on the host cell/host organism used.

The amino acid sequence, Nanobody or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, Nanobody or polypeptide of the invention) and/or preparative immunological techniques (i.e. using antibodies against the amino acid sequence to be isolated).

Generally, for pharmaceutical use, the polypeptides of the invention may be formulated as a pharmaceutical preparation or compositions comprising at least one amino acid sequence, Nanobody or polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one amino acid of the invention, at least one Nanobody of the invention or at least one polypeptide of the invention and at least one suitable carrier, diluent or excipient (i.e. suitable for pharmaceutical use), and optionally one or more further active substances. In a particular aspect, the invention relates to a pharmaceutical composition that contains SEQ ID NO: 70 and at least one suitable carrier, diluent or excipient (i.e. suitable for pharmaceutical use), and optionally one or more further active substances. In another particular aspect, the invention relates to a pharmaceutical composition that contains SEQ ID NO: 71 and at least one suitable carrier, diluent or excipient (i.e. suitable for pharmaceutical use), and optionally one or more further active substances.

Generally, the amino acid sequences, Nanobodies and polypeptides of the invention can be formulated and administered in any suitable manner known per se, for which reference is for example made to the general background art cited above (and in particular to WO 04/041862, WO 04/041863, WO 04/041865 and WO 04/041867) as well as to the standard handbooks, such as Remington's Pharmaceutical Sciences, 18$^{th}$ Ed., Mack Publishing Company, USA (1990) or Remington, the Science and Practice of Pharmacy, 21th Edition, Lippincott Williams and Wilkins (2005).

For example, the amino acid sequences, Nanobodies and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, sterile water and aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The amino acid sequences, Nanobodies and polypeptides of the invention can also be administered using gene therapy methods of delivery. See, e.g., U.S. Pat. No. 5,399,346, which is incorporated by reference in its entirety. Using a gene therapy method of delivery, primary cells transfected with the gene encoding an amino acid sequence, Nanobody or polypeptide of the invention can additionally be transfected with tissue specific promoters to target specific organs, tissue, grafts, tumors, or cells and can additionally be transfected with signal and stabilization sequences for subcellularly localized expression.

Thus, the amino acid sequences, Nanobodies and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the amino acid sequences, Nanobodies and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, Nanobody or polypeptide of the invention. Their percentage in the compositions and preparations may, of course, be varied and may conveniently be between about 2 to about 60% of the weight of a given unit dosage form. The amount of the amino acid sequence, Nanobody or polypeptide of the invention in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the amino acid sequences, Nanobodies and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the amino acid sequences, Nanobodies and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The amino acid sequences, Nanobodies and polypeptides of the invention may also be administered intravenously or intraperitoneally by infusion or injection. Solutions of the amino acid sequences, Nanobodies and polypeptides of the invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the amino acid sequences, Nanobodies and polypeptides of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the amino acid sequences, Nanobodies and polypeptides of the invention may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the amino acid sequences, Nanobodies and polypeptides of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the amino acid sequences, Nanobodies and polypeptides of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the amino acid sequences, Nanobodies and polypeptides of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the amino acid sequence, Nanobodies and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the amino acid sequences, Nanobodies and polypeptides of the invention required for use in treatment will vary not only with the particular amino acid sequence, Nanobody or polypeptide selected but also with the route of administration, the nature of the condition being treated and the age and condition of the patient and will be ultimately at the discretion of the attendant physician or clinician. Also the dosage of the amino acid sequences, Nanobodies and polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one IL-6R related disease and/or disorders, said method comprising administering, to a subject in need thereof, a pharmaceutically active amount of an amino acid sequence of the invention, of a Nanobody of the invention, of a polypeptide of the invention, of a compound of the invention, of a construct of the invention and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease and/or disorder that is associated with IL-6, with IL-6R, with the IL-6/IL-6R complex, with its biological or pharmacological activity, and/or with the biological pathways or signalling in which IL-6, IL-6R and/or the IL-6/IL-6R complex are involved, said method comprising administering, to a subject in need thereof, a pharmaceutically active amount of an amino acid sequence of the invention, of a Nanobody of the invention, of a polypeptide of the invention, of a compound of the invention, of a construct of the invention and/or of a pharmaceutical composition comprising the same. In particular, the invention relates to a method for the prevention and/or treatment of at least one disease and/or disorder that can be prevented and/or treated by modulating IL-6, IL-6R, the IL-6/IL-6R complex, its biological or pharmacological activity, and/or the biological pathways or signalling in which IL-6, IL-6R and/or the IL-6/IL-6R complex is involved, said method comprising administering, to a subject in need thereof, a pharmaceutically active amount of an amino acid sequence of the invention, of a Nanobody of the invention, of a polypeptide, of a compound of the invention, of a construct of the invention of the invention, and/or of a pharmaceutical composition comprising the same. In particular, said pharmaceutically effective amount may be an amount that is sufficient to modulate IL-6, IL-6R, the IL-6/IL-6R complex, its biological or pharmacological activity, and/or the biological pathways or signalling in which IL-6. IL-6R and/or the IL-6/IL-6R complex are involved.

The invention also relates to a method for the prevention and/or treatment of at least one disease and/or disorder that can be prevented and/or treated by administering of an amino acid sequence of the invention, a Nanobody of the invention or a polypeptide of the invention to a patient, said method comprising administering, to a subject in need thereof, a pharmaceutically active amount of an amino acid sequence of the invention, of a Nanobody of the invention, of a polypeptide of the invention, of a compound of the invention, of a construct of the invention and/or of a pharmaceutical composition comprising the same.

More in particular, the invention relates to a method for the prevention and/or treatment of at least one disease and/or disorder chosen from the group consisting of the diseases and disorders listed herein, said method comprising administering, to a subject in need thereof, a pharmaceutically active amount of an amino acid sequence of the invention, of a Nanobody of the invention, of a polypeptide of the invention, of a compound of the invention, of a construct of the invention and/or of a pharmaceutical composition comprising the same.

In particular, the present invention relates to a method for the prevention and/or treatment of sepsis, various forms of cancer, bone resorption, osteoporosis, cachexia, psoriasis, mesangial proliferative glomerulonephritis, Kaposi's sarcoma, AIDS-related lymphoma, and inflammatory diseases, said method comprising administering a pharmaceutically active amount of an amino acid sequence of the invention, of a Nanobody of the invention, of a polypeptide of the invention, and/or of a pharmaceutical composition comprising the same. The various forms of cancer may be chosen from the same. group consisting of multiple myeloma disease (MM), renal cell carcinoma (RCC), plasma cell leukaemia, lymphoma, B-lymphoproliferative disorder (BLPD), and prostate cancer. The inflammatory diseases may be chosen from the group consisting of rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus.

In another particular aspect, the present invention relates to a method for the prevention and/or treatment of sepsis, various forms of cancer, bone resorption, osteoporosis, cachexia, psoriasis, mesangial proliferative glomerulonephritis, Kaposi's sarcoma, AIDS-related lymphoma, and inflammatory diseases, said method comprising administering a pharmaceutically active amount of SEQ ID NO: 70, and/or of a pharmaceutical composition comprising the same. In another particular aspect, the present invention relates to a method for the prevention and/or treatment of sepsis, various forms of cancer, bone resorption, osteoporosis, cachexia, psoriasis, mesangial proliferative glomerulonephritis, Kaposi's sarcoma, AIDS-related lymphoma, and inflammatory diseases, said method comprising administering a pharmaceutically active amount of SEQ ID NO: 71, and/or of a pharmaceutical composition comprising the same. The various forms of cancer may be chosen from the group consisting of multiple myeloma disease (MM), renal cell carcinoma (RCC), plasma cell leukaemia, lymphoma, B-lymphoproliferative disorder (BLPD), and prostate cancer. The inflammatory diseases may be chosen from the group consisting of rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus.

In another embodiment, the invention relates to a method for immunotherapy, and in particular for passive immunotherapy, which method comprises administering, to a subject suffering from or at risk of the diseases and disorders mentioned herein, a pharmaceutically active amount of an amino acid sequence of the invention, of a Nanobody of the invention, of a polypeptide of the invention, of a compound of the invention, of a construct of the invention and/or of a pharmaceutical composition comprising the same.

In the above methods, the amino acid sequences, Nanobodies, polypeptides, compounds and/or constructs of the invention and/or the compositions comprising the same can be administered in any suitable manner, depending on the specific pharmaceutical formulation or composition to be used. Thus, the amino acid sequences, Nanobodies, polypeptides, compounds and/or constructs of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease and/or disorder to be prevented or treated and other factorse well known to the clinician.

The amino acid sequences, Nanobodies, polypeptides, compounds and/or constructs of the invention and/or the compositions comprising the same are administered according to a regime of treatment that is suitable for preventing and/or treating the disease and/or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequences, Nanobody, polypeptide, compound or construct of the invention to be used, the specific route of administration and farmaceutical formulation or composition to be used, the age, gender, weight, diet, general condition of the patient, and similar factors well known to the clinician.

Generally, the treatment regimen will comprise the administration of one or more amino acid sequences, Nanobodies, polypeptides, compounds and/or constructs of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific amino acid sequence, Nanobody, polypeptide, compound and construct of the invention to be used, the specific route of administration and the specific pharmaceutical formulation or composition used, the amino acid sequences, Nanobodies, polypeptides, compounds and constructs of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, Nanobody, polypeptide, compound or construct of the invention will be used. It is however within the scope of the invention to use two or more amino acid sequences, Nanobodies, polypeptides, compounds and/or constructs of the invention in combination.

The amino acid sequences, Nanobodies, polypeptides, compounds and constructs of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, Nanobodies, polypeptides, compounds and constructs of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease and/or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, Nanobody, polypeptide, compound or (monovalent) construct of the invention in the preparation of a pharmaceutical composition for prevention and/or treatment of at least one IL-6R related disorders.

The invention also relates to the use of an amino acid sequence, Nanobody, polypeptide, compound or (monovalent) construct of the invention, in the preparation of a pharmaceutical composition for prevention and/or treatment of at least one of the diseases and disorders associated with IL-6, with IL-6R, with the IL-6/IL-6R complex and/or with the signalling pathways and/or the biological functions and responses in which IL-6, IL-6R and/or the IL-6/IL-6R complex are involved; and/or for use in one or more of the methods described herein.

The invention also relates to the use of an amino acid sequence, Nanobody, polypeptide, compound or construct of the invention in the preparation of a pharmaceutical composition for the prevention and/or treatment of at least one disease or disorder that can be prevented and/or treated by modulating IL-6, IL-6R, the IL-6/IL-6R complex, its biological or pharmacological activity, and/or the biological pathways or signalling in which IL-6, IL-6R and/or the IL-6/IL-6R complex is involved.

The invention also relates to the use of an amino acid sequence, Nanobody, polypeptide, compound or construct of the invention in the preparation of a pharmaceutical composition for the prevention and/or treatment of at least one disease or disorder that can be prevented and/or treated by administering an amino acid sequence, Nanobody, polypeptide, compound or construct of the invention to a patient.

More in particular, the invention relates to the use of an amino acid sequence, Nanobody, polypeptide, compound or construct of the invention in the preparation of a pharmaceutical composition for the prevention and/or treatment of IL-6R related disorders, and in particular for the prevention and treatment of a sepsis, various forms of cancer, bone resorption, osteoporosis, cachexia, psoriasis, mesangial proliferative glomerulonephritis, Kaposi's sarcoma, AIDS-related lymphoma, and inflammatory diseases, said method comprising administering a pharmaceutically active amount of an amino acid sequence of the invention, of a Nanobody of the invention, of a polypeptide of the invention, and/or of a pharmaceutical composition comprising the same. The various forms of cancer may be chosen from the group consisting of multiple myeloma disease (MM), renal cell carcinoma (RCC), plasma cell leukaemia, lymphoma, B-lymphoproliferative disorder (BLPD), and prostate cancer. The inflammatory diseases may be chosen from the group consisting of rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus.

The invention further relates to an amino acid sequence, a Nanobody, a compound or construct, a polypeptide, monovalent construct of the invention or a pharmaceutical composition comprising the same for use in the prevention and/or treatment of at least one IL-6R related disease and/or disorder.

The invention further relates to an amino acid sequence, a Nanobody, a compound or construct, a polypeptide, monovalent construct of the invention or a pharmaceutical composition comprising the same for use in the prevention and/or treatment of at least one disease and/or disorder associated with IL-6, with IL-6R, with the IL-6/IL-6R complex, with its biological or pharmacological activity, and/or with the biological pathways or signalling in which IL-6, IL-6R and/or the IL-6/IL-6R complex are involved.

The invention further relates to an amino acid sequence, a Nanobody, a compound or construct, a polypeptide, monovalent construct of the invention or a pharmaceutical composition comprising the same for use in the prevention and/or treatment of at least one disease and/or disorder that can be prevented and/or treated by modulating IL-6, IL-6R, the IL-6/IL-6R complex, its biological or pharmacological activity, and/or the biological pathways or signalling in which IL-6, IL-6R and/or the IL-6/IL-6R complex is involved.

The invention further relates to an amino acid sequence, a Nanobody, a compound or construct, a polypeptide, monovalent construct of the invention or a pharmaceutical composition comprising the same for use in the prevention and/or treatment of at least one disease and/or disorder that can be prevented and/or treated by administering of an amino acid sequence of the invention, a Nanobody of the invention or a polypeptide of the invention to a patient.

The invention further relates to an amino acid sequence, a Nanobody, a compound or construct, a polypeptide, monovalent construct of the invention or a pharmaceutical composition comprising the same for use in the prevention and/or treatment of sepsis, various forms of cancer, bone resorption, osteoporosis, cachexia, psoriasis, mesangial proliferative glomerulonephritis, Kaposi's sarcoma, AIDS-related lymphoma, and inflammatory diseases, said method comprising administering a pharmaceutically active amount of an amino acid sequence of the invention, of a Nanobody of the invention, of a polypeptide of the invention, and/or of a pharmaceutical composition comprising the same. The various forms of cancer may be chosen from the group consisting of multiple myeloma disease (MM), renal cell carcinoma (RCC), plasma cell leukaemia, lymphoma, B-lymphoproliferative disorder (BLPD), and prostate cancer. The inflammatory diseases may be chosen from the group consisting of rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

Again, in such a pharmaceutical composition, the one or more amino acid sequences, Nanobodies, polypeptides, compounds or constructs of the invention may also be suitably combined with one or more other active principles, such as those mentioned herein.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

ASPECTS

Aspect 1. Amino acid sequence directed against IL-6R, that comprises one or more stretches of amino acid residues chosen from the following:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;
and/or
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;

and/or e) SEQ ID NO's: 93-95; or f) a stretch of amino acid residues that has no more than 2, preferably no more than 1 amino acid difference with one of SEQ ID NO's: 93-95, provided that the amino acid sequence comprising said stretch of amino acid residues binds IL-6R with about the same or a higher affinity compared to the amino acid sequence comprising said stretch of amino acid residues without the 1 or 2 amino acid difference, said affinity as measured by surface plasmon resonance.

Aspect 2. Amino acid sequence according to aspect 1, that comprises two or more stretches of amino acid residues chosen from the following:

a) SEQ ID NO's: 80-82; or b) a stretch of amino acid residues that has no more than 2, preferably no more than 1 amino acid difference with one of SEQ ID NO's: 80-82, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;

and/or c) SEQ ID NO's: 84-91; or d) a stretch of amino acid residues that has no more than 2, preferably no more than 1 amino acid difference with one of SEQ ID NO's: 84-91, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;

and/or e) SEQ ID NO's: 93-95; or f) a stretch of amino acid residues that has no more than 2, preferably no more than 1 amino acid difference with one of SEQ ID NO's: 93-95, provided that the amino acid sequence comprising said stretch of amino acid residues binds IL-6R with about the same or a higher affinity compared to the amino acid sequence comprising said stretch of amino acid residues without the 1 or 2 amino acid difference, said affinity as measured by surface plasmon resonance.

such that (i) when the first stretch of amino acid residues corresponds to one of the amino acid sequences according to a), or b), the second stretch of amino acid residues corresponds to one of the amino acid sequences according to c), d), e) or f); (ii) when the first stretch of amino acid residues corresponds to one of the amino acid sequences according to c) or d), the second stretch of amino acid residues corresponds to one of the amino acid sequences according to a), b), e) or f); or (iii) when the first stretch of amino acid residues corresponds to one of the amino acid sequences according to e) or f), the second stretch of amino acid residues corresponds to one of the amino acid sequences according to a), b), c) or d).

Aspect 3. Amino acid sequence according to any of aspects 1 or 2, that comprises three or more stretches of amino acid residues, in which the first stretch of amino acid residues is chosen from the group consisting of:

a) SEQ ID NO's: 80-82; or b) a stretch of amino acid residues that has no more than 2, preferably no more than 1 amino acid difference with one of SEQ ID NO's: 80-82, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;

the second stretch of amino acid residues is chosen from the group consisting of:

c) SEQ ID NO's: 84-91; or d) a stretch of amino acid residues that has no more than 2, preferably no more than 1 amino acid difference with one of SEQ ID NO's: 84-91, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;

and the third stretch of amino acid residues is chosen from the group consisting of:

e) SEQ ID NO's: 93-95; or f) a stretch of amino acid residues that has no more than 2, preferably no more than 1 amino acid difference with one of SEQ ID NO's: 93-95, provided that the amino acid sequence comprising said stretch of amino acid residues binds IL-6R with about the same or a higher affinity compared to the amino acid sequence comprising said stretch of amino acid residues without the 1 or 2 amino acid difference, said affinity as measured by surface plasmon resonance.

Aspect 4. Amino acid sequence according to any of aspects 1 to 3, which comprises an immunoglobulin fold or which under suitable conditions is capable of forming an immunoglobulin fold.

Aspect 5. Amino acid sequence according to any of aspects 1 to 4, which is an immunoglobulin sequence.

Aspect 6. Amino acid sequence according to any of aspects 1 to 5, which essentially consists of 4 framework regions (FR1 to FR4, respectively) and 3 complementarity determining regions (CDR1 to CDR3, respectively), in which:

CDR1 is chosen from the group consisting of:

a) SEQ ID NO's: 80-82; or b) a stretch of amino acid residues that has no more than 2, preferably no more than 1 amino acid difference with one of SEQ ID NO's: 80-82, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;

and/or

CDR2 is chosen from the group consisting of:

c) SEQ ID NO's: 84-91; or d) a stretch of amino acid residues that has no more than 2, preferably no more than 1 amino acid difference with one of SEQ ID NO's: 84-91, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;
and/or
CDR3 is chosen from the group consisting of:
e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with about the same or a higher affinity compared to the amino acid sequence comprising said stretch of amino acid residues without the 1 or 2 amino acid difference, said affinity as measured by surface plasmon resonance.

Aspect 7. Amino acid sequence according to aspect 6, which essentially consists of 4 framework regions (FR1 to FR4, respectively) and 3 complementarity determining regions (CDR1 to CDR3, respectively), in which:
CDR1 is chosen from the group consisting of:
a) SEQ ID NO's: 80-82; or
b) a stretch of amino acid residues that has no more than 2, preferably no more than 1 amino acid difference with one of SEQ ID NO's: 80-82, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;
and
CDR2 is chosen from the group consisting of:
c) SEQ ID NO's: 84-91; or
d) a stretch of amino acid residues that has no more than 2, preferably no more than 1 amino acid difference with one of SEQ ID NO's: 84-91, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance;
and
CDR3 is chosen from the group consisting of:
e) SEQ ID NO's: 93-95; or
f) a stretch of amino acid residues that has no more than 2, preferably no more than 1 amino acid difference with one of SEQ ID NO's: 93-95, provided that the amino acid sequence comprising said stretch of amino acid residues binds IL-6R with about the same or a higher affinity compared to the amino acid sequence comprising said stretch of amino acid residues without the 1 or 2 amino acid difference, said affinity as measured by surface plasmon resonance.

Aspect 8. Amino acid sequence according to any of aspects 1 to 7, which comprises at least:
a) SEQ ID NO: 80; or
b) a stretch of amino acid residues that has no more than 2, preferably no more than 1 amino acid difference with SEQ ID NO: 80, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance.

Aspect 9. Amino acid sequence according to any of aspects 1 to 8, which comprises at least a stretch of amino acid residues chosen from the following:
a) SEQ ID NO's: 84, 89 or 91; or
b) a stretch of amino acid residues that has no more than 2, preferably no more than 1 amino acid difference with one of SEQ ID NO's: 84, 89 or 91, provided that the amino acid sequence comprising said stretch of amino acid residues binds IL-6R with about the same or a higher affinity compared to the amino acid sequence comprising said stretch of amino acid residues without the 1 or 2 amino acid difference, said affinity as measured by surface plasmon resonance.

Aspect 10. Amino acid sequence according to any of aspects 1 to 9, which comprises at least:
a) SEQ ID NO: 84; or
b) a stretch of amino acid residues that has no more than 2, preferably no more than 1 amino acid difference with SEQ ID NO: 84, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance.

Aspect 11. Amino acid sequence according to any of aspects 1 to 10, which comprises at least a stretch of amino acid residues chosen from the following:
a) SEQ ID NO's: 93-94; or
b) a stretch of amino acid residues that has no more than 2, preferably no more than 1 amino acid difference with one of SEQ ID NO's: 93-94, provided that the amino acid sequence comprising said stretch of amino acid residues binds IL-6R with about the same or a higher affinity compared to the amino acid sequence comprising said stretch of amino acid residues without the 1 or 2 amino acid difference, said affinity as measured by surface plasmon resonance.

Aspect 12. Amino acid sequence according to any of aspects 1 to 11, which comprises at least:
a) SEQ ID NO: 93; or
b) a stretch of amino acid residues that has no more than 2, preferably no more than 1 amino acid difference with SEQ ID NO: 93, provided that the amino acid sequence comprising said stretch of amino acid residues binds IL-6R with about the same or a higher affinity compared to the amino acid sequence comprising said stretch of amino acid residues without the 2 or 1 amino acid difference, said affinity as measured by surface plasmon resonance.

Aspect 13. Amino acid sequence according to any of aspects 1 to 12, which comprises at least two stretches of amino acid residues selected from:
a) SEQ ID NO: 80 and SEQ ID NO: 84;
b) SEQ ID NO: 80 and SEQ ID NO: 93; or
c) SEQ ID NO: 84 and SEQ ID NO: 93.

Aspect 14. Amino acid sequence according to any of aspects 1 to 13, which comprises SEQ ID NO: 80, SEQ ID NO: 84 and SEQ ID NO: 93.

Aspect 15. Amino acid sequence according to any of aspects 1 to 14, which essentially consists of a heavy chain variable domain sequence that is derived from a conventional four-chain antibody or which essentially consist of a heavy chain variable domain sequence that is derived from heavy chain antibody.

Aspect 16. Amino acid sequence according to any of aspects 1 to 15, which essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody.

Aspect 17. Amino acid sequence according to any of aspects 1 to 16 selected from the group consisting of:
a) SEQ ID NO's: 60-69;
b) a sequence that has no more than 2, preferably no more than 1 amino acid difference in one, two or all of its CDRs with one of SEQ ID NO's: 60-69, provided that the amino acid sequence with no more than 2, preferably no more than 1 amino acid difference in one, two or all of its CDRs binds IL-6R with about the same or a higher affinity compared to the binding by the one of SEQ ID NO's: 60-69, said affinity as measured by surface plasmon resonance;
c) a sequence that has no more than 2, preferably no more than 1 amino acid difference with one of SEQ ID NO's: 60-69, provided that the amino acid sequence with no more than 2, preferably no more than 1 amino acid difference with one of SEQ ID NO's: 60-69 binds IL-6R with about the same or a higher affinity compared to the binding by the one of SEQ ID NO's: 60-69, said affinity as measured by surface plasmon resonance.

Aspect 18. Amino acid sequence according to aspect 17 selected from the group consisting of:
a) SEQ ID NO's: 65-69;
b) a sequence that has no more than 2, preferably no more than 1 amino acid difference in one, two or all of its CDRs with one of SEQ ID NO's: 65-69, provided that the amino acid sequence with no more than 2, preferably no more than 1 amino acid difference in one, two or all of its CDRs binds IL-6R with about the same or a higher affinity compared to the binding by the one of SEQ ID NO's: 65-69, said affinity as measured by surface plasmon resonance;
c) a sequence that has no more than 2, preferably no more than 1 amino acid difference with one of SEQ ID NO's: 65-69, provided that the amino acid sequence with no more than 2, preferably no more than 1 amino acid difference with one of SEQ ID NO's: 65-69 binds IL-6R with about the same or a higher affinity compared to the binding by the one of SEQ ID NO's: 65-69, said affinity as measured by surface plasmon resonance.

Aspect 19. Amino acid sequence according to aspect 18 selected from the group consisting of:
a) SEQ ID NO: 66;
b) a sequence that has no more than 2, preferably no more than 1 amino acid difference in one, two or all of its CDRs with SEQ ID NO: 66, provided that the amino acid sequence with no more than 2, preferably no more than 1 amino acid difference in one, two or all of its CDRs binds IL-6R with about the same or a higher affinity compared to the binding by SEQ ID NO: 66, said affinity as measured by surface plasmon resonance;
c) a sequence that has no more than 2, preferably no more than 1 amino acid difference with SEQ ID NO: 66, provided that the amino acid sequence with no more than 2, preferably no more than 1 amino acid difference with SEQ ID NO: 66 binds IL-6R with about the same or a higher affinity compared to the binding by SEQ ID NO:66, said affinity as measured by surface plasmon resonance.

Aspect 20. Amino acid sequence according to any of aspects 1 to 19, that specifically binds to hIL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less.

Aspect 21. Amino acid sequence according to any of aspects 1 to 20, that specifically binds to cyno IL-6R with a dissociation constant ($K_D$) of 1 nM to 1 pM or less, preferably 500 pM to 1 pM or less, more preferably 100 pM to 1 pM or less, or even more preferably about 50 pM to 1 pM or less.

Aspect 22. Amino acid sequence according to any of aspects 1 to 21, that specifically binds to hIL-6R with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect 23. Amino acid sequence according to any of aspects 1 to 22, that specifically binds to cyno IL-6R with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect 24. Amino acid sequence according to any of aspects 1 to 23, that specifically binds to hIL-6R with a $k_{off}$ rate between $10^{-3}$ $s^{-1}$ ($t_{1/2}$=0.69 s) and $10^{-6}$ $s^{-1}$ (providing a near irreversible complex with a $t_{1/2}$ of multiple days), preferably between $10^{-4}$ $s^{-1}$ and $10^{-6}$ $s^{-1}$, more preferably between $10^{-5}$ $s^{-1}$ and $10^{-6}$ $s^{-1}$, such as about $10^{-5}$ $s^{-1}$ or lower.

Aspect 25. Amino acid sequence according to any of aspects 1 to 24, that specifically binds to cyno IL-6R with a $k_{off}$ rate between $10^{-3}$ $s^{-1}$ ($t_{1/2}$=0.69 s) and $10^{-6}$ $s^{-1}$ (providing a near irreversible complex with a $t_{1/2}$ of multiple days), preferably between $10^{-4}$ $s^{-1}$ and $10^{-6}$ $s^{-1}$, more preferably between $10^{-5}$ $s^{-1}$ and $10^{-6}$ $s^{-1}$, such as about $10^{-5}$ $s^{-1}$ or lower.

Aspect 26. Amino acid sequence according to any of aspects 1 to 25, that, in the TF-1 assay, has IC50 values (at 100 IU/mL IL-6) between 10 nM and 50 pM, preferably between 5 nM and 50 pM, more preferably between 1 nM and 50 pM or less, such as about 750 or 500 pM or less.

Aspect 27. Amino acid sequence according to any of aspects 1 to 26, that, in the TF-1 assay, has IC50 (at 5000 IU/mL IL-6) between 50 nM and 1 nM, preferably between 25 nM and 1 nM, more preferably between 10 nM and 1 nM or less, such as about 8 nM or less.

Aspect 28. Amino acid sequence according to any of aspects 1 to 27, that, in the TF-1 assay, has IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4

Aspect 29. Amino acid sequence according to any of aspects 1 to 28, that, in the TF-1 assay, has IC50 values that are at least the same and preferably better, at least two times, preferably three times, more preferably four times, even more preferably 5 times, 7 times or more than 7 times better compared to the IC50 value obtained for Tocilizumab (MRA).

Aspect 30. Amino acid sequence according to any of aspects 1 to 29, that has, in a plasma potency assay at EC50 values of IL-6, IC50 values between 500 pM and 50 pM, preferably between 250 pM and 50 pM, more preferably between 200 pM and 50 pM or less, such as 150 pM or less.

Aspect 31. Amino acid sequence according to any of aspects 1 to 30, that has, in a plasma potency assay at EC95 values of IL-6, IC50 values between 1000 pM and 100 pM, preferably between 750 pM and 100 pM, more preferably between 500 pM and 100 pM or less, such as 400 pM or less.

Aspect 32. Amino acid sequence according to any of aspects 1 to 31, that has, in a plasma potency assay of aspects 30 or 31, IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4.

Aspect 33. Amino acid sequence according to any of aspects 1 to 32, that has, in a plasma potency assay of aspects 30 or 31, IC50 values that are at least the same and preferably better, at least two times, preferably three times, more preferably four times, even more preferably 5 times, 7 times or more than 7 times better compared to the IC50 value obtained for Tocilizumab (MRA).

Aspect 34. Amino acid sequence according to any of aspects 1 to 33, that has, for binding to membrane IL-6R on CHO cells, IC50 values between 10 nM and 100 pM, preferably between 5 nM and 100 pM, more preferably between 2 nM and 10 nM, such as 2 nM or less.

Aspect 35. Compound or construct, that comprises or essentially consists of one or more amino acid sequences according to any of aspects 1 to 34, and optionally further comprises one or more other groups, residues, moieties or binding units, optionally linked via one or more linkers.

Aspect 36. Compound or construct according to aspect 35, in which said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Aspect 37. Compound or construct according to any of aspects 35 or 36, which is a multivalent construct, such as e.g. a bivalent or trivalent construct.

Aspect 38. Compound or construct according to any of aspects 35 to 37, which is a multispecific construct, such as e.g. a bispecific or trispecific construct.

Aspect 39. Compound or construct according to any of aspects 35 to 38, which has an increased half-life, compared to the corresponding amino acid sequence according to any of aspects 1 to 34 per se.

Aspect 40. Compound or construct according to aspect 39, in which said one or more other groups, residues, moieties or binding units provide the compound or construct with increased half-life, compared to the corresponding amino acid sequence according to any of aspects 1 to 20.

Aspect 41. Compound or construct according to aspect 39, in which said one or more other groups, residues, moieties or binding units that provide the compound or construct with increased half-life is chosen from the group consisting of serum proteins or fragments thereof, binding units that can bind to serum proteins, an Fc portion, and small proteins or peptides that can bind to serum proteins.

Aspect 42. Compound or construct according to aspect 39, in which said one or more other groups, residues, moieties or binding units that provide the compound or construct with increased half-life is chosen from the group consisting of human serum albumin or fragments thereof.

Aspect 43. Compound or construct according to aspect 39, in which said one or more other groups, residues, moieties or binding units that provides the compound or construct with increased half-life are chosen from the group consisting of binding units that can bind to serum albumin (such as human serum albumin) or a serum immunoglobulin (such as IgG).

Aspect 44. Compound or construct according to aspect 39, in which said one or more other groups, residues, moieties or binding units that provides the compound or construct with increased half-life are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum albumin (such as human serum albumin) or a serum immunoglobulin (such as IgG).

Aspect 45. Compound or construct according to aspect 39, in which said one or more other binding units that provides the compound or construct with increased half-life are chosen from SEQ ID NO's: 97-99.

Aspect 46. Compound or construct according to any of aspects 35 to 45, selected from the following polypeptide sequences:
a) SEQ ID NO's 70-72;
b) a polypeptide sequence that has no more than 2, preferably no more than 1 amino acid difference in one, two or all of its CDRs of the invention with one of SEQ ID NO's: 70-72, provided that the polypeptide sequence with no more than 2, preferably no more than 1 amino acid difference in one, two or all of its CDRs of the invention binds IL-6R with about the same or a higher affinity compared to the binding by the one of SEQ ID NO's: 70-72, said affinity as measured by surface plasmon resonance;
c) a polypeptide sequence that has no more than 2, preferably no more than 1 amino acid difference with one of SEQ ID NO's: 70-72, provided that the amino acid sequence with no more than 2, preferably no more than 1 amino acid difference with one of SEQ ID NO's: 70-72 binds IL-6R with about the same or a higher affinity compared to the binding by the one of SEQ ID NO's: 70-72, said affinity as measured by surface plasmon resonance.

Aspect 47. Compound or construct according to any of aspects 35 to 46, selected from the following polypeptide sequences:
a) SEQ ID NO's 70-71;
b) a polypeptide sequence that has no more than 2, preferably no more than 1 amino acid difference in one, two or all of its CDRs of the invention with one of SEQ ID NO's: 70-71, provided that the polypeptide sequence with no more than 2, preferably no more than 1 amino acid difference in one, two or all of its CDRs of the invention binds IL-6R with about the same or a higher affinity compared to the binding by the one of SEQ ID NO's: 70-71, said affinity as measured by surface plasmon resonance;
c) a polypeptide sequence that has no more than 2, preferably no more than 1 amino acid difference with one of SEQ ID NO's: 70-71, provided that the amino acid sequence with no more than 2, preferably no more than 1 amino acid difference with one of SEQ ID NO's: 70-71 binds IL-6R with about the same or a higher affinity compared to the binding by the one of SEQ ID NO's: 70-71, said affinity as measured by surface plasmon resonance.

Aspect 48. Compound or construct according to any of aspects 35 to 47, that has or essentially consists of the amino acid sequence of SEQ ID NO: 70.

Aspect 49. Compound or construct according to any of aspects 35 to 47, that has or essentially consists of the amino acid sequence of SEQ ID NO: 71.

Aspect 50. Compound or construct according to any of aspects 35 to 49, that specifically binds to hIL-6R with a dissociation constant ($K_D$) of 1 nM to 1 pM moles/liter or less, preferably 500 pM to 1 pM moles/liter or less, more preferably 100 pM to 1 pM moles/liter or less, or even more preferably about 50 pM to 1 pM or less.

Aspect 51. Compound or construct according to any of aspects 35 to 50, that specifically binds to cyno IL-6R with a dissociation constant ($K_D$) of 1 nM to 1 pM or less, preferably 500 pM to 1 pM or less, more preferably 100 pM to 1 pM or less, or even more preferably about 50 pM to 1 pM or less.

Aspect 52. Compound or construct according to any of aspects 35 to 51, that specifically binds to hIL-6R with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect 53. Compound or construct according to any of aspects 35 to 52, that specifically binds to cyno IL-6R with a $k_{on}$-rate of between $10^4$ $M^{-1}$ $s^{-1}$ to about $10^7$ $M^{-1}$ $s^{-1}$, preferably between $10^5$ $M^{-1}$ $s^{-1}$ and $10^7$ $M^{-1}$ $s^{-1}$, more preferably about $10^6$ $M^{-1}$ $s^{-1}$ or more.

Aspect 54. Compound or construct according to any of aspects 35 to 53, that specifically binds to hIL-6R with a $k_{off}$ rate between $10^{-3}$ $s^{-1}$ ($t_{1/2}$=0.69 s) and $10^{-6}$ $s^{-1}$ (providing a near irreversible complex with a $t_{1/2}$ of multiple days), preferably between $10^{-4}$ $s^{-1}$ and $10^{-6}$ $s^{-1}$, more preferably between $10^5$ $s^{-1}$ and $10^{-6}$ $s^{-1}$, such as about $10^{-5}$ $s^{-1}$ or lower.

Aspect 55. Compound or construct according to any of aspects 35 to 54, that specifically binds to cyno IL-6R with a $k_{off}$ rate between $10^{-3}$ $s^{-1}$ ($t_{1/2}$=0.69 s) and $10^{-6}$ $s^{-1}$ (providing a near irreversible complex with a $t_{1/2}$ of multiple days), preferably between $10^{-4}$ $s^{-1}$ and $10^{-6}$ $s^{-1}$, more preferably between $10^{-5}$ $s^{-1}$ and $10^{-6}$ $s^{-1}$, such as about $10^{-5}$ $s^{-1}$ or lower.

Aspect 56. Compound or construct according to any of aspects 35 to 55, that, in the TF-1 assay, has IC50 values (at 100 IU/mL IL-6) between 10 nM and 50 pM, preferably between 5 nM and 50 pM, more preferably between 1 nM and 50 pM or less, such as about 750 or 500 pM or less.

Aspect 57. Compound or construct according to any of aspects 35 to 56, that, in the TF-1 assay, has IC50 (at 5000 IU/mL IL-6) between 50 nM and 1 nM, preferably between 25 nM and 1 nM, more preferably between 10 nM and 1 nM or less, such as about 8 nM or less.

Aspect 58. Compound or construct according to any of aspects 35 to 57, that, in the TF-1 assay, has IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4

Aspect 59. Compound or construct according to any of aspects 35 to 58, that, in the TF-1 assay, has IC50 values that are at least the same and preferably better, at least two times, preferably three times, more preferably four times, even more preferably 5 times, 7 times or more than 7 times better compared to the IC50 value obtained for Tocilizumab (MRA).

Aspect 60. Compound or construct according to any of aspects 35 to 59, that has, in a plasma potency assay at EC50 values of IL-6, IC50 values between 500 pM and 50 pM, preferably between 250 pM and 50 pM, more preferably between 200 pM and 50 pM or less, such as 150 pM or less.

Aspect 61. Compound or construct according to any of aspects 35 to 60, that has, in a plasma potency assay at EC95 values of IL-6, IC50 values between 1000 pM and 100 pM, preferably between 750 pM and 100 pM, more preferably between 500 pM and 100 pM or less, such as 400 pM or less.

Aspect 62. Compound or construct according to any of aspects 35 to 61, that has, in a plasma potency assay of aspects 60 or 61, IC50 values that are at least the same and preferably better, at least two times, preferably three times, more preferably four times, even more preferably 5 times, 7 times or more than 7 times better compared to the IC50 value obtained for the reference IgG as defined by SEQ ID NO's: 1 and 2 or the reference Fab as defined by SEQ ID NO's: 3 and 4.

Aspect 63. Compound or construct according to any of aspects 35 to 62, that has, in a plasma potency assay of aspects 60 or 61, IC50 values that are at least the same and preferably better, at least two times, preferably three times, more preferably four times, even more preferably 5 times, 7 times or more than 7 times better compared to the IC50 value obtained for Tocilizumab (MRA).

Aspect 64. Compound or construct according to any of aspects 35 to 63, that has, for binding to membrane IL-6R on CHO cells, IC50 values between 10 nM and 100 pM, preferably between 5 nM and 100 pM, more preferably between 2 nM and 10 pM or less, such as 2 nM or less.

Aspect 65. Monovalent construct, comprising or essentially consisting of one amino acid sequence according to any of aspects 1 to 34.

Aspect 66. Use of an amino acid sequence according to any of aspects 1 to 34 or a monovalent construct according to aspect 65, in preparing a multivalent compound or construct according to any of aspects 37 to 64.

Aspect 67. Method for the preparation of a multivalent compound or construct according to any of aspects 37 to 64, comprising the linking of an amino acid sequence according to any of aspects 1 to 34 or a monovalent construct according to aspect 65 to one or more groups, residues, moieties or binding units.

Aspect 68. Method according to aspect 67, for the preparation of a multivalent compound or construct according to any of aspects 37 to 64, comprising the linking of an amino acid sequence according to any of aspects 1 to 34 or a monovalent construct according to aspect 65 to other groups, residues, moieties or binding units via one or more linkers.

Aspect 69. Nucleic acid or nucleotide sequence, that encodes an amino acid sequence according to any of aspects 1 to 34, a compound or construct according to any of aspects 35 to 64 that is such that it can be obtained by expression of a nucleic acid or nucleotide sequence encoding the same, or a monovalent construct according to aspect 65.

Aspect 70. Nucleic acid or nucleotide sequence according to aspect 69, that is in the form of a genetic construct.

Aspect 71. Host or host cell that expresses, or that under suitable circumstances is capable of expressing, an amino acid sequence according to any of aspects 1 to 34, a compound or construct according to any of aspects 35 to 64 that is such that it can be obtained by expression of a nucleic acid or nucleotide sequence encoding the same, or a monovalent construct according to aspect 65; and/or that comprises a nucleic acid or nucleotide sequence according to aspect 69, or a genetic construct according to aspect 70.

Aspect 72. Method for producing an amino acid sequence according to any of aspects 1 to 34, a compound or construct according to any of aspects 35 to 64 that is such that it can be obtained by expression of a nucleic acid or nucleotide sequence encoding the same, or a monovalent construct according to aspects 65, said method at least comprising the steps of:
a) expressing, in a suitable host cell or host organism or in another suitable expression system, a nucleic acid or nucleotide sequence according to aspect 69, or a genetic construct according to aspect 70;
optionally followed by:
b) isolating and/or purifying the amino acid sequence according to any of aspects 1 to 34, the compound or construct according to any of aspects 35 to 64 that is such that it can be obtained by expression of a nucleic acid or nucleotide sequence encoding the same, or the monovalent construct according to aspect 65 thus obtained.

Aspect 73. Method for producing an amino acid sequence according to any of aspects 1 to 34, a compound or construct according to any of aspects 35 to 64 that is such that it can be obtained by expression of a nucleic acid or nucleotide sequence encoding the same, or a monovalent construct according to aspect 65, said method at least comprising the steps of:
a) cultivating and/or maintaining a host or host cell according to aspect 71 under conditions that are such that said host or host cell expresses and/or produces at least one amino acid sequence according to any of aspects 1 to 34, compound or construct according to any of aspects 35 to 64 that is such that it can be obtained by expression of a nucleic acid or nucleotide sequence encoding the same, or a monovalent construct according to aspect 65,
optionally followed by:
b) isolating and/or purifying the amino acid sequence according to any of aspects 1 to 34, the compound or construct according to any of aspects 35 to 64 that is such that it can be obtained by expression of a nucleic acid or nucleotide sequence encoding the same, or the monovalent construct according to aspect 65 thus obtained.

Aspect 74. Composition, comprising at least one amino acid sequence according to any of aspects 1 to 34, compound or construct according to any of aspects 35 to 64, monovalent construct according to aspect 65, or nucleic acid or nucleotide sequence according to aspects 69 or 70.

Aspect 75. Composition according to aspect 74, which is a pharmaceutical composition.

Aspect 76. Composition according to aspect 74, which is a pharmaceutical composition, that further comprises at least one pharmaceutically acceptable carrier, diluent or excipient and/or adjuvant, and that optionally comprises one or more further pharmaceutically active polypeptides and/or compounds.

Aspect 77. Method for the prevention and/or treatment of at least one of the diseases and disorders associated with IL-6, with IL-6R, with the IL-6/IL-6R complex and/or with the signalling pathways and/or the biological functions and responses in which IL-6, IL-6R and/or the IL-6/IL-6R complex are involved, said method comprising administering, to a subject in need thereof, a pharmaceutically active amount of at least one amino acid sequence according to any of aspects 1 to 34, a compound or construct according to any of aspects 35 to 64, or a monovalent construct according to aspect 65, or composition according to any of aspects 75 to 76.

Aspect 78. Method according to aspect 77, wherein said diseases and disorders associated with IL-6R and/or with the IL-6/IL-6R complex and/or with the signaling pathways and/or the biological functions and responses in which IL-6 and/or the IL-6/IL-6R complex are involved are chosen from the group consisting of sepsis, various forms of cancer, bone resorption, osteoporosis, cachexia, psoriasis, mesangial proliferative glomerulonephritis, Kaposi's sarcoma, AIDS-related lymphoma, and inflammatory diseases.

Aspect 79. Method according to aspect 78, wherein said various forms of cancer are chosen from the group consisting of multiple myeloma disease (MM), renal cell carcinoma (RCC), plasma cell leukaemia, lymphoma, B-lymphoproliferative disorder (BLPD), and prostate cancer.

Aspect 80. Method according to aspect 78, wherein said inflammatory diseases are chosen from the group consisting of rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus.

Aspect 81. Method for the prevention and/or treatment of at least one disease or disorder that can be prevented and/or treated by administering, to a subject in need thereof, an amino acid sequence according to any of aspects 1 to 34, a compound or construct according to any of aspects 35 to 64, or a monovalent construct according to aspect 65, said method comprising administering, to a subject in need thereof, a pharmaceutically active amount of at least one amino acid sequence according to any of aspects 1 to 34, compound or construct according to any of aspects 35 to 64, or monovalent construct according to aspect 65, or composition according to any of aspects 75 to 76.

Aspect 82. Use of an amino acid sequence according to any of aspects 1 to 34, compound or construct according to any of aspects 35 to 64, or monovalent construct according to aspect 65, in the preparation of a pharmaceutical composition for prevention and/or treatment of at least one of the diseases and disorders associated with IL-6, with IL-6R, with the IL-6/IL-6R complex and/or with the signalling pathways and/or the biological functions and responses in which IL-6, IL-6R and/or the IL-6/IL-6R complex are involved; and/or for use in one or more of the methods according to aspects 77 to 81.

Aspect 83. An amino acid sequence according to any of aspects 1 to 34, a compound or construct according to any of aspects 35 to 64, or monovalent construct according to aspect 65 for use in the prevention and/or treatment of at least one of the diseases and disorders associated with IL-6, with IL-6R, with the IL-6/IL-6R complex and/or with the signalling pathways and/or the biological functions and responses in which IL-6, IL-6R and/or the IL-6/IL-6R complex are involved; and/or for use in one or more of the methods according to aspects 77 to 81.

Aspect 84. Derivative of an amino acid sequence according to any of aspects 1 to 34, a compound or construct according to any of aspects 35 to 64, or monovalent construct according to aspect 65.

Aspect 85. Derivative according to aspect 84, that can specifically bind to IL-6R.

Aspect 86. Derivative according to any of aspects 84 to 85, that has a serum half-life that is at least 1.5 times, preferably at least 2 times, such as at least 5 times, for example at least 10 times or more than 20 times, greater than the half-life of the amino acid sequence according to any of aspects 1 to 34 per se, compound or construct according to any of aspects 35 to 64 per se, or monovalent construct according to aspect 65 per se.

Aspect 87. Derivative according to any of aspects 84 to 86, that has a serum half-life that is increased with more than 1 hours, preferably more than 2 hours, more preferably more than 6 hours, such as more than 12 hours, or even more than 24, 48 or 72 hours, compared to the corresponding amino acid sequence according to any of aspects 1 to 34 per se, a compound or construct according to any of aspects 35 to 64 per se, or monovalent construct according to aspect 65 per se.

Aspect 88. Derivative according to any of aspects 84 to 87, that has a serum half-life in human of at least about 12 hours, preferably at least 24 hours, more preferably at least 48 hours, even more preferably at least 72 hours or more; for example, at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect 89. Derivative according to any of aspects 84 to 88, that is a pegylated derivative.

Aspect 90. Composition, comprising at least one derivative according to any of aspects 84 to 89.

EXAMPLES

I. Isolation of IL-6R Binding Nanobodies

Example 1

Materials

The materials used for the isolation of IL-6R binding Nanobodies are given in Table C-1.

Two representative anti-human IL-6R immunoglobulins described in EP 0628639 (a Fab fragment and a full-sized IgG) were generated and used as reference compounds. The Fab fragment and full-sized IgG were constructed based on the L-chain called "$RV_La$" (see EP 0628639 B1, Table 2, version (a)) and the H-chain called "$RV_Hf$" (see EP 0628639 B1, Table 3, version (f)). These particular L-chain and H-chain were chosen for the purposes of constructing the reference compounds because, according to EP 0628639 B1 (see for example paragraph [0074]), a reshaped human antibody comprising said L-chain and said H-chain exhibited an ability to bind to human IL-6R at the same level as PM1, a mouse monoclonal antibody against human IL-6R (see again EP 0628639 B1, paragraph and the further references cited therein).

The full-length reference IgG consisted of the amino acid sequences of SEQ ID NO: 1 (heavy chain) and SEQ ID NO: 2 (light chain). The Fab fragment consisted of the amino acid sequences of SEQ ID NO: 3 (heavy chain regions $V_Lb$ and $V_Hf$ fused to the CH1 region of human IgG1) and SEQ ID NO: 4 (reshaped human PM-1 variable light chain fused to human Ckappa).

Encoding DNA fragments were generated by assembly PCR using partially overlapping oligonucleotides. PCR products were cloned into a single, bi-cistronic vector which enables expression of functional, disulphide-linked Fab fragments in the periplasm of E. coli. Full-length IgG was produced in CHO cells transfected with 2 expression vectors containing the genes for the light and heavy chains. The gene encoding the heavy chain was created by fusing $V_Hf$ to the constant region of human IgG1. The light chain was as described in EP 0628639.

Example 2

Immunizations

Two llamas (81 and 82) were immunized with human IL-6R (Peprotech) according to the immunization schedule described in Table C-2.

After completion of the immunization schedule the immune response in each animal was analyzed by ELISA. To this end, biotinylated IL-6R (2 μg/ml) was captured in a neutravidin coated microtiter plate. Serial dilutions of serum samples collected at days 0, 28, 39 and 43 were added (starting dilution: 1/500) and bound llama IgG was detected by addition of goat anti-llama IgG HRP labeled. TMB was used as a substrate. Results are shown in FIG. 1.

Figures 1, 27:
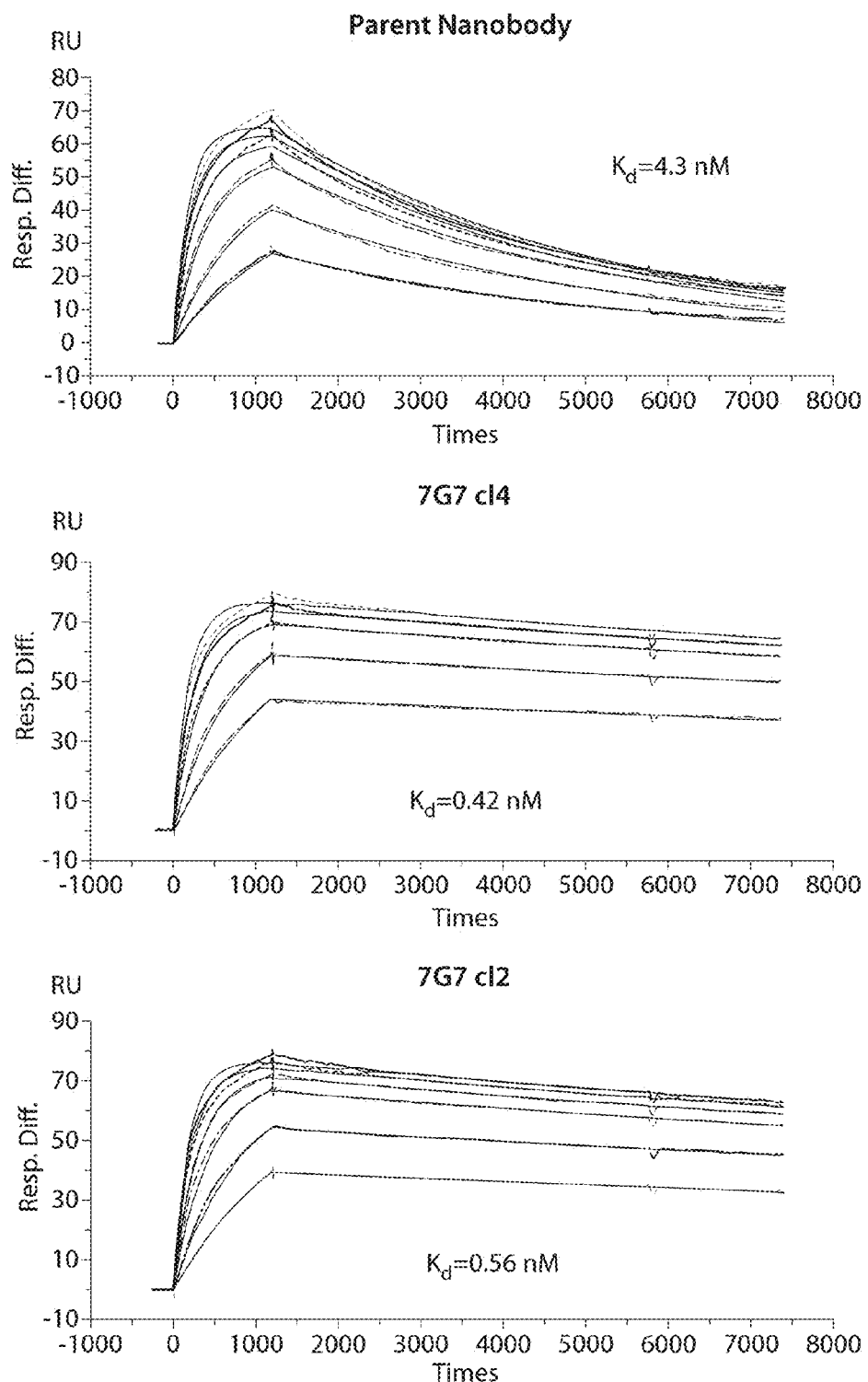
Figures 2, 27:
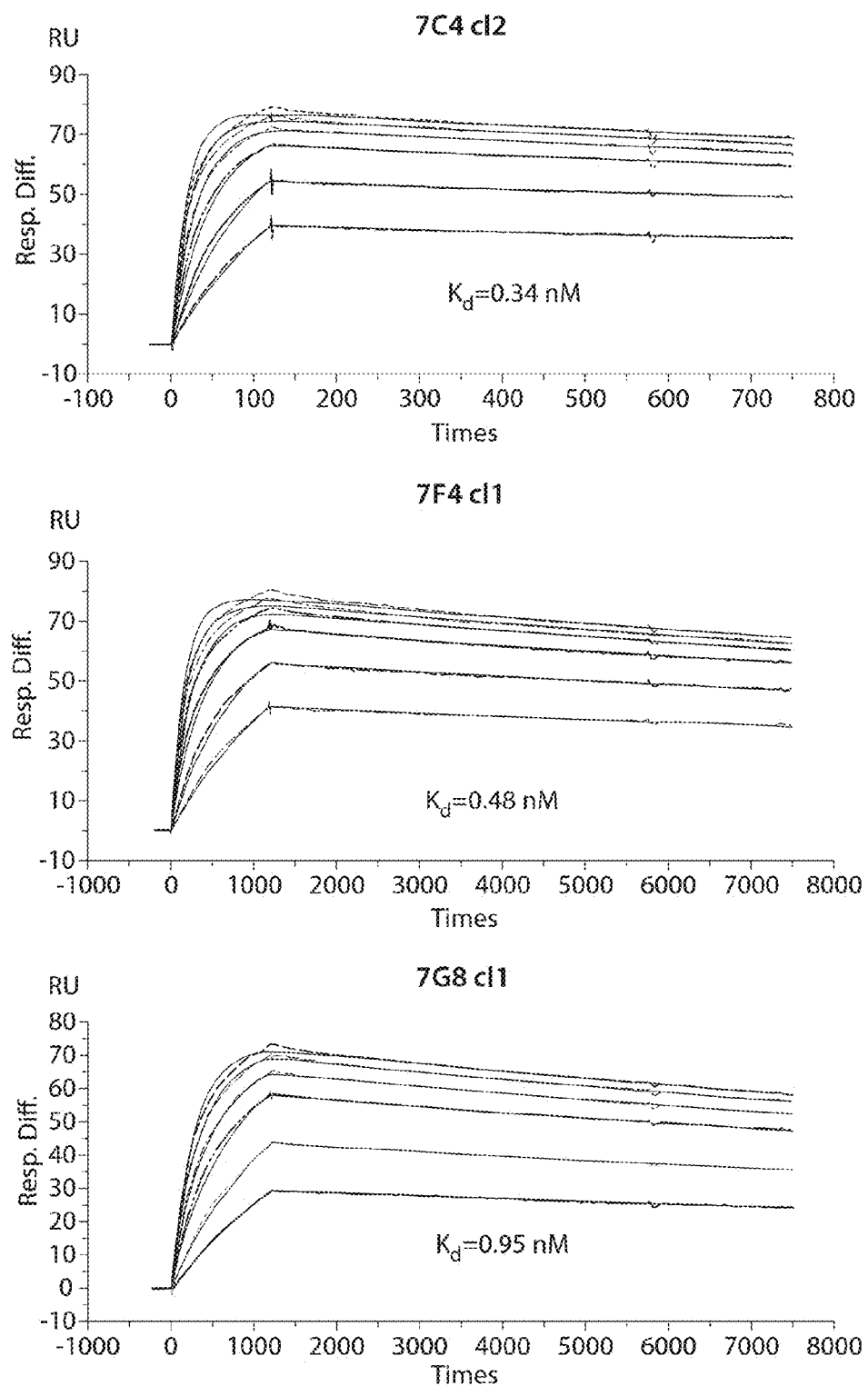

Immune responses were also analyzed by FACS: serial dilutions (starting dilution: 1/100) of serum samples collected at days 0, 28 and 43 were incubated with U266 cells (human myeloma). Bound llama IgG was detected by goat anti-llama IgG FITC labeled. Results are shown in FIG. 2.

Together these data show that both animals generated a good immune response against IL-6R and that at least a fraction of llama IgG recognize IL-6R on the surface of U266 cells.

Example 3

Library Construction

RNA extracted from PBLs and lymph node was used as starting material for RT-PCR to amplify Nanobody encoding gene fragments. These fragments were cloned into an expression vector derived from pUC119 which contained the LacZ promoter, a coliphage pIII protein coding sequence, a resistance gene for ampicillin or carbenicillin, a multicloning site and the gen3 leader sequence. In frame with the Nanobody coding sequence, the vector coded for a C-terminal c-myc tag and a (His)$_6$ tag. Phage was prepared according to a standard protocol and stored after filter sterilization at 4° C. for further use. The characteristics of the constructed libraries are shown in Table C-3.

Example 4

Selections

Selections were carried out with the above libraries using various conditions as summarized in Table C-4.

Only a single round of selection was performed for all conditions. Each selection output was analyzed for enrichment factor (# phage present in eluate relative to control), diversity (HinfI profiling) and percentage of IL-6R positive clones (ELISA). Based on these parameters the best selections were chosen for further analysis. To this end, the output from each selection was recloned as a pool into an expression vector derived from pUC119 which contained the LacZ promoter, a resistance gene for ampicillin or carbenicillin, a multicloning site and the gen3 leader sequence. In frame with the Nanobody coding sequence, the vector coded for a C-terminal c-myc tag and a (His)$_6$ tag. Colonies were picked and grown in 96 deep well plates (1 ml volume) and induced by adding IPTG for Nanobody expression. Periplasmic extracts were prepared according to the standard protocol.

Example 5

Screening

Figure 3:
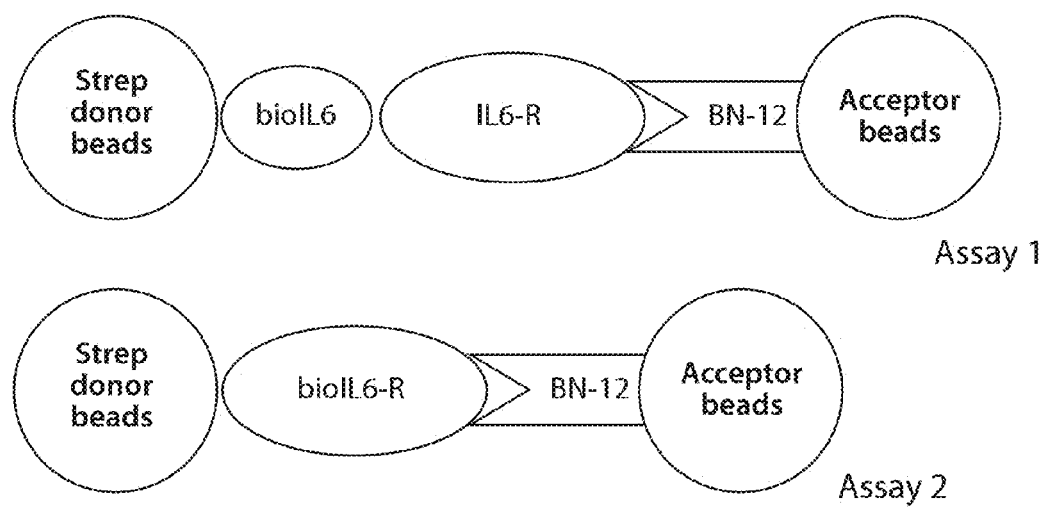
FIG. 3: Schematic representation of the Alphascreen assays used to identify Nanobodies against the IL-6 binding site on IL-6R.

The periplasmic extracts were analyzed first for their ability to inhibit the IL-6-IL-6R interaction. To this end, 2 independent Alphascreen assays were set up which are depicted schematically in FIG. 3. In assay 1, the periplasmic extracts were incubated with soluble IL-6 receptor (1 nM), biotinylated IL-6 (3 nM), streptavidin coated donor beads and MAb BN-12 coated acceptor beads (20 µg/ml). Nanobodies positive in this assay could either inhibit the IL-6/IL-6R interaction or IL-6R-MAb BN-12 interaction. To discriminate between these 2 possibilities a second assay was set up (Assay 2). In this assay the periplasmic extract were incubated with bio-IL-6R (0.3 nM), streptavidin coated donor beads and MAb BN-12 coated acceptor beads (10 µg/ml). Nanobodies positive in assay 1 but negative in assay 2 were considered as IL-6-IL-6R inhibitors.

Periplasmic extracts were diluted 25-fold in both assays which corresponds roughly to a final concentration of 40 nM. A statistical overview of the screening effort is shown in Table C-5 below. Nanobodies showing the strongest inhibition were selected for off-rate analysis on Biacore and DNA sequencing. FIG. 4 shows protein sequences of inhibitory Nanobodies that were selected for further analysis in cell based assays. Table C-6 shows $k_{off}$-values of these inhibitory Nanobodies.

Example 6

Nanobody Expression and Purification

Figure 5:
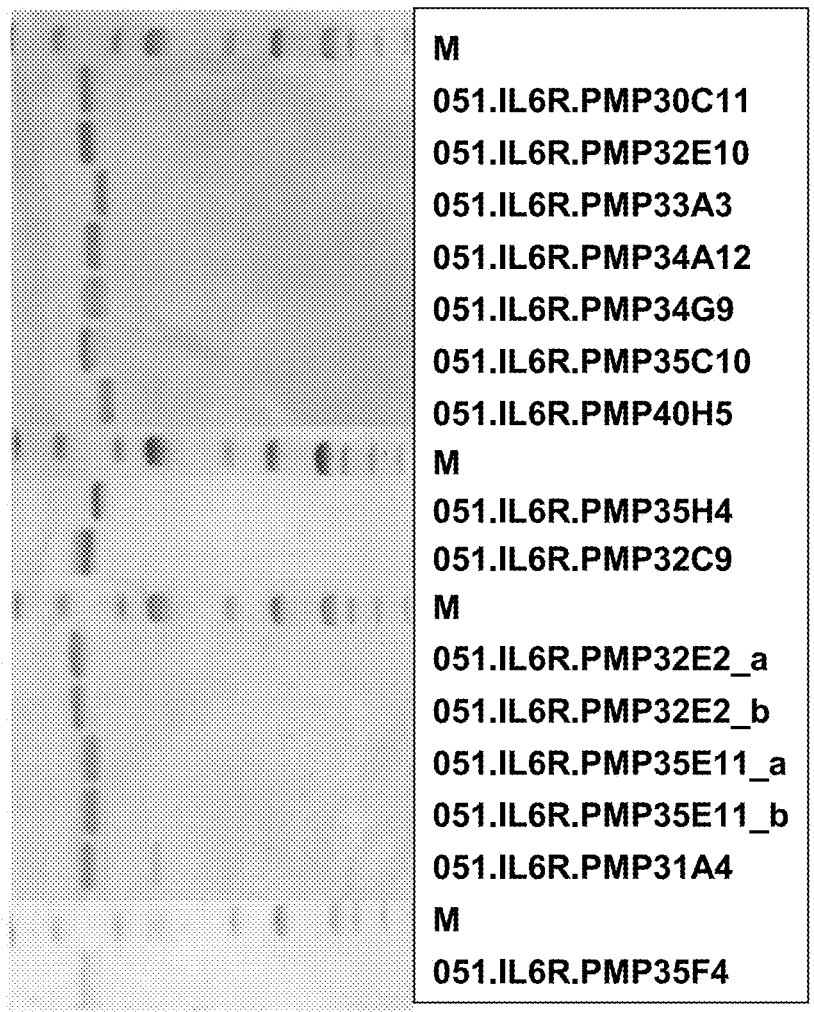
FIG. 5: SDS-PAGE of purified Nanobodies obtained as described in Example 6.

Selected Nanobodies were expressed in *E. coli* as c-myc, (His)6-tagged proteins in a culture volume of 50 or 250 ml. Expression was induced by addition of 1 mM IPTG and allowed to continue for 4 h at 37° C. After spinning the cell cultures, periplasmic extracts were prepared by freeze-thawing the pellets. These extracts were used as starting material for immobilized metal affinity chromatography (IMAC). Nanobodies were eluted from the column with 150 mM imidazole and subsequently dialyzed against PBS. Total yield and yield per liter of cell culture are listed in Table C-7. SDS-PAGE of purified Nanobodies (except for PMP28E11) is shown in FIG. 5.

Example 7

Protein Based Competition Assay

Figure 6B:
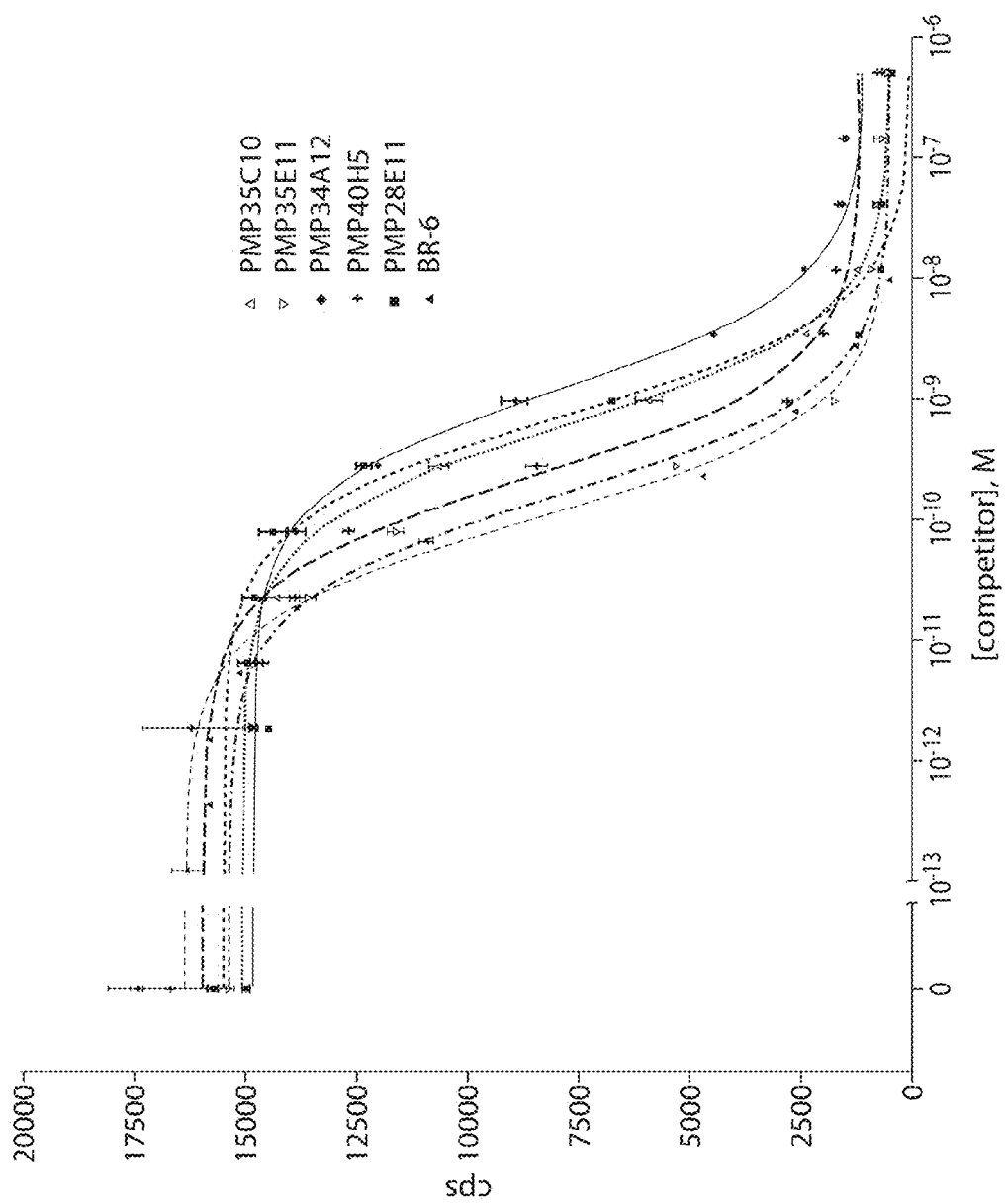
Figure 6C:
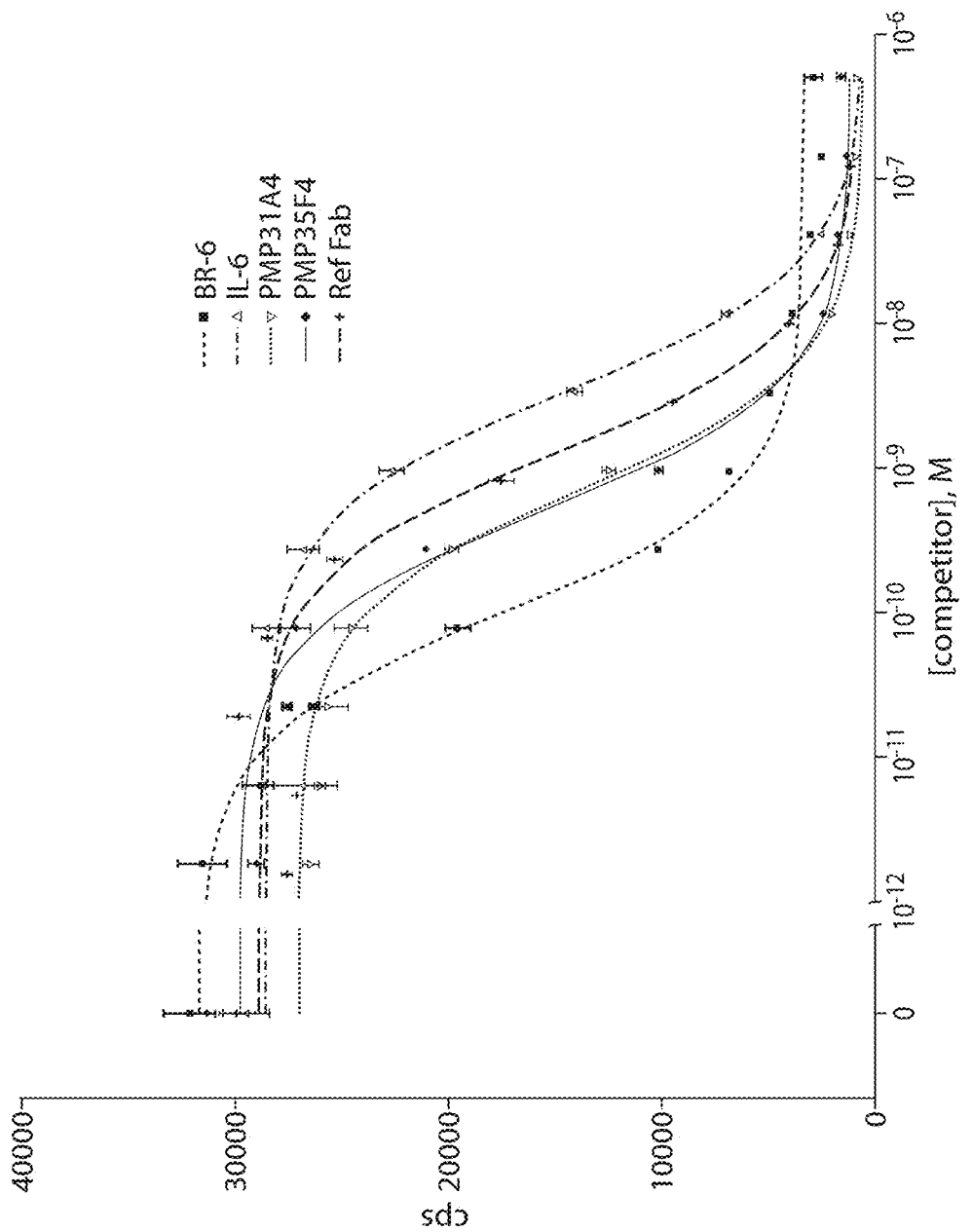
Figure 7A:
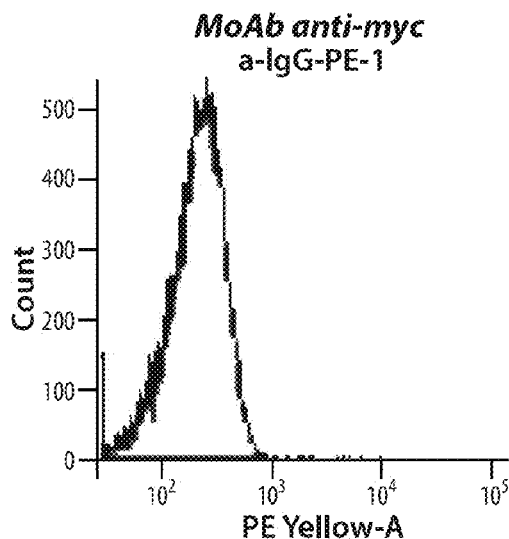
FIG. 7A-H: Binding of the anti-IL-6R Nanobodies to U266 cells analyzed by FACS. (A) MOAb antimyc; (B) BR6; (C) MoAb anti-IgG; (D) IL6R11; (E) IL6R04; (F) IL6R13; (G) IL6R14; (H) IL6R09.
Figure 7B:
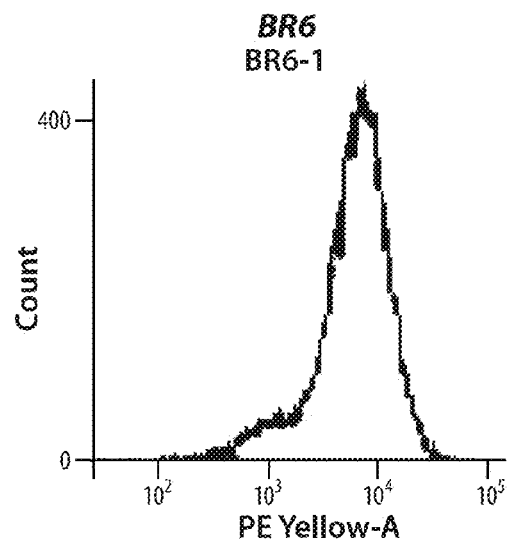
Figure 7C:
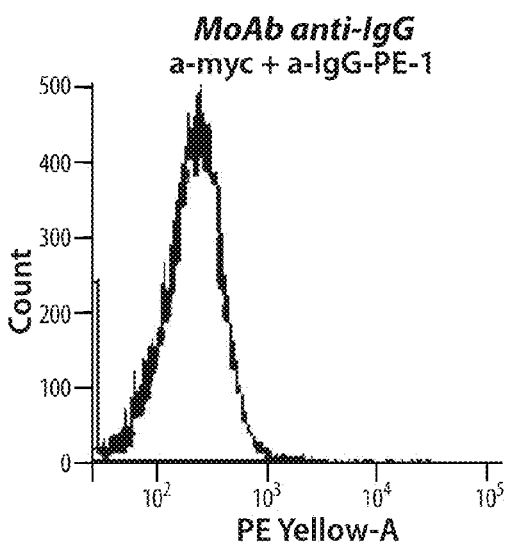
Figure 7D:
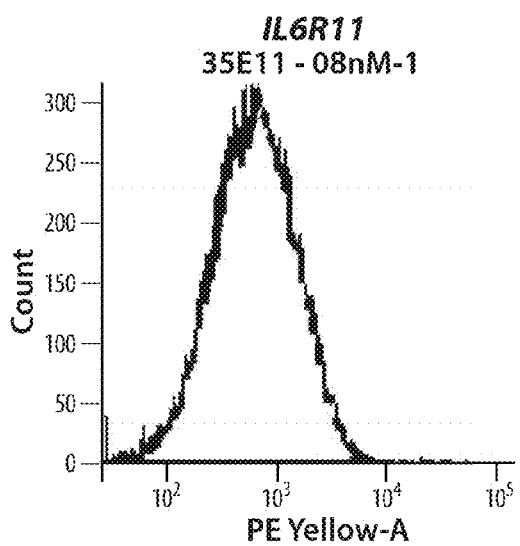
Figure 7E:
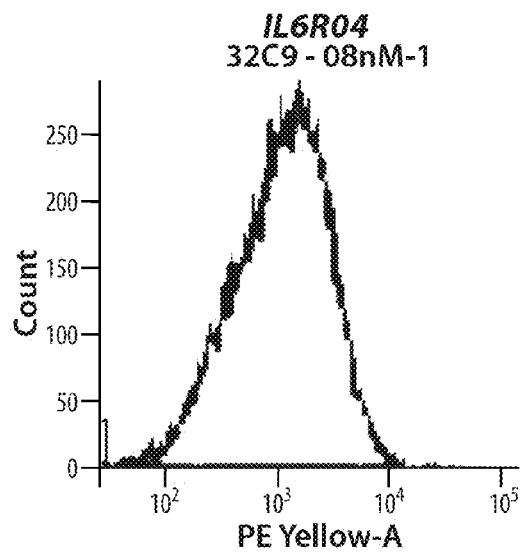
Figure 7F:
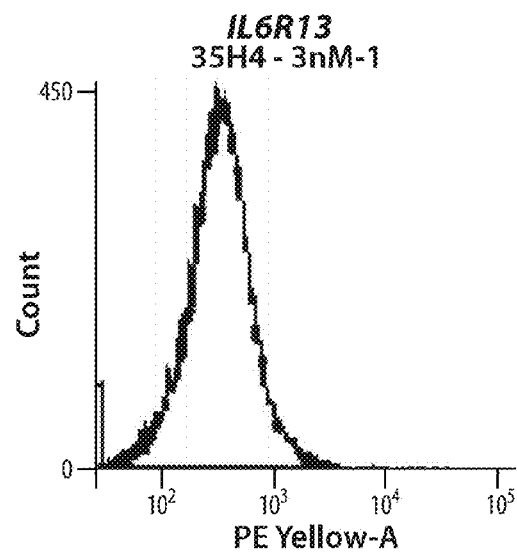
Figure 7G:
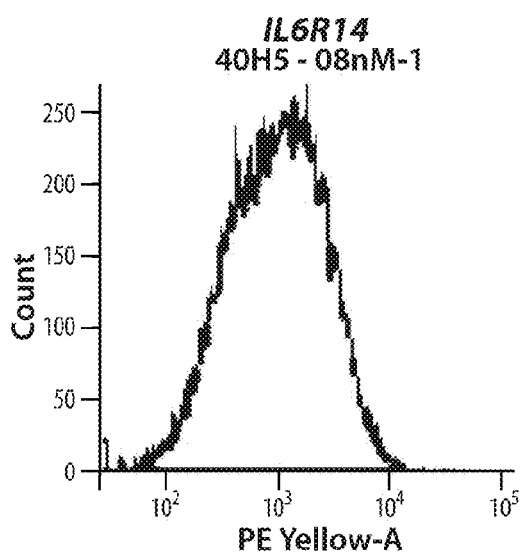
Figure 7H:
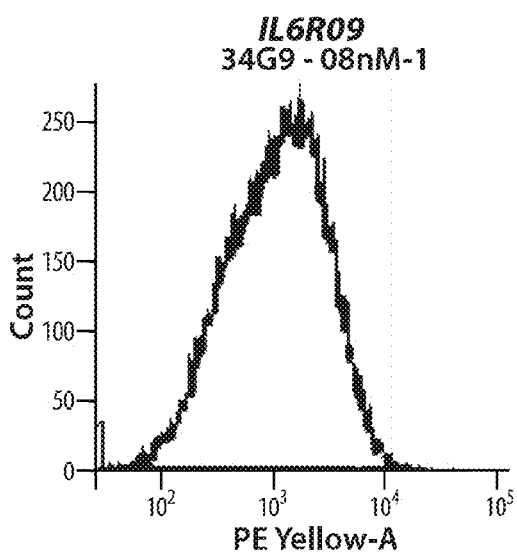
Figure 8F:
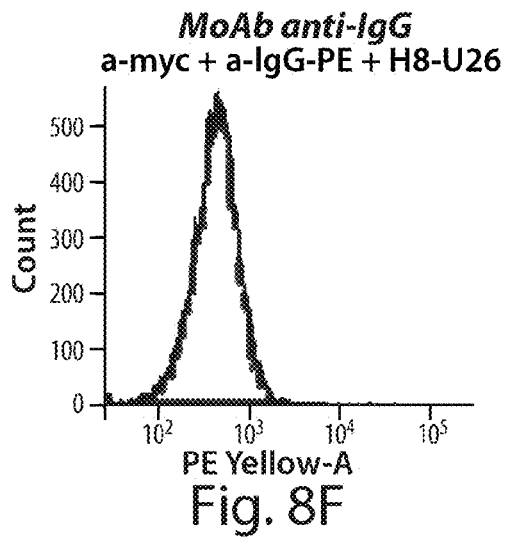
Figure 8G:
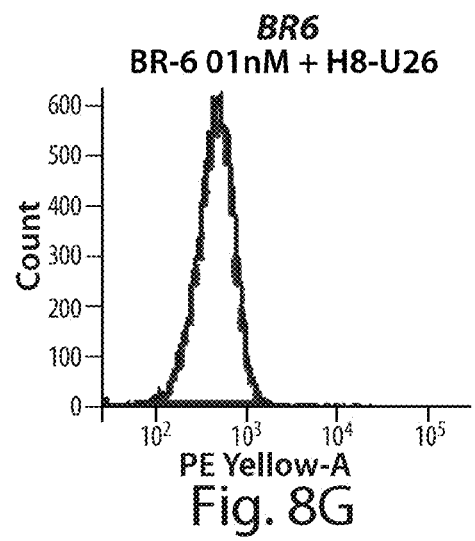
Figure 8H:
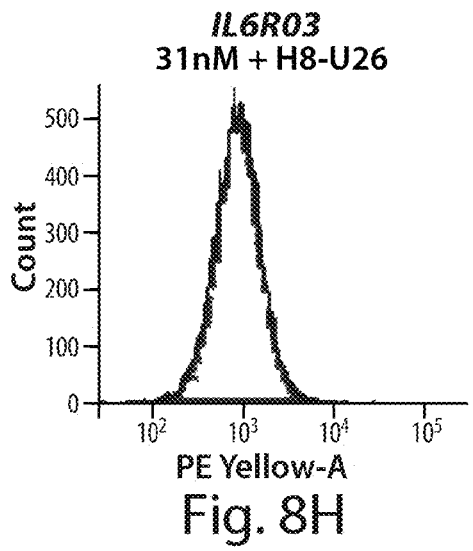
Figure 8I:
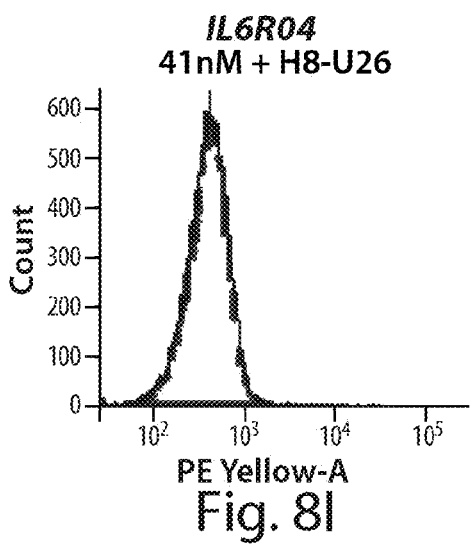
Figure 8J:
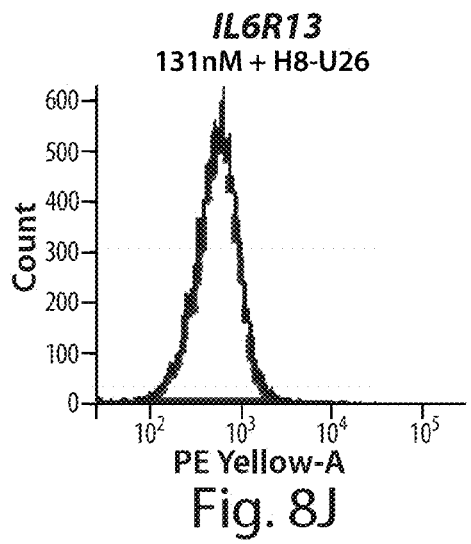
Figure 9:
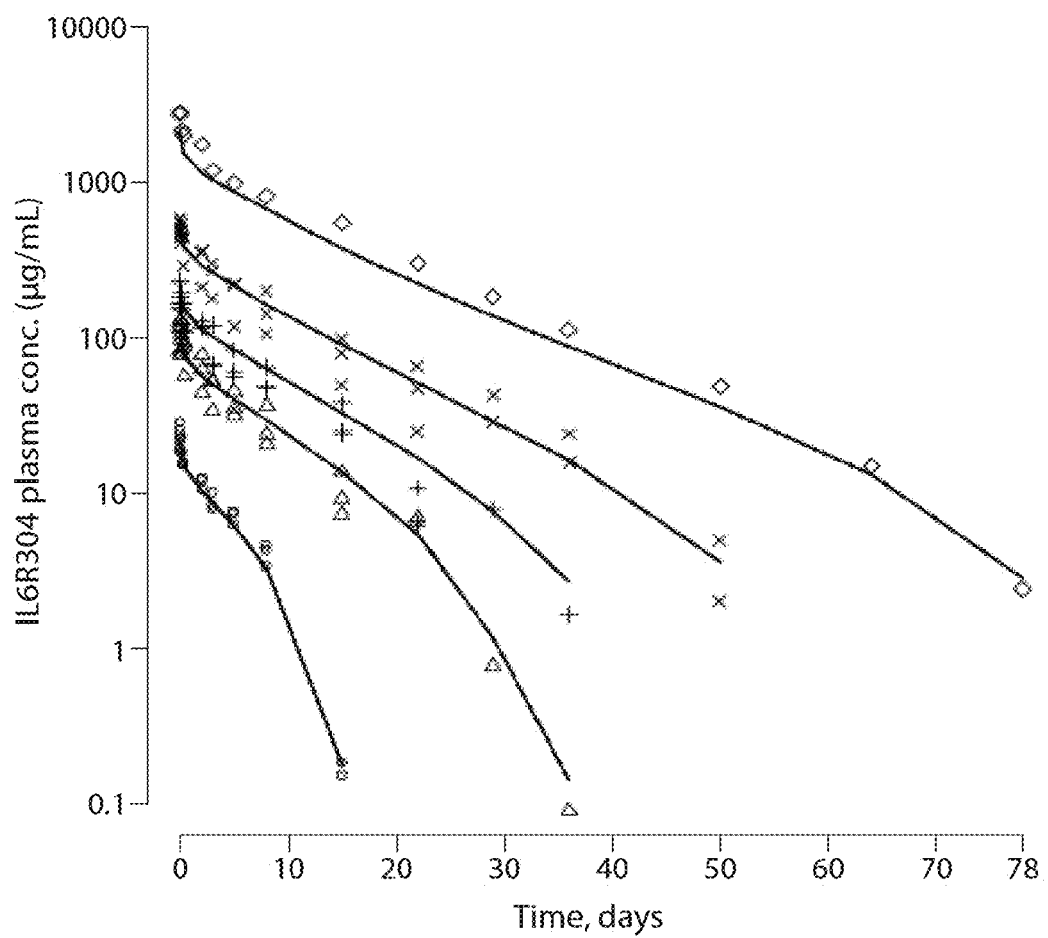
FIG. 9: Individual observed (symbols) and model predicted (solid line) plasma concentration-time profiles of IL6R304 in cynomolgus monkey after i.v. administration with 1 mg/kg (○), 5 mg/kg (Δ), 10 mg/kg (+), 25 mg/kg (×) and 100 mg/kg (◇).

The 14 purified Nanobodies were tested in Alphascreen for inhibition of the IL-6/IL-6R interaction. Serial dilutions of purified proteins (concentration range: 500 nM-10 pM) were added to IL-6R (0.3 nM) and incubated for 15 min. Subsequently 3 nM bio-IL-6 and BN-12-coated acceptor beads were added and this mixture was incubated for 1 hour. Finally streptavidin donor beads were added and after 1 hour incubator the plate was read on the Envision microplate reader. BR-6 and the Fab fragment described in Example 1 were included as reference. Results are shown in FIG. 6.

Dose-response curves were observed for all 14 Nanobodies with $IC_{50}$-values ranging from 48 pM to 1.7 nM (Table C-8). The most potent Nanobodies in this assay were PMP32C9 and PMP35H4. For PMP33A3 only partial (~50%) inhibition of IL-6/IL-6R interaction could be achieved.

Example 8

Affinity Determination of the Nanobodies Obtained

Affinity constants (Kd) of individual Nanobodies and the reference Fab fragment described in Example 1 were determined by surface plasmon resonance (SPR) on a Biacore 3000 instrument. In brief, IL-6R was amine-coupled to a CM5 sensor chip at a density of 800-1000 RU. Nanobodies were injected at 5 different concentrations between 1 and 50 nM. Flow rate was 45 µl/min in all experiments. Association and dissociation phase were 3 and 10 min, respectively. The chip was regenerated using Glycine/HCl pH 1.5. Binding curves at different concentrations of Nanobody were used to calculate the kinetic parameters $k_{on}$, $k_{off}$ and $K_d$ (Table C-9).

Example 9

Cell Based Potency of the Nanobodies in XG1 Assay

All purified Nanobodies were tested in the XG1 assay. XG1 is an IL-6-dependent human myeloma cell line. Half-maximal proliferation is achieved at ~20 pg/ml of IL-6. Assays were essentially performed as described by Zhang et al. (1994, Blood 83: 3654-3663). The reference Fab fragment as described in Example 1 was included as a reference. IC50 values ranged from 90 pM to 50 nM as listed in Table C-10. A small subset of Nanobodies was also tested in this assay in the presence of 1 mg/ml HSA.

Example 10

Cell Based Potency of the Nanobodies in TF1 Assay

Nanobodies were also tested for their ability to inhibit IL-6-dependent proliferation of TF-1 cells (ECACC no. 93022307; 1989, J. Cell Physiol., 140: 323; 1993, Exp. Cell Res., 208: 35) by blocking of IL-6 binding to IL-6R on the cell-surface. To this end, serial dilutions of Nanobody were pre-incubated with a fixed amount of TF-1 cells for 2 hours at 37° C. Subsequently IL-6 was added to a final concentration of 2 ng/ml. IL-6-dependent cell proliferation was allowed to continue for 72 hours and was measured by the incorporation of tritium labeled thymidine. IC50 values are listed in Table C-11.

Example 11

Competition with the Reference Fab for Binding to IL-6R

All 14 Nanobodies were analyzed for their ability to inhibit the binding of the reference Fab as described in Example 1 to IL-6R in an Alphascreen based assay. In this assay, 100 nM of purified Nanobody was incubated with 0.4 nM of biotinylated IL-6R. Reference-Fab coated acceptor beads and streptavidin coated donor beads were added and the concentration of Reference-Fab/IL-6R complex was measured. Values obtained in the presence of Nanobody were compared to a control where no Nanobody was added and the ratios between the 2 values, expressed as %, are listed in Table C-12. All Nanobodies, except IL6R03, show no or only partial inhibition of the reference Fab binding to IL-6R, suggesting that their epitopes do not or only partially overlap with the epitope of the reference Fab.

Example 12

Binding of the Nanobodies to U266 Cells

Binding of the Nanobodies to membrane-bound IL-6R expressed on U266 cells was analyzed in FACS. The analysis was done for purified Nanobodies from selected clones (IL6R04, IL6R09, IL6R11, IL6R13 and IL6R14). Results are shown in FIG. 7. All Nanobodies were able to bind to cell-surface expressed human IL-6R.

Example 13

Binding of the Nanobodies to Plasma-Derived Human IL-6R

Soluble IL-6R is present in human plasma at a concentration of 80-400 ng/ml. To determine whether Nanobodies IL6R03, IL6R04 and IL6R13 are able to bind plasma derived IL-6R, the effect of human plasma on Nanobody binding to U266 cells was evaluated. Human plasma inhibited binding to U266 cells, indicating that all 3 Nanobodies are able to bind to plasma-derived human IL-6R (see FIG. 8).

Example 14

Cross-Reactivity of the Nanobodies to Mouse IL-6R

Figure 10:
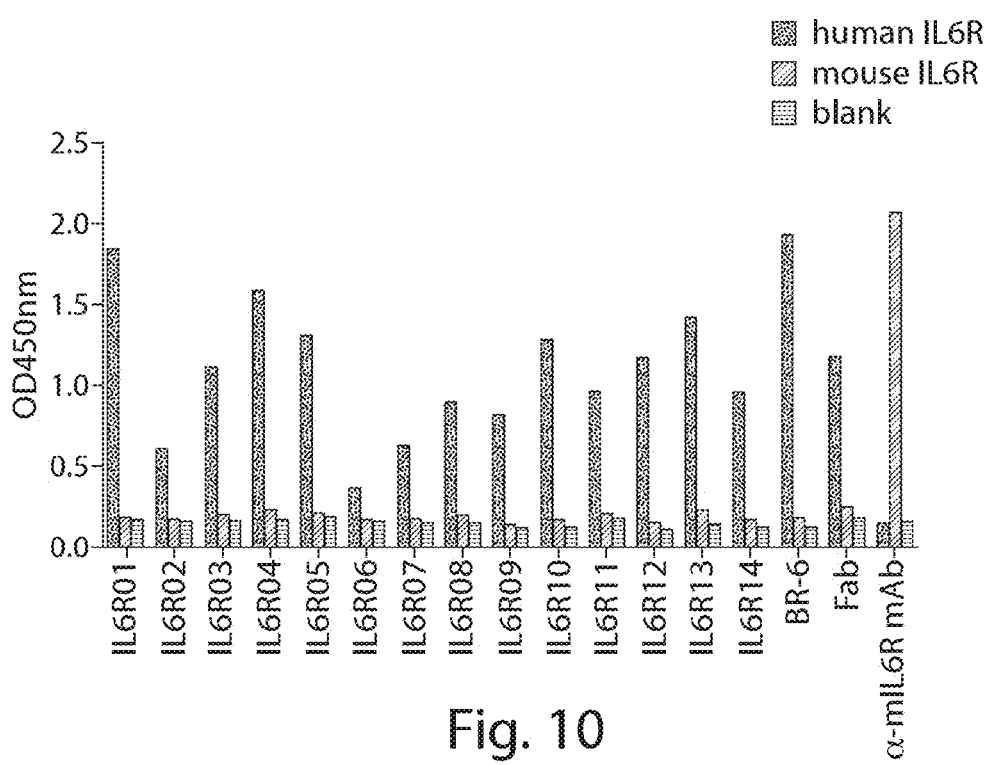
FIG. 10: Binding of the Nanobodies to mouse and human IL-6R. In each group of three bars, the bar on the left indicates human IL 6R, the middle bar indicates mouse IL 6R and the bar on the right indicates the blank.

Cross-reactivity of the Nanobodies to mouse IL-6R was analyzed in ELISA. To this end, 500 nM of the Nanobodies was applied to a microtiter plate coated with 1 μg/ml mouse and human IL-6R. Detection was performed with anti-myc and anti-mouse-HRP as first and second antibody respectively. Optical densities are shown in FIG. 10. No binding to mouse IL-6R was observed for any of the Nanobodies tested.

Example 15

Summary of the Isolation of IL-6R Binding Nanobodies

Immunization of 2 llamas with recombinant IL-6R resulted in a panel of 14 unique Nanobodies which were able to block the interaction between IL-6 and IL-6R. This panel was analyzed in detail and based on all the experimental data Nanobodies IL6R03, IL6R04 and IL6R13 were selected for further development. The most important Nanobody characteristics are summarized in Table C-13.

II. Formatting of the anti-IL-6R Nanobodies

Example 16

Preparation of Multivalent Constructs

The anti-IL-6R Nanobodies described in the previous paragraphs were also expressed as bispecific constructs consisting of a C-terminal anti-SA Nanobody (ALB1), a 9 amino acid Gly/Ser linker and an N-terminal anti-IL-6R Nanobody. In addition, 4 trivalent, bispecific Nanobodies were constructed consisting of a C-terminal and N-terminal anti-IL-6R Nanobody, an anti-SA Nanobody (ALB1) in the middle, all connected via 9 amino acid Gly/Ser linkers. The IDs of these Nanobodies are listed in Table C-14.

Example 17

Expression of Bispecific Anti-IL-6R Nanobodies

Figure 11:
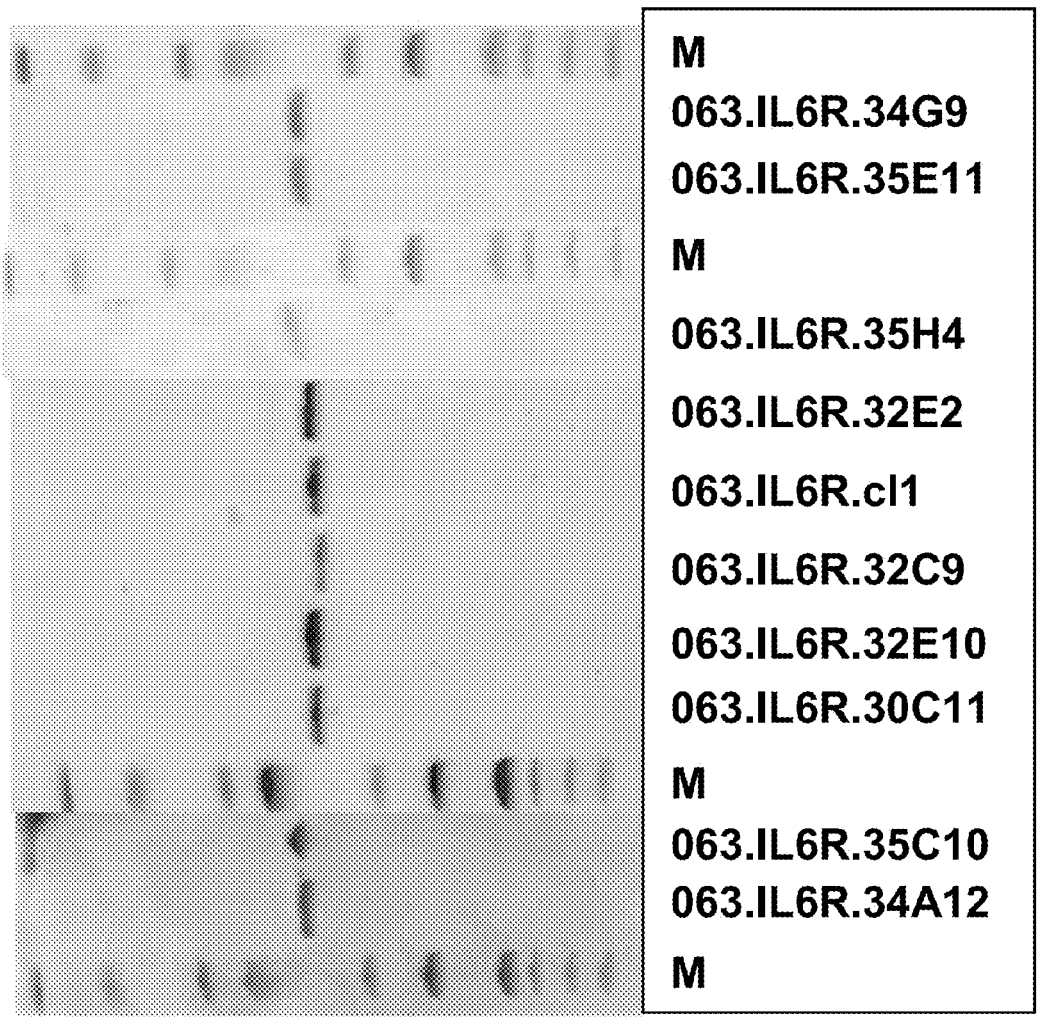
FIG. 11: SDS-PAGE of purified bispecific Nanobodies.

Bispecific Nanobody constructs were expressed in *E. coli* as c-myc, (His)6-tagged proteins and subsequently purified from the culture medium by immobilized metal affinity chromatography (IMAC) and size exclusion chromatography (SEC). Total yield and yield per liter of cell culture are listed in the Table C-15. SDS-PAGE of purified Nanobodies is shown in FIG. 11.

Example 18

Protein Based Competition Assay

Figure 12:
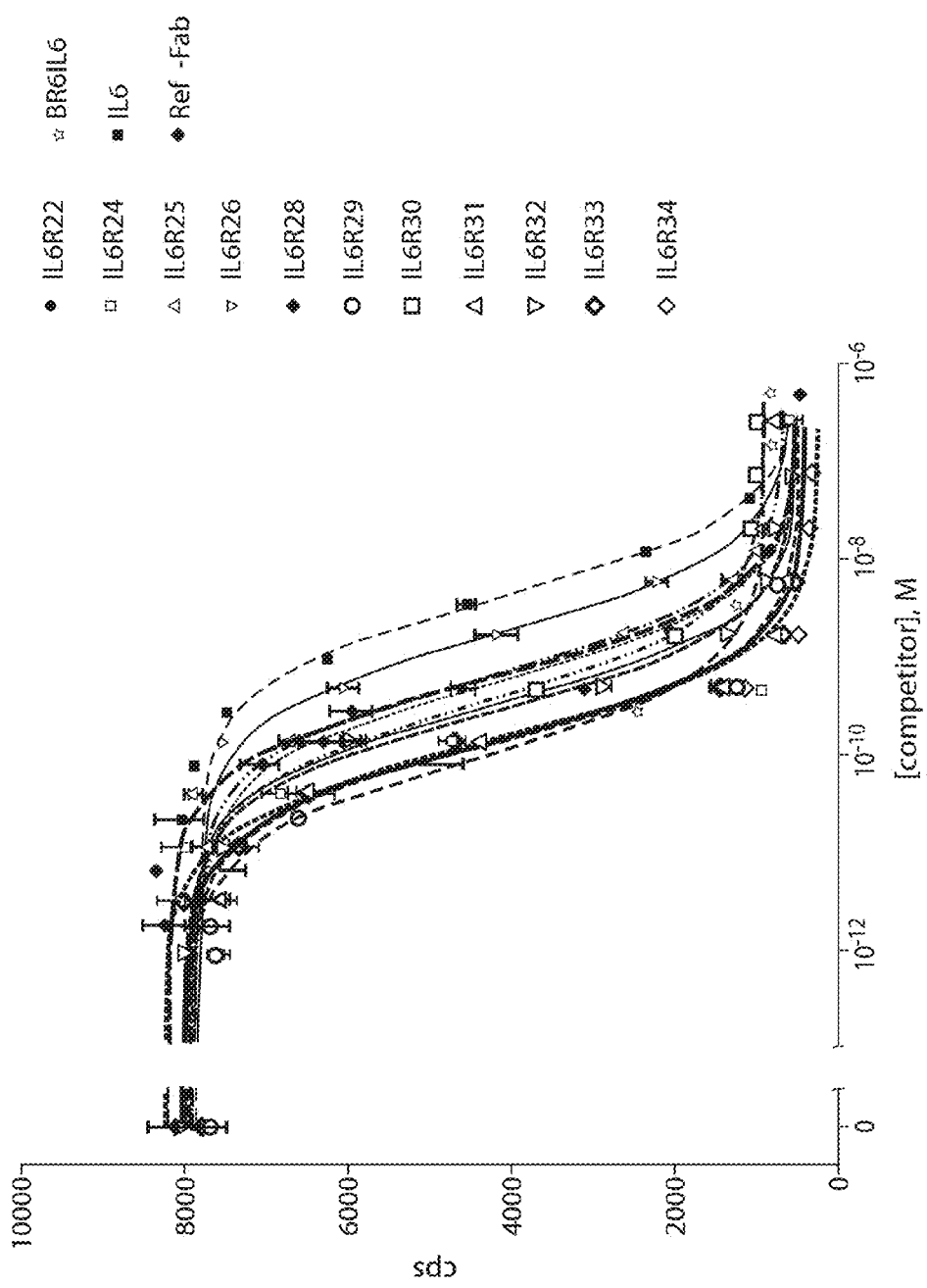
FIG. 12: Inhibition of IL-6/IL-6R interaction by bispecific Nanobodies as measured in alphascreen.
Figure 13A:
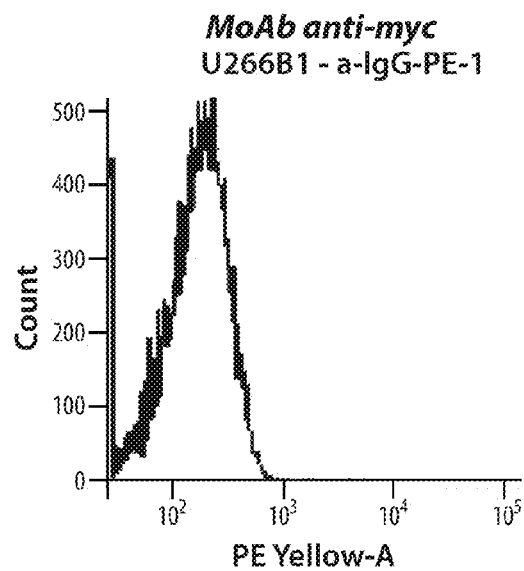
FIG. 13A-G: FACS analysis of bivalent Nanobodies binding to U266 cells. (A) MoAb anti-myc; (B) BR6; (C) MoAb anti-IgG; (D) IL6R23; (E) IL6R24; (F) IL6R29; (G) IL6R33.
Figure 13B:
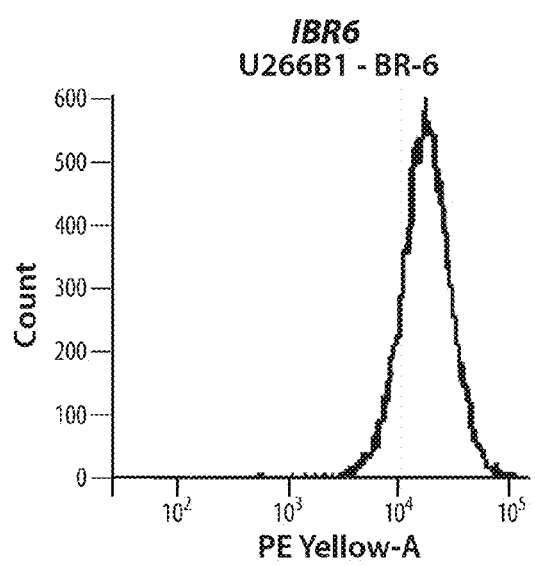
Figure 13C:
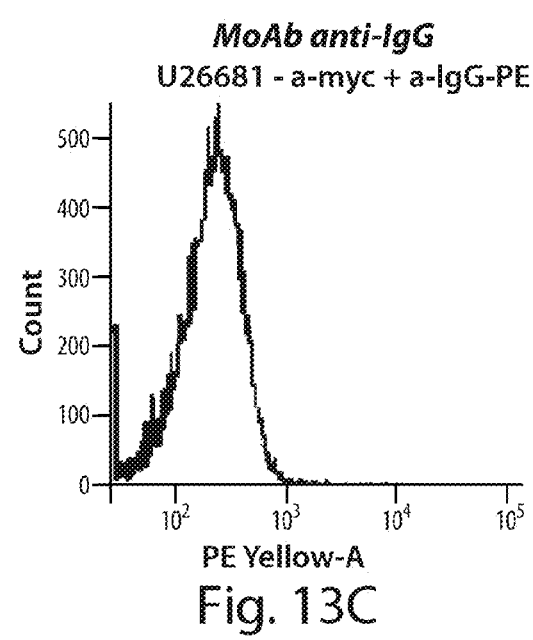
Figure 13D:
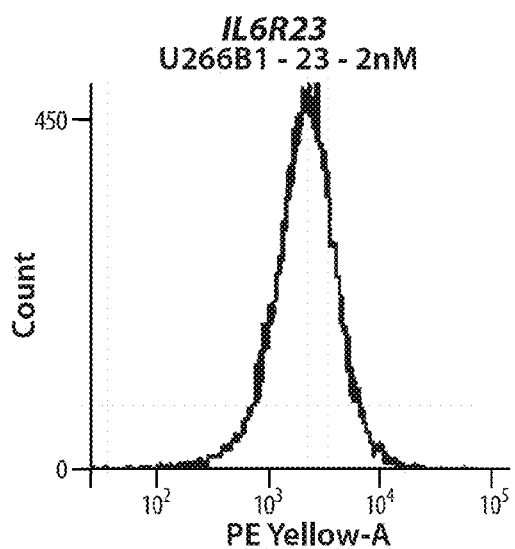
Figure 13E:
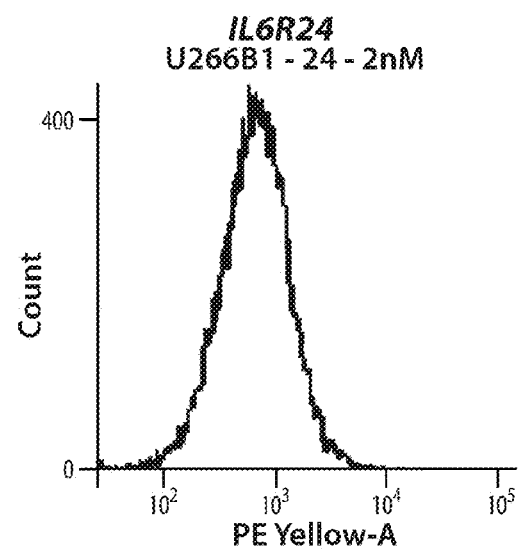
Figure 13F:
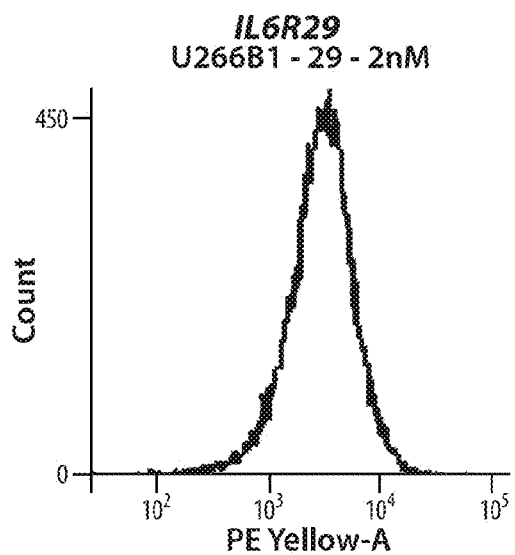
Figure 13G:
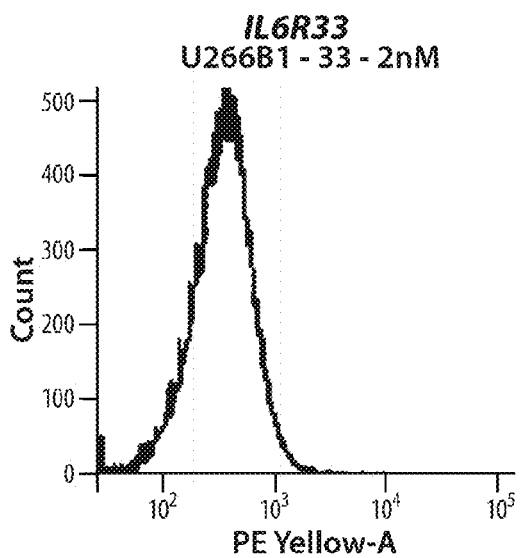
Figure 14A:
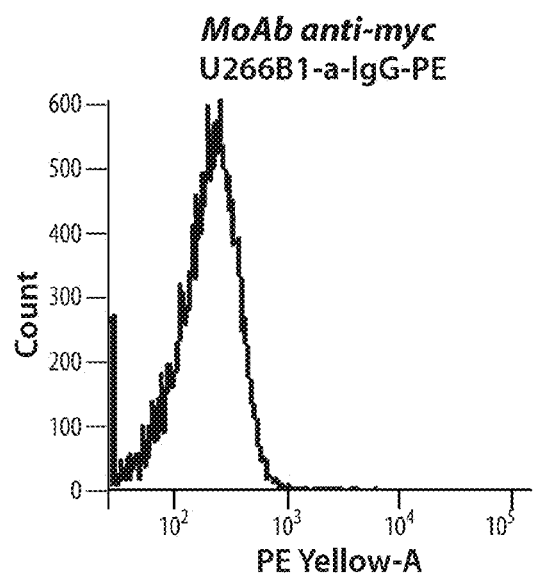
FIG. 14A-D: FACS analysis of trivalent Nanobodies binding to U266 cells. (A) MoAb anti-myc; (B) BR6; (C) IL6R44; (D) IL6R53.
Figure 14B:
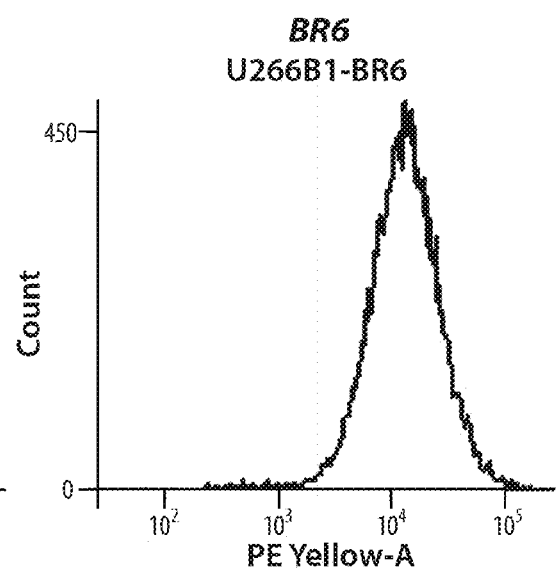
Figure 14C:
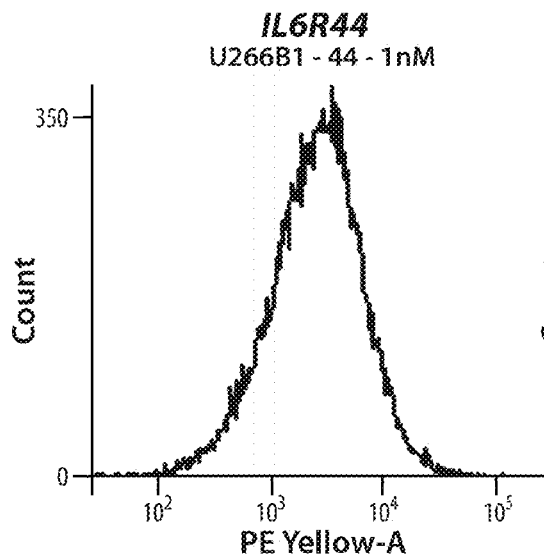
Figure 14D:
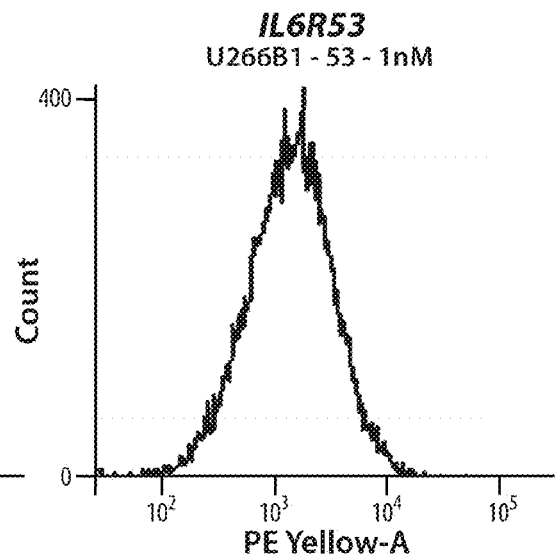

The purified bispecific Nanobodies were tested in Alphascreen for inhibition of the IL-6/IL-6R interaction. Serial dilutions of purified proteins (concentration range: 250 nM-5 pM) were added to IL-6R (0.3 nM) and incubated for 15 min. Subsequently 3 nM bio-IL-6 and BN-12-coated acceptor beads were added and this mixture was incubated for 1 hour. Finally streptavidin donor beads were added and after 1 hour incubator the plate was read on the Envision microplate reader. BR-6 and the Fab fragment described in Example 1 were included as reference. Results are shown in FIG. 12.

Dose-response curves were observed for all Nanobodies with $IC_{50}$-values ranging from 123 pM to 1.67 nM (Table C-16).

Example 19

Cell Based Potency of the Nanobodies in XG1 Assay

Bispecific Nanobodies were tested in the XG1 proliferation assay. IC50 values ranged from 60 pM to 65 nM. Nanobodies were also analyzed in this assay in the presence of 1 mg/mL human serum albumin. IC50 values range from 190 pM to 90 nM for bispecific Nanobodies. The reference IgG as described in Example 1 was included as reference. IC50 values are listed in Table C-17.

A loss in potency was observed when formatted Nanobodies were tested in the XG1 assay in the presence of albumin. Potencies of formatted Nanobodies IL6R24, IL6R44 and IL6R49 were superior to or in the same range as the reference IgG in the presence of serum albumin.

Example 20

Determination of Affinity for IL-6R

Binding of bispecific Nanobodies to IL-6R was analyzed by surface plasmon resonance. Kinetic parameters were determined and are listed in Table C-18. No significant loss in affinity for IL-6R was observed for the Nanobodies in bivalent format (IL6R23, IL6R24, IL6R33).

Example 21

Determination of Affinity for Serum Albumin

Binding of formatted Nanobodies to serum albumin was analyzed by surface plasmon resonance. Affinity constants (Kd) were determined and are listed in Table C-19. The albumin binding Nanobody Alb-1 (SEQ ID NO: 97) was included for comparison. The affinities were in the range of previously formatted Nanobodies containing the same anti-serum albumin building block, however in general a lower affinity was observed. This was particularly the case for mouse serum albumin affinity.

Example 22

Binding of the Formatted Nanobodies to U266 Cells

Binding of formatted Nanobodies from selected clones (IL6R23, IL6R24, IL6R29, IL6R33, IL6R44 and IL6R53) to U266 cells was analyzed by FACS. Results are shown in FIGS. 13 and 14. Bivalent Nanobodies IL6R23, IL6R24, IL6R29 and IL6R33 show reduced binding as compared to the monovalent building blocks, whereas similar binding was observed for trivalent Nanobodies IL6R44 and IL6R53.

III. Sequence Optimization of Anti-IL-6R Nanobodies

Example 23

Sequence Optimization Strategy

Protein sequences of Nanobodies IL6R03, IL6R04 and IL6R13 were each aligned with the 5 closest human germlines sharing the highest degree of homology (FIG. 15). Amino acid differences in the framework regions relative to the human germline consensus sequence are color coded. Amino acid differences highlighted in light gray were selected for conversion into the human counterpart whereas amino acids highlighted in dark gray were left untouched. Initially a panel of 4 sequence optimized variants was generated for each of the 3 Nanobodies (Stage 1). These variants were analyzed for a number of parameters and the results obtained were used to design a second set of Nanobodies (Stage 2). Protein sequences of all sequence optimized variants are shown in FIG. 16.

Example 24

Sequence Optimization Stage 1

Figure 17:
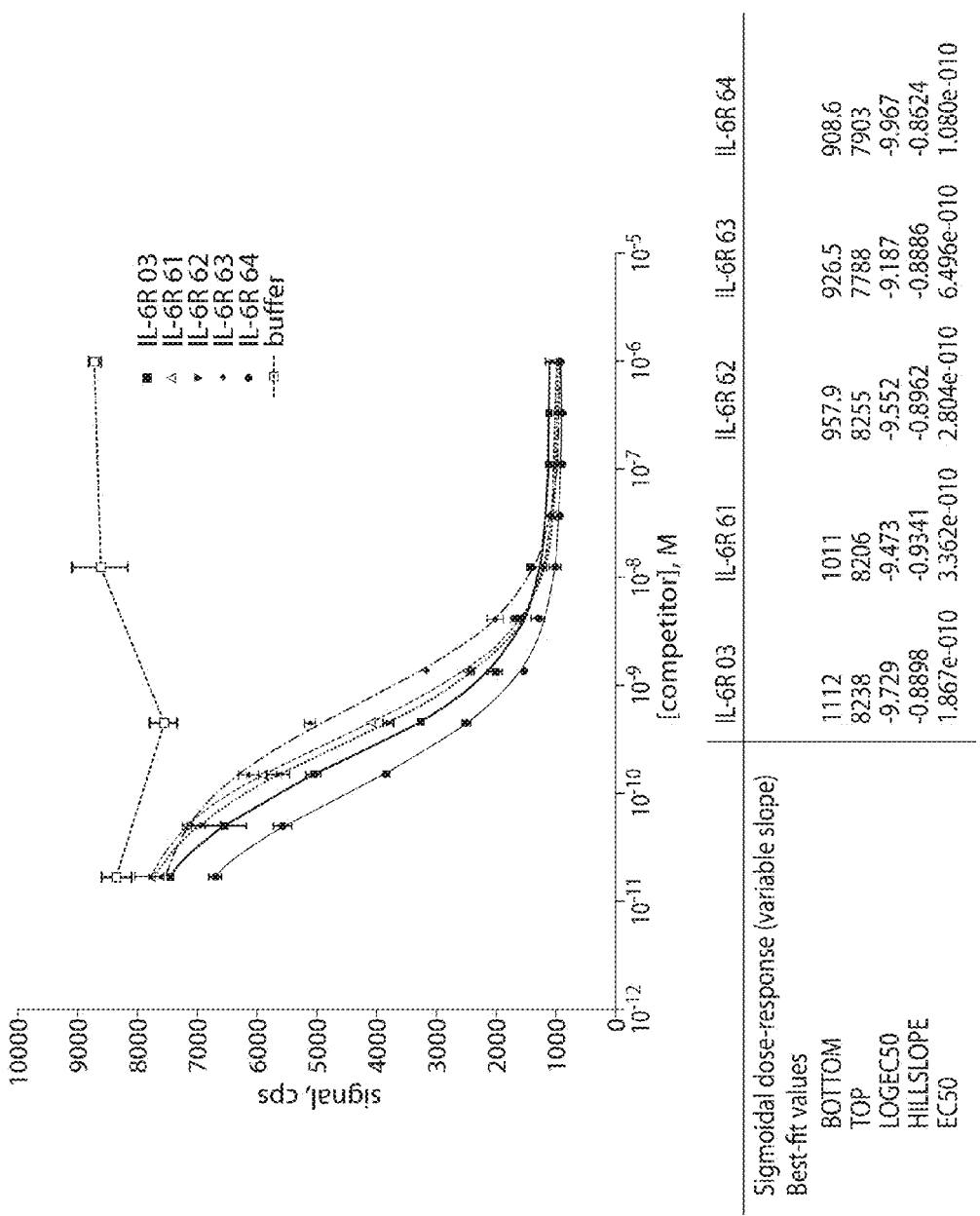
FIG. 17: Inhibition of the IL-6/IL-6R interaction by sequence optimized variants of IL6R03.
Figure 18:
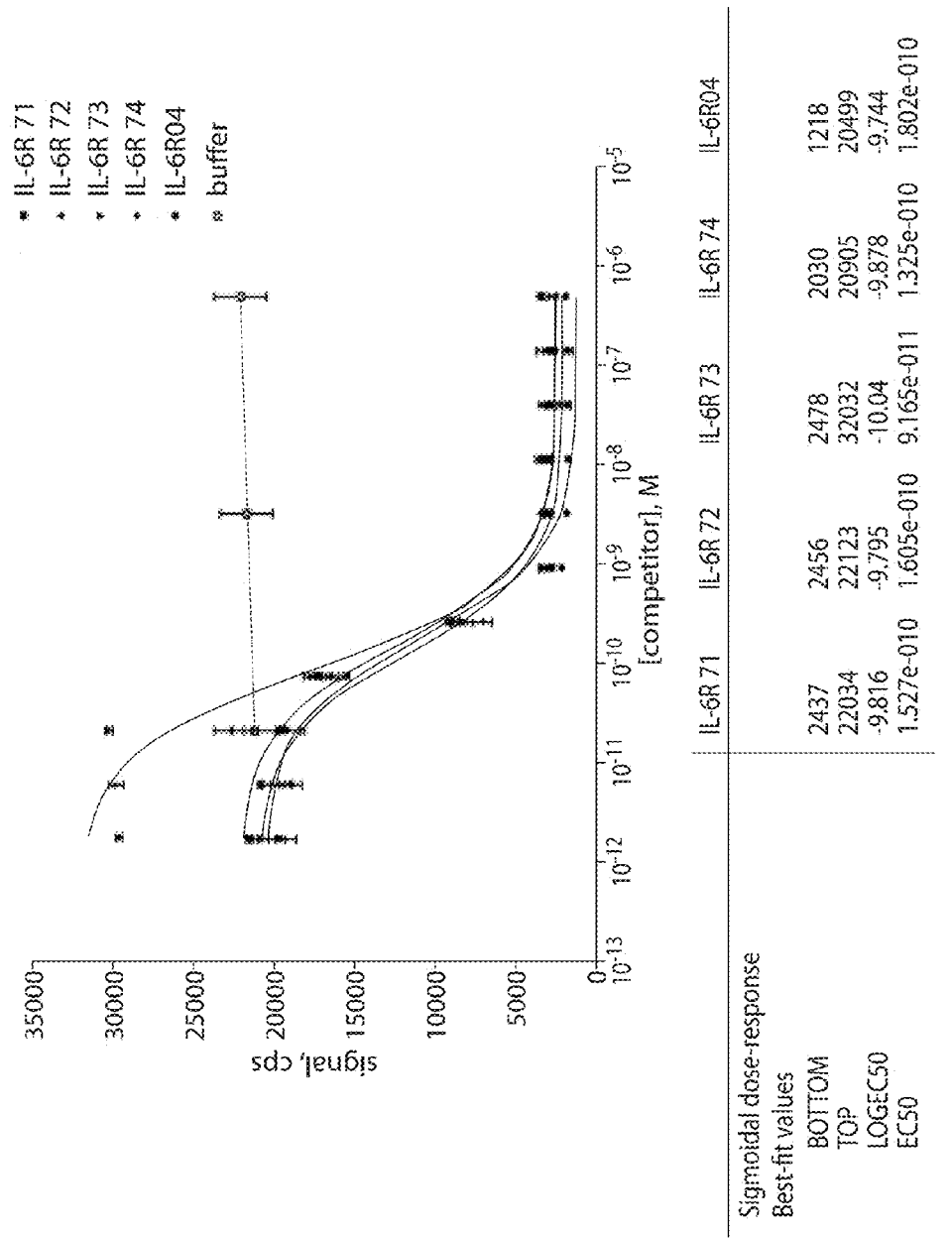
FIG. 18: Inhibition of the IL-6/IL-6R interaction by sequence optimized variants of IL6R04.
Figure 19:
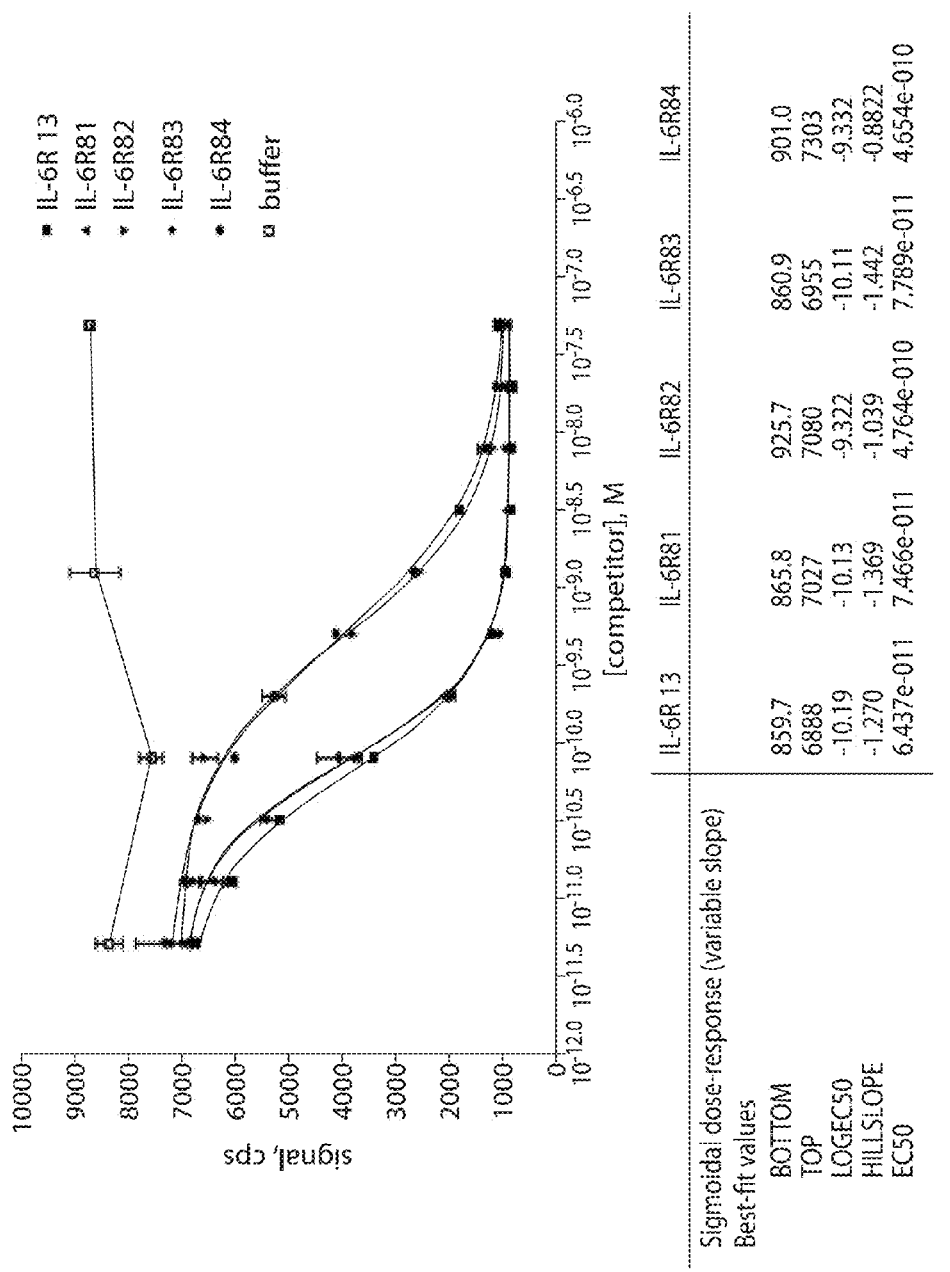
FIG. 19: Inhibition of the IL-6/IL-6R interaction by sequence optimized variants of IL6R13.

In stage 1 of the sequence optimization process the following 12 variants were created and analyzed:
IL6R03: IL6R61, IL6R62, IL6R63 and IL6R64
IL6R04: IL6R71, IL6R72, IL6R73 and IL6R74
IL6R13: IL6R81, IL6R82, IL6R83 and IL6R84
Amino acid sequences of these different variants are shown in FIG. 16.
Evaluation of Sequence Optimized Nanobodies in the IL-6/IL-6R Competition Assay
Sequence optimized clones of IL6R03, IL6R04 and IL6R13 were tested in Alphascreen for inhibition of the IL-6/IL-6R interaction. Serial dilutions of purified Nanobodies were added to IL-6R (0.3 nM) and incubated for 15 min. Subsequently 3 nM bio-IL-6 and BN-12-coated acceptor beads were added and this mixture was incubated for 1 hour. Finally streptavidin donor beads were added and after 1 hour incubation the plate was read on the Envision microplate reader. Parental clones were included as reference. Results are shown in FIG. 17, FIG. 18 and FIG. 19.
The sequence optimized variants of IL6R03 (IL6R61, 62 and 64) have IC50 values all within 2-fold of the IC50 value of IL6R03, whereas IL6R63 displays a ~4-fold lower IC50 value.

For the sequence optimized variants of IL6R04, no significant differences were observed in IC50 values between IL6R04 and the 4 sequence optimized variants.
For the sequence optimized variants of IL6R13, the IC50 values of IL6R81 and IL6R83 were almost identical to that of IL6R13 while the 2 variants carrying the RAT→KGL mutation in framework 2 (IL6R82 and IL6R84) had a drop in potency.
Affinity Determination
The sequence optimized variants of IL6R03, IL6R04 and IL6R13 were also analyzed on Biacore for binding to IL-6R. Kinetic parameters are listed in Table C-20.
For the sequence optimized variants of IL6R03, $K_d$ values of IL6R61, 62 and 63 were all within 2-fold of the $K_d$ value of IL6R03. The $K_d$ of IL6R64 was not determined.
For the sequence optimized variants of IL6R04, no significant differences were observed in $K_d$ values between IL6R04 and the 4 sequence optimized variants.
For the sequence optimized variants of IL6R13, $K_d$ values of IL6R81 and IL6R83 are very similar to the $K_d$ of IL6R13 while the 2 variants carrying the RAT→KGL mutation in framework 2 (IL6R82 and IL6R84) displayed a serious drop in affinity.
Overall, these observations are in perfect agreement with the results obtained in the Alphascreen based competition assay.

Example 25

Sequence Optimization Stage 2

Figure 20:
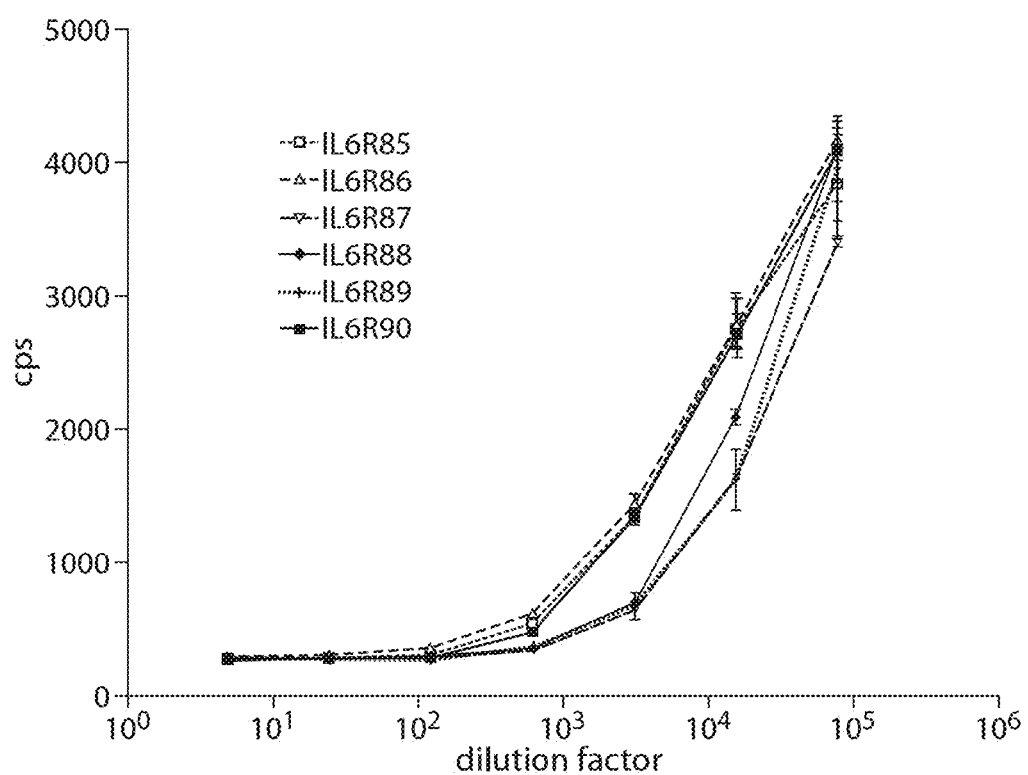
FIG. 20: Inhibition of the IL-6/IL-6R interaction by sequence optimized variants of IL6R13.
Figure 21:
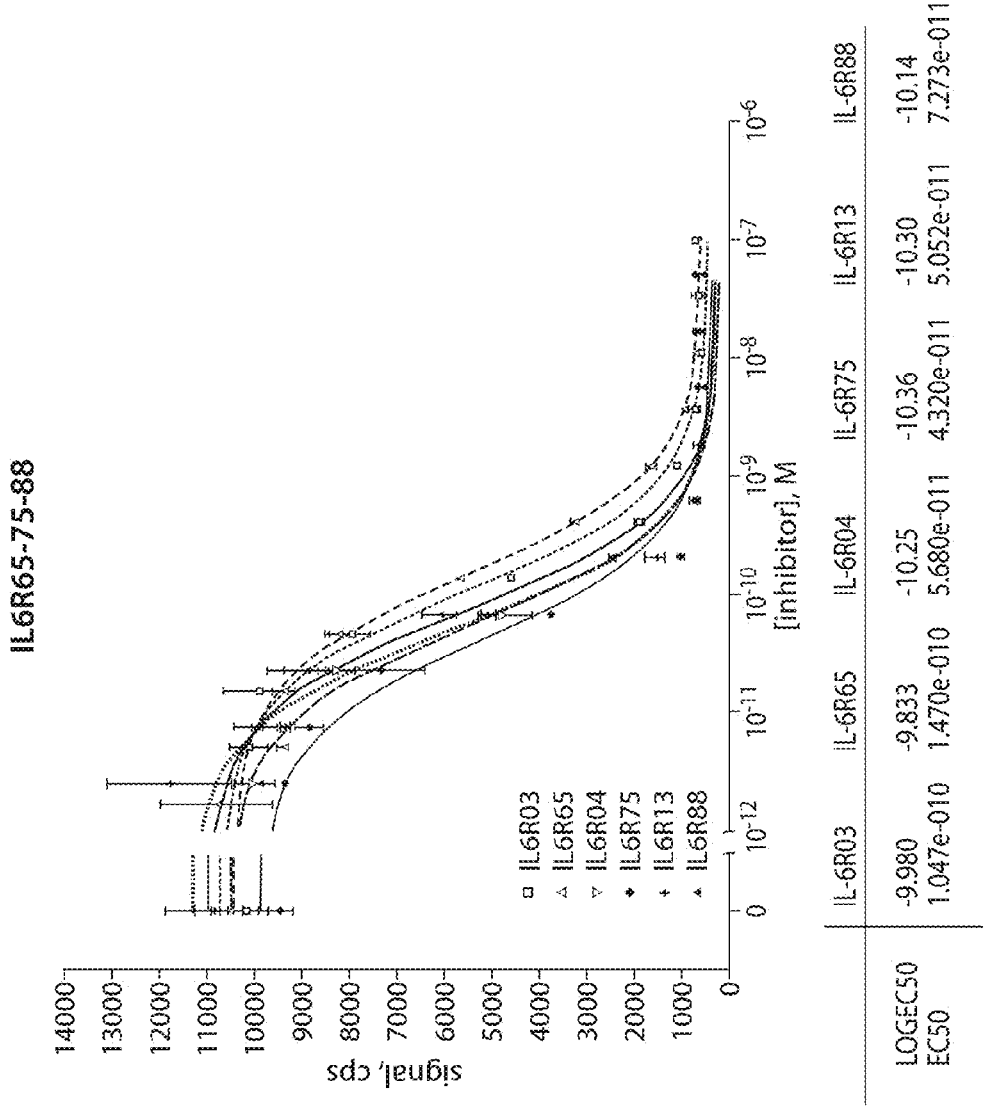
FIG. 21: Inhibition of the IL-6/IL-6R interaction by wild-type and sequence optimized anti-IL-6R Nanobodies.

Based on the affinity and potency data of stage 1 it was decided to generate the following set of variants:
For IL6R03 all mutations present in variants IL6R61, 62, 63 and 64 were combined to yield ILR65.
For IL6R04 all mutations present in variants IL6R71, 72, 73 and 74 were combined to yield ILR75.
For IL6R13 a set of 6 new variants (IL6R85-90) was created carrying different (combinations of) mutations in the RAT sequence in FR2. These mutations were introduced in the IL6R83 background as this sequence optimized variant was indistinguishable from IL6R13 in both affinity and potency.
Off-rate Analysis of Sequence Optimized IL6R13 Variants
Sequence optimized variants IL6R85-90 were analyzed as periplasmic extracts on Biacore. Dissociation curves were used to calculate $k_{off}$ values (Table C-21). Off-rates of Nanobodies IL6R87-89 were similar to that of IL6R13 while Nanobodies IL6R85, 86 and 90 had a 10-fold higher off-rate.
Evaluation of Sequence Optimized Nanobodies in the IL-6/IL-6R Competition Assay
Sequence optimized variants IL6R85-90 were tested as periplasmic extracts for their ability to block the IL-6/IL-6R interaction in Alphascreen. Results are shown in FIG. 20.
Nanobodies IL6R87, 88 and 89 were more potent than IL6R13 variants 85, 86 and 90 in blocking the IL-6/IL-6R interaction. These results are in perfect agreement with the observations on Biacore. Comparison of the amino acid sequence of the sequence optimized IL6R13 variants revealed that mutation T45L was responsible for the reduction in off-rate and potency. Therefore the most human variant without the T45L mutation, i.e. IL6R88, was selected for further characterization.
This variant was expressed, purified and analyzed for inhibition of the IL-6/IL-6R interaction along with purified clones IL6R65 and IL6R75. No significant differences between the different sequence optimized clones (IL6R65, IL6R75 and IL6R88) and their corresponding non-sequence optimized versions (IL6R03, IL6R04 and IL6R13, respectively) was observed (FIG. 21).

Affinity Determination

Affinity constants ($K_d$) of sequence optimized clones of IL6R65, 75 and 88 for human IL-6R were determined by surface plasmon resonance on a Biacore 3000 instrument. In brief, human IL-6R was amine-coupled to a CM5 sensor chip at a density of 800-1000 RU. Remaining reactive groups were inactivated. Nanobody binding was assessed at various concentrations ranging from 0.5 to 50 nM. Each sample was injected for 4 min at a flow rate of 45 µl/min to allow for binding to chip-bound antigen. Next, binding buffer without Nanobody was sent over the chip at the same flow rate to allow for dissociation of bound Nanobody. Kinetic parameters of the sequence optimized variants of IL6R03, 04 and 13 are given in Table C-22.

No major differences in affinity constants were observed between parental and sequence optimized Nanobodies.

Cell-Based Potency Assay

Figure 22A:
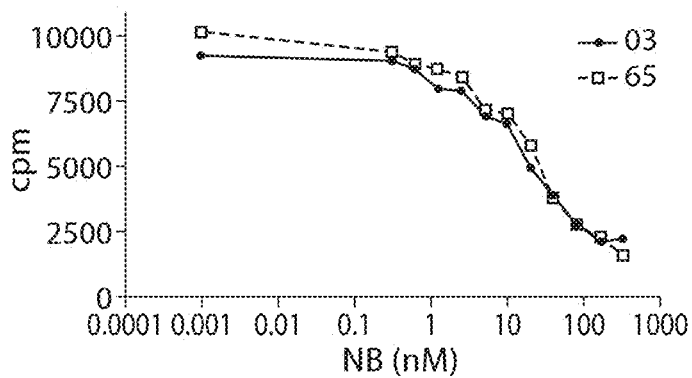
FIG. 22A-C: Cell-based potency of sequence optimized Nanobodies versus wildtype Nanobodies.
Figure 22B:
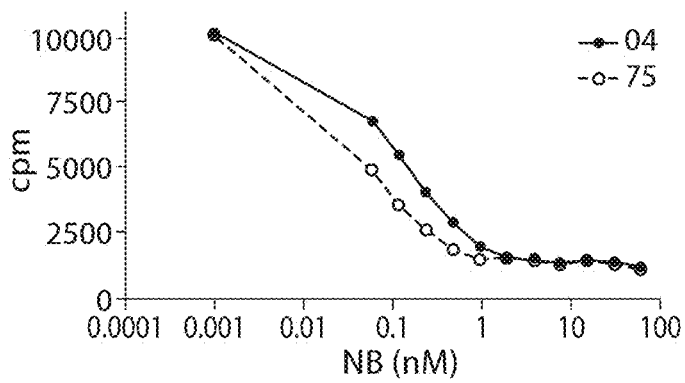
Figure 22C:
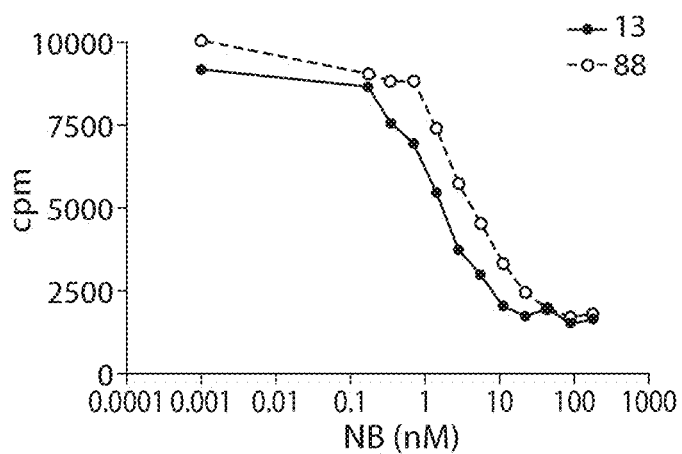

Sequence optimized Nanobodies were analyzed in the XG-1 assay. Results are shown in FIG. 22. IC50 values are summarized in Table C-23. Sequence optimization had no significant effect on the potency to neutralize IL-6-induced proliferation in cell-based assay.

IV. Additional Characterization of Sequence Optimized Nanobodies

Example 26

Affinity Determination for Cyno IL-6R

Affinity of IL6R03-IL6R65, IL6R04-IL6R75 and IL6R13-IL-6R88 for cyno IL-6R was determined by SPR on a Biacore 3000 instrument. In brief, cyno IL-6R was amine-coupled to a CM5 sensor chip at a density of 760 RU. Remaining reactive groups were inactivated. Nanobody binding was assessed at various concentrations ranging from 1.25 to 100 nM. Each sample was injected for 4 min at a flow rate of 45 µl/min to allow for binding to chip-bound antigen. Next, binding buffer without Nanobody was sent over the chip at the same flow rate to allow for dissociation of bound Nanobody. The kinetic parameters are summarized in Table C-24.

Although there was quite some difference in the affinity constants of IL6R04 and IL6R75, from this experiment it was clear that the affinity of both molecules for cyno IL-6R was much lower than for human. In contrast, the affinity constants of IL6R03 and IL6R65 for cyno IL-6R were in the same range as for human IL-6R. Strikingly, the crystal structure of the IL-6/IL-6R/gp130 complex (Boulanger et al.) reveals that the IL-6 binding site on IL-6R is completely conserved between human and cyno, suggesting that IL6R04 is binding to a different epitope.

Example 27

Testing of the Sequence Optimized Nanobodies in Plasma Potency Assay Using Human and Cyno Plasma In order to assess the cross-reactivity of IL6R65 and IL6R75 with cynomolgus monkey IL-6R the plasma potency ELISA was performed using either human or cyno plasma as a source of sIL-6R. In this assay, a dilution series of the Nanobodies was pre-incubated with plasma and human IL-6 (50 ng/mL). Subsequently, plasma sIL-6R was captured on a BN-12 coated plate and bound IL-6 was detected using biotinylated polyclonal antibodies and streptavidin-HRP.

Figure 23A:
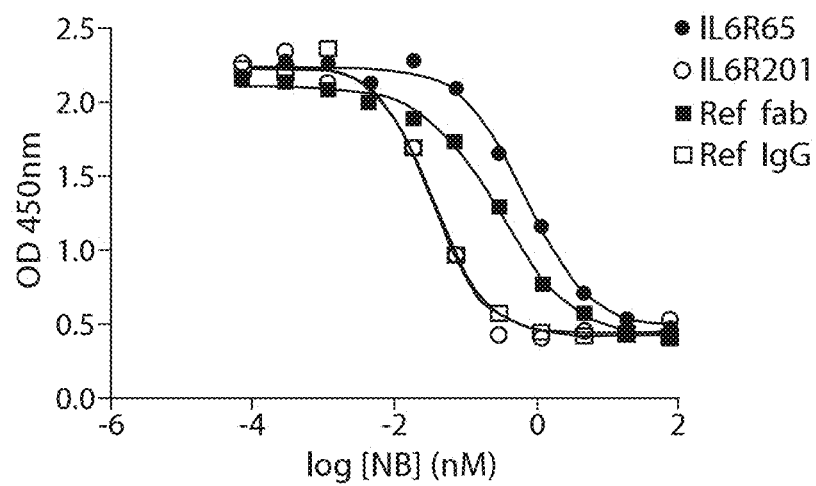
FIGS. 23A and B: Plasma potency ELISA of sequence optimized Nanobodies in human (A) and cyno (B) plasma.
Figure 23B:
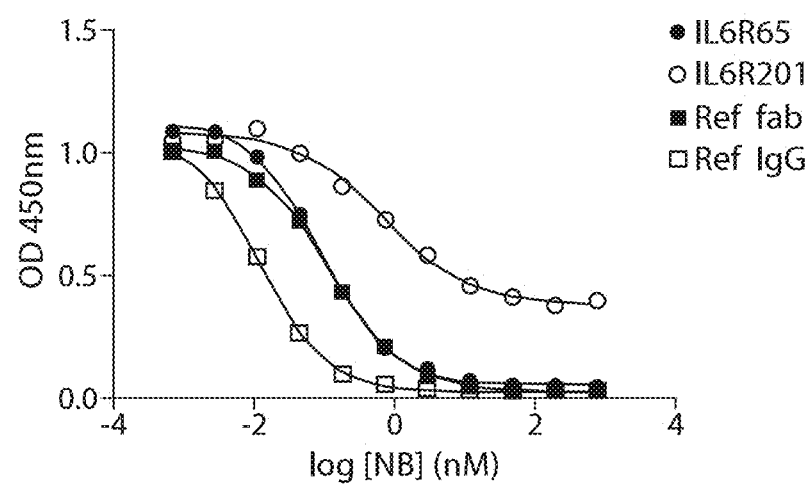

As can be observed in FIG. 23A, both IL6R201 and IL6R65 were able to completely block the binding of IL-6 to human sIL-6R, but IL6R65 appeared to be less potent than IL6R201, and than the reference IgG and reference Fab described in Example 1. As can be observed in FIG. 23B, IL6R65 was able to completely block the binding of IL-6 to cyno sIL-6R with a potency comparable to the reference Fab described in Example 1.

Example 28

Figure 24:
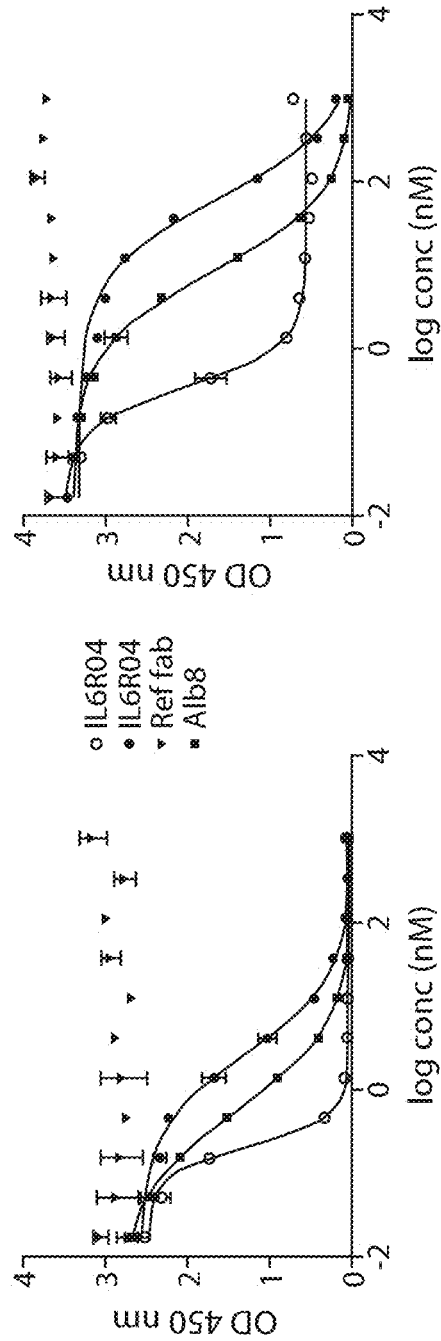
FIG. 24: Plasma potency ELISA of sequence optimized Nanobodies at the EC50 (left) and the EC95 (right) of IL-6.

Testing of the Sequence Optimized Nanobodies in Plasma Potency Assay at High IL-6 Concentration The plasma potency assay in human plasma was also used to test the ability of the Nanobodies to block high concentrations of IL-6. IL6R04, IL6R65 and the reference Fab described in Example 1 were tested at the EC50 of IL-6 (50 ng/mL) and at the EC95 of IL-6 (885 ng/mL). The results are depicted in FIG. 24. Clearly, IL6R04 appeared to be the most potent compound at the EC50 of IL-6. At the EC95 the reference Fab and IL6R65 could still completely block plasma sIL-6R, albeit at higher concentrations, indicating that these 2 molecules bind to an epitope that overlaps with the IL-6 binding site. The IC50 of the reference Fab increased from 0.55 nM to 8.47 nM and the IC50 of IL6R65 increased from 2.61 nM to 66.25 nM.

Example 29

Biacore Competition Studies

Figure 25A:
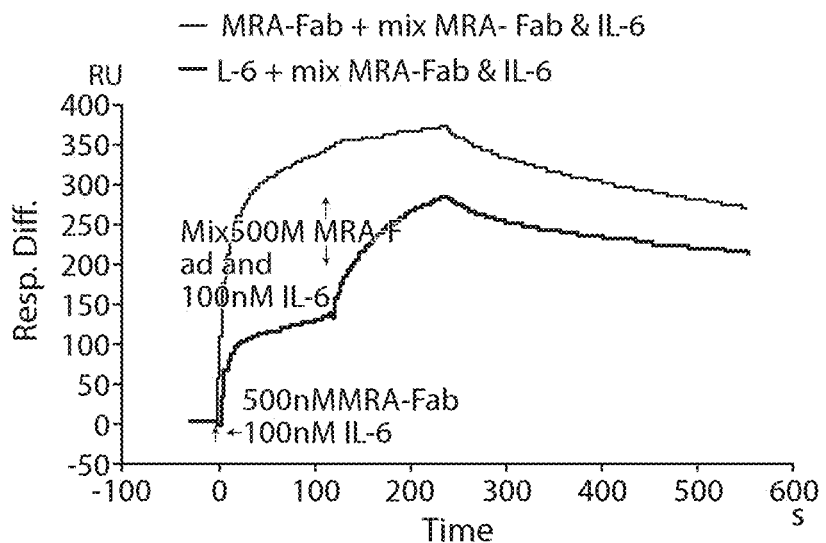
FIG. 25A-D: Epitope mapping of IL-6R Nanobodies as described in Example 29: competition assay on an IL-6R-coated (A-C) or an IL-6-coated chip (D).
Figure 25B:
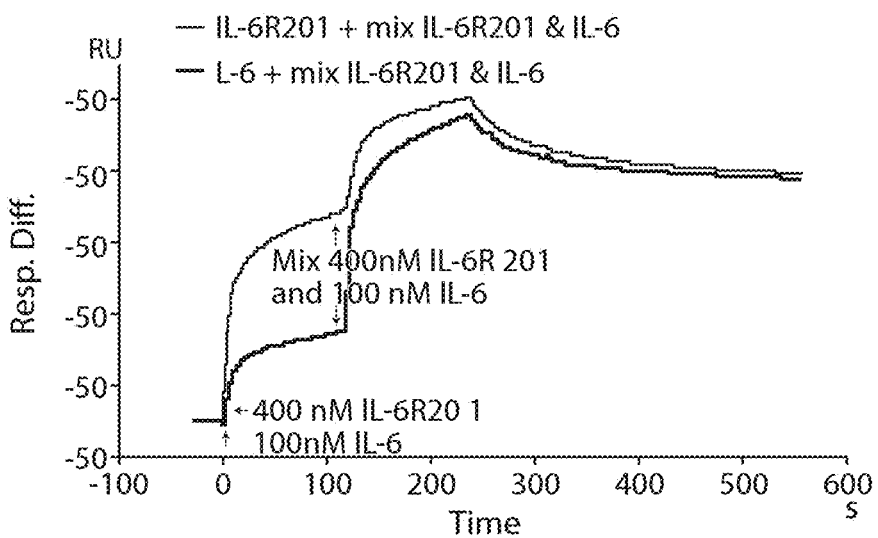
Figure 25C:
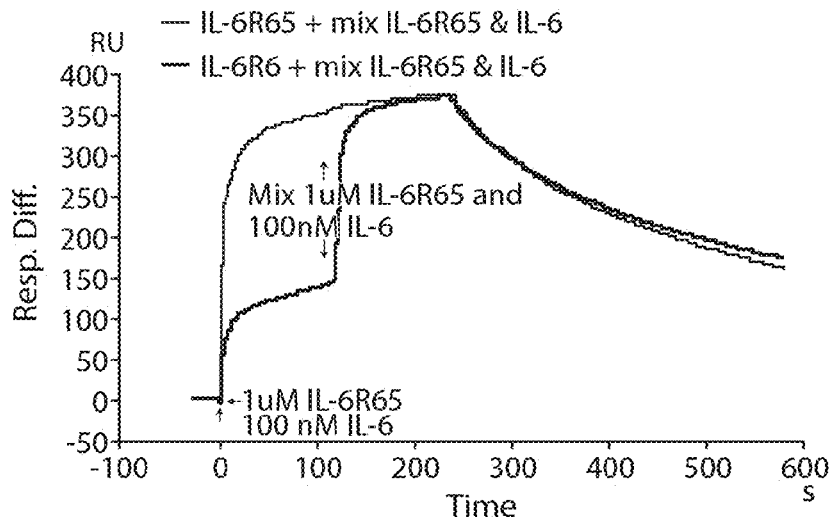

Biacore experiments were carried out to investigate whether IL-6 and IL6R65 were able to bind to IL-6R simultaneously. The reference Fab (FIG. 25A), IL6R201/75 (FIG. 25B) or IL6R65 (FIG. 25C) were captured on IL-6R, after which IL-6 was allowed to bind to the complex. With the reference Fab and IL6R65 almost no binding of IL-6 could be observed. When IL-6 was captured on IL-6R and the Nanobodies were injected, all three Nanobodies seemed to be able to bind to the complex. However, in the case of the reference Fab and IL-6R65 this was probably because IL-6 was displaced due to the lower affinity of IL-6 for IL-6R.

Figure 25D:
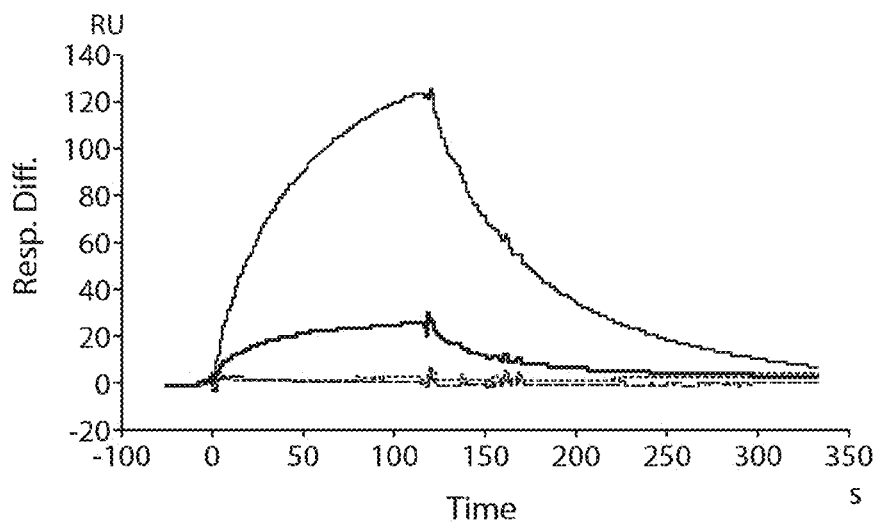

Finally, IL-6R was allowed to bind to an IL-6 coated chip in the presence or absence of Nanobodies (FIG. 25D). This confirmed the earlier results, namely IL-6R could not be captured in the presence of the reference Fab or IL6R65.

In conclusion, the Biacore epitope mapping experiments showed that both the reference Fab and IL6R65 target the same epitope as IL-6. While IL6R65 and the reference Fab were able to block the binding of IL-6 to IL-6R completely, IL6R201 was unable to prevent binding of IL-6 to IL-6R when this Nanobody was bound to the receptor.

V. Affinity Maturation of IL6R65

Example 30

Diversification Strategy for Affinity Maturation

CDR regions of the Nanobody IL6R65 were randomized using the 2 following strategies:
1. Each CDR residue was replaced by a set of residues with similar side-chain chemistries:
   K↔HR
   A↔S↔T I↔L↔V
F↔Y
N↔D
Q↔E
G→A
M→L
H,C,W,P were kept constant
2. Each CDR residue was replaced by a panel of amino acids which naturally occur on that position.
Only the most frequently occurring amino acids on each position were introduced in order to limit the diversity per position. This approach was only used for randomization of CDR1 and CDR2.

Concurrent randomization of CDR1 and 2 was performed using the 2 strategies described above and CDR3 was randomized separately following strategy 1 resulting in a total number of 3 libraries. All 3 libraries were made in-house by PCR overlap extension using degenerate oligos. Theoretical diversity for each of the libraries was approximately 1×10e6. Fragments encoding the Nanobody variants were cloned into the phage display vector. The actual size of all 3 libraries was around 1×10e8 (100× coverage of theoretical diversity). One round of selection was performed using different concentration of biotinylated IL-6R (0, 1, 10 and 100 pM) in solution. No enrichment was observed for the CDR3 library under these conditions while dose-dependent enrichment was observed for both CDR1/2 libraries. Outputs from the CDR1/2 libraries were analyzed as periplasmic extracts in ELISA and clones with highest signals were subsequently tested on Biacore. The top 30 clones in ELISA showed off-rates between 2.1×10e-3 and 2.6×10e-4 $s^{-1}$. The 5 Nanobodies with the slowest off-rates were sequenced, expressed and purified (FIG. 26).

Example 31

Nanobody Expression and Purification

Affinity matured Nanobodies were expressed in *E. coli* as c-myc, (His)6-tagged proteins in a culture volume of 250 ml. Expression was induced by addition of 1 mM IPTG and allowed to continue for 4 h at 37° C. After spinning the cell cultures, periplasmic extracts were prepared by freeze-thawing the pellets. These extracts were used as starting material for immobilized metal affinity chromatography (IMAC). Nanobodies were eluted from the column with 150 mM imidazole and subsequently desalted on a Hiprep26/10 column.

Example 32

Affinity Determination of the Affinity Matured Variants on Biacore

Nanobody IL6R65 (sequence optimized) and the 5 affinity matured variants were analyzed on Biacore. Binding curves at different concentrations of purified Nanobody were recorded and used to calculate the affinity constants. Kd-values for these 5 clones were between 0.34 and 0.95 nM which corresponds to a 13-fold improvement relative to IL6R65 (parent Nanobody) for the best variant (FIG. 27).

Example 33

Evaluation of the Affinity Matured Variants in Plasma Potency Assay

Figure 28A:
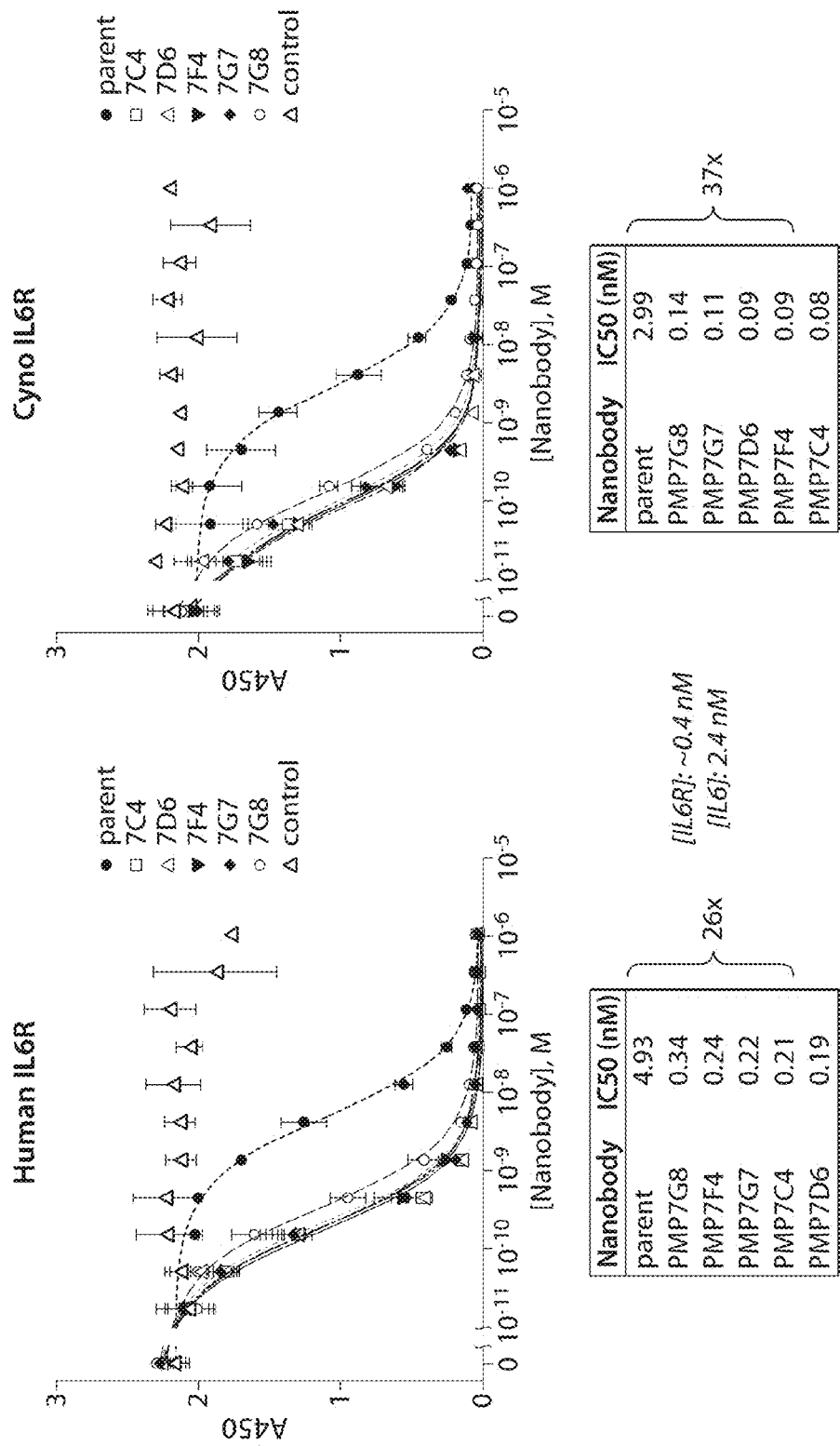
FIG. 28A: Evaluation of IL6R65 and 5 affinity matured variants in a human and cyno plasma potency assay. Human IL6R (left) and Cyno IL6R (right).
Figure 28B:
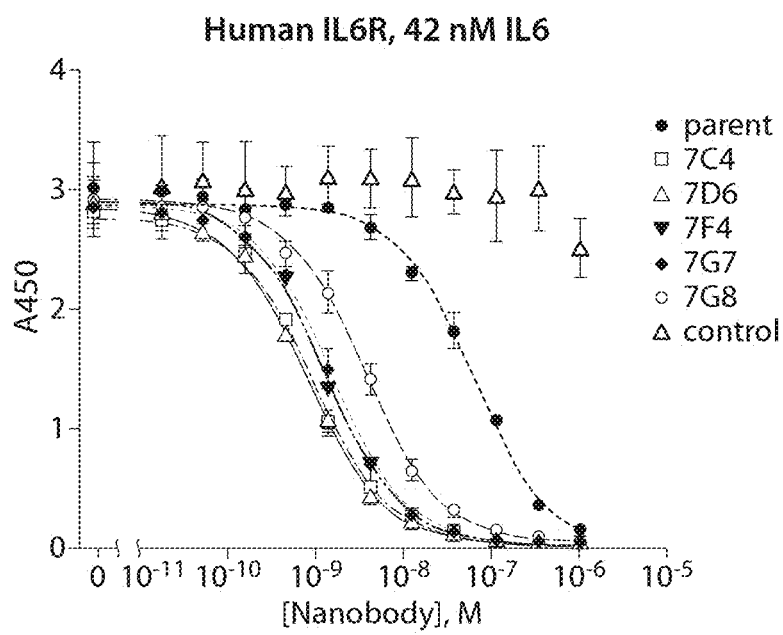
FIG. 28B: Evaluation of IL6R65 and 5 affinity matured variants in a human and cyno plasma potency assay. Human IL6R, 42 nM IL6.

All 5 affinity matured Nanobodies and the sequence optimized Nanobody were also tested in a plasma potency assay. In this assay different concentrations of Nano body were mixed with soluble IL-6R containing plasma from either human or cynomolgus monkey and a fixed concentration of human IL-6 (2.4 or 42 nM). After 1 hour of incubation the mixture was transferred to a Maxisorp plate coated with the anti-IL-6R MAb BN-12 (Diaclone). The amount of IL-6 bound was determined by subsequent addition of biotinylated anti-IL-6 polyclonal antibody (R&D Systems) and streptavidin-HRP. TMB was used as substrate. Substrate conversion was measured at 450 nm (FIG. 28).

Example 34

Evaluation of the Affinity Matured Variants in TF-1 Assay

Figure 29:
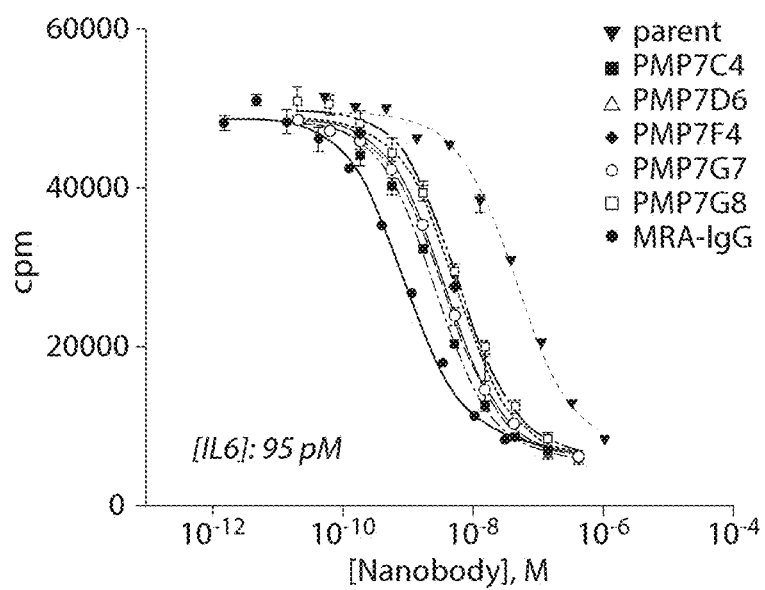
FIG. 29: Inhibition of IL-6-dependent proliferation of TF-1 cells by affinity matured Nanobodies. Cells were grown in the presence of 2 ng/ml human IL-6 and various concentrations of Nanobody. Proliferation was measured by 3H-thymidine incorporation.

The affinity matured Nanobodies were also tested for their ability to inhibit IL-6-dependent proliferation of TF-1 cells (ECACC no. 93022307; 1989, J. Cell Physiol. 140: 323; 1993, Exp. Cell Res. 208: 35) due to blocking of IL-6 binding to IL-6R on the cell-surface. To this end, serial dilutions of Nanobody were pre-incubated with a fixed amount of TF-1 cells for 2 hours at 37 C. Subsequently IL-6 was added to a final concentration of 2 ng/ml. IL-6-dependent cell proliferation was allowed to continue for 72 hours and was measured by the incorporation of tritium labeled thymidine (FIG. 29).

IC50 values of affinity matured Nanobodies were up to 17-fold better than that of IL6R65 but all variants were still less potent than the reference-IgG.

Example 35

Biacore Competition Studies

Figure 30A:
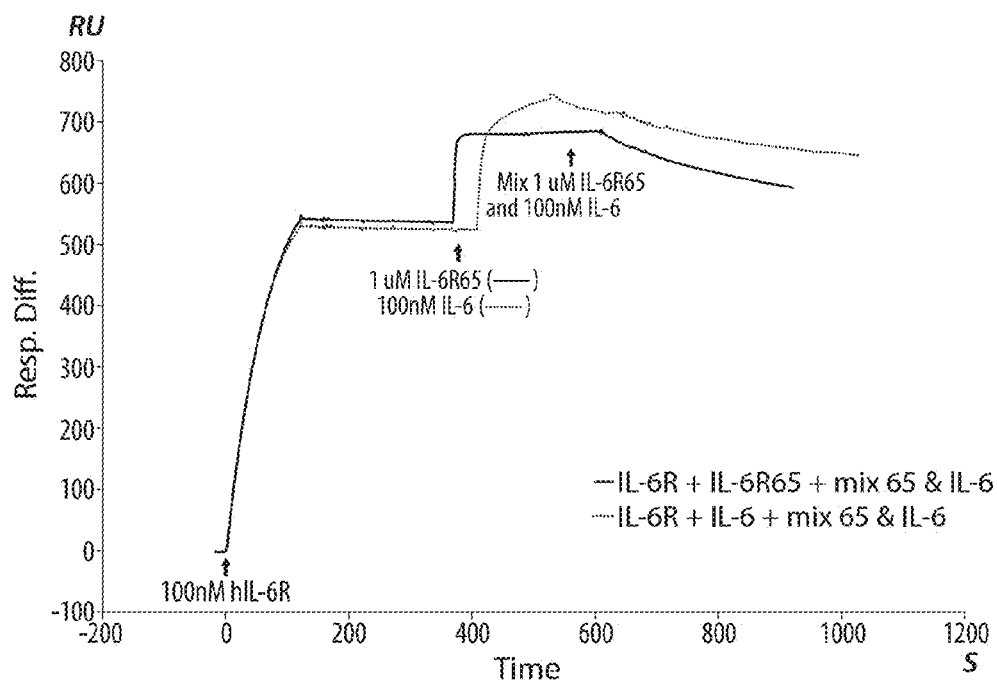
FIG. 30A-C: Competition of IL-6 with two affinity matured Nanobodies (B-C) in comparison with the competition of IL-6 with the IL6R65 (A) as measured in Biacore.
Figure 30B:
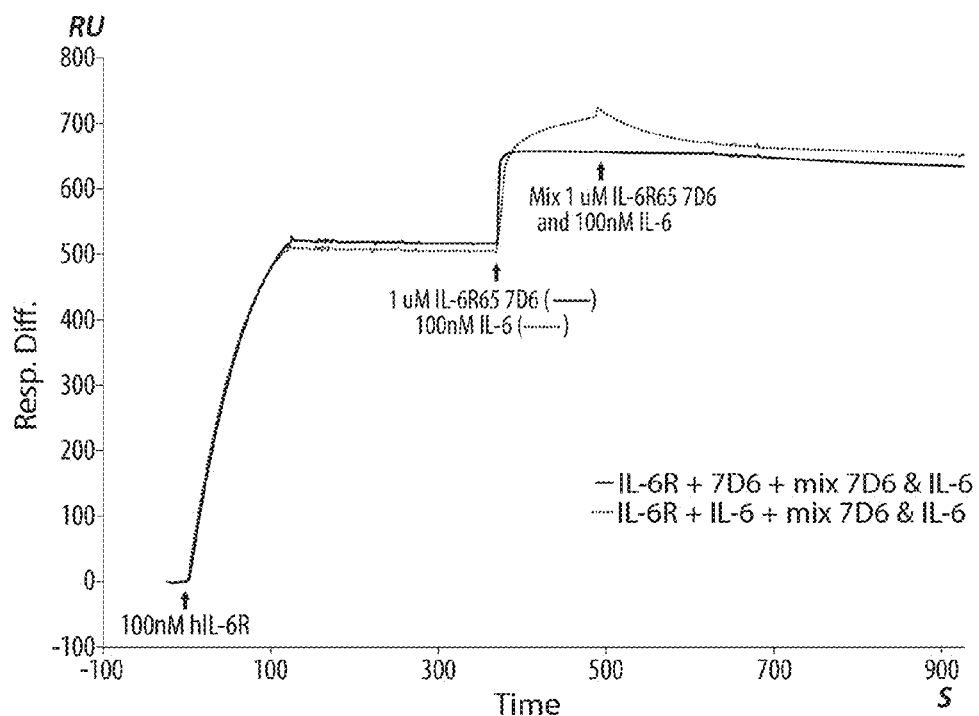
Figure 30C:
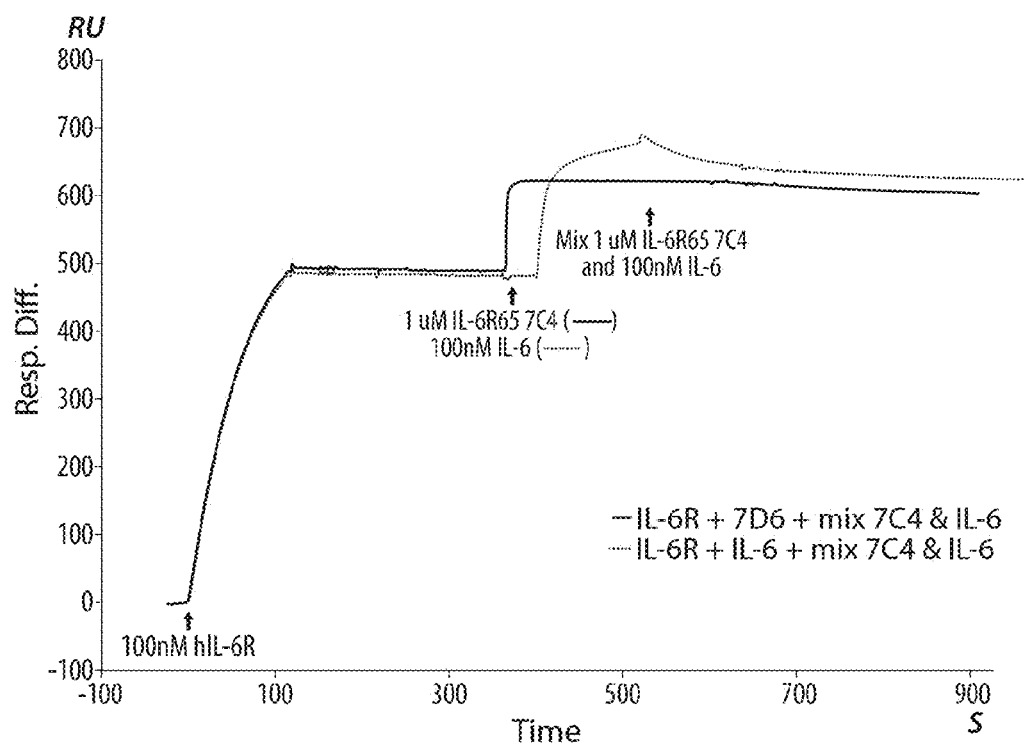

Biacore experiments were carried out to investigate whether IL-6 is able to bind to IL-6R simultaneously with IL6R65 and with 2 of its affinity matured variants (7D6 and 7C4). In these experiments IL-6R was captured on a BN-12 coated chip and saturated with Nanobody IL6R65 (FIG. 30A), 7D6 (FIG. 30B) or 7C4 (FIG. 30C). Next, binding of IL-6 to the IL-6R-Nanobody complex was assessed by injection of the cytokine at a concentration of 100 nM. In addition, also binding of the 3 Nanobodies to IL-6R in complex with IL-6 was determined.

The results for IL6R65 (FIG. 30A) are comparable to the results observed previously and confirm that IL6R65 and IL-6 recognize the same epitope on IL-6R. As expected the IL6R65 affinity matured variants and IL-6 also recognized the same epitope on IL-6R (FIG. 30B-C).

Example 36

Further Affinity Maturation

Next, a panel of 47 Nanobodies was generated containing different combinations of beneficial mutations in CDR1/2 and CDR3. These mutations were identified by thorough analysis of protein sequences and off-rates of all Nanobody clones isolated from the CDR randomization libraries. Off-rates of these $2^{nd}$ generation clones ranged from 4.2E-04 to 4.5E-05 $s^{-1}$. 5 clones showing the slowest off-rates were selected for further analysis (20F6, 20A11, 20E10, 21A10, 21D11). Sequences are listed in FIG. 31.

Example 37

Nanobody Expression and Purification of Second Round Variants

Affinity matured Nanobodies were expressed in *E. coli* as c-myc, (His)6-tagged proteins in a culture volume of 250 ml. Expression was induced by addition of 1 mM IPTG and allowed to continue for 4 h at 37° C. After spinning the cell cultures, periplasmic extracts were prepared by freeze-thawing the pellets. These extracts were used as starting material for immobilized metal affinity chromatography (IMAC). Nanobodies were eluted from the column with 150 mM imidazole and subsequently desalted on a Hiprep26/10 column.

Example 38

Determination of Melting Temperatures

Temperature stability of the Nanobodies was analyzed in the thermal shift assay. The Tm values were similar for all affinity matured Nano bodies and slightly higher as compared to IL6R65. Tm values are listed in Table C-25.

Example 39

Affinity Determination of $2^{nd}$ Round Variants on Biacore

Kinetic parameters for Nanobody IL6R65 (sequence optimized) and the 5 affinity matured variants were determined on Biacore T100. Association rates ($k_a$) were determined from binding curves at 2 different concentrations of purified Nanobody and a fixed concentration of IL-6R which was captured on the chip via mAb BN-12. Off-rates were determined at a single Nanobody concentration using IL-6R covalently coupled to the chip. Values for ka, kd and Kd are listed in Table C-26.

Example 40

Evaluation of $2^{nd}$ Round Variants in TF-1 Assay

Figure 32:
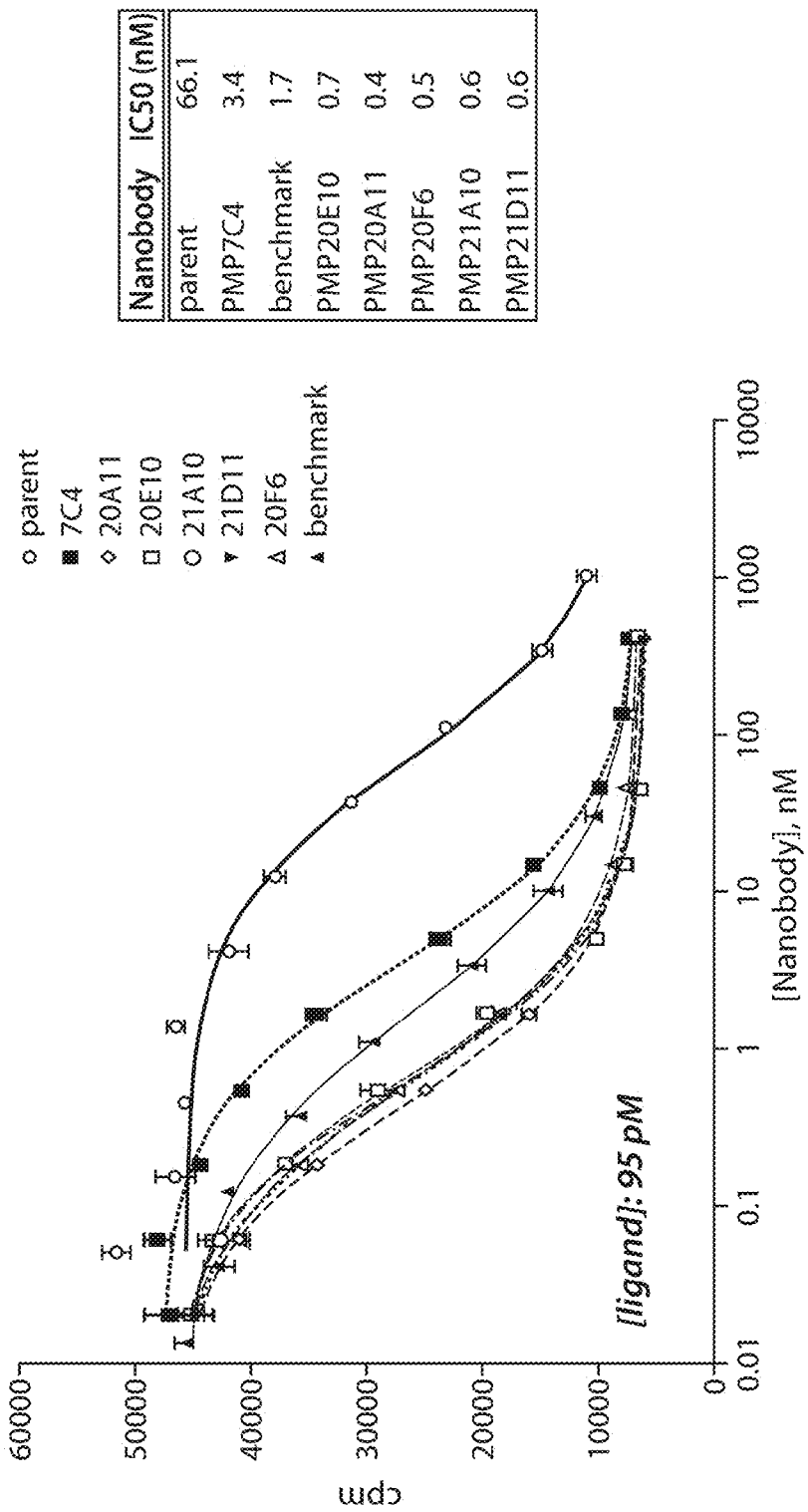
FIG. 32: Inhibition of IL-6-dependent proliferation of TF-1 cells. Cells were grown in the presence of 2 ng/ml human IL-6 and various concentrations of Nanobody. Proliferation was measured by 3H-thymidine incorporation.

Biological activity of the $2^{nd}$ round variants was evaluated in the TF1 assay and data are presented in FIG. 32. The 2nd round affinity matured clones had a 5-8 fold higher potency than 1st round clone 7C4 and were 2.5-4 fold more potent than the benchmark reference IgG described in Example 1. Best performing clone was 20A11 with an IC50 of 0.4 nM (4-fold more potent as compared to benchmark).

Example 41

Evaluation of $2^{nd}$ Round Variants in Plasma Potency Assays

Figure 33A:
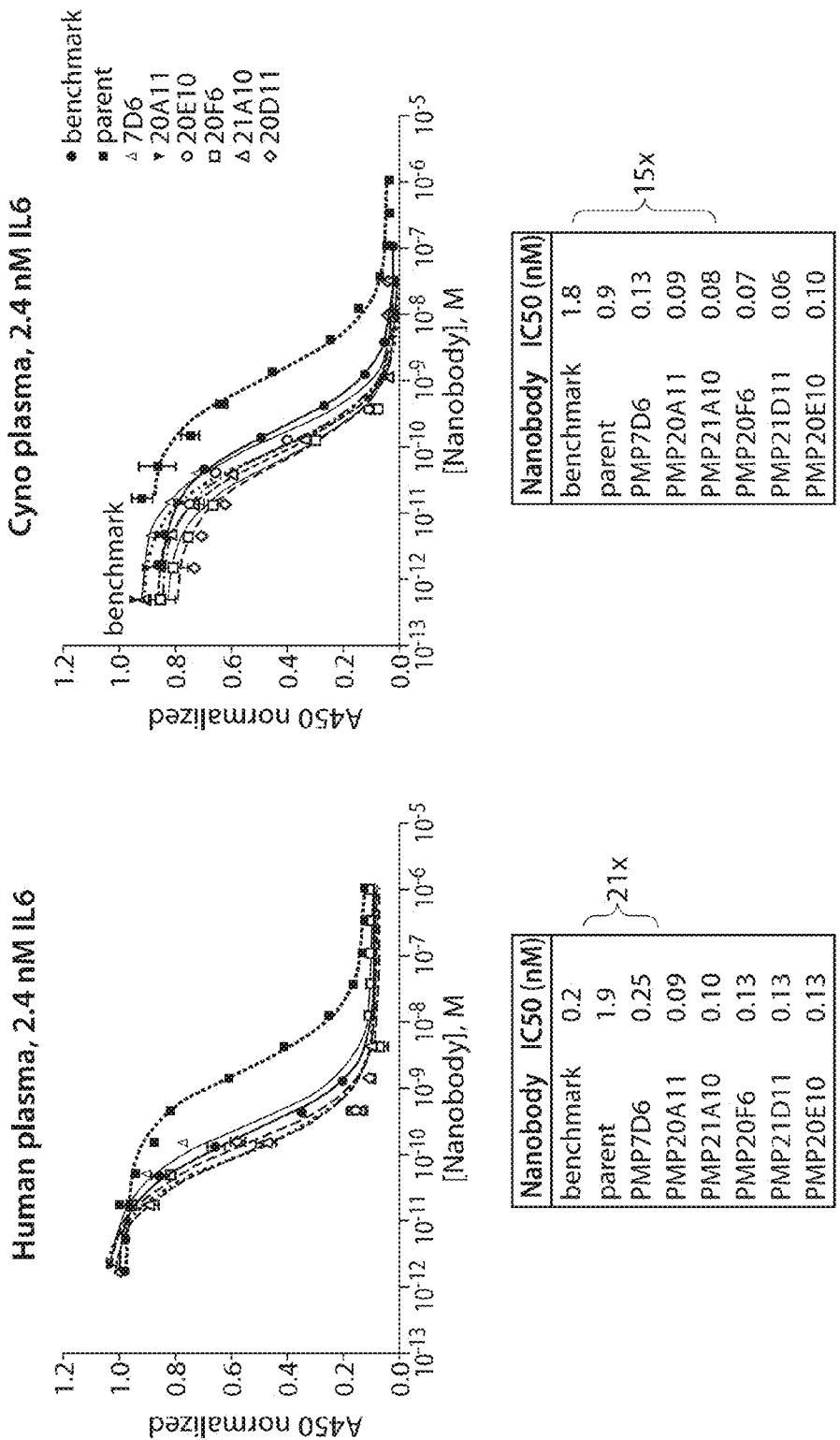
FIG. 33A-B: Evaluation of IL6R65 and 2nd round affinity matured variants in a human and cyno plasma potency assay. Parent=IL6R65.
Figure 33B:
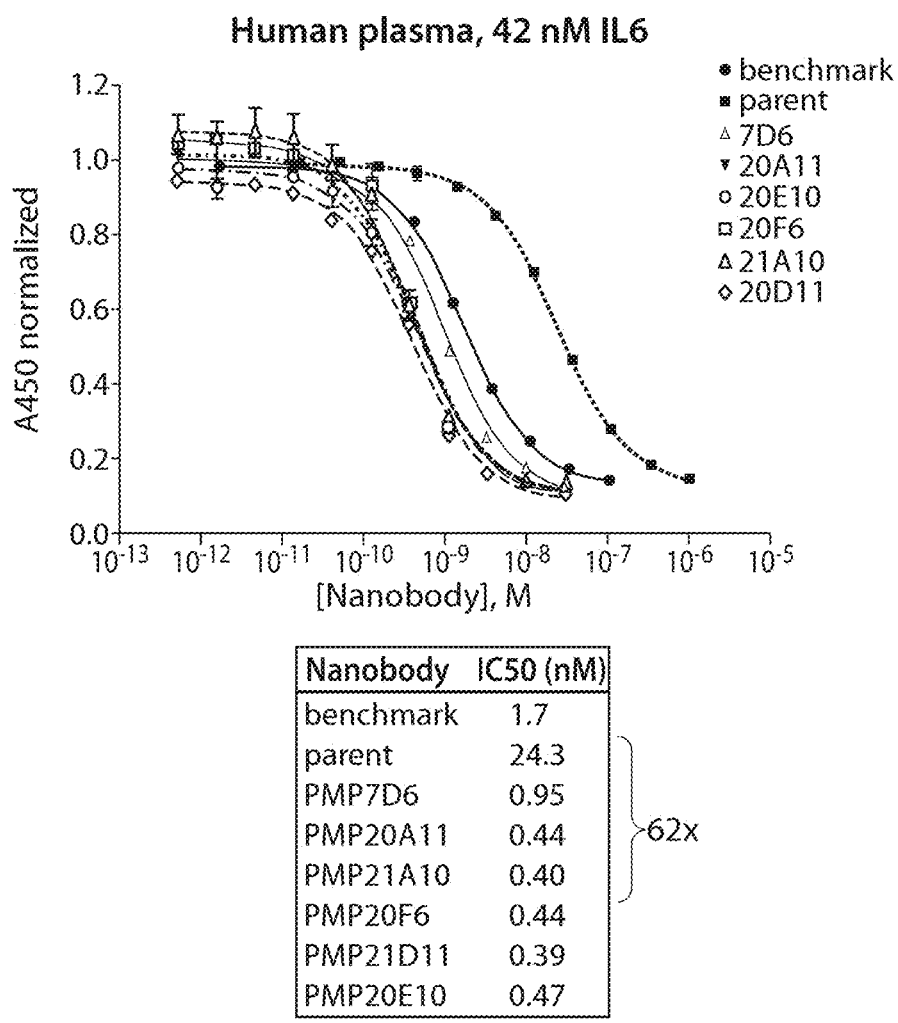

Inhibition of soluble IL-6R was analyzed in the plasma potency assay at high and low IL-6 concentrations. The $2^{nd}$ round variants were at least as potent as the reference IgG in the plasma potency assay (0.1-0.2 nM), which was at the sensitivity limit of this assay. At high IL-6 concentration (EC95), the affinity mutants were still able to block binding of IL-6 to sIL-6R and appeared to be 3-4 fold more potent than the reference IgG. No difference could be observed between 1st and 2nd round variants in this assay. As expected, all tested clones were cyno cross-reactive (FIG. 33).

Example 42

Binding to Human PBMCs in Full Blood

Figure 34:
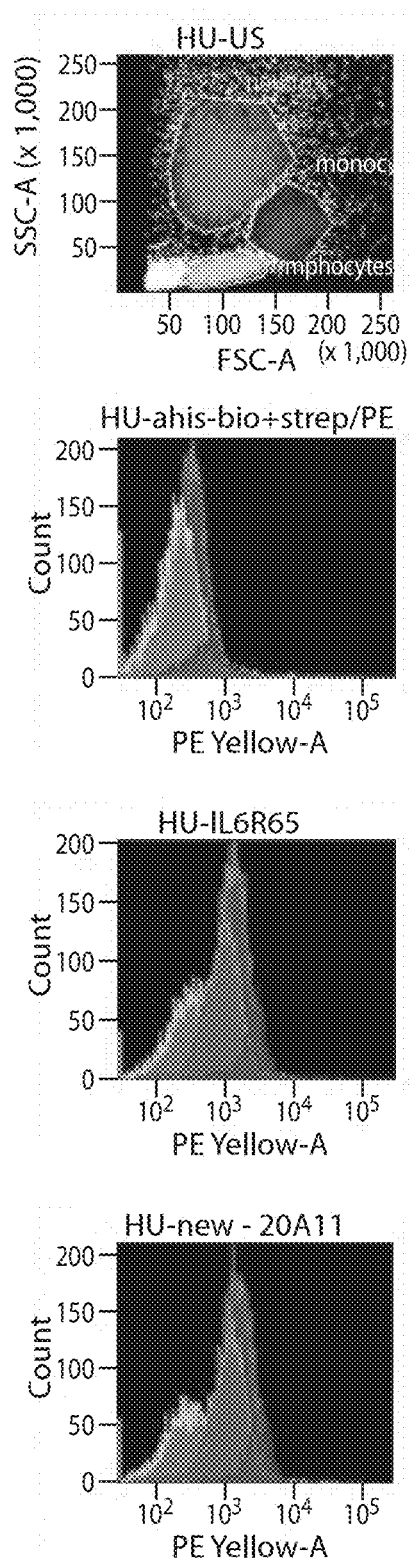
FIG. 34: Binding of IL6R65 and PMP20A11 to human PBMCs in full blood.

Purified Nano bodies IL6R65 and PMP20A11 were tested in FACS for binding to human PBMCs. Cell binding was detected using a biotinylated anti-His mAb and PE-labelled streptavidin (FIG. 34). Both IL6R65 and the affinity matured variant PMP20A11 could bind to neutrophils, monocytes and a subpopulation of lymphocytes. This is in agreement with the expression profile of IL-6R.

VI. Formatting of Affinity Matured Nanobody

Example 43

Preparation of Multivalent Constructs

PMP20A11 was formatted as bivalent and trivalent Nanobodies with the albumin-binding Nanobody ALB8. An overview of the different Nanobodies is presented in Table C-27.

Example 44

Neutralization of Membrane IL-6R in the TF-1 Assay

Figure 35:
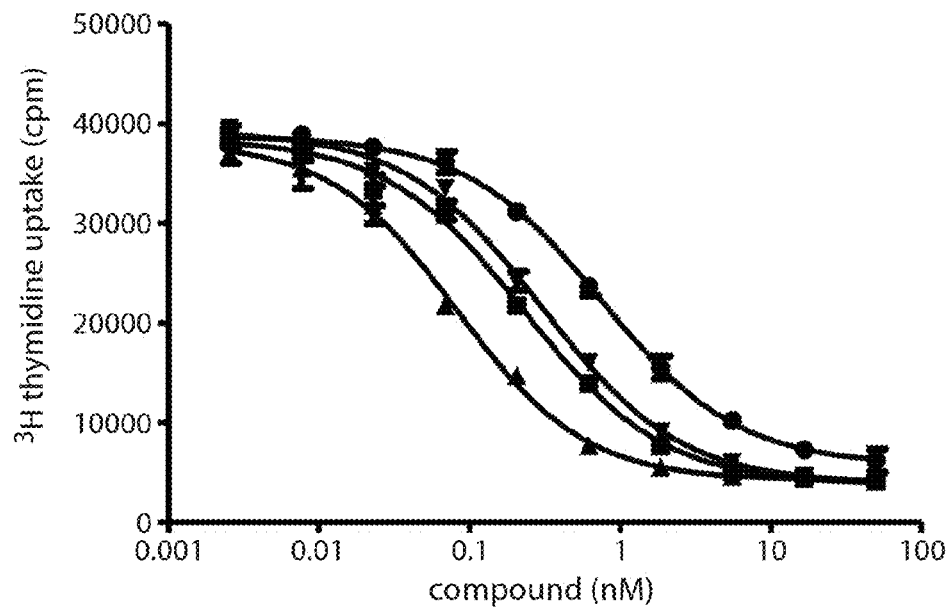
FIG. 35: Inhibition of membrane IL-6R activity by formatted Nanobodies and reference IgG. TF-1 cells were pre-incubated with a dilution series of IL6R304(■), IL6R305(▲), IL6R306(▼) or reference IgG(•) after which proliferation was induced with 100 IU/mL IL-6. After 72 h incubation, cell proliferation was assessed by incorporation of $^3$H thymidine. Mean+s.e. of triplicate measurements is shown.

In a first experiment, it was verified if the formatted Nanobodies inhibit the signalization through IL-6R using the TF-1 cell line as model system. Nanobodies 20A11, IL6R304, IL6R305 and IL6R306 dose-dependently and completely block the IL-6 induced proliferation of TF-1 cells mediated by membrane IL-6R (FIG. 35, Table C-28).

These results demonstrate that all formatted Nanobodies are more potent compared to the reference IgG as described in Example 1 for inhibiting membrane IL-6R activity. Compared to its monovalent equivalent IL6R304, IL6R305 inhibits ~7-fold more potently the IL-6 mediated responses, demonstrating avid interaction of IL6R305 with membrane IL-6R. IL6R306 is less potent than IL6R305 and only shows a 2-fold better potency than IL6R304. This demonstrates that the format of IL6R306 is less favorable and moreover indicates that avid binding of IL6R306 is not possible.

Figure 36:
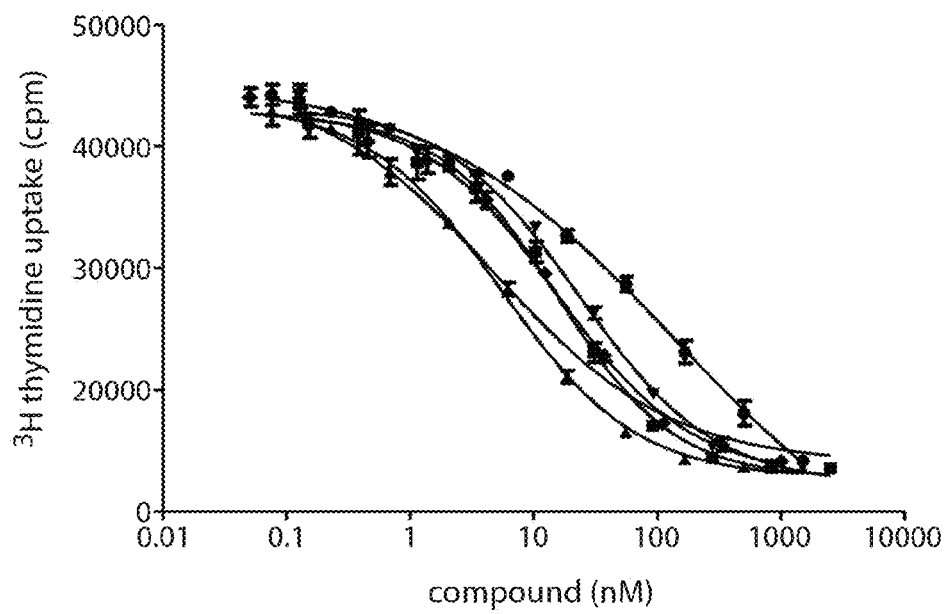
FIG. 36: Inhibition of membrane IL-6R by the formatted Nanobodies and the reference IgG at high levels of IL-6. TF-1 cells were pre-incubated with a dilution series of 20A11 (▲), IL6R304(■), IL6R305(▲), IL6R306(▼) or the reference IgG (•) after which proliferation was induced with 5000 IU/mL IL-6. After 72 h incubation, cell proliferation was assessed by incorporation of $^3$H thymidine. Mean+s.e. of triplicate measurements is shown.

Next, it was verified if the formatted Nanobodies could still completely inhibit the signalization through IL-6R at pathological concentrations of IL-6. Indeed, 20A11, IL6R304, IL6R305 and IL6R306 dose-dependently and completely blocked the proliferation of TF-1 cells induced by 5000 IU/mL IL-6 (FIG. 36, Table C-29). As expected, IC50s did shift compared to the experiments performed with 100 IU/mL. In agreement with the previous results, IL6R305 was most potent in blocking the IL-6 induced signalization through membrane IL-6R.

Figure 37:
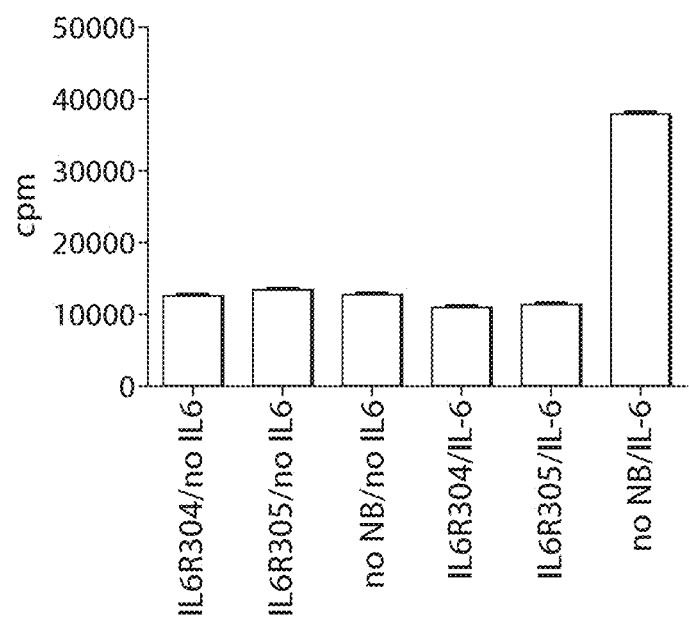
FIG. 37: Effect of IL6R304 and IL6R305 on proliferation of TF-1 cells. TF-1 cells were seeded at a density of 12500 cells/well and incubated with or without 50 nM IL6R304 or IL6R305. Proliferation was induced with 100 IU/mL IL-6 or cells were incubated in the absence of growth factors. After 72 h incubation, cell proliferation was assessed by incorporation of $^3$H thymidine. Each data point was measured 30 times. Mean+s.e. is shown.

As the Nanobodies do interact with IL-6R, it was verified if binding of Nanobodies to this receptor might induce cell activation leading to cell proliferation. TF-1 cells were incubated with an excess of Nanobody in the presence or absence of 100 IU/mL IL-6 (FIG. 37). As expected, both IL6R304 and IL6R305 completely prevented the IL-6 mediated proliferation. Indeed, IL6R305 and IL6R306 inhibited the IL-6 proliferation to the same level as the background ($^3$H-thymidine incorporation measured in the absence of growth factors), demonstrating that IL6R304 and IL6R305 completely blocked the effect of IL-6.

IL6R304 and IL6R305 did not induce proliferation of TF-1 cells in the absence of growth factors, suggesting that these compounds do not have an agonistic effect on TF-1 cells.

Example 45

Neutralization of sIL-6R in ELISA by the Formatted Affinity Matured Nanobodies

The ability of the building block IL6R20A11 and its formatted variants to prevent binding of human IL-6 to plasma sIL-6R was analyzed in the plasma potency ELISA. Since the concentration of plasma sIL-6R is variable, the same plasma needed to be used across the different assays for comparing the potency of the Nanobodies. Also, a titration of IL-6 was first incubated in the plasma to determine the concentration of IL-6 that would be used with the Nanobodies. The EC50 and EC95 values of IL-6 in human plasma were determined to be 27.29 ng/mL and 885 ng/mL, respectively. These concentrations were subsequently used to test the potency of the Nanobodies at normal and high concentrations of IL-6.

IL6R20A11 and the formatted variants were compared to the reference IgG as described in Example 1. The resulting IC50 values for the different Nanobodies are summarized in Table C-30. At the EC50 of IL-6 (FIG. 38A, B) both the monovalent and bivalent IL-6R Nanobodies were in the same range as the reference IgG. Although IL6R304 has only one binding site, it had a similar IC50 as the reference IgG (0.229 nM vs. 0.258 nM). IL6R305 appeared to be twice as potent as IL6R304 (IC50 of 0.137 nM), which is in line with its two binding sites. However, IL6R306 appeared to be less potent than IL6R304 and the reference IgG and had an IC50 of 0.412 nM.

Most probably the assay limit was reached in terms of sensitivity. Indeed, the concentration of plasma sIL-6R was ~30 ng/mL or 0.6 nM. Therefore, only 0.3 nM of sIL-6R needed to be blocked by the Nanobodies (50% plasma), which means that the minimum IC50 that can be obtained is 0.15 nM. This corresponds to the IC50 values that were obtained. However, if the IL-6 concentration would be increased to 885 ng/mL it would be more difficult for the Nanobodies to compete with IL-6 and a larger difference in potency could be detected. Indeed, at high IL-6 concentrations IL6R20A11, IL6R304 and IL6R305 were clearly more potent than the reference IgG, whereas IL6R306 was not (FIG. 38 C, D). The ratio of the IC50 at high and low concentrations of IL-6 is shown in Table C-30. Clearly, the reference IgG and IL6R306 were more affected by increasing IL-6 than the other Nanobodies. This was also observed in the TF-1 assay (see Example 44).

Example 46

Binding of the Formatted Affinity Matured Nanobodies to Membrane IL-6R

In order to block signaling of IL-6, both soluble and membrane IL-6R need to be neutralized by the Nanobodies. Therefore, binding of the different formatted Nanobodies to IL-6R-expressing cells was analyzed by flow cytometry.

Binding to IL-6R-Expressing CHO Cells

Stably transfected CHO cells expressing human IL-6R were used to analyze the binding of the anti-IL-6R Nanobodies to membrane IL-6R (FIG. 39A). IL-6R negative CHO cells were used as a negative control (FIG. 39B). All 4 Nanobodies showed saturated binding to IL-6R-expressing cells, whereas only very low signals were detected at high Nanobody concentrations on IL-6R-negative cells.

The median PE fluorescence was exported to GraphPad and 4PL curves were fitted to determine the EC50 values. These are summarized in Table C-31. In contrast to the TF-1 assay, IL6R305 did not seem to benefit from an avidity effect in this setup: it was only a factor 2 more potent than IL6R304 (0.8984 vs. 1.939 nM). As was also the case in the TF-1 and in the plasma ELISA, IL6R306 bound less well to IL-6R-positive cells.

Binding to Peripheral Blood Leukocytes

Human PBL were used to demonstrate binding of the Nanobodies to membrane IL-6R under physiological conditions. This matrix is highly relevant for the in vivo situation, since it contains HSA (~50 mg/mL), sIL-6R (~30 ng/mL), cells expressing membrane IL-6R($CD4^+$ T cells, monocytes, granulocytes) and IL-6R-negative cells (most circulating B cells, $CD8^+$ T cells). The Nanobodies were incubated in EDTA-treated blood from 2 donors and bound Nanobody was detected by flow cytometry. Lymphocytes, monocytes and granulocytes were gated based on FSC/SSC properties (FIG. 40) and bound Nanobodies were detected in the PE channel.

Figure 40:
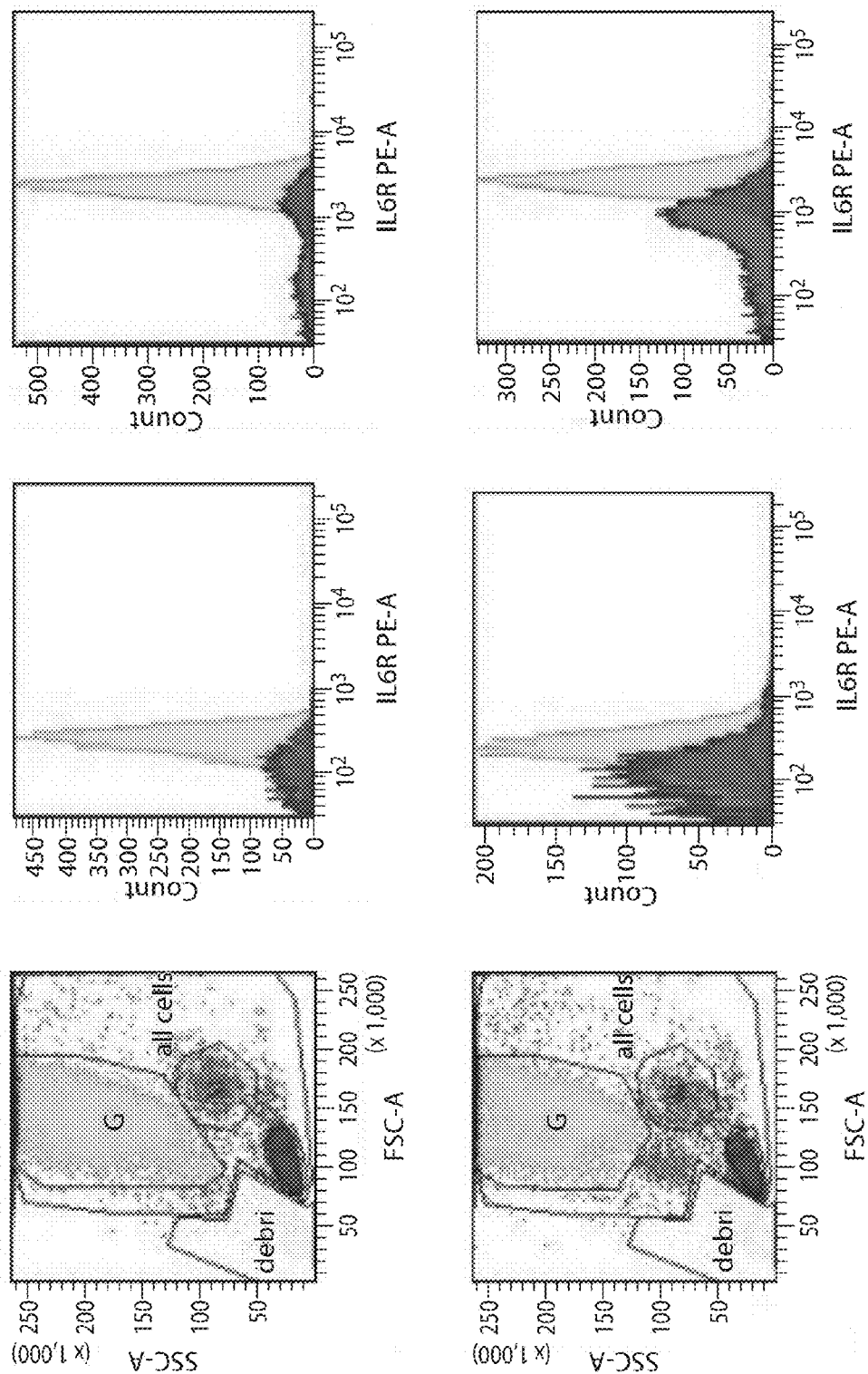
FIG. 40: Binding of IL-6R Nanobodies on human PBL in full blood. Left: lymphocytes (L, black), monocytes (M, dark gray) and granulocytes (G, light gray) were gated based on FSC/SSC properties. Middle: background PE fluorescence of the three gated populations. Right: PE fluorescence after incubation with 1 pM of IL6R305. FSC-A (left column); IL6R PE-A (middle and right columns).

As can be observed in FIG. 40 (right), the granulocytes and monocytes were uniformly stained by the Nanobodies. In contrast, only a part of the lymphocytes were stained. This can be observed as a double peak in the PE histogram. The mean fluorescence of the 3 gated populations after incubation with different concentrations of the Nanobodies is depicted in FIG. 41 and the resulting EC50 values are summarized in Table C-32.

Example 47

Figures 1, 42:
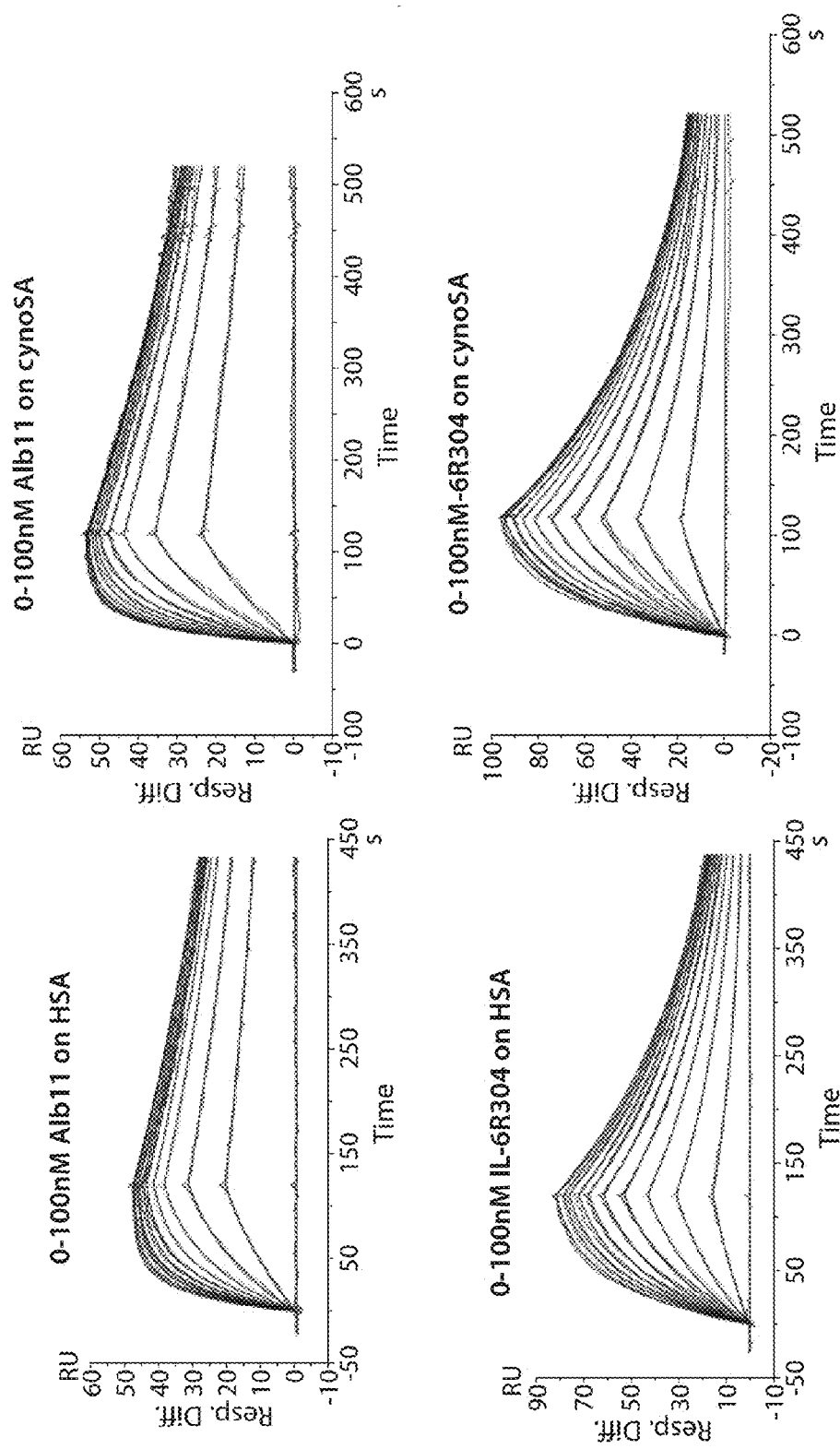
Figures 2, 42:
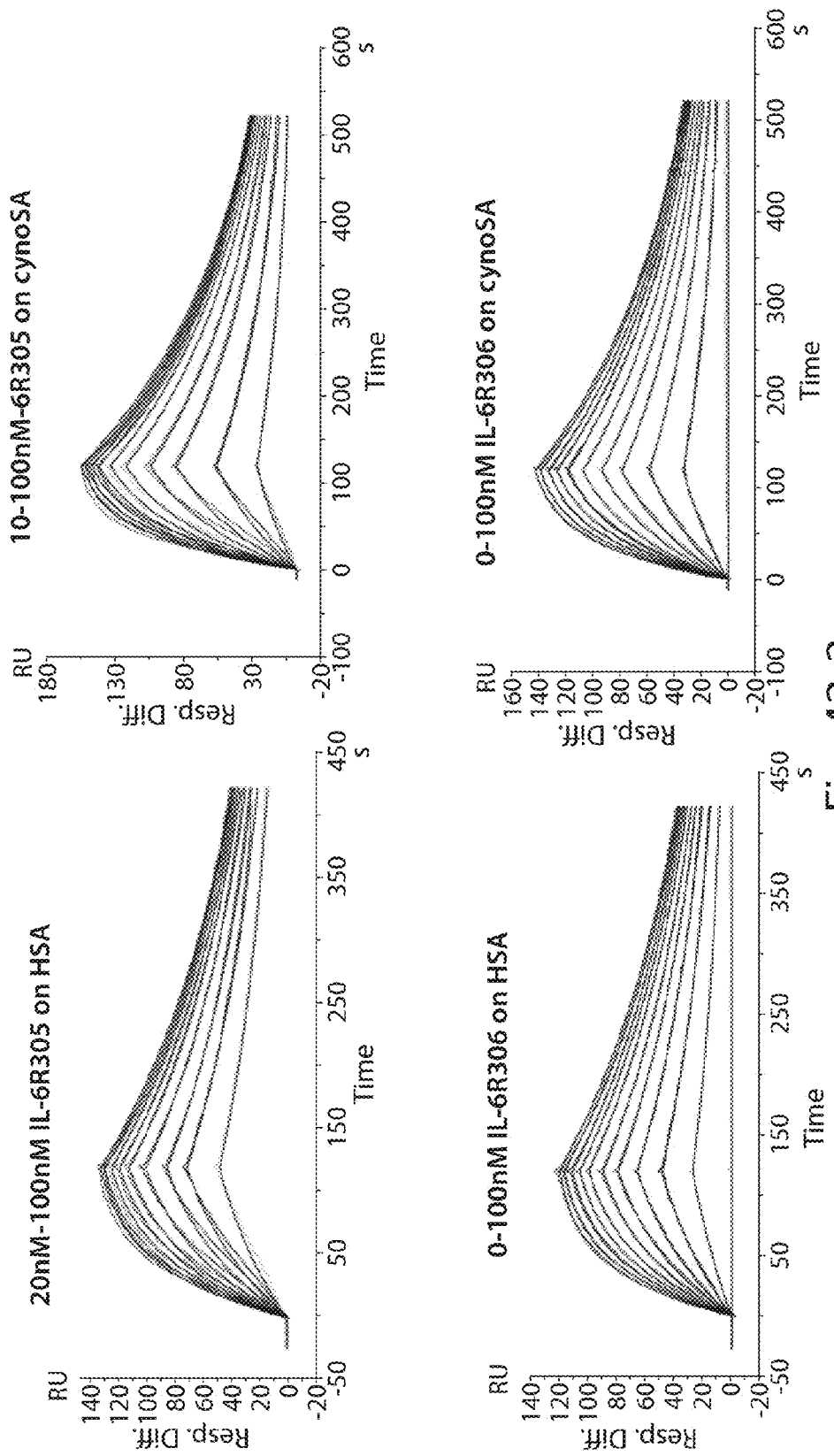

Affinity of the Formatted Affinity Matured Nanobodies for Human and Cyno Serum Albumin Kinetic analysis of the bi-specific, bivalent and trivalent Nanobodies IL6R304, IL6R305 and IL6R306 on human and cyno serum albumin was performed by SPR on a Biacore 3000 instrument. Results are shown in FIG. 42 and summarized in Table C-33. Nanobodies IL6R304, 305 and 306 showed similar kinetic rate constants and affinities (17-23 nM) for human and cyno SA. The affinity of the formatted IL-6R Nanobodies for SA was 6.5× lower as compared to the monovalent anti-SA Nanobody ALB11 by a decrease of a factor 2.5 in association rate and an increase of a factor 2.5 in dissociation rate.

Example 48

Affinity for Human and Cyno IL-6R

Figure 43:
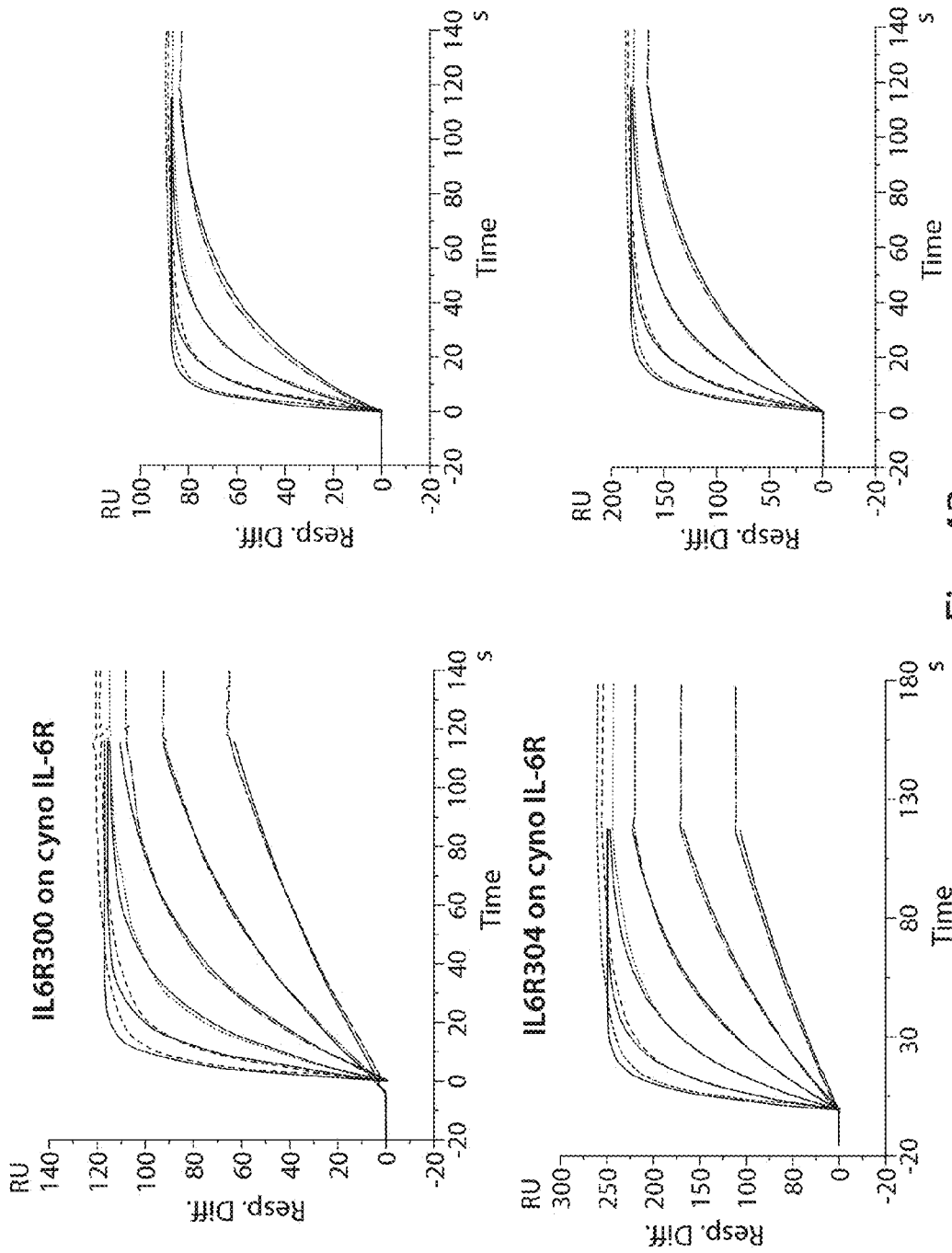
FIG. 43: Binding curves of formatted affinity matured Nanobodies to human and cyno IL-6R.

Kinetic analysis on human and cyno IL-6R was performed by SPR on a Biacore T100 instrument. Because of indications of a conformational change of IL-6R when immobilizing it directly to the chip on-rates were measured on IL-6R captured by BN-12. Off-rates were measured on directly immobilized IL-6R, because of the lack of availability of a capturing tool with a lower dissociation rate than the Nanobody-IL-6R interaction. Results are shown in Table C-34 and FIG. 43.

The on-rate of 20A11 (IL6R300; SEQ ID NO: 66) decreased by less than a factor 2 by formatting with an anti-SA building block (IL6R304). The off-rate for IL6R304 on human IL-6R was at or below the detection limit of the Biacore instrument. The off-rate on cyno IL-6R was ≥2 times higher than on human IL-6R, but still near the detection limit. Calculated affinities for IL6R304 were ≤14 pM on human IL-6R and 25 pM on cyno IL-6R.

Example 49

Species Cross-Reactivity of IL6R20A11

Cross-reactivity of IL6R20A11 and its formatted variants with cynomolgus sIL-6R was analyzed in the plasma potency ELISA using cyno plasma. Also, a competition ELISA was used to determine the cross-reactivity of IL6R20A11 with cyno and mouse sIL-6R.

Plasma Potency ELISA

Figure 44:
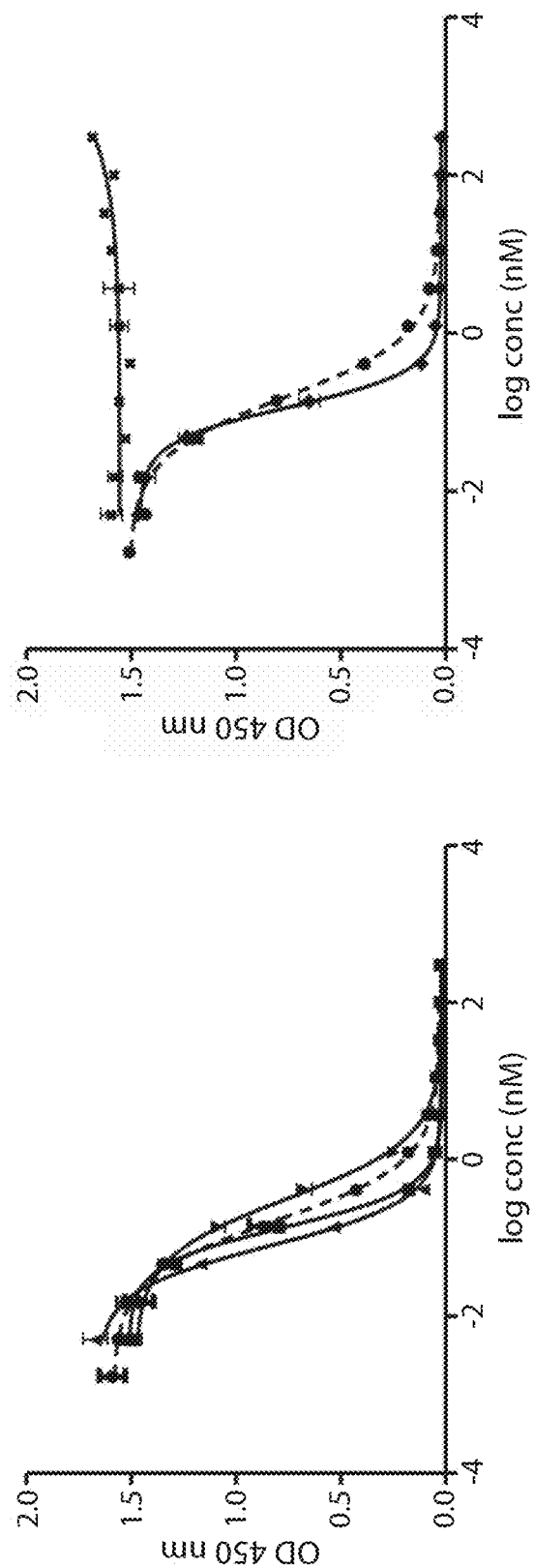
FIG. 44: Plasma potency ELISA in cyno plasma. Neutralization of binding of human IL-6 to cyno plasma sIL-6R by the reference IgG (•), IL6R20A11 (♦), IL6R304 (■), IL6R305 (▲), IL6R306 (▼) or an irrelevant NB (x).

A titration of human IL-6 was first incubated in cyno plasma and the EC50 value of IL-6 was determined to be 50.11 ng/mL. This concentration of IL-6 was subsequently used to test the cross-reactivity of the Nanobodies with cyno plasma sIL-6R. As can be observed in FIG. 44, IL6R20A11 and the formatted variants were clearly cross-reactive with cynomolgus sIL-6R. The same ranking can be observed as in human plasma and the ratio of the IC50 values in human vs. cyno plasma was similar for all compounds (Table C-35).

Competition ELISA

The plasma potency ELISA can only be used if BN-12 is able to capture plasma sIL-6R from that particular species and if binding of IL-6 to sIL-6R can be detected. Therefore, a more generic competition ELISA was developed. This assay was based on binding of IL6R20A11 to neutravidin-captured IL-6R-bio. Briefly, 0.4 nM of IL6R20A11 was pre-incubated with a titration series of plasma from the different species containing endogenous sIL-6R, after which free IL6R20A11 was captured on biotinylated human sIL-6R immobilized on a neutravidin-coated plate, and detected with an anti-VHH mAb:FITC and anti-FITC-HRP. The concentration of IL6R20A11 of 0.4 nM corresponds to the concentration that yields 50% of the maximal signal (EC$_{50}$ of 0.35±0.021 nM; n=4).

Figure 45:
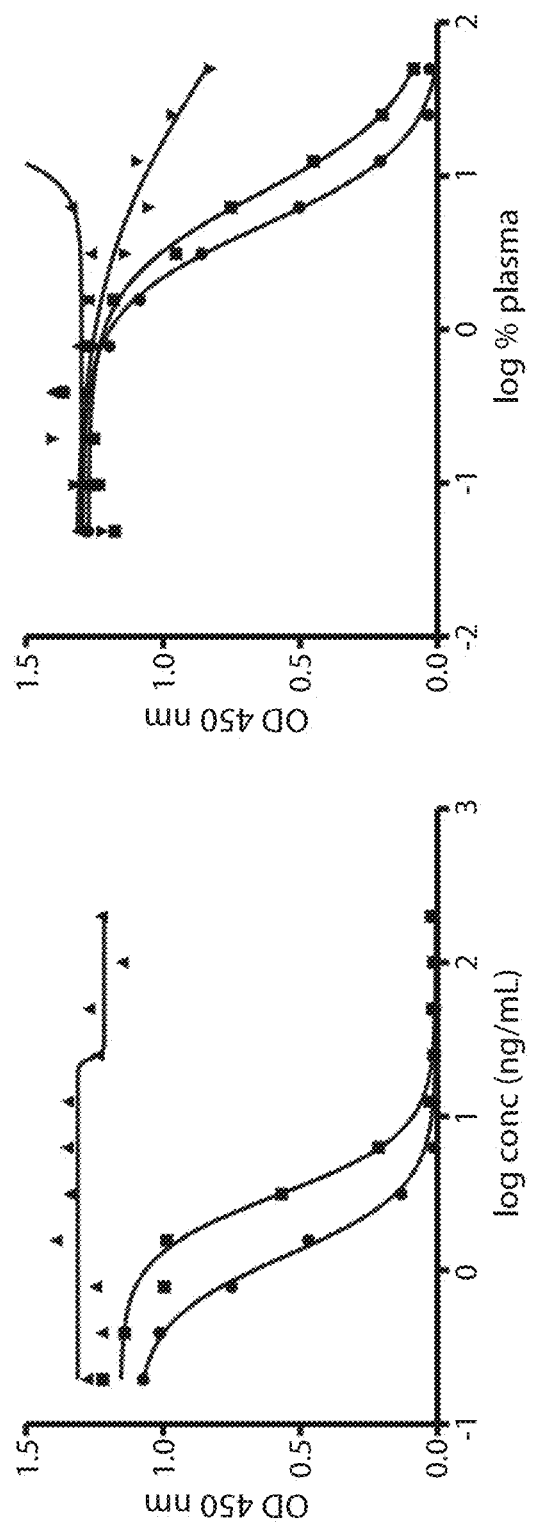
FIG. 45: Cross-reactivity of IL6R20A11 with sIL-6R from other species. Left: binding of IL6R20A11 to human sIL-6R on the plate after pre-incubation with recombinant sIL-6R from human (•), cyno (■) or mouse (▲). Right: binding of IL6R20A11 to human sIL-6R after pre-incubation with human (•), cyno (■), mouse (▲) or guinea pig (▼) plasma.

As can be observed in FIG. 45, IL6R20A11 was clearly cross-reactive with cyno sIL-6R, which confirms the Biacore results. In contrast, no binding to mouse sIL-6R could be observed. Human and cyno plasma also competed with binding of IL6R20A11 to recombinant sIL-6R, whereas mouse plasma did not. In fact, increasing signals were observed at high concentrations of mouse plasma, which was probably due to the detection of mouse immunoglobulins in the assay.

Example 50

Specificity of IL6R20A11 for IL-6R

Figure 46:
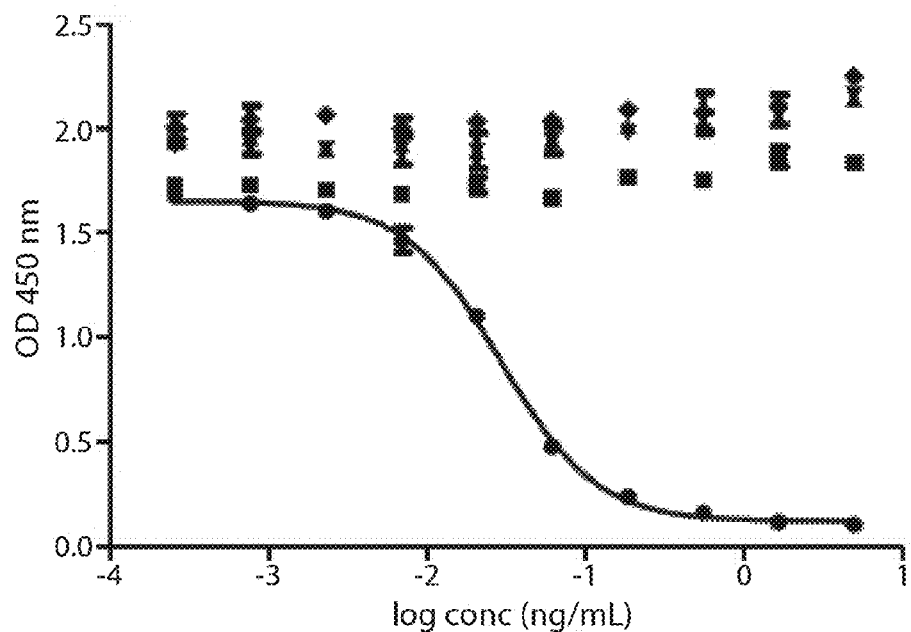
FIG. 46: Competitive binding ELISA. IL6R20A11 (0.05 nM) was pre-incubated with different concentrations of IL-6R (•), LIF-R (■), CNTF-R (▲), OSM-R (▼) or IL-11R/Fc (♦). Free IL6R20A11 was captured on sIL-6R and detected via anti-His.

IL-6R belongs to the family of type I cytokine receptors. Since the cytokine binding region of these receptors is conserved, the specificity of IL6R20A11 for IL-6R was analyzed by analyzing binding to receptors related to IL-6R. Binding of IL6R20A11 to LIF-R, CNTF-R, OSM-R and IL-11R/Fc was analyzed in a competitive binding ELISA. As can be observed in FIG. 46, the positive control sIL-6R inhibited binding of IL6R20A11 to the plate. The IC50 for sIL-6R (0.03 nM) was in line with the expected IC50 based on the amount of IL6R20A11 that was used (0.025 nM vs. 0.05 nM). None of the IL-6R-related proteins seemed to compete with binding of IL6R20A11 to sIL-6R, even at a 100-fold molar excess (5 nM). In a similar setup, it was shown that CLF-1/CLC, IL12-p40, IL-27B and gp130/Fc also did not interact with 0.05 nM of IL6R20A11, even at concentrations as high as 100 nM (results not shown).

VII. In Vivo PK/PD Analysis of IL6R304 and IL6R305

The aim of this study was to analyze the plasma pharmacokinetics (PK), pharmacodynamics (PD) and immunogenicity of two sequence optimized, affinity maturated anti-interleukin 6 receptor (IL-6R) Nanobodies, namely IL6R304 and IL6R305, in cynomolgus monkey after a single intravenous bolus administration. Administration of Nanobodies was followed by 7 daily subcutaneous injections of recombinant human (h) IL-6 starting 24 hours post Nanobody administration. The ultimate goal of this in vivo efficacy study was to assess the ability of these anti-IL-6R Nanobodies to inhibit hIL-6-induced parameters and compare their efficacy with each other and with the benchmark reference of Example 1.

In non-human primates and in humans, recombinant hIL-6 has been reported to induce the synthesis of acute phase proteins. Acute phase proteins are defined as a class of plasma proteins, such as C-reactive protein (CRP), serum amyloid A, haptoglobin, fibrinogen, albumin and transferrin, whose plasma concentrations increase or decrease by at least 25% in response to inflammation, mainly due to changes in their production by hepatocytes. Patterns of cytokine production and acute phase response differ in different inflammatory conditions. Therefore, acute phase changes reflect the presence and intensity of inflammation, making them diagnostically relevant. The main stimulators of the production of acute phase proteins are the inflammation-associated cytokines, which are produced during inflammatory processes: IL-6, IL-1β, tumor necrosis factor-α(TNF-α), interferon-γ (INF-γ), transforming growth factor β (TGF-β) and possibly IL-8.

Example 51

Study Design

In this study 6 groups (groups 6 to 11, Table C-36) of 2-3 animals received a single i.v. injection of IL6R304 or IL6R305. Of both Nanobodies, 3 different doses were tested, namely 0.4, 2 or 10 mg/kg. In addition, animals in group 12 (n=3) received vehicle and served as negative control, while animals of group 13 (n=3) were injected with 5 mg/kg reference IgG (Table C-36).

Figure 47:
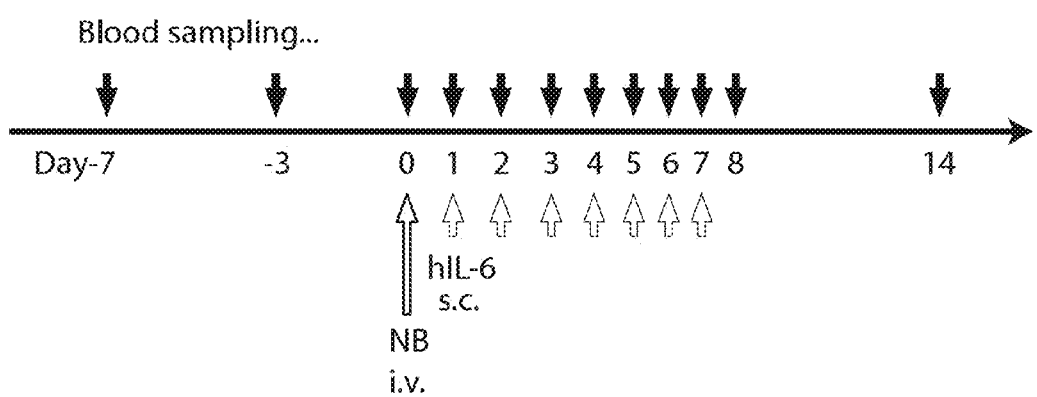
FIG. 47: Study design for in vivo PK/PD analysis of IL6R304 and IL6R305.

Starting on TD1, i.e. 24 hours after test item administration, all animals were injected once daily for 7 days with hIL-6 (5 µg/kg; FIG. 47).

Blood samples were collected via the vena cephalica or saphena magna before and after injection of hIL-6 on predetermined time points (see FIG. 47). Extra blood samples were taken on TD0 for PK analysis (see Table C-37).

Example 52

The Effect of the Nanobodies on an hIL-6-Induced Acute Phase Response (Phase 2)

The effect of the Nanobodies and the positive reference IgG was analyzed on the induction of an acute phase response by 7 consecutive daily injections of hIL-6. Read-outs were CRP levels, fibrinogen levels and platelet count.

Figure 48A:
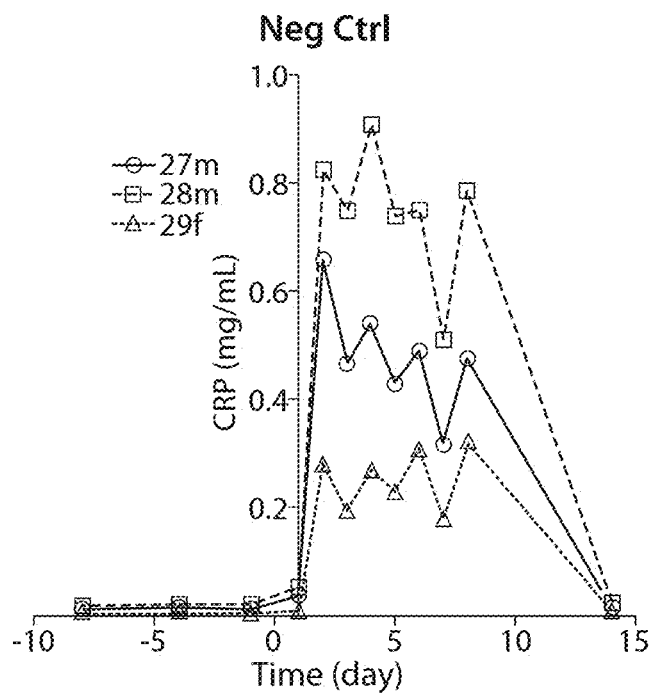
FIG. 48A-D: Effect of the reference IgG, IL6R304 and IL6R305 on CRP levels increased by hIL-6 in individual cynomolgus monkeys. (A) Animals 27, 28 and 29 served as negative controls and received only hIL-6. The reference IgG (B, closed black symbols), different doses of IL6R304 (C, blue symbols) and different doses of IL6R305 (D, red symbols) were i.v. administered followed by s.c. injections of hIL-6 at a dose of 5 µg/kg once a day for 7 days.

In the negative control group (group 12), CRP levels were immediately elevated after the first injection of hIL-6 and maximum levels were already reached on day 2. The maximum levels attained were between 0.2-0.8 mg/mL and this plateau was maintained until day 8, which is the day after the last hIL-6 injection (FIG. 48A).

Figure 48B:
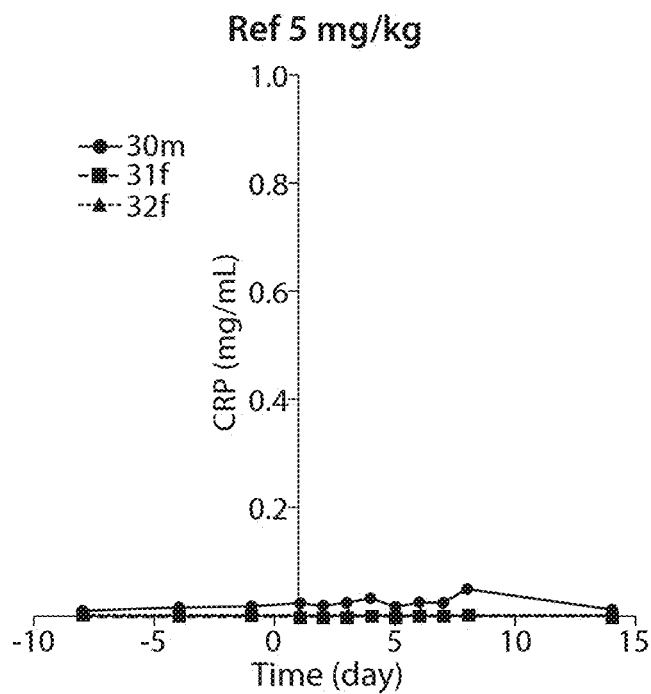
Figure 48C:
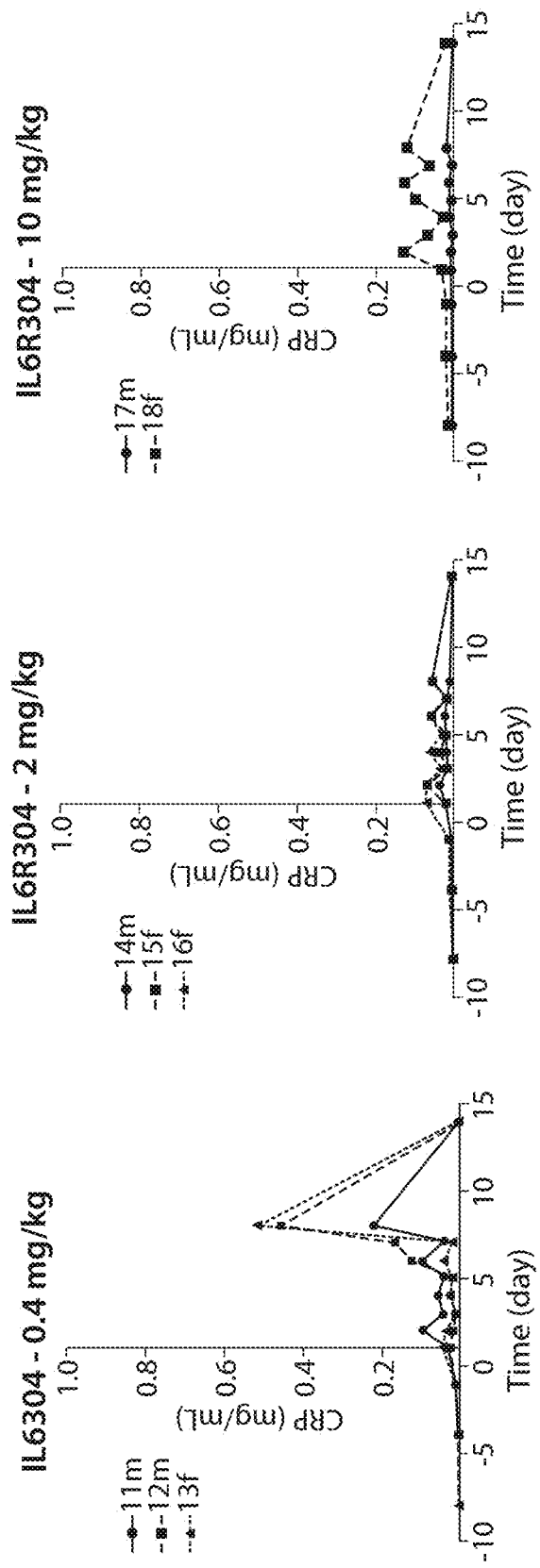
Figure 48D:
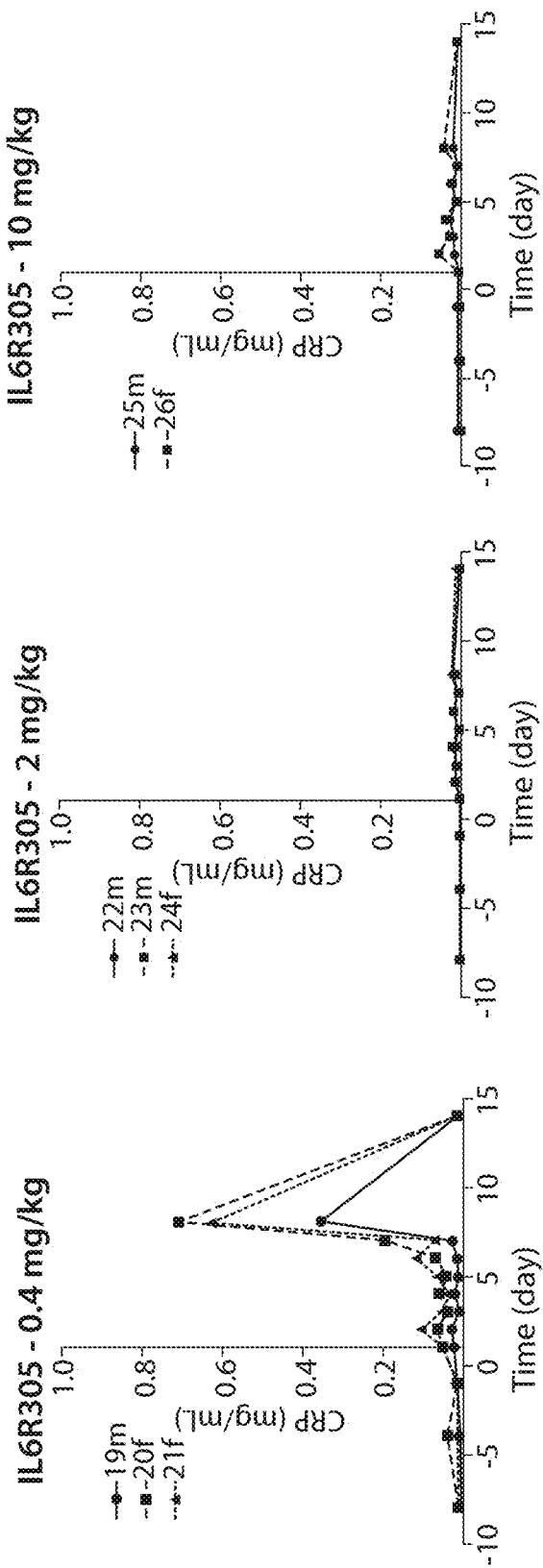
Figure 49:
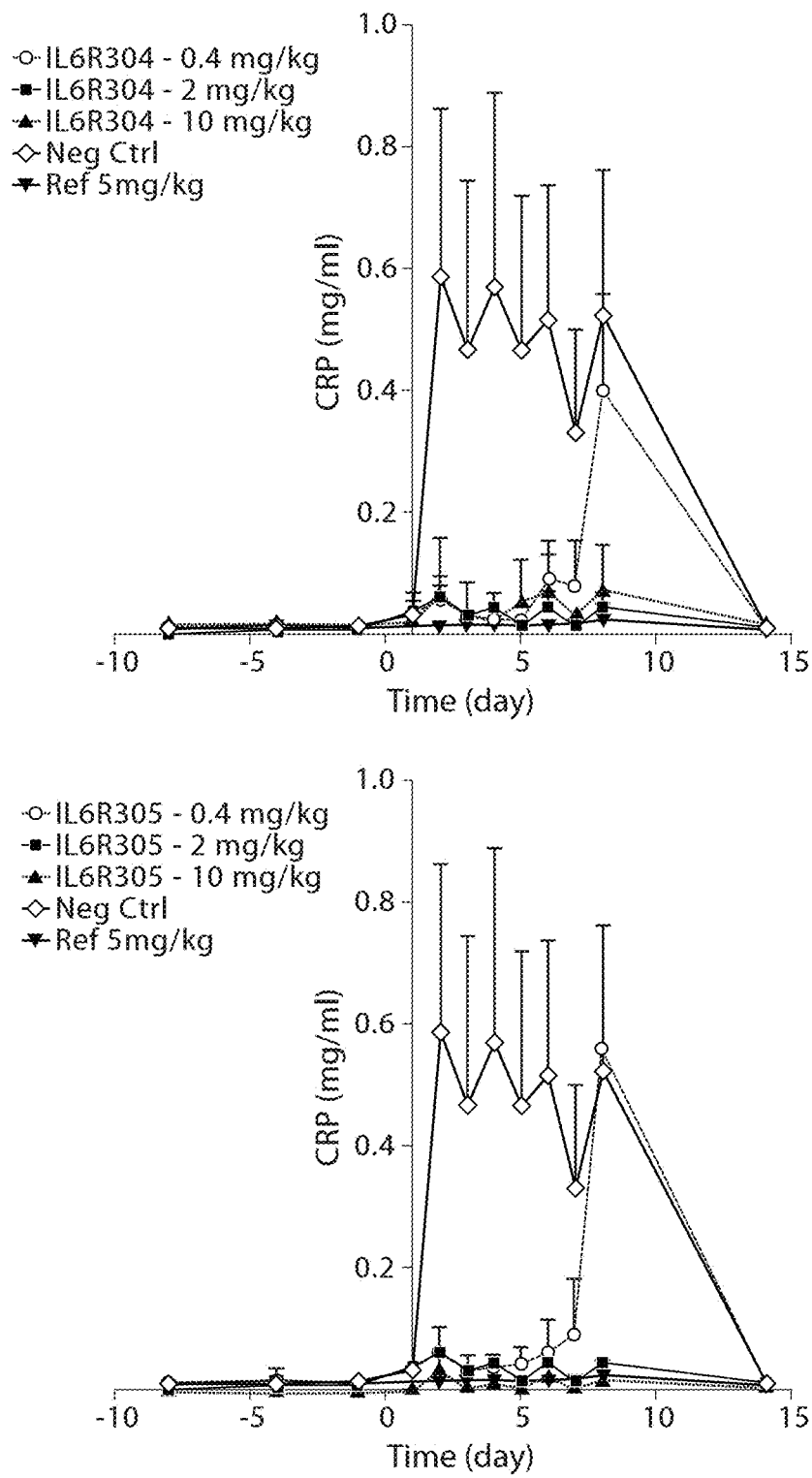
FIG. 49: Mean CRP levels for all groups obtained in the in vivo PK/PD study with IL6R304 and IL6R305.

These changes were completely inhibited by pretreatment with 5 mg/kg reference IgG (FIG. 48B). Also a single pretreatment with a comparable dose (2 mg/kg) or a 5-fold higher dose (10 mg/kg) of the Nanobodies IL6R304 and IL6R305 gave almost complete inhibition of CRP induction during the whole course of the experiment (FIGS. 48C and D). Only animal No. 18 in the highest dose group of IL6R304 showed some induction, reaching maximum serum CRP levels around 0.1 mg/mL. In the lowest dose group (0.4 mg/kg), both Nanobodies gave complete inhibition for 7 days. CRP levels increased only on day 8 to comparable levels as in the negative control group (FIG. 48) The mean CRP levels of all groups can be found in FIG. 49.

Figure 50A:
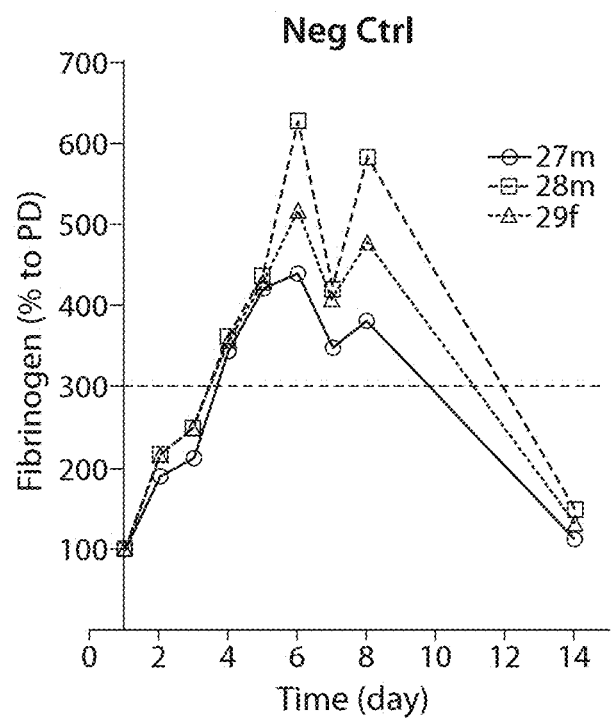
FIG. 50A-D: Effect of the reference IgG, IL6R304 and IL6R305 on fibrinogen levels increased by hIL-6 in individual cynomolgus monkeys. (A) Animals 27, 28 and 29 served as negative controls and received only hIL-6. Reference IgG (B, closed black symbols), different doses of IL6R304 (C, blue symbols) and different doses of IL6R305 (D, red symbols) were i.v. administered followed by s.c. injections of hIL-6 at a dose of 5 µg/kg once a day for 7 days. Results were normalized to the basal levels.
Figure 50B:
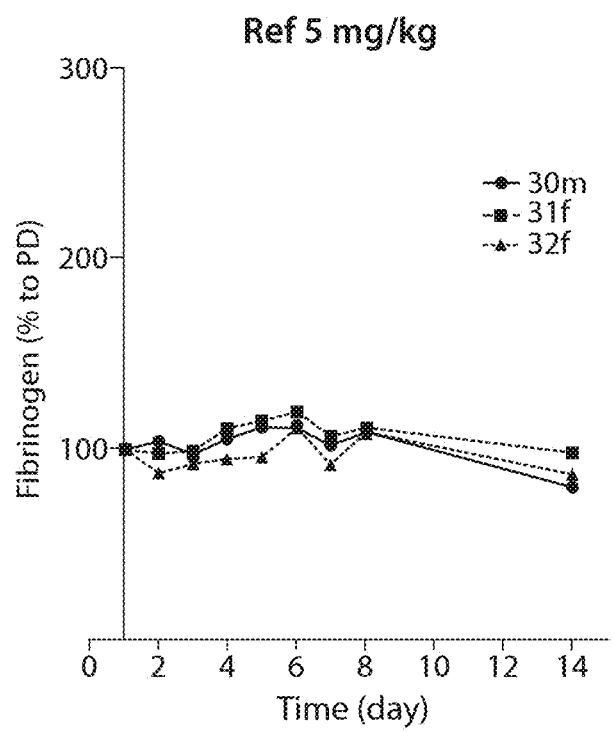
Figure 50C:
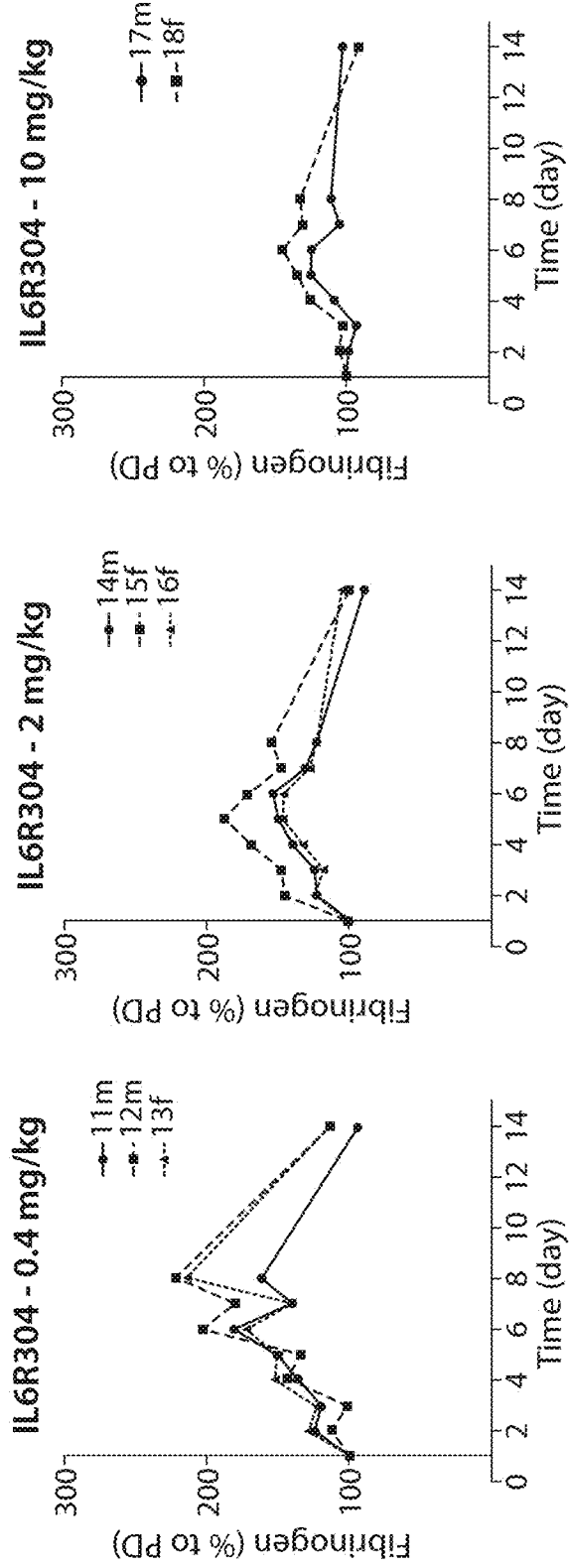
Figure 50D:
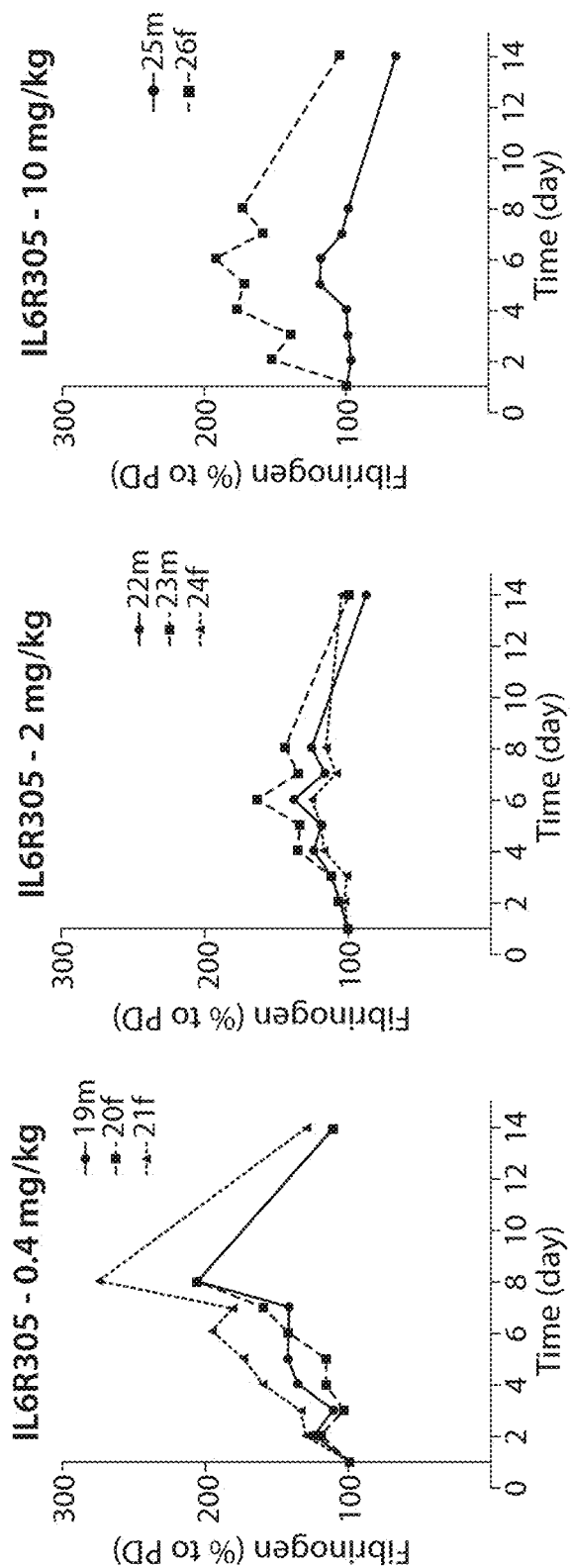
Figure 51:
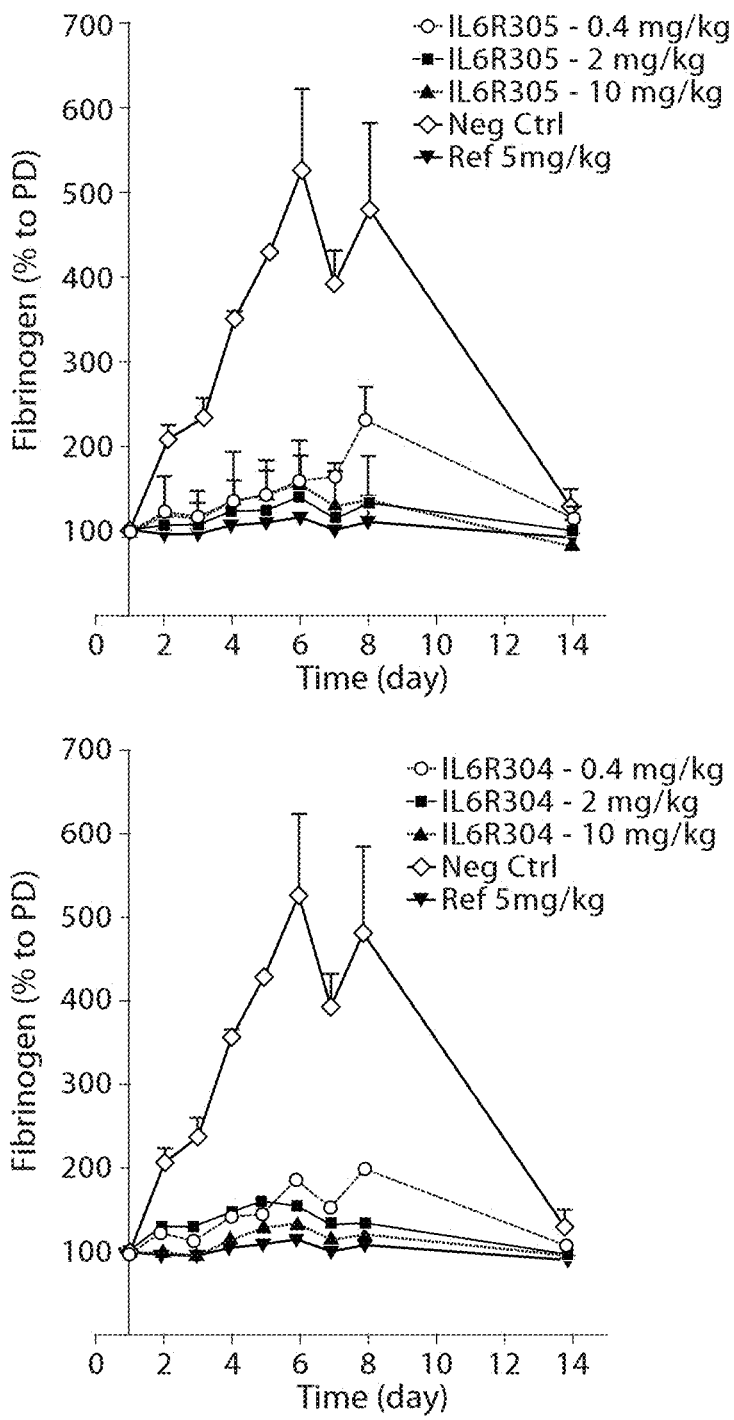
FIG. 51: Mean fibrinogen levels for all groups obtained in the in vivo PK/PD study with IL6R304 and IL6R305.
Figure 52A:
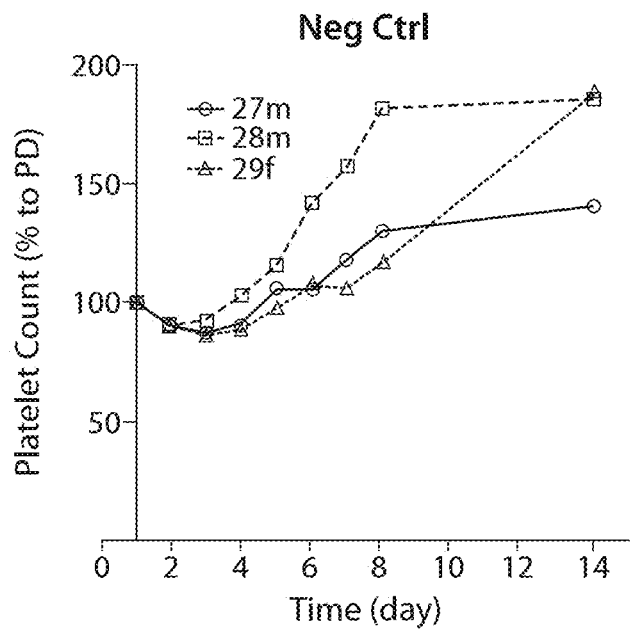
FIG. 52A-D: Effect of the reference IgG, IL6R304 and IL6R305 on platelet counts increased by hIL-6 in individual cynomolgus monkeys. (A) Animals 27, 28 and 29 served as negative controls and received only hIL-6. Reference IgG (B, closed black symbols), different doses of IL6R304 (C, blue symbols) and different doses of IL6R305 (D, red symbols) were i.v. administered followed by s.c. injections of hIL-6 at a dose of 5 µg/kg once a day for 7 days. Results were normalized to the basal levels.
Figure 52B:
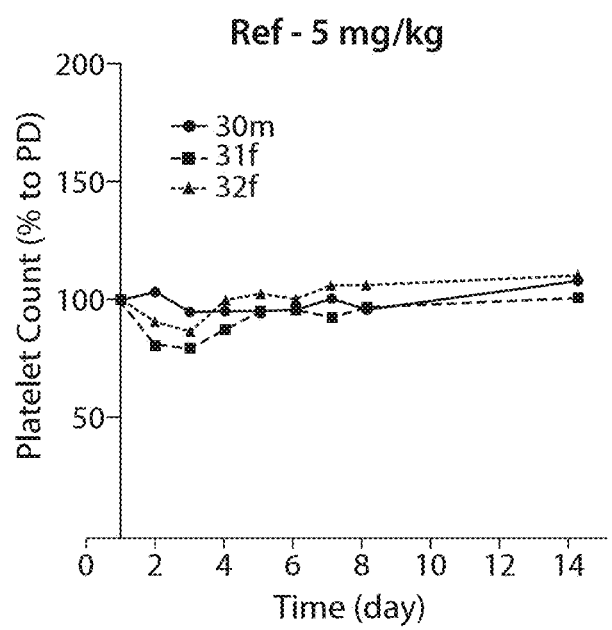
Figure 52C:
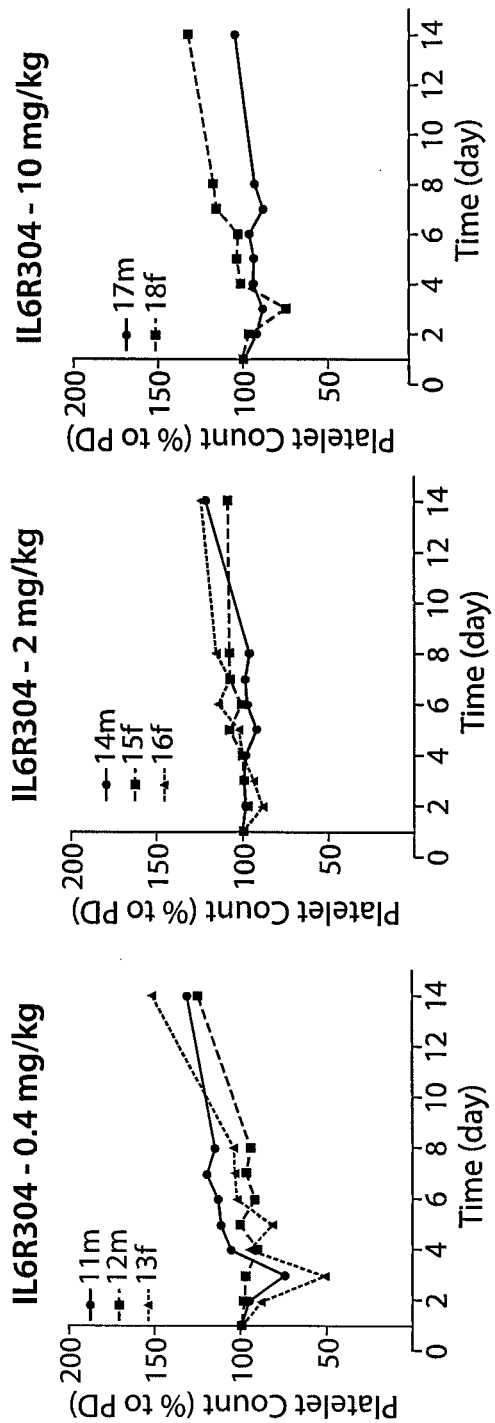
Figure 52D:
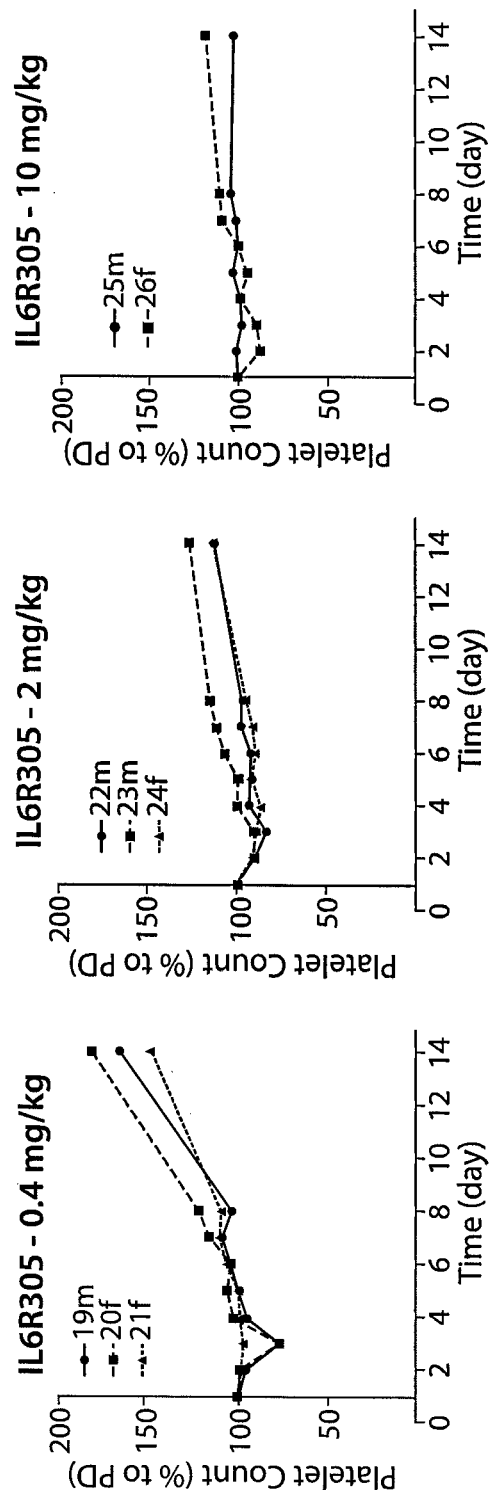

Fibrinogen levels increased slowly in the negative control group to an average maximum of 5 times the basal levels (FIG. 50A). This maximum was reached on day 6 and was maintained for 2 more days. On day 14, fibrinogen levels were back to basal levels. The reference IgG was capable to completely inhibit the induction of fibrinogen (FIG. 50B). Both Nanobodies showed a dose-dependent inhibition of fibrinogen induction (FIGS. 50C and D). In the highest dose groups, inhibition was almost complete for both animals pretreated with IL6R304 and for 1 out of 2 animals pretreated with IL6R305. There was some minor increases in fibrinogen levels of animal No. 25 (10 mg/kg IL6R305) and of all animals of the middle and lowest dose groups of both Nanobodies. In these animals, however, fibrinogen levels never exceeded 2-3 times the basal levels. The mean fibrinogen levels of all groups can be found in FIG. 51.

Figure 53:
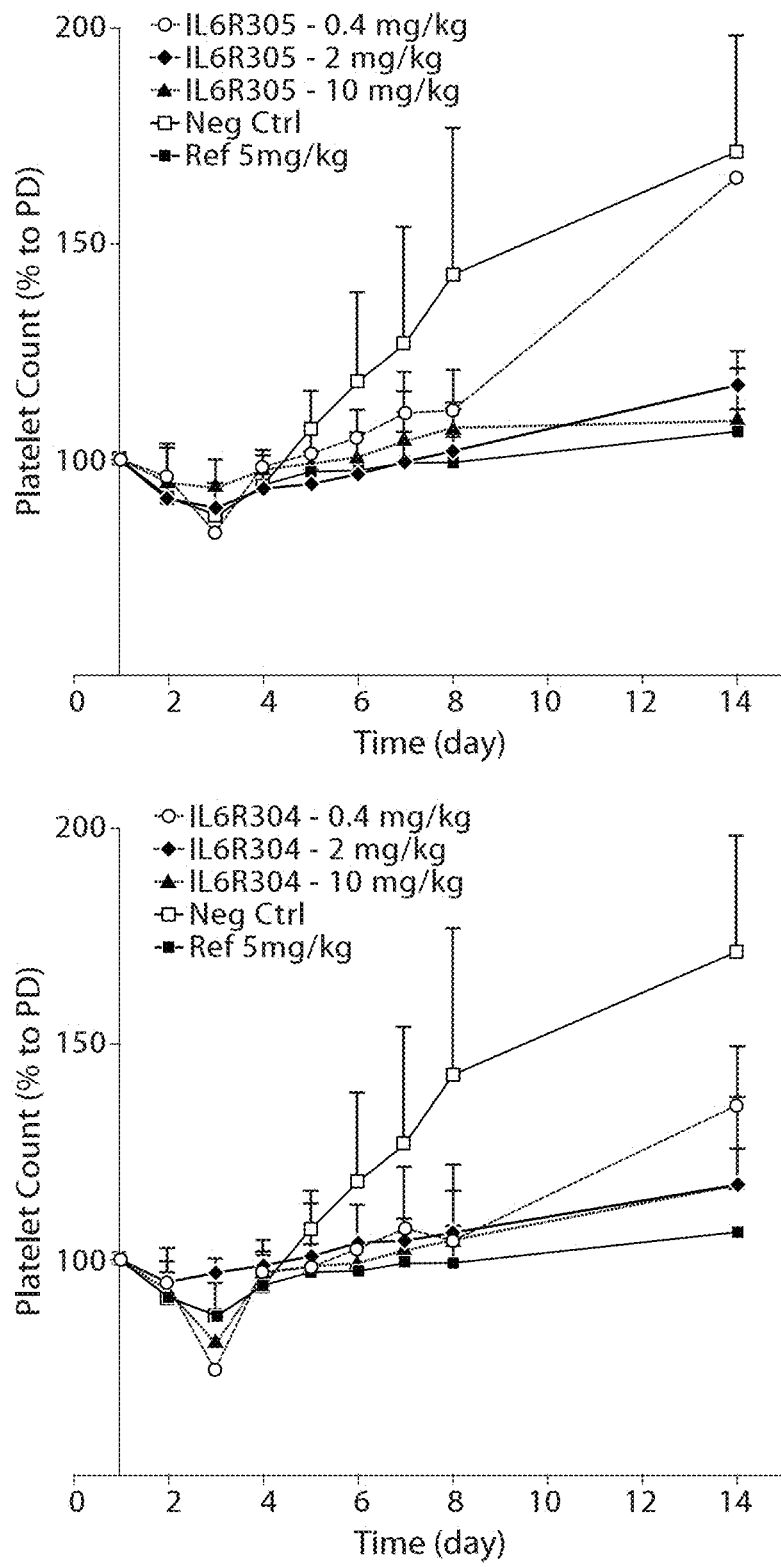
FIG. 53: Mean platelet counts for all groups obtained in the in vivo PK/PD study with IL6R304 and IL6R305.

For all animals in the negative control group, platelet counts increased slowly from day 5 onwards. Maximum levels were reached at day 8 to day 14 and were between 160-190% of basal levels. The effect of hIL-6 on platelet counts was completely blocked by a single pretreatment with 5 mg/kg reference IgG or ≥2 mg/kg of the Nanobodies. An induction in platelet count was only observed in the lowest dose groups of the Nanobodies, starting in all animals on day 8. Maximal induction was around 120-150% of basal levels for IL6R304, while maximum platelet counts for IL6R305 were between 160-180% of basal levels (FIGS. 52 and 53).

In conclusion, IL6R304 and IL6R305 showed a similar dose-dependent and complete inhibition of all three acute phase response parameters.

Example 53

Plasma Concentrations after i.v. Administration of IL6R304 or IL6R305 (0.4-2-10 Mg/Kg) in Cynomolgus Monkeys Blood samples for plasma pharmacokinetic (PK) analysis ELISA sample analysis were taken at pre-dose and at following time points post administration of IL6R304 or IL6R305: 5 and 30 minutes, 3 and 8 hours, day 1, 2, 3, 4, 5, 6, 7, 8, 14, 21 and 29.

Figure 54:
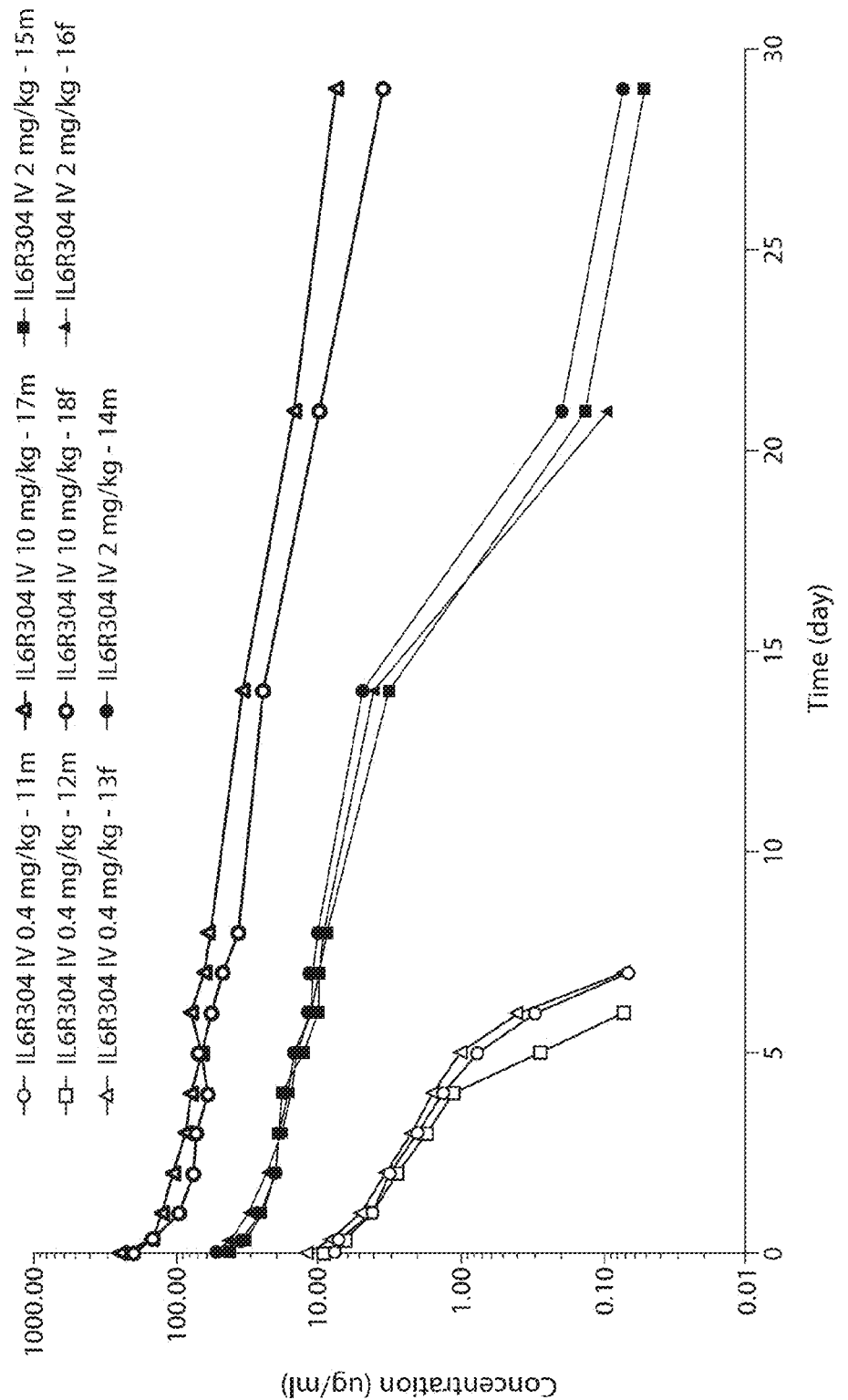
FIG. 54: Individual observed plasma concentration-time plots after i.v. bolus administration of IL6R304 (0.4-2-10 mg/kg) in cynomolgus monkeys. 11m, 12m and 13f are the three graphs on the left hand side; 17m, 18f and 14m are the middle graphs and 15m and 16f are the graphs on the right hand side.
Figure 55:
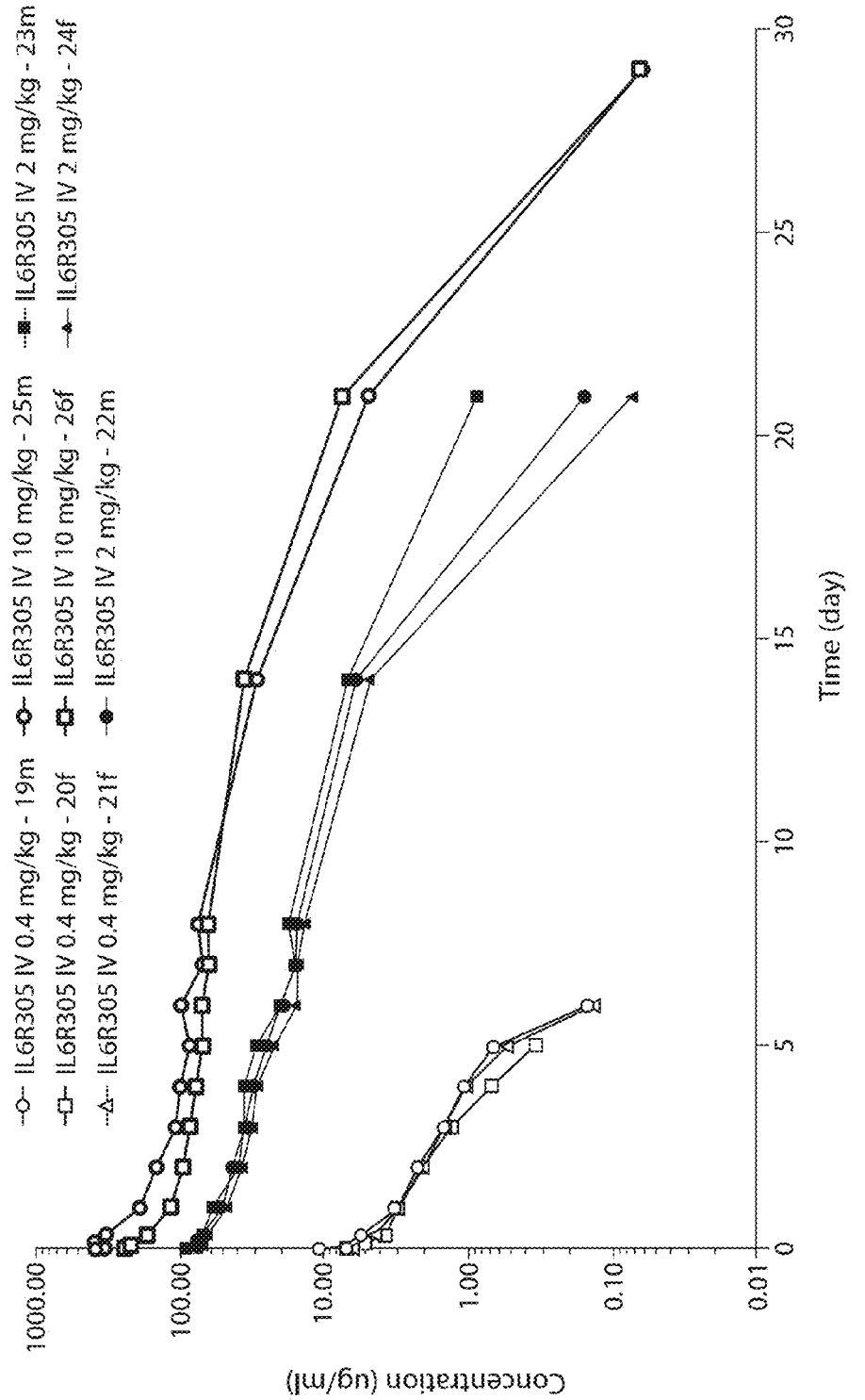
FIG. 55: Individual observed plasma concentration-time plots after i.v. bolus administration of IL6R305 (0.4-2-10 mg/kg) in cynomolgus monkeys. 19m, 20f and 21f are the three graphs on the left hand side; 25m, 26f and 22m are the middle graphs and 23m and 24f are the graphs on the right hand side.

Individual observed plasma concentration-time plots after i.v. administration of IL6R304 (0.4-2-10 mg/kg) and IL6R305 (0.4-2-10 mg/kg) to cynomolgus monkeys are shown in FIG. 54 and FIG. 55, respectively.

Example 54

Non-Compartmental Pharmacokinetics Analysis of IL6R304 and IL6R305 (0.4-2-10 mg/kg) in Cynomolgus Monkeys An overview of the basic PK parameters obtained by non-compartmental PK analysis of IL6R304 (0.4-2-10 mg/kg) and IL6R305 (0.4-2-10 mg/kg) in cynomolgus monkeys is given in Table C-38, Table C-39, Table C-40, Table C-41, Table C-42 and Table C-43. The PK parameters discussed herein are obtained using non-compartmental analysis (NCA) using WinNonlin Professional Software Version 5.1 (Pharsight Corp). The terminal parameters for some of the animals were calculated with two data-points only ($R^2$ is 1 by default).

For both Nanobodies administered intravenously in cynomolgus monkeys, plasma concentrations seemed to decline in a triphasic manner. During the first two days post administration there was an initial disposition phase, followed by a slower dominant phase. A gradual decline at the lower concentrations resulted in a terminal phase characterized by a short half-life.

Since anti-drug antibodies were detected in the plasma samples of most cynomolgus monkeys, the change in terminal half-life at lower concentrations could be linked to an immune-mediated clearance mechanism. This is however unlikely upon examining the PK profiles: at the lowest dose the shortest half-life has been observed at time points where no immunogenicity is detected. Moreover, despite the presence of detectable titers at the higher doses, there is still a tendency towards longer half-lives (f.e. IL6R304 10 mg/kg i.v.).

Based on PK profile observations, it is expected that both Nanobodies are cleared from the circulation via at least two mechanisms. In such a situation, a linear non-saturable clearance mechanism would represent the non-specific degradation of compound. A second saturable clearance mechanism would be target mediated (f.e. internalization of drug binding to membrane bound IL-6R and subsequent clearance). At higher Nanobody concentrations, the latter clearance mechanism is expected to be saturated and negligible compared with the non-saturable linear clearance: the linear clearance is dominant (resulting in a dominant half-life). However, at lower concentrations the rate of metabolism is higher for a given Nanobody concentration, resulting in a change of terminal slope.

Because of target mediated clearance, PK parameters obtained via NCA analysis such as clearance and half-life appear to be dose and time dependent. The total clearance is the highest at the lowest dose: 24.8 and 35 mL/day/kg for IL6R304 and IL6R305 after 0.4 mg/kg i.v. compared with 10.4-9.00 and 5.93-7.76 mL/day/kg for IL6R304 and IL6R305 at the higher doses. Correspondingly, the dose normalized exposure will be lower at the lowest dose (Dose=CL× AUC).

The dominant half-life of IL6R304 decreased from 6.61 days to 5.00 days and 1.73 days after i.v. administration of 10, 2 and 0.4 mg/kg. The dominant half-life of IL6R305 decreased from 7.37 days to 4.29 days and 1.64 days after i.v. administration of 10, 2 and 0.4 mg/kg. Since more data points are available at earlier time points, the terminal phase was best characterized at the lowest dose: a short terminal half-life of 0.530 days and 0.470 days was observed after i.v. administration of 0.4 mg/kg IL6R304 and IL6R305, respectively.

Based on these PK findings, the pharmacokinetic properties of IL6R304 and IL6R305 are considered to be similar.

At test day 29 for monkey 14m and monkey 15f (i.v. 2 mg/kg) low IL6R304 concentration levels were still detectable. Based on the PK profiles of the other monkeys, these observations were unexpected. It is possible that this indicates a second type of saturable target binding, which only becomes apparent at very low concentrations. However, these observations could also be an artifact of the PK ELISA sample analysis.

The reported volumes of distribution calculated via NCA analysis were low ranging from once to twice the plasma volume of approximately 40 mL/kg for both Nanobodies, suggesting limited distribution outside the vascular space. However, the true Vss may be underestimated due to methodological errors linked to NCA (f.e. Nanobody distribution and subsequent degradation in the peripheric space would not be attributed to the distribution term but to the total systemic clearance). The Vss seems fairly constant across the different dose levels.

Figure 56:
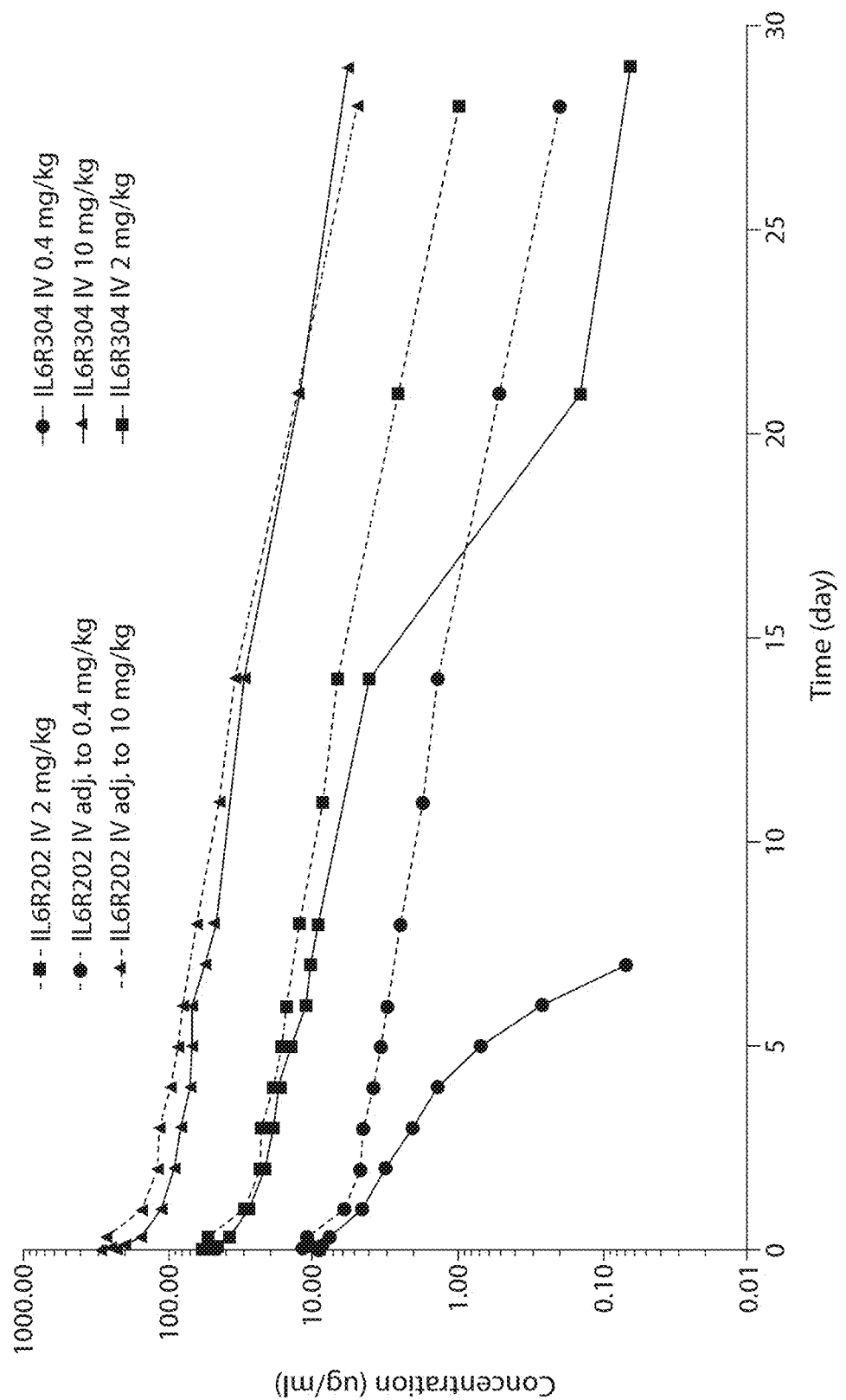
FIG. 56: Mean observed plasma concentration vs. time plots after i.v. bolus administration of IL6R304 (0.4-2-10 mg/kg) and IL6R202 (2 mg/kg, dose-normalized to 0.4-10 mg/kg) in cynomolgus monkeys.

To illustrate the possible effects of target binding on the PK profile, FIG. 56 compares the mean PK profiles of IL6R304 (i.v. 0.4-2-10 mg/kg) and IL6R202 (i.v. 2 mg/kg, SEQ ID ON: 73). For illustrative purposes the IL6R202 (i.v. 2 mg/kg) PK profile was normalized to a 0.4 mg/kg and 10 mg/kg dose as well. IL6R304 was shown to bind to IL-6R in cynomolgus monkey, while for IL6R202 there was a lack of target binding in cynomolgus monkey (WO 09/010,539). Correspondingly, at high concentrations where linear clearance is dominant, the profiles (and corresponding half-lives) of both Nanobodies are similar. At lower concentrations, a gradual change in slope is observed for IL6R304 most likely due to target mediated clearance, while for IL6R202 there is no change in terminal slope. However, the lower concentrations of IL6R304 and IL6R305 could also be somewhat underestimated due to IL-6R interference in the PK ELISA, especially if high IL-6R levels are present.

Example 55

Detection of Anti-IL6R304 and Anti-IL6R305 Antibodies

Figure 57:
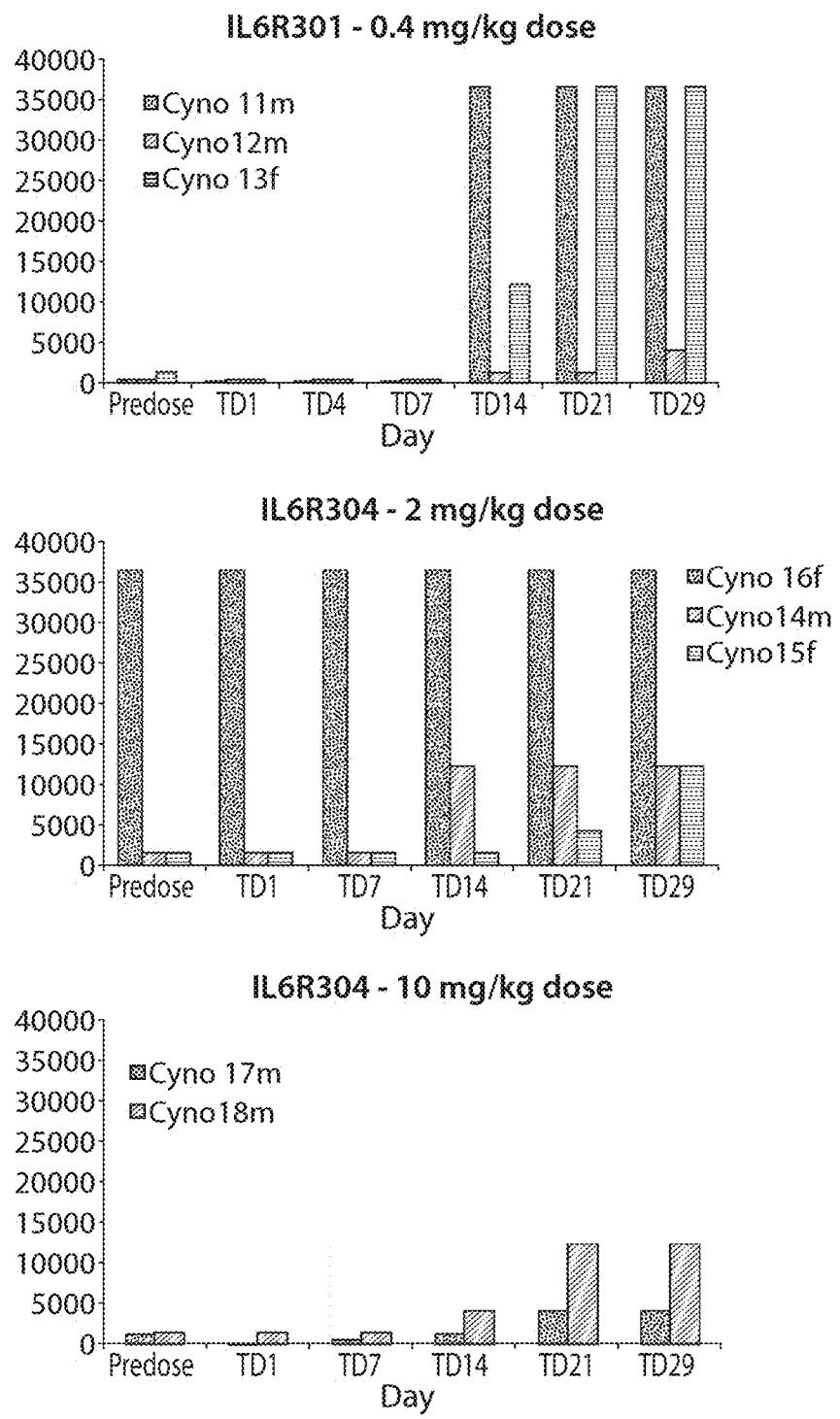
FIG. 57: Immunodetection of anti-IL6R304 antibodies at pre-dose and different days post i.v. administration of IL6R304. ELISA plates were coated with IL6R304. The legend in each of the figures corresponds to the bar graph groupings starting from left to right.
Figure 58:
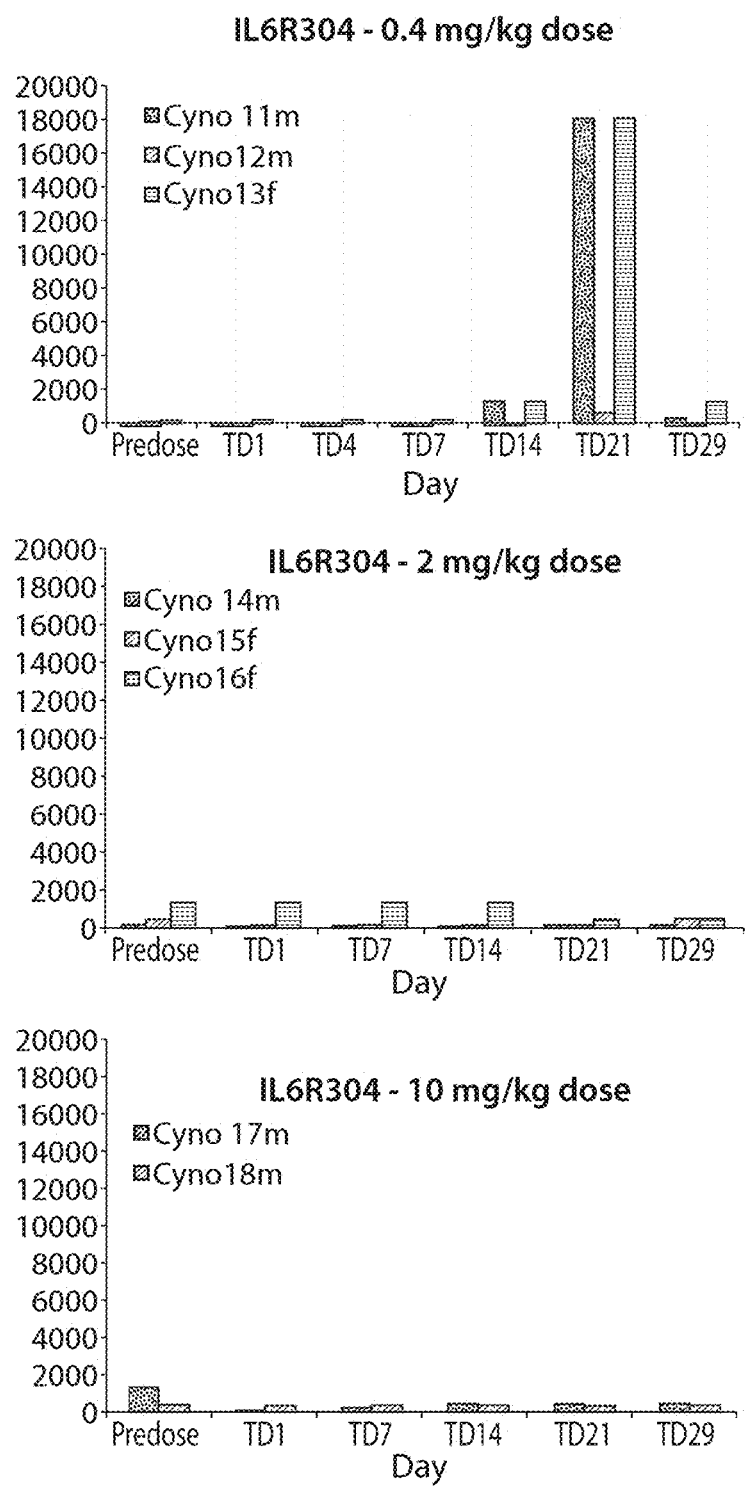
FIG. 58: Immunodetection of anti-IL6R304 antibodies at pre-dose and different days post i.v. administration of IL6R304. ELISA plates were coated with IL6R300. The legend in each of the figures corresponds to the bar graph groupings starting from left to right.
Figure 59:
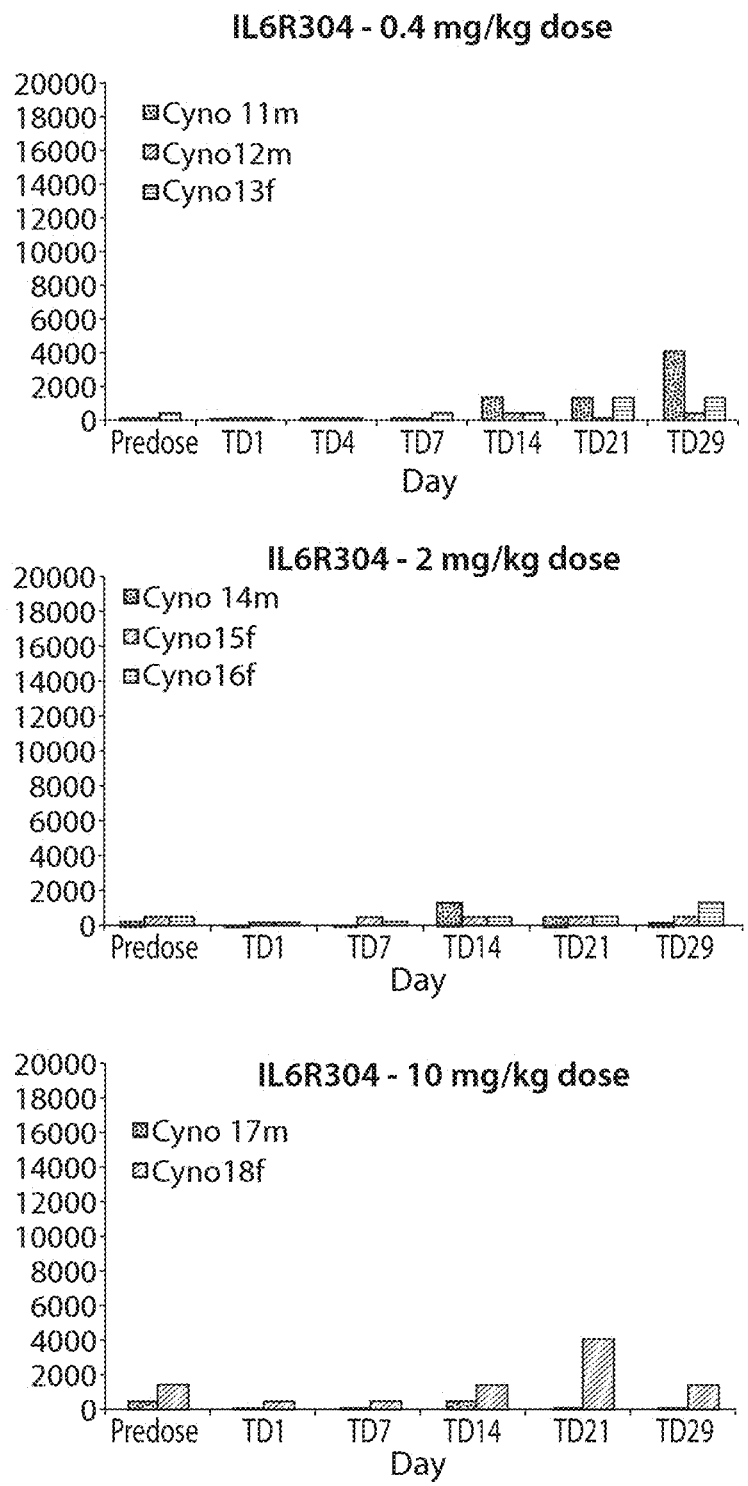
FIG. 59: Immunodetection of anti-IL6R304 antibodies at pre-dose and different days post i.v. administration of IL6R304. ELISA plates were coated with ALB8. The legend in each of the figures corresponds to the bar graph groupings starting from left to right.
Figure 60:
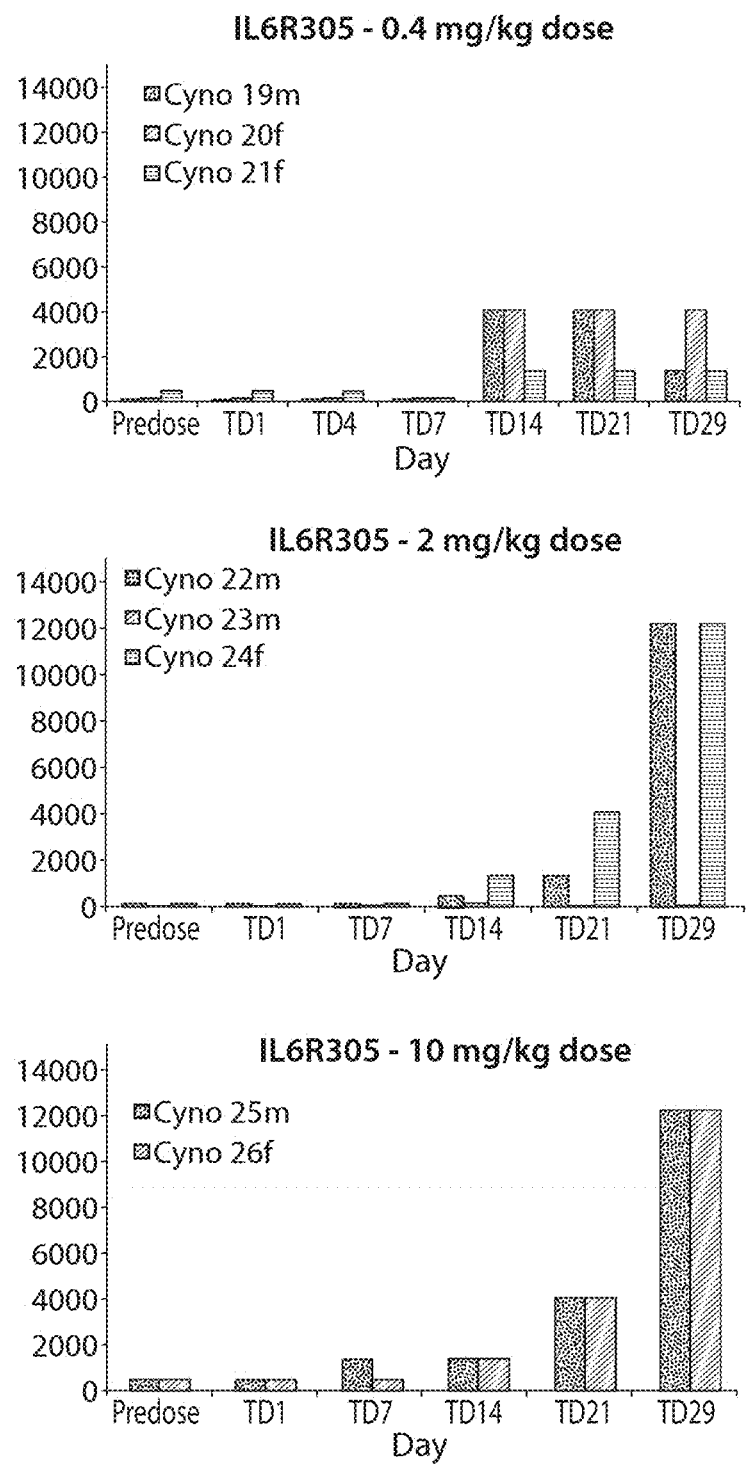
FIG. 60: Immunodetection of anti-IL6R305 antibodies at pre-dose and different days post i.v. administration of IL6R305. ELISA plates were coated with IL6R305. The legend in each of the figures corresponds to the bar graph groupings starting from left to right.
Figure 61:
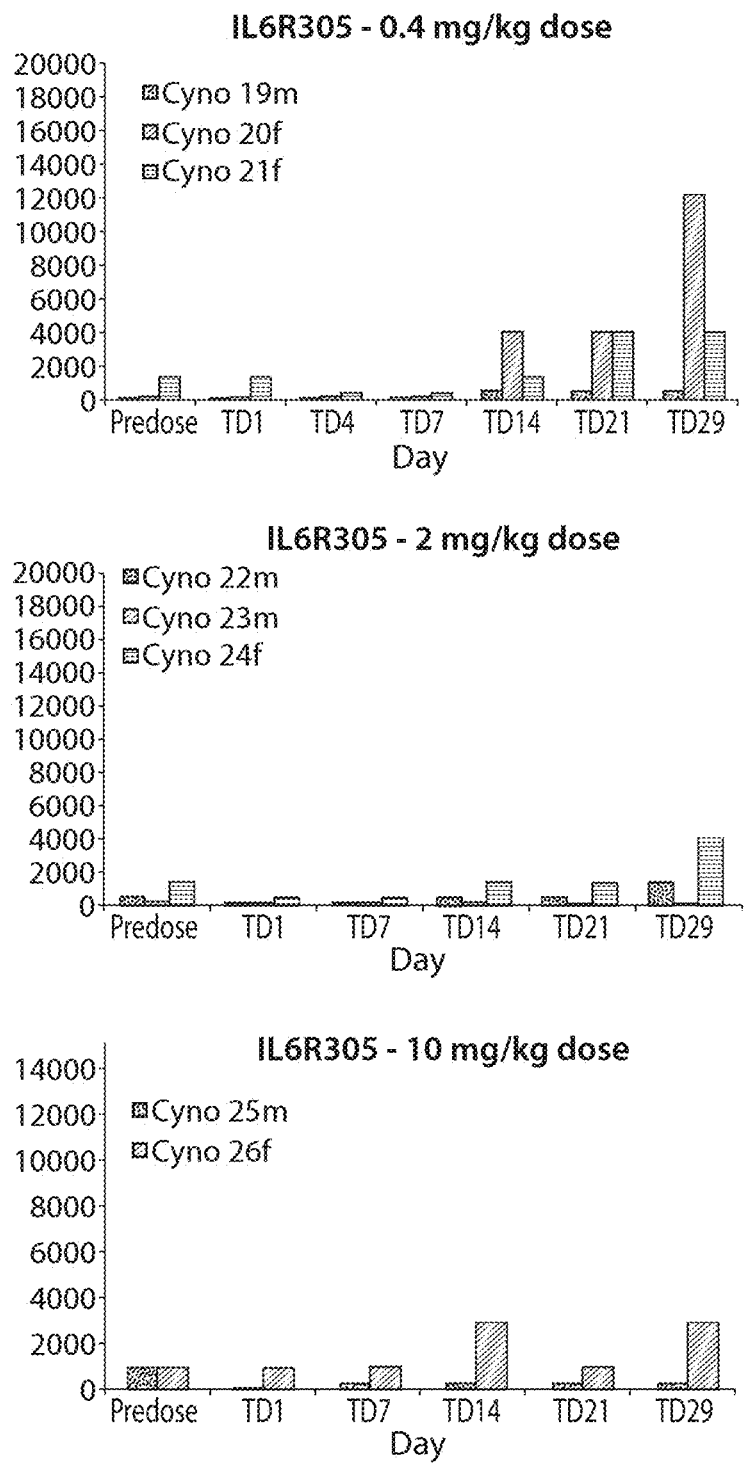
FIG. 61: Immunodetection of anti-IL6R305 antibodies at pre-dose and different days post i.v. administration of IL6R305. ELISA plates were coated with IL6R300. The legend in each of the figures corresponds to the bar graph groupings starting from left to right.
Figure 62:
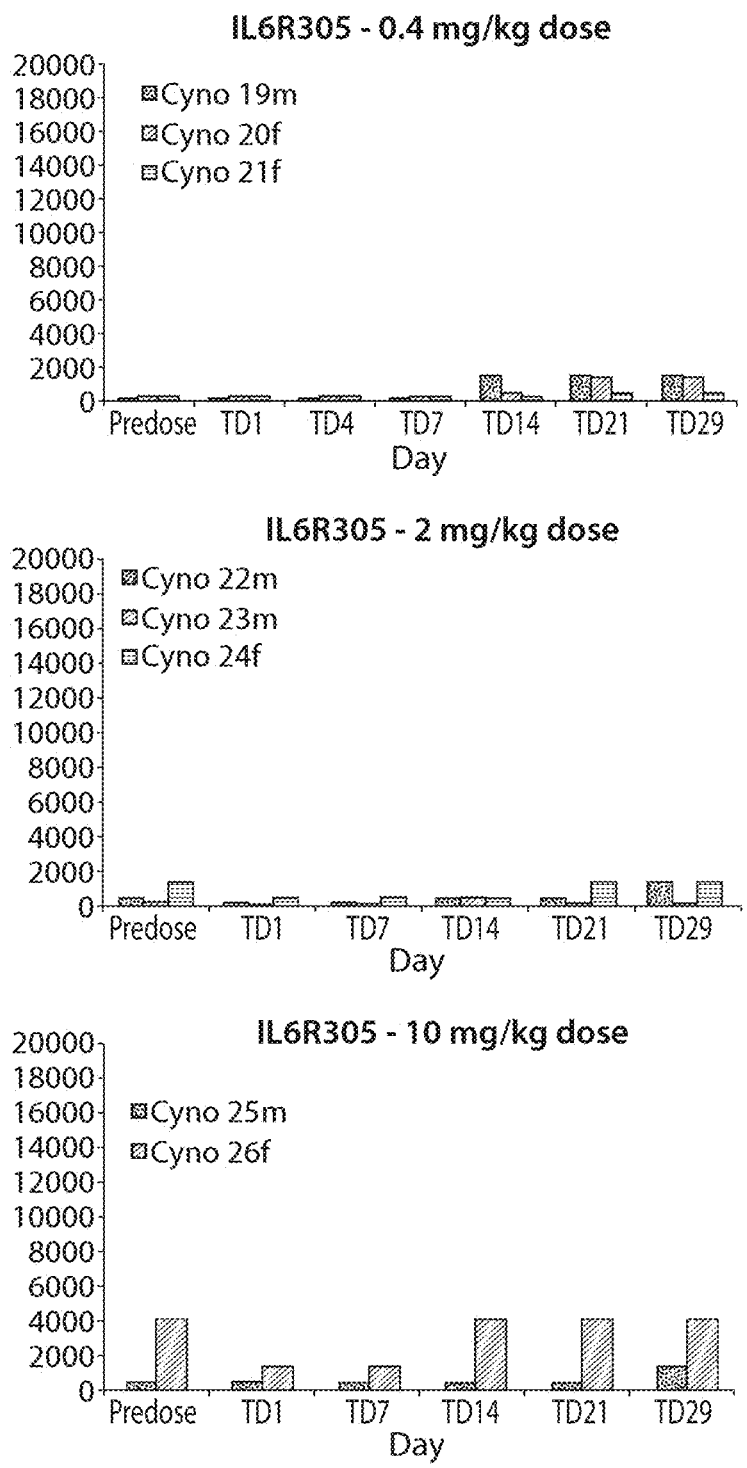
FIG. 62: Immunodetection of anti-IL6R305 antibodies at pre-dose and different days post i.v. administration of IL6R305. ELISA plates were coated with ALB8. The legend in each of the figures corresponds to the bar graph groupings starting from left to right.

A series of plasma samples taken at predose and at different days post administration of IL6R304 or IL6R305 were screened for the presence of monkey antibodies (IgG isotype) capable of binding to the Nanobody or one or more of its building blocks. Samples from animals dosed with IL6R304 were analyzed on plates coated with either IL6R304 (FIG. 57), IL6R300 (FIG. 58) or ALB8 (FIG. 59). Samples from animals dosed with IL6R305 were analyzed on plates which were coated with either IL6R305 (FIG. 60), IL6R300 (FIG. 61) or ALB8 (FIG. 62).

A summary of the anti-drug antibody (ADA) appearance to full Nanobody (IL6R304 and IL6R305) is given in Table C-44. Lower or no response was observed to IL6R300 and Alb8. In conclusion, after i.v. injection of IL6R304, ADA were detectable in all monkeys (except for Animal No. 16 in which no ADA determination could be determined due to high predose values). Antibodies appeared after 1 week post administration for the monkeys dosed at 0.4 mg/kg and after 2 weeks post administration for the monkeys dosed at 2 mg/kg and 10 mg/kg. Highest ADA titers were obtained in animals No. 11 and 13 (both from the 0.4 mg/kg dose). After i.v. injection of IL6R305, ADA were detectable in all monkeys (except for animal No. 23 in which no ADA was detected). Antibodies appeared after 1 week post administration for the monkeys dosed at 0.4 mg/kg and after 2 weeks post administration for the monkeys dosed at 2 mg/kg and 10 mg/kg. Highest ADA titers were obtained in animals No. 22 and 24 (both from the 2 mg/kg dose) and in animals No. 25 and 26 (both from the 10 mg/kg dose).

Example 56

The Effect of the Nanobodies on sIL-6R Levels

Figure 63A:
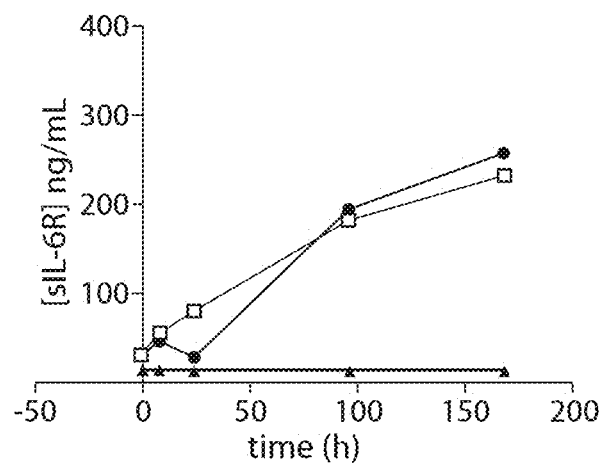
FIG. 63A-C: Plasma sIL-6R levels in cynomolgus monkeys after a single IV bolus dose of IL6R Nanobodies. A: 2 animals treated with Ref IgG at 5 mg/kg (▨, ❋) or vehicle (▲), B: 3 animals with IL6R304 at 0.04 mg/kg, C: 3 animals with IL6R305 at 0.04 mg/kg.
Figure 63B:
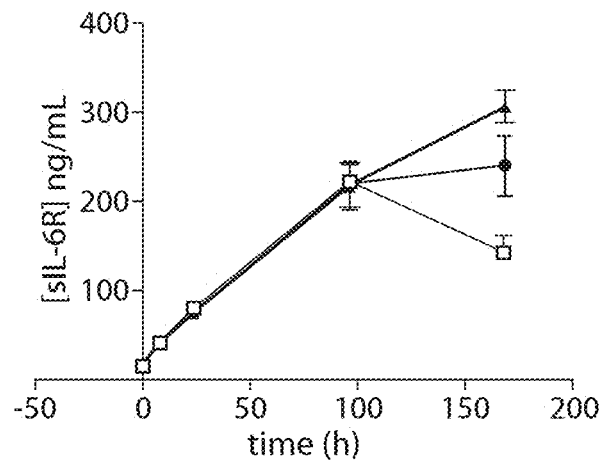
Figure 63C:
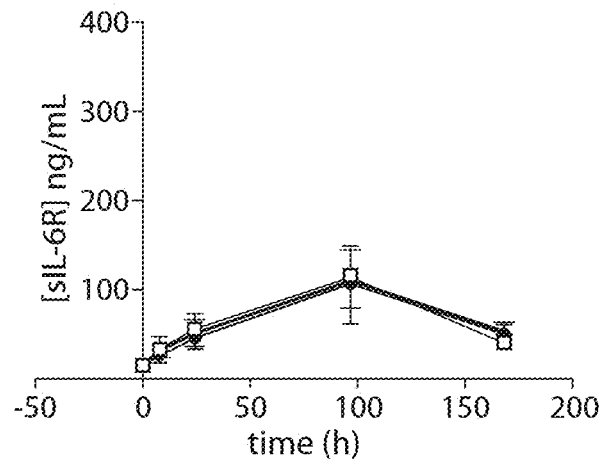

As expected based on publicly available data (Nishimoto et al., 2008, Blood 112(10): 3959-64), treatment with Ref IgG lead to an increase in plasma sIL-6R, whereas treatment with vehicle did not (FIG. 63A). Similarly, the low dose of IL6R304 induced a rapid increase in sIL-6R levels in all three monkeys (FIG. 63B). In the IL6R305-treated animals plasma sIL-6R also increased, but not as pronounced as in the other treatment groups (FIG. 63C).

VIII. Efficacy of IL6R304

Example 57

The Effect of the Nanobodies on sIL-6R Levels in the Efficacy Study

Figure 64A:
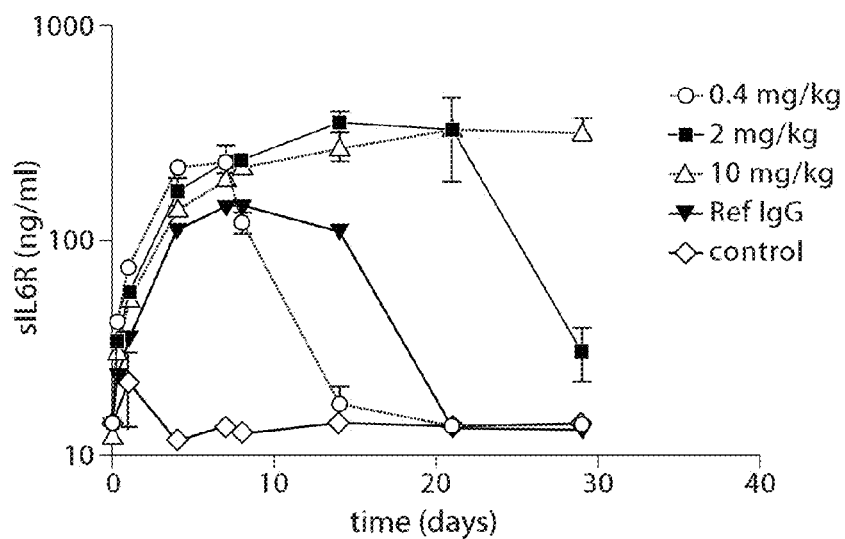
FIG. 64A-B: Total plasma sIL-6R levels in cynomolgus monkeys after a single IV bolus dose of IL6R Nanobodies. A: animals treated with IL6R304 (▨, ▲, ❋), Ref IgG (▼) or vehicle (◇); B: animals treated with IL6R305, (▲, ❋, ▨), Ref IgG (▲) or vehicle (◇). The mean±s.e. per group is shown.

The total sIL-6R levels in plasma (free, Nanobody-bound and IL-6-bound) were measured via ELISA. As expected based on published data (Nishimoto et al., 2008, Blood 112 (10): 3959-64), treatment with Ref IgG led to an increase in plasma sIL-6R, whereas treatment with vehicle did not (FIG. 64A). Similarly, all Nanobody-treated animals showed a rapid increase in sIL-6R levels. This can be explained by a slower clearance of the Ref IgG- or NB-sIL-6R complex compared to free sIL-6R.

Figure 64B:
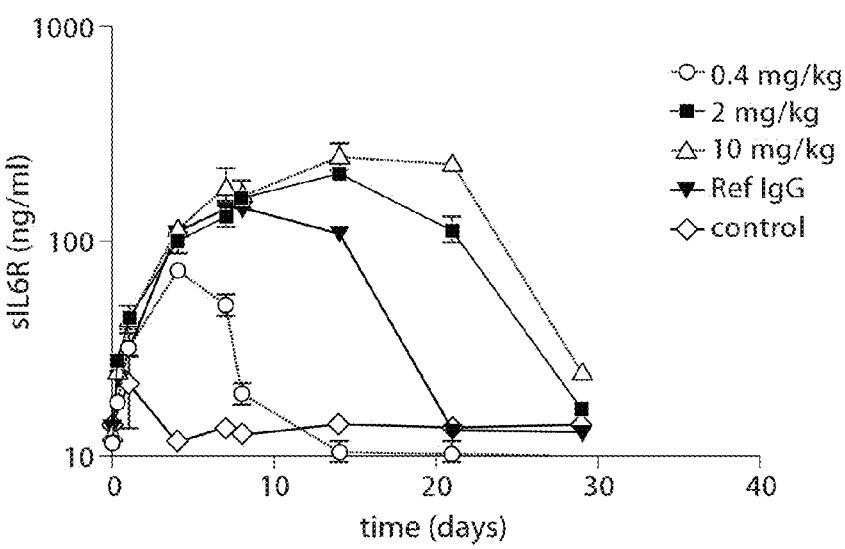

The maximum sIL-6R level and the duration of the effect were clearly dose dependent. Also, the effect of the Nanobodies seems to be more pronounced than for the Ref IgG (compare the 2 mg/kg dose of the Nanobodies to Ref IgG in FIG. 64). This can possibly be explained due to faster Fc-mediated clearing of antibody immune complexes. Surprisingly however, the increase in sIL-6R and the duration of the effect were more pronounced for IL6R304 (FIG. 64A) compared to IL6R305 (FIG. 64B).

Example 58

The Effect of the Nanobodies on IL-6 Levels in the Efficacy Study

The total IL-6 levels in plasma (free, sIL-6R-bound) were measured via the Gyrolab platform. For this assay, a biotinylated rat anti-human IL-6 mAb was used to capture IL-6 and an Alexa-labeled mouse anti-human IL-6 mAb for detection. The assay measures both endogenous cynomolgus monkey IL-6 and recombinant human IL-6 that is injected daily from days 1-8. Therefore, a distinction needs to be made between the IL-6 that can be measured until day 1 (=Only endogenous cyno IL-6) and from days 2-29 (=administered human IL-6+ endogenous cyno IL-6).

As can be observed in FIG. 65, administration of IL6R304, IL6R305, Ref IgG and to a minor extent placebo, led to a transient increase in IL-6 which peaked at 8 h post administration. However, this increase was markedly higher in the Nanobody-treated groups. The effect on IL-6 did not seem to be specific for IL-6R targeting Nanobodies, since administration of an irrelevant Nanobody also led to a transient IL-6 response (FIG. 65D). The early increase in IL-6 can most probably be explained by stress because of handling of the animals and potentially a further increase in IL-6 production by minute amounts of endotoxins in the Nanobody preparations.

Figure 65A:
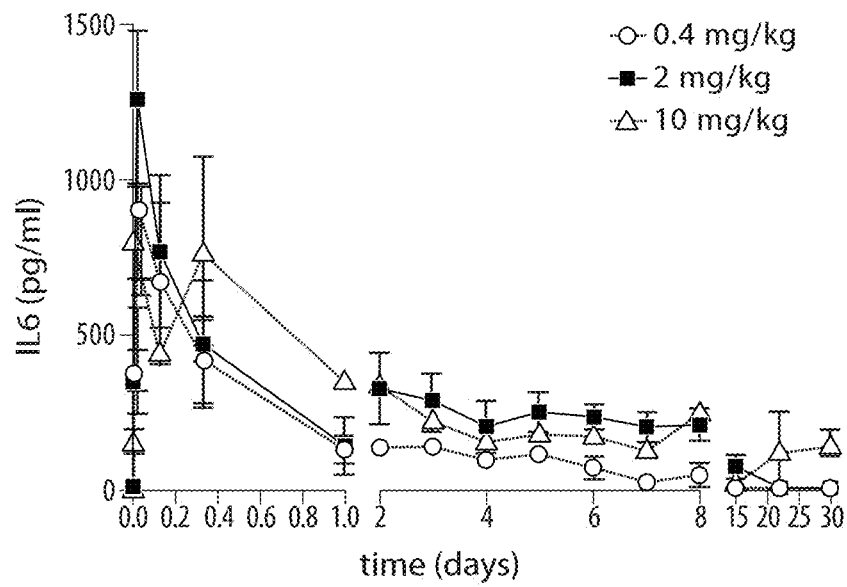
FIG. 65A-D: Total plasma IL-6 levels in cynomolgus monkeys after a single IV bolus dose of IL6R Nanobodies. Total plasma IL-6 concentrations, both endogenous cyno and injected human IL-6, were measured via the Gyrolab platform. Samples that were below the limit of quantification are depicted as 9.6 pg/mL. A: IL6R304; B: IL6R305; C: positive (Ref IgG) and negative (buffer) control. The mean per treatment group±s.e. (n=3 for 0.4 and 2 mg/kg; n=2 for 10 mg/kg) is depicted. D: endogenous cyno plasma IL-6 concentrations in individual animals after IV bolus injection of 10 mg/kg IL6R304 (▨, ❋), IL6R305, (▲, ▽) or irrelevant Nanobody (◇, •). The mean±s.e. of 2 measurements is shown.
Figure 65B:
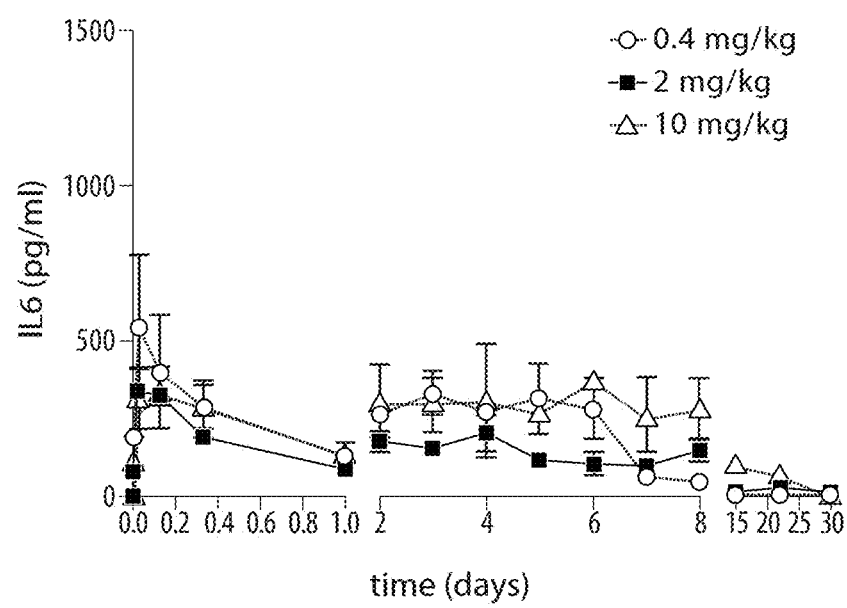
Figure 65C:
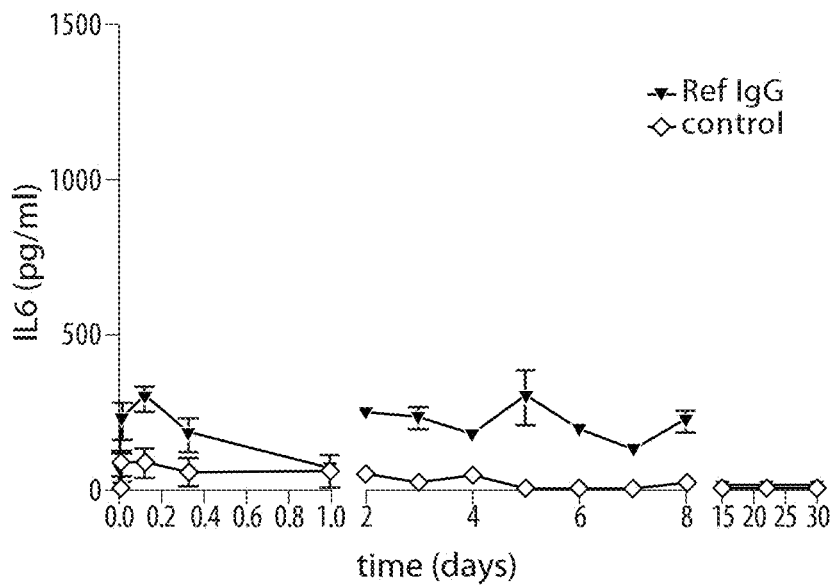
Figure 65D:
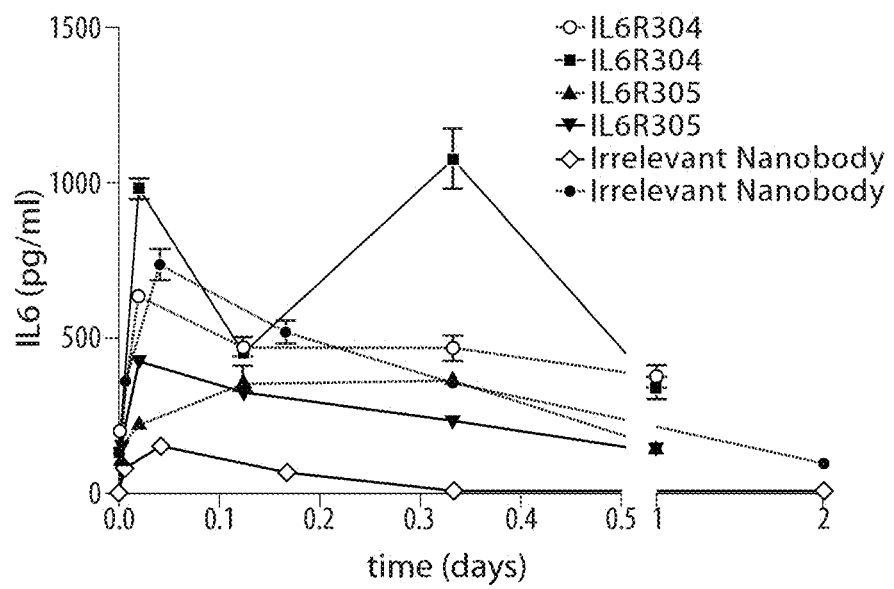

During the IL-6 treatment phase, blood was sampled before each daily injection of IL-6. In the placebo group, which received IL-6 but not the Nano bodies or Ref IgG, almost no IL-6 was detected (FIG. 65C). This is in line with the short half life of human IL-6 after SC injection (Tsigos, et al., 1997, J. Clin. Endocrinol. Metab. 82: 4167-70). However, in all animals treated with 2-10 mg/kg Ref IgG, IL6R304 or IL6R305, IL-6 was detected from days 2-8. This can be explained by blocking of receptor-mediated clearance of IL-6, thereby prolonging its half life (Nishimoto et al., 2008, Blood 112(10): 3959-64). Hence, circulating IL-6 could serve as a pharmacodynamic biomarker for neutralization of IL-6R.

IX. Pharmacodynamics of IL6R304

Example 59

Pharmacodynamic Effects after Single Dosing in Cynomolgus Monkey

Changes in sIL6R plasma concentrations were also measured after single i.v. administration of IL6R304 in healthy (i.e. non-stimulated) cynomolgus monkeys. In this single dose PK/PD study, doses ranged from 1-100 mg/kg. Blood sampling was performed for pharmacokinetic, immunogenicity and pharmacodynamic analysis. An ELISA-based assay was used to measure total sIL6R levels and a ligand binding assay using the Gyrolab™ platform was used to measure free sIL6R levels. For the total sIL6R assay, a non-neutralizing anti-IL6R monoclonal antibody was used to capture sIL6R (free+in complex) and a polyclonal biotinylated anti-IL6R tool in combination with streptavidin-HRP for detection. For the free sIL6R assay, the biotinylated 20A11 building block was used to capture the free sIL6R and an Alexa-labeled non-neutralizing anti-IL6R monoclonal antibody for detection.

Figure 66A:
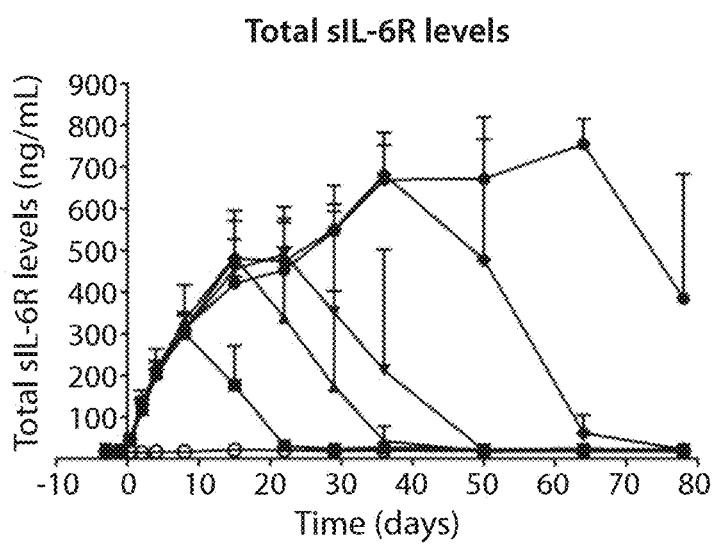
FIG. 66A-B: Total (A) and free (B) sIL6R plasma levels in cynomolgus monkey after a single i.v. administration of different doses of IL6R304. Mean plasma concentrations of either biomarker ±SD per group is shown. Vehicle or IL6R304 at given doses were administered at time point 0. For the legend, see FIG. 66B.
Figure 66B:
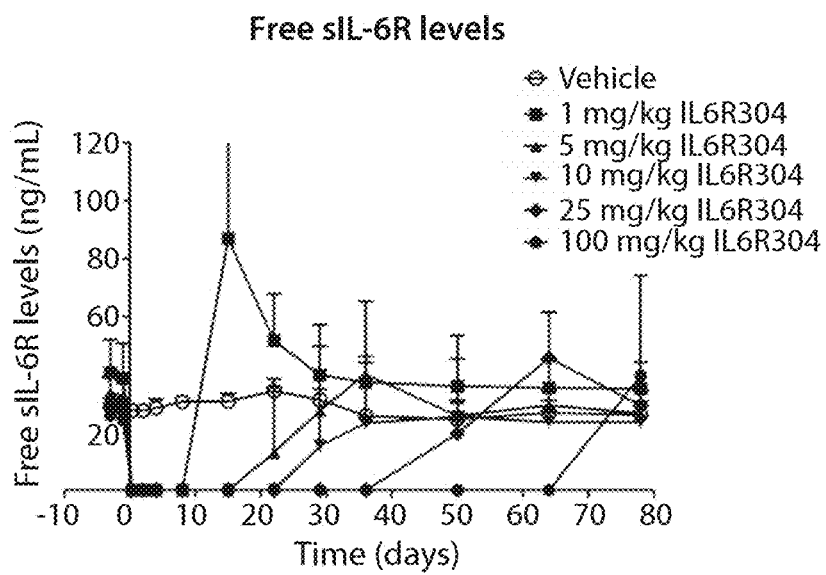

The results of the single dose PK/PD study confirmed the dose-dependent effect of IL6R304 on (i) the maximal total sIL6R concentrations (FIG. 66A), (ii) the duration of (increased total sIL6R (FIG. 66A) and (iii) the duration of the suppression of free sIL6R (FIG. 66B). In general, total and free sIL6R concentrations returned to baseline levels after a given time (dependent on the dose, longest elevation and suppression is seen with highest dose). Concentrations of free sIL6R after administration of a low dose of 1 mg/kg IL6R304 were decreased for approximately 8 days and then increased to concentrations above those of vehicle treated animals.

Figure 67:
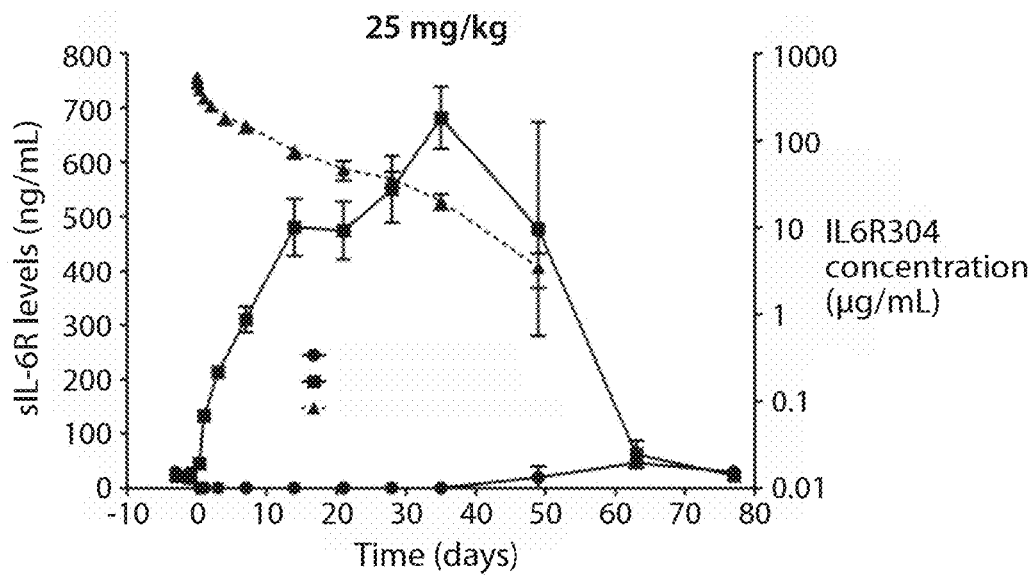
FIG. 67: Total and free sIL6R plasma levels and IL6R304 concentration in cynomolgus monkey after a single i.v. administration of 25 mg/kg IL6R304. The mean±SD for the specific dose group is shown. Total sIL6R (solid line, square symbols), free sIL6R (solid line, round symbols) and IL6R304 concentrations (dotted line, delta) are plotted versus time (days).

A good inverse correlation was observed between total sIL6R levels, free sIL6R levels (PD) and IL6R304 concentrations confirming that sIL6R can be used as a biomarker for the presence of active drug. FIG. 67 shows one example to elucidate the interplay between the 3 parameters (the mid dose group was selected as the return to baseline can be demonstrated in this group): administration of IL6R304 lead to an increase in total sIL6R concentrations and a stabilized drug-sIL6R complex was formed. As IL6R304 plasma concentrations decreased, concentrations of total sIL6R also decreased in parallel as most of the total sIL6R constituted of complexed receptor. This is confirmed by low free sIL6R concentrations which return to baseline levels upon elimination of IL6R304 from the circulation. Low free sIL6R concentrations confirm that measured total sIL6R is indeed inactive and complexed with IL6R304 (FIG. 67).

Example 60

Description of Pharmacodynamic Effects via PK/PD Modeling

The influence of IL6R304 administration on total sIL6R levels can be explained by direct binding of IL6R304 to the receptor—the complex stays in circulation via the half-life extension moiety of IL6R304 (i.e. albumin binding). As the measurable changes in total sIL6R concentrations follow a time-delayed kinetic, an indirect response model best describes the PK/PD relationship and was used to describe the effect of i.v. administered IL6R304 on the accumulation of sIL6R-IL6R304 complex levels. The model describes a drug response that results from the inhibition of the elimination of sIL6R when bound to IL6R304. In this indirect response model, the rate of change of total sIL6R-IL6R304 complex (Response R) is described by:

$$\frac{dR}{dt} = Kin - Kout * \left[1 - Imax * \frac{C^n}{IC50^n + C^n}\right] * R$$

With $K_{in}$, the zero order synthesis rate; R, the total sIL6R; $I_{max}$, the maximum inhibition; C, the IL6R304 plasma concentration; n, the dose-response shape factor; and $K_{out}$, the first order elimination rate constant of sIL6R.

All available i.v. total sIL6R data from the single dose PK/PD study were fitted simultaneously to the model (WinNonlin Professional Software Version 5.1, Pharsight Corporation, Mountain View Calif., USA) using the pharmacokinetic function as described in Example 61 as input function for the indirect response PK/PD model.

Figure 68:
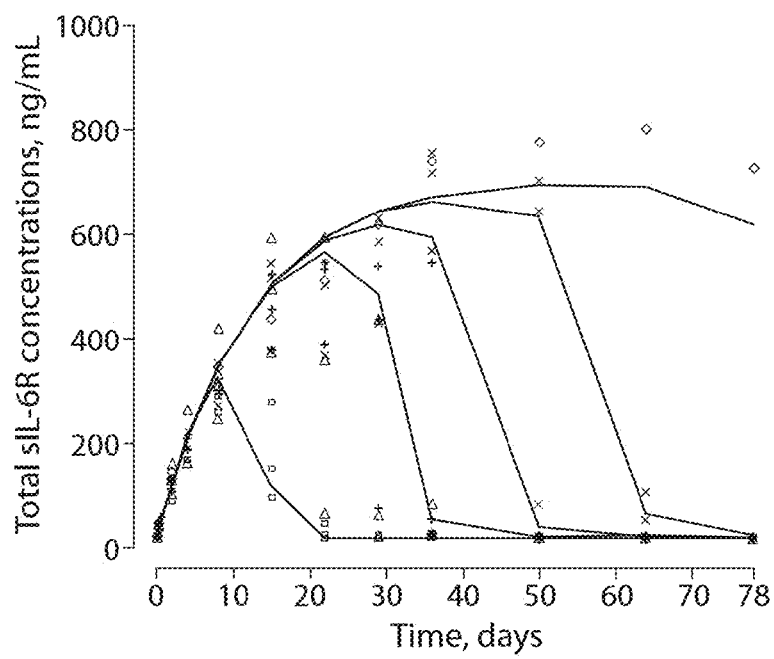
FIG. 68: Individual observed (symbols) and model-predicted (solid lines) total sIL6R concentration-time plots after i.v. administration with 1 mg/kg (•), 5 mg/kg (Δ), 10 mg/kg (+), 25 mg/kg (×) and 100 mg/kg (◇) of IL6R304.

FIG. 68 shows the individual observed and model-predicted total sIL6R concentration-time data in cynomolgus monkey after i.v. administration of 1, 5, 10, 25 or 100 mg/kg. The estimated pharmacodynamic parameters of IL6R304, in cynomolgus monkey, are listed in Table C-45. All parameters were estimated with a sufficient degree of precision as indicated by CV % values below 50%.

All data after i.v. administration, from the single dose PK/PD study, were fitted simultaneously to an indirect response model describing the behavior of sIL6R, IL6R304 and the complex of sIL6R-IL6R304.

The average half-life of sIL6R was estimated to be approximately 5.8 h (=ln 2/$K_{out}$ with $K_{out}$=$K_{in}$/$R_0$) and an estimated production rate of 2.49 ng/mL/h. IL6R304 was able to almost completely inhibit the elimination of sIL6R via the primary pathway ($I_{max}$=97%). Therefore the elimination rate changed to a new maximum decreased $k_{out}$ which correlated with that of cynomolgus monkey serum albumin. Subsequently a new baseline level of total sIL6R was established. With an estimated $IC_{50}$ of 125 ng/mL or 4.48 nM, IL6R304 was shown to be a potent inhibitor of the elimination of non-complexed sIL6R in cynomolgus monkey.

X. Pharmacokinetics of IL6R304

Example 61

Pharmacokinetics in the Cynomolgus Monkey

This section summarizes data characterizing the pharmacokinetic behavior of i.v. administered IL6R304 in 1 cross-reactive species (cynomolgus monkey).

In healthy (non-induced) cynomolgus monkeys, the concentrations of IL6R304 were measured using a qualified DELFIA (dissociation enhanced lanthanide fluoro-immunoassay) method. Total active IL6R304 concentrations were measured by means of an IL6R dependent assay.

In a single dose PK/PD study, IL6R304 was administered to healthy male cynomolgus monkeys as a single i.v. bolus of 0, 1, 5, 10, 25 and 100 mg/kg. Blood samples for PK, ADA (anti-drug antibodies) and PD analysis purposes were collected from all animals at predose and at selected time points postdose. Samples were analysed for PK, PD and ADA (see also Example 62).

A validated electrochemiluminescent (ECL) bridging screening and confirmation assay was used to detect anti-IL6R304 antibodies. Briefly, IL6R304 was used to capture and detect anti-drug antibodies (ADAs) in an homogenous assay format using a MSD Sector Imager 2400.

For the PK analysis, IL6R304 was captured via a biotinylated anti-Nano body tool (3E8biv-bio) on streptavidin coated plates. After a complexation step with the target IL6R, an Europium-labeled mAb against IL6R was used to generate a fluorescence signal in enhancement solution.

Figure 69:
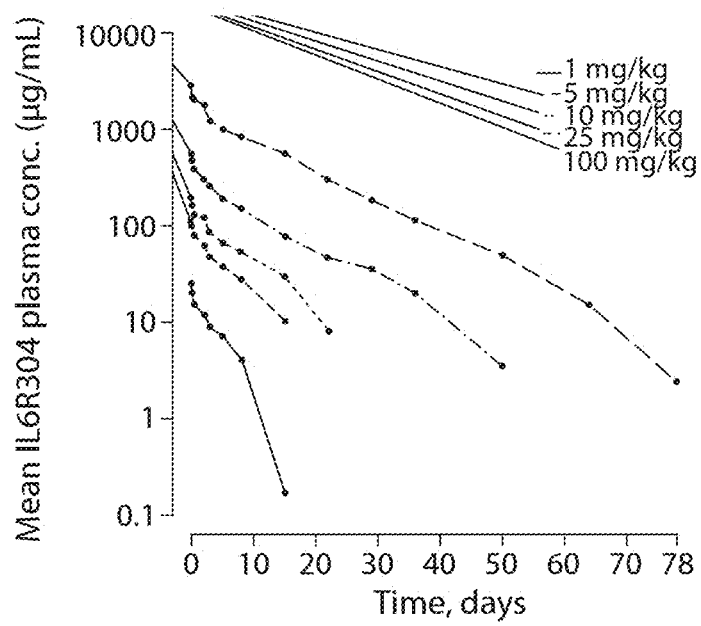
FIG. 69: Mean plasma concentration-time profiles of IL6R304 in cynomolgus monkey after i.v. bolus injection with 1, 5, 10, 25 or 100 mg/kg of IL6R304.

The mean plasma concentration-time profiles of IL6R304 are displayed in FIG. 69. A summary of the key pharmacokinetic parameters of IL6R304, after a single i.v. bolus of 1, 5, 10, 25 or 100 mg/kg, are provided in Table C-46.

The pharmacokinetic profile, after i.v. administration, showed a triphasic decline. During the first two post administration days, a distribution phase was observed followed by a slower dominant phase and a faster terminal phase. The distribution phase can be further divided in a fast (shallow compartment) and a slow distribution (deep compartment). Based on the elimination phase, IL6R304 is presumably cleared via two mechanisms, a linear non-saturable (non-specific elimination or $CL_{NON-IL6R}$) and a non-linear saturable (target mediated or specific elimination or $CL_{IL6R}$) clearance mechanism. The latter could be the result of the internalization of IL6R304 bound to membrane bound IL6R and subsequent clearance of the IL6R304-mIL6R complex.

As the clearance of IL6R304 is a combination of saturable and non-saturable pathways, the plasma kinetics in cynomolgus monkey showed a non-linear behavior with a half-life which is dose-dependent and at a given dose level, also time-dependent.

When the $CL_{IL6R}$ is saturated, and the overall CL is mainly determined by $CL_{NON-IL6R}$, the reported half-life of IL6R304 in cynomolgus monkey ranged from 5.8 to 8.9 days and was similar to that reported for cynomolgus monkey serum albumin (Nguyen et al., 2006, Protein Eng. Des. Sel. 19: 291). This was in line with expectations and with the confirmed cross-reactivity of IL6R304's albumin binding moiety to cynomolgus monkey albumin.

Average exposures, after single dose administration, increased somewhat more than dose-proportional between 1 and 5 mg/kg and 10 and 25 mg/kg and dose-proportional between 5 and 10 mg/kg. The result of the 100 mg/kg dose group has to be taken with caution as only one animal was included in this dose group. Overall, due to the limited number of monkeys per dose group, the dose-proportionality assessment was exploratory.

The binding of IL6R304 to sIL6R resulted in an increase of the measured total concentration of sIL6R, which comprised of sIL6R and sIL6R-IL6R304 complex; this increase is thought to be due to a slower clearance of the complex compared to the sIL6R alone.

Based on the available immunogenicity, PK and PD data, it was concluded that emerging ADAs likely have impacted the PK/PD profile of IL6R304 in two animals from the highest dose group (animal 15 and 17). Both animals showed an unexpected decrease in IL6R304 plasma levels concurrent to the emergence of measurable ADA and with a reduced pharmacodynamic effect. Therefore, these animals were not considered in the PK/PD analysis. Emerging ADAs in the other animals did not seem to have an obvious effect on the PK/PD profiles, therefore these data were included in the analysis.

For one animal (animal 3) in the 1 mg/kg dose group, no target mediated clearance was observed, although this was expected for this low dose. For one animal (animal 6) in the 5 mg/kg dose group, target mediated clearance was still observed despite the higher dose and expected saturation of this pathway. As the variability for endogenous IL6R concentrations between animals can be high, the target mediated clearance can be subjected to a high inter-individual variability. Additionally, when the IL6R304 concentrations are close to the estimated KM value (here: 0.718 µg/mL), a small change in the IL6R304 concentration results in a large change in nonlinear clearance. The combination of both can lead to a measurable evidence of target or only non-target mediated clearance in the lower dose groups which is reflected in a high variability in terminal half-life values. The PK parameters of the animals 3 and 6 were excluded from descriptive statistics as the biologic variability excludes meaningful assessment of the precision of applied methods (Table C-46).

None of the animals from the placebo group were systematically exposed to IL6R304. All predose samples of the IL6R304 treated animals were below the lower limit of quantification (LLOQ). Animals from the active treated groups, showed an increase in plasma concentrations of IL6R304 with an increase in dose level. The highest mean total exposure ($AUC_{inf}$) was observed in the highest dose group (100 mg/kg) and was 540612 µg·h/mL.

Mean dose-normalized $AUC_{inf}$ values increased dose proportionally over the 5 to 10 mg/kg dose range and somewhat more than dose proportional between 1 and 5 mg/kg and 10 and 25 mg/kg (1.3 and 1.4, respectively). The more than dose-proportional increase from 25 to 100 mg/kg has to be taken with caution as only one animal was included in the highest dose group. Overall, due to the limited number of monkeys per dose group, the dose-proportionality assessment was exploratory.

Notably, data from the non-compartmental analysis indicated a difference in half-life at the 1 mg/kg dose level compared to higher dose levels tested. This is attributable to the higher contribution of saturatable target mediated clearance mechanisms as compared to higher doses where non-saturable mechanisms prevail.

Based on the elimination phase, IL6R304 is presumably cleared via two mechanisms, a linear and a non-linear clearance mechanism. The linear clearance mechanism is likely related to the non-saturable, and non-IL6R mediated removal of IL6R304 and corresponds to the slow and non-specific proteolytic degradation of IL6R304. The non-linear and IL6R-mediated clearance process is a saturable clearance mechanism; most probably representing binding of IL6R304 to membrane bound IL6R and subsequent internalization and clearance.

Figure 70:
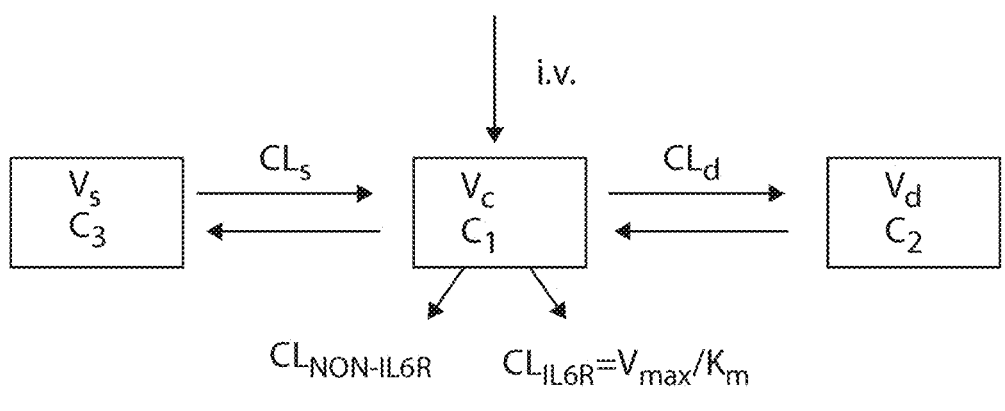
FIG. 70: Open three-compartmental pharmacokinetic model with linear and non-linear clearance from the central compartment. $CL_{NON-IL6R}$ is the linear non-IL6R mediated clearance, $V_c$ the volume of the central compartment, $V_d$ the volume of the deep peripheral compartment, $CL_d$ the inter-compartmental flow between central and deep compartment, $V_5$ the volume of the shallow peripheral compartment, $CL_s$ the inter-compartmental flow between central and shallow compartment and $CL_{IL6R}$ is the non-linear IL6R-mediated clearance (with $V_{max}$ the maximum metabolic rate and $K_m$ the IL6R304 concentration corresponding to 50% of $V_{max}$).

The non-linear pharmacokinetic behavior of IL6R304 in the cynomolgus monkey was captured by fitting the data to an open three-compartmental pharmacokinetic model with linear and a non-linear clearance from the central compartment. The structural model is depicted in FIG. 70.

All available individual i.v. plasma concentration data from a single dose PK/PD study were fitted simultaneously to the model (WinNonlin Professional Software Version 5.1

(Pharsight Corporation, Mountain View Calif., USA) using iterative re-weighting (1/ŷ*ŷ), where ŷ is the predicted plasma concentration. FIG. 71 displays the individual observed and model-predicted plasma concentration-time plots of IL6R304 in cynomolgus monkey after i.v. administration of 1, 5, 10, 25 or 100 mg/kg. The estimated pharmacokinetic parameters of IL6R304 are listed in Table C-47.

All data from single dose PK/PD study, were fitted simultaneously to an open three-compartmental model with linear ($CL_{NON-IL6R}$) and non-linear ($CL_{IL6R}$) clearance from the central compartment. At low IL6R304 concentrations ($C<<<K_m$) the contribution of the IL6R-mediated clearance ($CL_{IL6R}$) is predominant and equals $V_{max}/K_m$. At high IL6R304 concentrations ($C>>>K_m$), the IL6R-mediated clearance pathway becomes saturated and will proceed at the maximum mass turnover (i.e. $V_{max}$). Consequently, the overall clearance (CL) is dominated by the linear, non-IL6R mediated pathway ($CL_{NON-IL6R}$).

The non-linear IL6R mediated component in the clearance explains both the time- and dose-dependency in the half-life of IL6R304 in cynomolgus monkey.

Tables

TABLE A-1

Preferred combinations of CDR sequences

| Nanobody | SEQ ID FR1 | SEQ ID CDR 1 | SEQ ID FR2 | SEQ ID CDR 2 | SEQ ID FR3 | SEQ ID CDR 3 | SEQ ID FR4 | SEQ ID |
|---|---|---|---|---|---|---|---|---|
| PMP7F4 | 60 EVQLVESGGGLVQPGGSLRLSCAASGTTFK | 74 VNVMA | 81 WYRQAPGKGRELVA | 83 GIINGGSTTYADSVKG | 90 RFTISRDNAKNTLYLQMNSLRPEDTAVYYCAF | 92 VTTNSDYDLGRDY | 95 WGQGTLVTVSS | 96 |
| PMP7C4 | 61 EVQLVESGGGLVQPGGSLRLSCAASGTTFR | 75 INVMA | 81 WYRQAPGKGRELVA | 83 GIITNGSTSYADSVKG | 85 RFTISRDNAKNTLYLQMNSLRPEDTAVYYCAF | 92 VTTNSDYDLGRDY | 95 WGQGTLVTVSS | 96 |
| PMP7D6 | 62 EVQLVESGGGLVQPGGSLRLSCAASGSIFR | 76 VNVMA | 81 WYRQAPGKGRELVA | 83 AVINGGTTTYADSVKG | 86 RFTISRDNAKNTLYLQMNSLRPEDTAVYYCAF | 92 VTTNSDYDLGRDY | 95 WGQGTLVTVSS | 96 |
| PMP7G7 | 63 EVQLVESGGGLVQPGGSLRLSCAASGTTFK | 74 INIMA | 82 WYRQAPGKGRELVA | 83 GVITGGNTTYADSVKG | 87 RFTISRDNAKNTLYLQMNSLRPEDTAVYYCAF | 92 VTTNSDYDLGRDY | 95 WGQGTLVTVSS | 96 |
| PMP7G8 | 64 EVQLVESGGGLVQPGGSLRLSCAASGSTFR | 77 INVMA | 80 WYRQAPGKGRELVA | 83 GVINDGSTTYADSVKG | 88 RFTISRDNAKNTLYLQMNSLRPEDTAVYYCAF | 92 VTTNSDYDLGRDY | 95 WGQGTLVTVSS | 96 |
| PMP20F6 | 65 EVQLVESGGGLVQPGGSLRLSCAASGSVFK | 78 INVMA | 80 WYRQAPGKGRELVA | 83 GIVSGGSTSYADSVKG | 89 RFTISRDNAKNTLYLQMNSLRPEDTAVYYCAF | 92 ITTNSDYDLGRRY | 94 WGQGTLVTVSS | 96 |
| PMP20A11 | 66 EVQLVESGGGLVQPGGSLRLSCAASGSVFK | 78 INVMA | 80 WYRQAPGKGRELVA | 83 GIISGGSTSYADSVKG | 84 RFTISRDNAKNTLYLQMNSLRPEDTAVYYCAF | 92 ITTESDYDLGRRY | 93 WGQGTLVTVSS | 96 |
| PMP20E10 | 67 EVQLVESGGGLVQPGGSLRLSCAASGSVFK | 78 INVMA | 80 WYRQAPGKGRELVA | 83 GIVSGGSTSYADSVKG | 89 RFTISRDNAKNTLYLQMNSLRPEDTAVYYCAF | 92 ITTESDYDLGRRY | 93 WGQGTLVTVSS | 96 |
| PMP21A10 | 68 EVQLVESGGGLVQPGGSLRLSCAASGSIFK | 79 INVMA | 80 WYRQAPGKGRELVA | 83 GIVTGGSTSYADSVKG | 91 RFTISRDNAKNTLYLQMNSLRPEDTAVYYCAF | 92 ITTESDYDLGRRY | 93 WGQGTLVTVSS | 96 |
| PMP21D11 | 69 EVQLVESGGGLVQPGGSLRLSCAASGSVFK | 78 INVMA | 80 WYRQAPGKGRELVA | 83 GIVTGGSTSYADSVKG | 91 RFTISRDNAKNTLYLQMNSLRPEDTAVYYCAF | 92 ITTESDYDLGRRY | 93 WGQGTLVTVSS | 96 |

TABLE B-1

Amino acid sequences that make up the reference compounds

REFERENCE IGG HEAVY CHAIN, SEQ ID NO: 1
QVQLQESGPGLVRPSQTLSLTCTVSGYSITSDHAWSWVRQPPGRGLEWIG
YISYSGITTYNPSLKSRVTMLRDTSKNQFSLRLSSVTAADTAVYYCARSL
ARTTAMDYWGQGSLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

REFERENCE IGG LIGHT CHAIN, SEQ ID NO: 2
DIQMTQSPSSLSASVGDRVTITCRASQDISSYLNWYQQKPGKAPKLLIYY
TSRLHSGVPSRFSGSGSGTDFTFTISSLQPEDIATYYCQQGNTLPYTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

REFERENCE FAB HEAVY CHAIN, SEQ ID NO: 3
QVQLQESGPGLVRPSQTLSLTCTVSGYSITSDHAWSWVRQPPGRGLEWIG
YISYSGITTYNPSLKSRVTMLRDTSKNQFSLRLSSVTAADTAVYYCARSL
ARTTAMDYWGQGSLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSC

REFERENCE FAB LIGHT CHAIN, SEQ ID NO: 4
DIQMTQSPSSLSASVGDRVTITCRASQDISSYLNWYQQKPGKAPKLLIYY
TSRLHSGVPSRFSGSGSGTDFTFTISSLQPEDIATYYCQQGNTLPYTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

TABLE B-2

Protein sequences of anti-IL-6R Nanobodies

PMP40H5, SEQ ID NO: 5
EVQLVESGGGLVQPGGSLRLSCAASGFSLDYYAIGWFRQAPGKEREGVSC
MDSSSGTTSTYYSDSVKGRFTISRDDAKNTVYLQMNSLKPEDTAVYYCAA
DGHLNWGQRYVPCSQISWRGWNDYWGQGTQVTVSS

PMP35E11, SEQ ID NO: 6
EVQLVESGGGLVQAGGSLRLSCAASGFTFDDYAIGWFRQAPGKEHEGVSC
ISSSDGSTYYADSVKGRFTISSDNAKNTVYLQMNSLKPEDTAVYYCAAER
DVPARSLCGSYYWYDYRGQGTQVTVSS

PMP32C9/IL6R04, SEQ ID NO: 7
EVQLVESGGGLVQAGGSLRLSCAASGFTFDDYDIGWFRQAPGKEREGVSG
ISSSDGNTYYADSVKGRFTISSDNAKNTVYLQMNSLKPEDTAVYYCAAEP
PDSSWYLDGSPEFFKYWGQGTQVTVSS

PMP35H4/IL6R13, SEQ ID NO: 8
EVQLVESGGGLVQPGGSLRLSCAASGFTFDDYGMSWVRQAPGRATEWVSA
ISWNGNNTYYTESMKGRFTISRDNAKNTVYLQMNSLKPEDTAVYYCVKGS
TAIVGVPPTYPDEYDYWGQGTQVTVSS

PMP32E10, SEQ ID NO: 9
EVQLVESGGGLVQPGGSLRLSCAASGFTFGSYDMSWVRQAPGKGPEWVSA
INSGGGSTYYADSVKGRFTISRDNAKNTLYLQMNSLKPEDTAVYYCATDW
RYSDYDLPLPPPGDYWGQGTQVTVSS

PMP30C11, SEQ ID NO: 10
EVQLVESGGGLVQAGGSLRLSCAASGRTFSSYDMGWYRQAPGKEREFVAV
ISRSGSSTYYADSVKGRFTISRDNAKNTVYLQMNSLKPEDTAIYYCKAEV
VAGDYDYWGQGTQVTVSS

PMP35C10, SEQ ID NO: 11
EVQLVESGGGLVQAGGSLRLSCAASGRTFSSYDMGWYRQAPGKEREFVAV
IHWSSGSTYYADPVKGRFTISRDNAKNTVYLQMNSLKPEDTAIYYCNAFL
PGPEGFHDYWGQGTQVTVSS

TABLE B-2-continued

Protein sequences of anti-IL-6R Nanobodies

PMP34G9, SEQ ID NO: 12
EVQLVESGGGLVQAGGSLRLSCAASGRTSSSYDMTWYRQVPGKEREFVAV
ISWSGGSTYYADSVKGRFTISRDNAKNTVYLQMNSLKPEDTAIYYCNAYT
GGGDDYWGQGTQVTVSS

PMP31A4/IL6R03, SEQ ID NO: 13
EVQLVESGGGLVQAGGSLRLSCAASGSIFKVNAMGWYRQAPGKQRELVAG
IISGGSTNYADSVKGRLTISRDNAKNTVYLQMNSLKPEDTAVYYCSFVTT
NSDYDLGRDYWGQGTQVTVSS

PMP32E2, SEQ ID NO: 14
EVQLVESGGGLVQAGGSLRLSCAASGNIFDDNTMGWTWNRQPPGKQRELV
AIIATDGSTNYADSVKGRFTISRDNAKNTVYLQMNSLKPEDTAVYYCNLF
SLRLGRDYWGQGTQVTVSS

PMP33A3, SEQ ID NO: 15
EVQLVESGGGLVQPGGSLRLSCAASGFTLDYGAIGWFRQAPGKEREGVSC
ISSSTGSTYYADSVKGRFTISRDNGKNTVYLQMNSLKPEDTAVYYCAADK
MWSPCLVAANEEALFEYDYWGQGTQVTVSS

PMP34A12, SEQ ID NO: 16
EVQLVESGGGLVQPGGSLRLSCVASGFSLDYYVIGWFRQAPGKEREGVSC
ISSSDGSTYYADSVKGRFTISRDNAKNTVYLQMNSLKPEDTAVYYCAADL
LRTPEFCVDSAPYDYWGQGTQVTVSS

PMP28E11, SEQ ID NO: 17
EVQLVESGGGLVQPGGSLRLSCAASGFPLDYYAIGWFRQAPGKEREGVSC
ISSSDGSTYYADSVKGRFTISRDNAKNTVYLQMNSLKPEDTAVYYCALVH
TTAQATGVPQREYEYEWWGQGTQVTVSS

PMP35F4, SEQ ID NO: 18
EVQLVESGGGLVQAGGSLRLSCAASGRTFSSYDMGWYRQAPGKEREFVAI
ITWNSSTYYADSVKGRFTISRDNAKNTVYLQMNSLKPEDTAIYYCNAQYG
LGYAEDYWGQGTQVTVSS

TABLE B-3

Protein sequences of multivalent anti-IL-6R Nanobodies

IL6R22, SEQ ID NO: 19
EVQLVESGGGLVQAGGSLRLSCAASGRTFSSYDMGWYRQAPGKEREFVAV
ISRSGSSTYYADSVKGRFTISRDNAKNTVYLQMNSLKPEDTAIYYCKAEV
VAGDYDYWGQGTQVTVSSGGGGSGGGSAVQLVESGGGLVQPGNSLRLSCA
ASGFTFRSFGMSWVRQAPGKEPEWVSSISGSGSDTLYADSVKGRFTISRD
NAKTTLYLQMNSLKPEDTAVYYCTIGGSLSRSSQGTQVTVSS

IL6R23, SEQ ID NO: 20
EVQLVESGGGLVQAGGSLRLSCAASGSIFKVNAMGWYRQAPGKQRELVAG
IISGGSTNYADSVKGRLTISRDNAKNTVYLQMNSLKPEDTAVYYCSFVTT
NSDYDLGRDYWGQGTQVTVSSGGGGSGGGSAVQLVESGGGLVQPGNSLRL
SCAASGFTFRSFGMSWVRQAPGKEPEWVSSISGSGSDTLYADSVKGRFTI
SRDNAKTTLYLQMNSLKPEDTAVYYCTIGGSLSRSSQGTQVTVSS

IL6R24, SEQ ID NO: 21
EVQLVESGGGLVQAGGSLRLSCAASGFTFDDYDIGWFRQAPGKEREGVSG
ISSSDGNTYYADSVKGRFTISSDNAKNTVYLQMNSLKPEDTAVYYCAAEP
PDSSWYLDGSPEFFKYWGQGTQVTVSSGGGGSGGGSAVQLVESGGGLVQP
GNSLRLSCAASGFTFRSFGMSWVRQAPGKEPEWVSSISGSGSDTLYADSV
KGRFTISRDNAKTTLYLQMNSLKPEDTAVYYCTIGGSLSRSSQGTQVTVS
S

IL6R25, SEQ ID NO: 22
EVQLVESGGGLVQPGGSLRLSCAASGFTFGSYDMSWVRQAPGKGPEWVSA
INSGGGSTYYADSVKGRFTISRDNAKNTLYLQMNSLKPEDTAVYYCATDW
RYSDYDLPLPPPGDYWGQGTQVTVSSGGGGSGGGSAVQLVESGGGLVQPG
NSLRLSCAASGFTFRSFGMSWVRQAPGKEPEWVSSISGSGSDTLYADSVK
GRFTISRDNAKTTLYLQMNSLKPEDTAVYYCTIGGSLSRSSQGTQVTVSS

IL6R26, SEQ ID NO: 23
EVQLVESGGGLVQAGGSLRLSCAASGNIFDDNTMGWTWNRQPPGKQRELV
AIIATDGSTNYADSVKGRFTISRDNAKNTVYLQMNSLKPEDTAVYYCNLF
SLRLGRDYWGQGTQVTVSSGGGGSGGGSAVQLVESGGGLVQPGNSLRLSC

TABLE B-3-continued

Protein sequences of multivalent
anti-IL-6R Nanobodies

AASGFTFRSFGMSWVRQAPGKEPEWVSSISGSGSDTLYADSVKGRFTISR
DNAKTTLYLQMNSLKPEDTAVYYCTIGGSLSRSSQGTQVTVSS

IL6R28, SEQ ID NO: 24
EVQLVESGGGLVQPGGSLRLSCVASGFSLDYYVIGWFRQAPGKEREGVSC
ISSSDGSTYYADSVKGRFTISRDNAKNTVYLQMNSLKPEDTAVYYCAADL
LRTPEFCVDSAPYDYWGQGTQVTVSSGGGGSGGGSAVQLVESGGGLVQPG
NSLRLSCAASGFTFRSFGMSWVRQAPGKEPEWVSSISGSGSDTLYADSVK
GRFTISRDNAKTTLYLQMNSLKPEDTAVYYCTIGGSLSRSSQGTQVTVSS

IL6R29, SEQ ID NO: 25
EVQLVESGGGLVQAGGSLRLSCAASGRTSSSYDMTWYRQVPGKEREFVAV
ISWSGGSTYYADSVKGRFTISRDNAKNTVYLQMNSLKPEDTAIYYCNAYT
GGGDDYWGQGTQVTVSSGGGGSGGGSAVQLVESGGGLVQPGNSLRLSCAA
SGFTFRSFGMSWVRQAPGKEPEWVSSISGSGSDTLYADSVKGRFTISRDN
AKTTLYLQMNSLKPEDTAVYYCTIGGSLSRSSQGTQVTVSS

IL6R30, SEQ ID NO: 26
EVQLVESGGGLVQAGGSLRLSCAASGRTFSSYDMGWYRQAPGKEREFVAV
IHWSSGSTYYADPVKGRFTISRDNAKNTVYLQMNSLKPEDTAIYYCNAFL
PGPEGFHDYWGQGTQVTVSSGGGGSGGGSAVQLVESGGGLVQPGNSLRLS
CAASGFTFRSFGMSWVRQAPGKEPEWVSSISGSGSDTLYADSVKGRFTIS
RDNAKTTLYLQMNSLKPEDTAVYYCTIGGSLSRSSQGTQVTVSS

IL6R31, SEQ ID NO: 27
EVQLVESGGGLVQAGGSLRLSCAASGFTFDDYAIGWFRQAPGKEHEGVSC
ISSSDGSTYYADSVKGRFTISRDNAKNTVYLQMNSLKPEDTAVYYCAAER
DVPARSLCGSYWYDYRGQGTQVTVSSGGGGSGGGSAVQLVESGGGLVQP
GNSLRLSCAASGFTFRSFGMSWVRQAPGKEPEWVSSISGSGSDTLYADSV
KGRFTISRDNAKTTLYLQMNSLKPEDTAVYYCTIGGSLSRSSQGTQVTV
SS

IL6R32, SEQ ID NO: 28
EVQLVESGGGLVQAGGSLRLSCAASGRTFSSYDMGWYRQAPGKEREFVAI
ITWNSSTYYADSVKGRFTISRDNAKNTVYLQMNSLKPEDTAIYYCNAQYG
LGYAEDYWGQGTQVTVSSGGGGSGGGSAVQLVESGGGLVQPGNSLRLSCA
ASGFTFRSFGMSWVRQAPGKEPEWVSSISGSGSDTLYADSVKGRFTISRD
NAKTTLYLQMNSLKPEDTAVYYCTIGGSLSRSSQGTQVTVSS

IL6R33, SEQ ID NO: 29
EVQLVESGGGLVQPGGSLRLSCAASGFTFDDYGMSWVRQAPGRATEWVSA
ISWNGNNTYYTESMKGRFTISRDNAKNTVYLQMNSLKPEDTAVYYCVKGS
TAIVGVPPTYPDEYDYWGQGTQVTVSSGGGGSGGGSAVQLVESGGGLVQP
GNSLRLSCAASGFTFRSFGMSWVRQAPGKEPEWVSSISGSGSDTLYADSV
KGRFTISRDNAKTTLYLQMNSLKPEDTAVYYCTIGGSLSRSSQGTQVTV
SS

IL6R34, SEQ ID NO: 30
EVQLVESGGGLVQPGGSLRLSCAASGFSLDYYAIGWFRQAPGKEREGVSC
MDSSGTTSTYYSDSVKGRFTISRDDAKNTVYLQMNSLKPEDTAVYYCAA
DGHLNWQRYVPCSQISWRGWNDYWGQGTQVTVSSGGGGSGGGSAVQLVE
SGGGLVQPGNSLRLSCAASGFTFRSFGMSWVRQAPGKEPEWVSSISGSGS
DTLYADSVKGRFTISRDNAKTTLYLQMNSLKPEDTAVYYCTIGGSLSRSS
QGTQVTVSS

IL6R43, SEQ ID NO: 31
EVQLVESGGGLVQAGGSLRLSCAASGSIFKVNAMGWYRQAPGKQRELVAG
IISGGSTNYADSVKGRLTISRDNAKNTVYLQMNSLKPEDTAVYYCSFVTT
NSDYDLGRDYWGQGTQVTVSSGGGGSGGGSAVQLVESGGGLVQPGNSLRL
SCAASGFTFRSFGMSWVRQAPGKEPEWVSSISGSGSDTLYADSVKGRFTI
SRDNAKTTLYLQMNSLKPEDTAVYYCTIGGSLSRSSQGTQVTVSSEVQLV
ESGGGLVQAGGSLRLSCAASGSIFKVNAMGWYRQAPGKQRELVAGIISGG
STNYADSVKGRLTISRDNAKNTVYLQMNSLKPEDTAVYYCSFVTTNSDYD
LGRDYWGQGTQVTVSS

IL6R44, SEQ ID NO: 32
EVQLVESGGGLVQAGGSLRLSCAASGFTFDDYDIGWFRQAPGKEREGVSG
ISSSDGNTYYADSVKGRFTISSDNAKNTVYLQMNSLRPEDTAVYYCAAEP
PDSSWYLDGSPEFFKYWGQGTLVTVSSGGGGSGGGSAVQLVESGGGLVQP
GNSLRLSCAASGFTFRSFGMSWVRQAPGKEPEWVSSISGSGSDTLYADSV
KGRFTISRDNAKTTLYLQMNSLKPEDTAVYYCTIGGSLSRSSQGTQVTVS
SGGGGSGGGSEVQLVESGGGLVQAGGSLRLSCAASGFTFDDYDIGWFRQA
PGKEREGVSGISSSDGNTYYADSVKGRFTISSDNAKNTVYLQMNSLKPED
TAVYYCAAEPPDSSWYLDGSPEFFKYWGQGTLVTVSS

TABLE B-3-continued

Protein sequences of multivalent
anti-IL-6R Nanobodies

IL6R49, SEQ ID NO: 33
EVQLVESGGGLVQAGGSLRLSCAASGRTSSSYDMTWYRQVPGKEREFVAV
ISWSGGSTYYADSVKGRFTISRDNAKNTVYLQMNSLKPEDTAIYYCNAYT
GGGDDYWGQGTQVTVSSGGGGSGGGSAVQLVESGGGLVQPGNSLRLSCAA
SGFTFRSFGMSWVRQAPGKEPEWVSSISGSGSDTLYADSVKGRFTISRDN
AKTTLYLQMNSLKPEDTAVYYCTIGGSLSRSSQGTQVTVSSGGGGSGGGS
EVQLVESGGGLVQAGGSLRLSCAASGRTSSSYDMTWYRQVPGKEREFVAV
ISWSGGSTYYADSVKGRFTISRDNAKNTVYLQMNSLKPEDTAIYYCNAYT
GGGDDYWGQGTQVTVSS

IL6R53, SEQ ID NO: 34
EVQLVESGGGLVQPGGSLRLSCAASGFTFDDYGMSWVRQAPGRATEWVSA
ISWNGNNTYYTESMKGRFTISRDNAKNTVYLQMNSLKPEDTAVYYCVKGS
TAIVGVPPTYPDEYDYWGQGTQVTVSSGGGGSGGGSAVQLVESGGGLVQP
GNSLRLSCAASGFTFRSFGMSWVRQAPGKEPEWVSSISGSGSDTLYADSV
KGRFTISRDNAKTTLYLQMNSLKPEDTAVYYCTIGGSLSRSSQGTQVTVS
SGGGGSGGGSEVQLVESGGGLVQPGGSLRLSCAASGFTFDDYGMSWVRQA
PGRATEWVSAISWNGNNTYYTESMKGRFTISRDNAKNTVYLQMNSLKPED
TAVYYCVKGSTAIVGVPPTYPDEYDYWGQGTQVTVSS

TABLE B-4

Protein sequences of sequence optimized Nanobodies

IL6R61, SEQ ID NO: 40
EVQLVESGGGLVQPGGSLRLSCAASGSIFKVNAMGWYRQAPGKGRELVAG
IISGGSTNYADSVKGRLTISRDNAKNTVYLQMNSLRPEDTAVYYCSFVTT
NSDYDLGRDYWGQGTLVTVSS

IL6R62, SEQ ID NO: 41
EVQLVESGGGLVQPGGSLRLSCAASGSIFKVNAMGWYRQAPGKGRELVAG
IISGGSTNYADSVKGRFTISRDNAKNTVYLQMNSLRPEDTAVYYCSFVTT
NSDYDLGRDYWGQGTLVTVSS

IL6R63, SEQ ID NO: 42
EVQLVESGGGLVQPGGSLRLSCAASGSIFKVNAMGWYRQAPGKGRELVAG
IISGGSTNYADSVKGRLTISRDNAKNTLYLQMNSLRPEDTAVYYCSFVTT
NSDYDLGRDYWGQGTLVTVSS

IL6R64, SEQ ID NO: 43
EVQLVESGGGLVQPGGSLRLSCAASGSIFKVNAMGWYRQAPGKGRELVAG
IISGGSTNYADSVKGRLTISRDNAKNTVYLQMNSLRPEDTAVYYCAFVTT
NSDYDLGRDYWGQGTLVTVSS

IL6R65, SEQ ID NO: 44
EVQLVESGGGLVQPGGSLRLSCAASGSIFKVNAMGWYRQAPGKGRELVAG
IISGGSTNYADSVKGRFTISRDNAKNTLYLQMNSLRPEDTAVYYCAFVTT
NSDYDLGRDYWGQGTLVTVSS

IL6R71, SEQ ID NO: 45
EVQLVESGGGLVQPGGSLRLSCAASGFTFDDYDIGWFRQAPGKGREGVSG
ISSSDGNTYYADSVKGRFTISSDNAKNTVYLQMNSLRPEDTAVYYCAAEP
PDSSWYLDGSPEFFKYWGQGTLVTVSS

IL6R72, SEQ ID NO: 46
EVQLVESGGGLVQPGGSLRLSCAASGFTFSDYDIGWFRQAPGKGREGVSG
ISSSDGNTYYADSVKGRFTISSDNAKNTVYLQMNSLRPEDTAVYYCAAEP
PDSSWYLDGSPEFFKYWGQGTLVTVSS

IL6R73, SEQ ID NO: 47
EVQLVESGGGLVQPGGSLRLSCAASGFTFDDYDIGWFRQAPGKGREGVSG
ISSSDGNTYYADSVKGRFTISRDNAKNTVYLQMNSLRPEDTAVYYCAAEP
PDSSWYLDGSPEFFKYWGQGTLVTVSS

IL6R74, SEQ ID NO: 48
EVQLVESGGGLVQPGGSLRLSCAASGFTFDDYDIGWFRQAPGKGREGVSG
ISSSDGNTYYADSVKGRFTISSDNAKNTLYLQMNSLRPEDTAVYYCAAEP
PDSSWYLDGSPEFFKYWGQGTLVTVSS

IL6R75, SEQ ID NO: 49
EVQLVESGGGLVQPGGSLRLSCAASGFTESDYDIGWERQAPGKGREGVSG
ISSSDGNTYYADSVKGRFTISRDNAKNTLYLQMNSLRPEDTAVYYCAAEP
PDSSWYLDGSPEFFKYWGQGTLVTVSS

TABLE B-4-continued

Protein sequences of sequence optimized Nanobodies

IL6R81, SEQ ID NO: 50
EVQLVESGGGLVQPGGSLRLSCAASGFTFDDYGMSWVRQAPGRATEWVSA
ISWNGNNTYYTESMKGRFTISRDNAKNTVYLQMNSLRPEDTAVYYCVKGS
TAIVGVPPTYPDEYDYWGQGTLVTVSS

IL6R82, SEQ ID NO: 51
EVQLVESGGGLVQPGGSLRLSCAASGFTFDDYGMSWVRQAPGKGLEWVSA
ISWNGNNTYYTESMKGRFTISRDNAKNTVYLQMNSLRPEDTAVYYCVKGS
TAIVGVPPTYPDEYDYWGQGTLVTVSS

IL6R83, SEQ ID NO: 52
EVQLVESGGGLVQPGGSLRLSCAASGFTFDDYGMSWVRQAPGRATEWVSA
ISWNGNNTYYTESMKGRFTISRDNAKNTLYLQMNSLRPEDTAVYYCVKGS
TAIVGVPPTYPDEYDYWGQGTLVTVSS

IL6R84, SEQ ID NO: 53
EVQLVESGGGLVQPGGSLRLSCAASGFTFDDYGMSWVRQAPGKGLEWVSA
ISWNGNNTYYTESMKGRFTISRDNAKNTLYLQMNSLRPEDTAVYYCVKGS
TAIVGVPPTYPDEYDYWGQGTLVTVSS

IL6R85, SEQ ID NO: 54
EVQLVESGGGLVQPGGSLRLSCAASGFTFDDYGMSWVRQAPGRGLEWVSA
ISWNGNNTYYTESMKGRFTISRDNAKNTLYLQMNSLRPEDTAVYYCVKGS
TAIVGVPPTYPDEYDYWGQGTLVTVSS

IL6R86, SEQ ID NO: 55
EVQLVESGGGLVQPGGSLRLSCAASGFTFDDYGMSWVRQAPGRALEWVSA
ISWNGNNTYYTESMKGRFTISRDNAKNTLYLQMNSLRPEDTAVYYCVKGS
TAIVGVPPTYPDEYDYWGQGTLVTVSS

IL6R87, SEQ ID NO: 56
EVQLVESGGGLVQPGGSLRLSCAASGFTFDDYGMSWVRQAPGKATEWVSA
ISWNGNNTYYTESMKGRFTISRDNAKNTLYLQMNSLRPEDTAVYYCVKGS
TAIVGVPPTYPDEYDYWGQGTLVTVSS

IL6R88, SEQ ID NO: 57
EVQLVESGGGLVQPGGSLRLSCAASGFTFDDYGMSWVRQAPGKGTEWVSA
ISWNGNNTYYTESMKGRFTISRDNAKNTLYLQMNSLRPEDTAVYYCVKGS
TAIVGVPPTYPDEYDYWGQGTLVTVSS

IL6R89, SEQ ID NO: 58
EVQLVESGGGLVQPGGSLRLSCAASGFTFDDYGMSWVRQAPGRGTEWVSA
ISWNGNNTYYTESMKGRFTISRDNAKNTLYLQMNSLRPEDTAVYYCVKGS
TAIVGVPPTYPDEYDYWGQGTLVTVSS

IL6R90, SEQ ID NO: 59
EVQLVESGGGLVQPGGSLRLSCAASGFTFDDYGMSWVRQAPGKALEWVSA
ISWNGNNTYYTESMKGRFTISRDNAKNTLYLQMNSLRPEDTAVYYCVKGS
TAIVGVPPTYPDEYDYWGQGTLVTVSS

TABLE B-5

Protein sequences of affinity matured Nanobodies

PMP7F4, SEQ ID NO: 60
EVQLVESGGGLVQPGGSLRLSCAASGTTFKVNVMAWYRQAPGKGRELVAG
IINGGSTTYADSVKGRFTISRDNAKNTLYLQMNSLRPEDTAVYYCAFVTT
NSDYDLGRDYWGQGTLVTVSS

PMP7C4, SEQ ID NO: 61
EVQLVESGGGLVQPGGSLRLSCAASGTTFRINVMAWYRQAPGKGRELVAG
IITNGSTSYADSVKGRFTISRDNAKNTLYLQMNSLRPEDTAVYYCAFVTT
NSDYDLGRDYWGQGTLVTVSS

PMP7D6, SEQ ID NO: 62
EVQLVESGGGLVQPGGSLRLSCAASGSIFRVNVMAWYRQAPGKGRELVAA
VINGGTTYADSVKGRFTISRDNAKNTLYLQMNSLRPEDTAVYYCAFVTT
NSDYDLGRDYWGQGTLVTVSS

PMP7G7, SEQ ID NO: 63
EVQLVESGGGLVQPGGSLRLSCAASGTTFKINIMAWYRQAPGKGRELVAG
VITGGNTTYADSVKGRFTISRDNAKNTLYLQMNSLRPEDTAVYYCAFVTT
NSDYDLGRDYWGQGTLVTVSS

TABLE B-5-continued

Protein sequences of affinity matured Nanobodies

PMP7G8, SEQ ID NO: 64
EVQLVESGGGLVQPGGSLRLSCAASGSTFRINVMAWYRQAPGKGRELVAG
VINDGSTTYADSVKGRFTISRDNAKNTLYLQMNSLRPEDTAVYYCAFVTT
NSDYDLGRDYWGQGTLVTVSS

PMP20F6, SEQ ID NO: 65
EVQLVESGGGLVQPGGSLRLSCAASGSVFKINVMAWYRQAPGKGRELVAG
IVSGGSTSYADSVKGRFTISRDNAKNTLYLQMNSLRPEDTAVYYCAFITT
NSDYDLGRRYWGQGTLVTVSS

PMP20A11, IL6R300, SEQ ID NO: 66
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSS

PMP20E10, SEQ ID NO: 67
EVQLVESGGGLVQPGGSLRLSCAASGSVFKINVMAWYRQAPGKGRELVAG
IVSGGSTSYADSVKGRFTISRDNAKNTLYLQMNSLRPEDTAVYYCAFITT
ESDYDLGRRYWGQGTLVTVSS

PMP21A10, SEQ ID NO: 68
EVQLVESGGGLVQPGGSLRLSCAASGSIFKINVMAWYRQAPGKGRELVAG
IVTGGSTSYADSVKGRFTISRDNAKNTLYLQMNSLRPEDTAVYYCAFITT
ESDYDLGRRYWGQGTLVTVSS

PMP21D11, SEQ ID NO: 69
EVQLVESGGGLVQPGGSLRLSCAASGSVFKINVMAWYRQAPGKGRELVAG
IVTGGSTSYADSVKGRFTISRDNAKNTLYLQMNSLRPEDTAVYYCAFITT
ESDYDLGRRYWGQGTLVTVSS

TABLE B-6

Protein sequences of formatted affinity matured/sequence optimized Nanobodies

IL6R304, SEQ ID NO: 70
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGGSEVQLVESGGGLVQPGNSLRL
SCAASGFTFSSFGMSWVRQAPGKGLEWVSSISGSGSDTLYADSVKGRFTI
SRDNAKTTLYLQMNSLRPEDTAVYYCTIGGSLSRSSQGTLVTVSS

IL6R305, SEQ ID NO: 71
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGGSEVQLVESGGGLVQPGGSLRL
SCAASGSVFKINVMAWYRQAPGKGRELVAGIISGGSTSYADSVKGRFTIS
RDNAKNTLYLQMNSLRPEDTAVYYCAFITTESDYDLGRRYWGQGTLVTVS
SGGGGSGGGSEVQLVESGGGLVQPGNSLRLSCAASGFTFSSFGMSWVRQA
PGKGLEWVSSISGSGSDTLYADSVKGRFTISRDNAKTTLYLQMNSLRPED
TAVYYCTIGGSLSRSSQGTLVTVSS

IL6R306, SEQ ID NO: 72
EVQLVESGGGLVQPGGSLRLSCAASGSVFKINVMAWYRQAPGKGRELVAG
IISGGSTSYADSVKGRFTISRDNAKNTLYLQMNSLRPEDTAVYYCAFITT
ESDYDLGRRYWGQGTLVTVSSGGGGSGGGGSEVQLVESGGGLVQPGNSLRL
SCAASGFTFSSFGMSWVRQAPGKGLEWVSSISGSGSDTLYADSVKGRFTI
SRDNAKTTLYLQMNSLRPEDTAVYYCTIGGSLSRSSQGTLVTVSSGGGGS
GGGSEVQLVESGGGLVQPGGSLRLSCAASGSVFKINVMAWYRQAPGKGRE
LVAGIISGGSTSYADSVKGRFTISRDNAKNTLYLQMNSLRPEDTAVYYCA
FITTESDYDLGRRYWGQGTLVTVSS

IL6R202, SEQ ID NO: 73
EVQLVESGGGLVQPGGSLRLSCAASGFTFSDYDIGWFRQAPGKGREGVSG
ISSSDGNTYYADSVKGRFTISRDNAKNTLYLQMNSLRPEDTAVYYCAAEP
PDSSWYLDGSPEFFKYWGQGTLVTVSSGGGGSGGGGSEVQLVESGGGLVQP
GNSLRLSCAASGFTFSSFGMSWVRQAPGKGLEWVSSISGSGSDTLYADSV
KGRFTISRDNAKTTLYLQMNSLRPEDTAVYYCTIGGSLSRSSQGTLVTV
SS

TABLE B-7

Preferred, but non-limiting examples of albumin-binding Nanobodies

ALB-1, SEQ ID NO: 97
AVQLVESGGGLVQPGNSLRLSCAASGFTFRSFGMSWVRQAPGKEPEWVSS
ISGSGSDTLYADSVKGRFTISRDNAKTTLYLQMNSLKPEDTAVYYCTIGG
SLSRSSQGTQVTVSS

ALB-8 (humanized ALB-1), SEQ ID NO: 98
EVQLVESGGGLVQPGNSLRLSCAASGFTFSSFGMSWVRQAPGKGLEWVSS
ISGSGSDTLYADSVKGRFTISRDNAKTTLYLQMNSLRPEDTAVYYCTIGG
SLSRSSQGTLVTVSS ALB-2, SEQ ID NO: 99
AVQLVESGGGLVQGGGSLRLACAASERIFDLNLMGWYRQGPGNERELVAT
CITVGDSTNYADSVKGRFTISMDYTKQTVYLHMNSLRPEDTGLYYCKIRR
TWHSELWGQGTQVTVSS

TABLE B-8

Sequence listing of linkers

GS30, SEQ ID NO: 101
GGGGSGGGGSGGGGSGGGGSGGGGSGGGGS

GS15, SEQ ID NO: 102
GGGGSGGGGSGGGGS

GS9, SEQ ID NO: 103
GGGGSGGGS

GS7, SEQ ID NO: 104
SGGSGGS

Llama upper long hinge region, SEQ ID NO: 105
EPKTPKPQPAAA

TABLE C-1

Materials used for the isolation of IL-6R binding Nanobodies

| | Supplier | Description |
|---|---|---|
| Human IL-6 | Diaclone | Recombinant protein produced in *E. coli* |
| Human bio-IL-6 | Diaclone/PE | Human IL-6 from Diaclone biotinylated by PE (6 biotins/molecule) |
| Human soluble IL-6R | Peprotech | Recombinant protein produced in HEK293 cells (cat.# 200-06R) |
| Human soluble IL-6R | R&D Systems | Recombinant protein produced in Sf21 cells (cat.#227-SR) |
| MAb BR-6 | Diaclone | Neutralizing anti-IL-6R MAb |
| MAb BN-12 | Diaclone | Non-neutralizing anti-IL-6R MAb |
| MAb M182 | BD Biosciences | Biotinylated anti-IL-6R MAb |
| Llama IgG (h&l) Antibody HRP conjugated | Bethyl Labs | PAb against llama IgG raised in goat |
| TF-1 cell line | ECACC no.93022307 | J Cell Physiol 1989;140:323; Exp Cell Res 1993:208:35 |

TABLE C-2

Immunization schedule

| Day | Llama 081 | Llama 082 | Tissue collection |
|---|---|---|---|
| 0 | 100 μg | 100 μg | 10 ml pre-immune blood |
| 7 | 100 μg | 100 μg | — |
| 14 | 50 μg | 50 μg | — |
| 21 | 50 μg | 50 μg | — |
| 28 | 50 μg | 50 μg | 10 ml immune blood |
| 35 | 50 μg | 50 μg | — |
| 39 | | | 150 ml immune blood PBL1 lymph node bow biopsy |
| 43 | | | 150 ml immune blood PBL2 |
| 52 | 50 μg | 50 μg | |
| 59 | | | 100 ml immune blood NC1 |

TABLE C-3

Characteristics of the Nanobody libraries obtained from the immunized llamas

| | Library size | % insert |
|---|---|---|
| Llama 81 | $6 \times 10^7$ | 87 |
| Llama 82 | $5 \times 10^7$ | 78 |

TABLE C-4

Conditions used for the selection of the Nanobodies

| Method | Immobilization/ capture | Antigen | Concentration/ amount | Elution |
|---|---|---|---|---|
| Magnetic beads | Streptavidin | bio-IL-6R | 0, 1, 10, 100 ng | Trypsin |
| Solution | Streptavidin beads | bio-IL-6R | 0, 0.01, 0.1, 1 nM | Trypsin |
| Plate | BN-12 | IL-6R (Peprotech) | 0, 1, 10, 100 nM | Trypsin |
| Plate | BN-12 | IL-6R (R&D) | 0, 1, 10, 100 nM | Trypsin |

TABLE C-5

Screening statistics

| Assay | Number of clones screened | Number of inhibitors (%) | Number of clones sequenced | Number of unique sequences |
|---|---|---|---|---|
| IL-6-IL-6R | 1536 | 72 (4.7%) | 46 | 14 |

TABLE C-6

$k_{off}$-values of inhibitory Nanobodies

| Nanobody ID | Nanobody ID | $k_{off}(s^{-1})$ | Nanobody ID | Nanobody ID | $k_{off}(s^{-1})$ |
|---|---|---|---|---|---|
| PMP40H5 | IL6R14 | 1.14E−04 | PMP34G9 | IL6R09 | 1.39E−03 |
| PMP35E11 | IL6R11 | 4.17E−04 | PMP31A4 | IL6R03 | 1.60E−03 |
| PMP32C9 | IL6R04 | 1.50E−04 | PMP32E2 | IL6R06 | 8.86E−04 |
| PMP35H4 | IL6R13 | 1.78E−04 | PMP33A3 | IL6R07 | 2.42E−04 |
| PMP32E10 | IL6R05 | 1.27E−03 | PMP34A12 | IL6R08 | ND |
| PMP30C11 | IL6R02 | 2.94E−03 | PMP28E11 | IL6R01 | ND |
| PMP35C10 | IL6R10 | 5.09E−04 | PMP35F4 | IL6R12 | 8.96E−04 |

TABLE C-7

Yields of Nanobody cell cultures

| Nanobody ID | yield (mg) | yield (mg/l) | Nanobody ID | yield (mg) | yield (mg/l) |
|---|---|---|---|---|---|
| PMP40H5 | 0.14 | 0.6 | PMP34G9 | 0.09 | 1.8 |
| PMP35E11 | 0.65 | 2.6 | PMP31A4 | 1.06 | 4.2 |
| PMP32C9 | 0.33 | 6.5 | PMP32E2 | 1.57 | 6.3 |
| PMP35H4 | 0.49 | 9.8 | PMP33A3 | 0.33 | 1.3 |
| PMP32E10 | 0.78 | 3.1 | PMP34A12 | 0.57 | 2.3 |
| PMP30C11 | 0.63 | 2.5 | PMP28E11 | 0.08 | 1.6 |
| PMP35C10 | 0.53 | 2.1 | PMP35F4 | 0.24 | 1.0 |

TABLE C-8

IC50-values of selected Nanobodies

| Nanobody ID | Sample | IC50 (M) |
|---|---|---|
| IL6R01 | PMP28E11 | 7.26E−10 |
| IL6R02 | PMP30C11 | 1.69E−09 |
| IL6R03 | PMP31A4 | 7.16E−10 |
| IL6R04 | PMP32C9 | 9.30E−11 |
| IL6R05 | PMP32E10 | 6.26E−10 |
| IL6R06 | PMP32E2 | 1.21E−09 |
| IL6R07 | PMP33A3 | 1.44E−09 |
| IL6R08 | PMP34A12 | 1.18E−09 |
| IL6R09 | PMP34G9 | 2.38E−10 |
| IL6R10 | PMP35C10 | 5.96E−10 |
| IL6R11 | PMP35E11 | 1.58E−10 |
| IL6R12 | PMP35F4 | 5.17E−10 |
| IL6R13 | PMP35H4 | 4.77E−11 |
| IL6R14 | PMP40H5 | 2.22E−10 |

TABLE C-9

Kinetic parameters for a selected subset of 14 inhibitory anti-IL-6R Nanobodies

| Nanobody ID | Nanobody ID | $k_{off}$ (s$^{-1}$) | $K_{on}$ (1/Ms) | $K_d$ (nM) |
|---|---|---|---|---|
| IL6R01 | PMP28E11 | 1.10E−04 | 2.62E+05 | 0.4 |
| IL6R02 | PMP30C11 | 2.94E−03 | 8.40E+05 | 5.9 |
| | | 4.95E−03 | | |
| IL6R03 | PMP31A4 | 1.47E−03 | 4.84E+05 | 3.0 |
| | | 1.60E−03 | | |
| IL6R04 | PMP32C9 | 9.42E−05 | 3.65E+05 | 0.3 |
| | | 1.50E−04 | | |
| IL6R05 | PMP32E10 | 1.41E−03 | 1.44E+05 | 9.8 |
| | | 1.27E−03 | | |
| IL6R06 | PMP32E2 | 8.86E−04 | 1.07E+06 | 7.1 |
| | | 7.57E−03 | | |
| IL6R07 | PMP33A3 | 2.42E−04 | ND | ND |
| IL6R08 | PMP34A12 | 1.97E−03 | 1.94E+05 | 10.2 |
| IL6R09 | PMP34G9 | 1.29E−03 | 6.41E+05 | 2.0 |
| | | 1.30E−03 | 1.11E+06 | 1.2 |
| | | 1.39E−03 | | |
| IL6R10 | PMP35C10 | 5.26E−04 | 4.14E+05 | 1.3 |
| | | 5.09E−04 | | |
| IL6R11 | PMP35E11 | 3.40E−04 | 3.91E+05 | 0.9 |
| | | 3.96E−04 | 2.15E+05 | 1.9 |
| | | 4.17E−04 | | |
| IL6R12 | PMP35F4 | 1.16E−03 | 6.78E+05 | 1.7 |
| | | 8.96E−04 | | |
| IL6R13 | PMP35H4 | 1.21E−04 | 2.31E+05 | 0.5 |
| | | 1.09E−04 | 1.37E+05 | 0.8 |
| | | 1.78E−04 | | |
| IL6R14 | PMP40H5 | 1.00E−04 | 4.02E+05 | 0.3 |
| | | 1.14E−04 | | |

TABLE C-10

IC50 values for Nanobody inhibition of XG-1 cell proliferation

| Nanobody ID | IC50 (nM) | IC50 (nM) + HSA |
|---|---|---|
| IL6R01 | ND | |
| IL6R02 | 31.0 | |
| IL6R03 | 16.2 | 17.5 |
| IL6R04 | 0.1 | 0.1 |
| IL6R05 | 7.3 | |
| IL6R06 | 42.1 | |
| IL6R07 | 50.5 | |
| IL6R08 | 36.6 | |
| IL6R09 | 2.7 | 3.0 |
| IL6R10 | 2.5 | |
| IL6R11 | 5.4 | |
| IL6R12 | 2.8 | |
| IL6R13 | 1.4 | 1.3 |
| IL6R14 | 0.6 | 0.8 |
| Reference Fab | 6.0 | |

TABLE C-11

IC50 values for Nanobody inhibition of TF1 cell proliferation

| Nanobody ID | IC50 (nM) |
|---|---|
| IL6R01 | ND |
| IL6R02 | 94.7 |
| IL6R03 | 62.1 |
| IL6R04 | 0.4 |
| IL6R05 | 38.0 |
| IL6R06 | 137.9 |
| IL6R07 | 374.9 |
| IL6R08 | 24.3 |
| IL6R09 | 8.7 |
| IL6R10 | 9.9 |
| IL6R11 | 9.9 |
| IL6R12 | 6.8 |
| IL6R13 | 5.2 |
| IL6R14 | 1.5 |
| Reference Fab | 9.2 |

TABLE C-12

Competition with the reference Fab for binding IL-6R as determined in an alphascreen assay

| Nanobody ID | Residual reference-Fab binding to IL-6R (%) |
|---|---|
| IL6R01 | 49 |
| IL6R02 | 86 |
| IL6R03 | 5 |
| IL6R04 | 50 |
| IL6R05 | 64 |
| IL6R06 | 36 |
| IL6R07 | 80 |
| IL6R08 | 99 |
| IL6R09 | 62 |
| IL6R10 | 102 |
| IL6R11 | 40 |
| IL6R12 | 103 |
| IL6R13 | 25 |
| IL6R14 | 96 |

TABLE C-13

Summary Nanobody characteristics

| ID | $K_d$ (nM) | IC50 (nM) (IL-6/IL-6R) | IC50 (nM) XG-1 | IC50 (nM) TF-1 | Ref Fab competition (%) |
|---|---|---|---|---|---|
| IL6R01 | 0.4 | 0.73 | ND | ND | 49 |
| IL6R02 | 5.9 | 1.69 | 31.0 | 94.7 | 86 |
| IL6R03 | 3.0 | 0.72 | 16.2 | 62.1 | 5 |
| IL6R04 | 0.3 | 0.09 | 0.1 | 0.4 | 50 |
| IL6R05 | 9.8 | 0.63 | 7.3 | 38.0 | 64 |
| IL6R06 | 7.1 | 1.21 | 42.1 | 137.9 | 36 |
| IL6R07 | ND | 1.44 | 50.5 | 374.9 | 80 |
| IL6R08 | 10.2 | 1.18 | 36.6 | 24.3 | 99 |
| IL6R09 | 2.0 | 0.24 | 2.7 | 8.7 | 62 |
| IL6R10 | 1.3 | 0.60 | 2.5 | 9.9 | 102 |
| IL6R11 | 0.9 | 0.16 | 5.4 | 9.9 | 40 |
| IL6R12 | 1.7 | 0.52 | 2.8 | 6.8 | 103 |
| IL6R13 | 0.5 | 0.05 | 1.4 | 5.2 | 25 |
| IL6R14 | 0.3 | 0.22 | 0.6 | 1.5 | 96 |

TABLE C-14

Nomenclature (ID) of formatted Nanobodies

| ID | format | SEQ ID NO |
|---|---|---|
| IL6R22 | PMP30C11-9GS-ALB1 | 19 |
| IL6R23 | PMP31A4-9GS-ALB1 | 20 |
| IL6R24 | PMP32C9-9GS-ALB1 | 21 |
| IL6R25 | PMP32E10-9GS-ALB1 | 22 |
| IL6R26 | PMP32E2-9GS-ALB1 | 23 |
| IL6R28 | PMP34A12-9GS-ALB1 | 24 |
| IL6R29 | PMP34G9-9GS-ALB1 | 25 |
| IL6R30 | PMP35C10-9GS-ALB1 | 26 |
| IL6R31 | PMP35E11-9GS-ALB1 | 27 |
| IL6R32 | PMP35F4-9GS-ALB1 | 28 |
| IL6R33 | PMP35H4-9GS-ALB1 | 29 |
| IL6R34 | PMP40H5-9GS-ALB1 | 30 |
| IL6R43 | PMP31A4-9GS-ALB1-9GS-31A4 | 31 |
| IL6R44 | PMP32C9-9GS-ALB1-9GS-32C9 | 32 |
| IL6R49 | PMP34G9-9GS-ALB1-9GS-34G9 | 33 |
| IL6R53 | PMP35H4-9GS-ALB1-9GS-35H4 | 34 |

TABLE C-15

Expression yields of bispecific anti-IL-6R Nanobodies

| Nanobody | ID | yield (mg) | yield (mg/l) |
|---|---|---|---|
| PMP30C11 | IL6R22 | 1.1 | 4.2 |
| PMP31A4 | IL6R23 | 0.3 | 0.6 |
| PMP32C9 | IL6R24 | 0.5 | 2.0 |
| PMP32E10 | IL6R25 | 1.3 | 5.0 |
| PMP32E2 | IL6R26 | 1.1 | 4.2 |
| PMP34A12 | IL6R28 | 2.1 | 8.4 |
| PMP34G9 | IL6R29 | 3.3 | 13.2 |
| PMP35C10 | IL6R30 | 0.9 | 3.7 |
| PMP35E11 | IL6R31 | 1.8 | 7.3 |
| PMP35F4 | IL6R32 | 0.5 | 1.1 |
| PMP35H4 | IL6R33 | 1.9 | 7.5 |
| PMP40H5 | IL6R34 | 0.4 | 0.9 |

TABLE C-16

IC50 values of bivalent Nanobodies in alphascreen competition assay

| Nanobody ID | IC50 (M) |
|---|---|
| IL6R22 | 5.59E−10 |
| IL6R24 | 1.45E−10 |
| IL6R25 | 6.43E−10 |
| IL6R26 | 1.67E−09 |
| IL6R28 | 3.26E−10 |
| IL6R29 | 1.23E−10 |
| IL6R30 | 3.43E−10 |
| IL6R31 | 1.31E−10 |
| IL6R32 | 2.68E−10 |
| IL6R33 | 1.39E−10 |
| IL6R34 | 1.46E−10 |
| reference-Fab | 5.92E−10 |

TABLE C-17

IC50 values of formatted Nanobodies in the XG-1 proliferation assay

| ID | IC50 (nM) | IC50 (nM) + HSA |
|---|---|---|
| IL6R22 | 50.2 | |
| IL6R23 | 16.9 | 90.4 |
| IL6R24 | 0.2 | 0.5 |
| IL6R25 | 8.4 | |
| IL6R26 | 65.3 | |
| IL6R28 | 4.4 | |
| IL6R29 | 3.6 | 13.4 |
| IL6R30 | 27.2 | |
| IL6R31 | 4.6 | |
| IL6R32 | 1.6 | |
| IL6R33 | 2.6 | 15.4 |
| IL6R34 | 0.8 | 2.5 |
| IL6R44 | 0.07 | 0.17 |
| IL6R49 | 0.06 | 0.19 |
| IL6R53 | 0.13 | 0.61 |
| Ref-IgG | | 0.47 |

TABLE C-18

Kinetic parameters of IL-6R binding

| Nanobody ID | $k_d$ (s$^{-1}$) | $k_a$ (1/Ms) | $K_d$ (nM) |
|---|---|---|---|
| IL6R22 | 5.7E−03 | 3.3E+05 | 16.9 |
| IL6R23 | 1.5E−03 | 3.2E+05 | 4.6 |
| IL6R24 | 1.1E−04 | 3.7E+05 | 0.3 |
| IL6R25 | 1.2E−03 | 1.2E+05 | 10.3 |

TABLE C-18-continued

Kinetic parameters of IL-6R binding

| Nanobody ID | $k_d$ ($s^{-1}$) | $k_a$ (1/Ms) | $K_d$ (nM) |
|---|---|---|---|
| IL6R26 | 6.9E−03 | 4.5E+05 | 15.5 |
| IL6R28 | 5.3E−04 | 2.4E+05 | 2.2 |
| IL6R29 | 1.5E−03 | 7.1E+05 | 2.1 |
| IL6R30 | 1.2E−03 | 1.6E+05 | 7.5 |
| IL6R31 | 3.8E−04 | 1.6E+05 | 2.3 |
| IL6R32 | 1.3E−03 | 1.0E+06 | 1.3 |
| IL6R33 | 1.25E−04 | 1.1E+05 | 1.1 |
| IL6R34 | 1.1E−04 | 2.6E+05 | 0.4 |

TABLE C-19

$K_d$ values of formatted Nanobodies for binding to serum albumin from different species

| ID | Human $K_d$ (nM) | Mouse $K_d$ (nM) | Cyno $K_d$ (nM) | Rhesus $K_d$ (nM) | Baboon $K_d$ (nM) |
|---|---|---|---|---|---|
| IL6R22 | 11.1 | 108 | | | |
| IL6R23 | 16 | 275 | 27.6 | 23.8 | 23.2 |
| IL6R24 | 15 | 122 | 28.3 | 28.3 | 40.3 |
| IL6R25 | 13.9 | 122 | | | |
| IL6R26 | 9.4 | 73 | | | |
| IL6R28 | 10.6 | 180 | | | |
| IL6R29 | 10.8 | 83 | 19 | 20.6 | 26.8 |
| IL6R30 | 12.1 | 113 | | | |
| IL6R31 | 13.4 | 86.8 | | | |
| IL6R32 | 10 | 179 | | | |
| IL6R33 | 27.3 | 98.6 | 24.5 | 24.6 | 32.3 |
| IL6R34 | 9.2 | 111 | 15 | 14.7 | 18.9 |
| IL6R44 | 51.4 | 993 | 43 | | |
| IL6R53 | 35 | 497 | | | |
| ALB-1 | 0.6 | 6.5 | | | |

TABLE C-20

Kinetic parameters of sequence optimized variants of IL6R03, 04 and 13

| | | | |
|---|---|---|---|
| IL6R03 (3.0 nM) | IL6R61 | KD (nM) | 2 |
| | | ka (1/Ms) | 8.50E+05 |
| | | kd (1/s) | 1.70E−03 |
| | IL6R62 | KD (nM) | 2.2 |
| | | ka (1/Ms) | 9.29E+05 |
| | | kd (1/s) | 2.07E−03 |
| | IL6R63 | KD (nM) | 3.7 |
| | | ka (1/Ms) | 9.90E+05 |
| | | kd (1/s) | 3.65E−03 |
| | IL6R64 | KD (nM) | ND |
| | | ka (1/Ms) | ND |
| | | kd (1/s) | 1.00E−03 |
| IL6R04 (0.3 nM) | IL6R71 | KD (nM) | 0.2 |
| | | ka (1/Ms) | 7.03E+05 |
| | | kd (1/s) | 1.53E−04 |
| | IL6R72 | KD (nM) | 0.3 |
| | | ka (1/Ms) | 5.43E+05 |
| | | kd (1/s) | 1.80E−04 |
| | IL6R73 | KD (nM) | 0.3 |
| | | ka (1/Ms) | 6.98E+05 |
| | | kd (1/s) | 2.33E−04 |
| | IL6R74 | KD (nM) | 0.2 |
| | | ka (1/Ms) | 7.67E+05 |
| | | kd (1/s) | 1.22E−04 |
| IL6R13 (0.7 nM) | IL6R81 | KD (nM) | 0.4 |
| | | ka (1/Ms) | 3.20E+05 |
| | | kd (1/s) | 1.28E−04 |
| | IL6R82 | KD (nM) | 5.1 |
| | | ka (1/Ms) | 6.19E+05 |
| | | kd (1/s) | 3.14E−03 |
| | IL6R83 | KD (nM) | 0.3 |
| | | ka (1/Ms) | 3.50E+05 |
| | | kd (1/s) | 1.20E−04 |
| | IL6R84 | KD (nM) | 5.4 |
| | | ka (1/Ms) | 7.62E+05 |
| | | kd (1/s) | 4.09E−03 |

TABLE C-21

$k_{off}$ values of sequence optimized variants of IL6R13

| ID | $k_{off}$ ($s^{-1}$) |
|---|---|
| IL6R13 | 2.1E−04 |
| IL6R85 | 2.1E−03 |
| IL6R86 | 1.7E−03 |
| IL6R87 | 1.1E−04 |
| IL6R88 | 2.6E−04 |
| IL6R89 | 1.9E−04 |
| IL6R90 | 1.9E−03 |

TABLE C-22

Kinetic parameters of sequence optimized variants of IL6R03, 04 and 13

| | | | |
|---|---|---|---|
| IL6R03 (3.0 nM) | IL6R65 | KD (nM) | 4 |
| | | ka (1/Ms) | 6.00E+05 |
| | | kd (1/s) | 2.35E−03 |
| IL6R04 (0.3 nM) | IL6R75 | KD (nM) | 0.1 |
| | | ka (1/Ms) | 1.00E+06 |
| | | kd (1/s) | 1E−04 |
| IL6R13 (0.7 nM) | IL6R88 | KD (nM) | 0.9 |
| | | ka (1/Ms) | 2.30E+05 |
| | | kd (1/s) | 2.13E−04 |

TABLE C-23

IC50 values of sequence optimized and WT Nanobodies in XG-1 assay

IC50 values (nM)

| Parental | | Sequence optimized | |
|---|---|---|---|
| IL6R03 | 17 | IL6R65 | 26 |
| IL6R04 | 0.1 | IL6R75 | 0.04 |
| IL6R13 | 1.4 | IL6R88 | 3.3 |

TABLE C-24

Kinetic parameters of Nanobody binding to cyno IL-6R

| ID | $k_a$ (1/Ms) | $k_d$ (1/s) | $K_D$ (nM) |
|---|---|---|---|
| IL6R03 | 3.70E+05 | 1.64E−03 | 4.4 |
| IL6R65 | 1.65E+05 | 1.97E−03 | 12 |
| IL6R04 | 5.86E+04 | 1.00E−02 | 171 |
| IL6R201* | 2.18E+05 | 6.11E−03 | 28.1 |

*IL6R201 is the tagless version of IL6R75

TABLE C-25

Tm values of ILR65 and affinity matured IL-6R Nanobodies

| | Tm first run | | Tm second run | | average Tm |
|---|---|---|---|---|---|
| IL6R65 | 70.44 | 70.64 | 70.54 | 71.07 | 70.67 |
| PMP7F4 | 76.68 | 76.55 | 76.58 | 76.44 | 76.56 |
| 21A10 | 74.56 | 74.22 | 74.39 | 74.39 | 74.39 |
| 20E10 | 75.29 | 75.22 | 75.31 | 75.38 | 75.30 |
| 20A11 | 74.42 | 74.03 | 74.12 | 74.19 | 74.19 |
| 21D11 | 74.03 | 74.29 | 74.45 | 74.25 | 74.26 |
| 20F6 | 74.36 | 74.29 | 74.45 | 74.32 | 74.36 |

TABLE C-26

Kinetic parameters for affinity of IL6R65 and affinity matured variants

| Nanobody | $k_a$ (M$^{-1}$·s$^{-1}$) | $k_d$ (s$^{-1}$) | $K_d$ (pM) |
|---|---|---|---|
| IL6R65 | 1.0E+06 | 3.8E-03 | 3800 |
| 20E10 | 1.0E+06* | 3.3E-05 | 33 |
| 21D11 | 1.0E+06* | 3.5E-05 | 35 |
| 21A10 | 1.0E+06* | 1.2E-05 | 12 |
| 20F6 | 1.0E+06* | 3.3E-05 | 33 |
| 20A11 | 1.0E+06 | 1.9E-5 | 19 |

*estimated

TABLE C-27

Formats of affinity matured anti-IL6R Nanobodies

| Format | Sequence optimized Nanobody | Name |
|---|---|---|
| 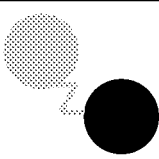 anti-IL6R / anti-HSA | 20A11-9GS-ALB8 | IL6R304 |
| 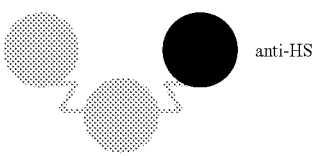 anti-IL6R / anti-HSA / anti-IL6R | 20A11-9GS-20A11-9GS-ALB8 | IL6R305 |
| 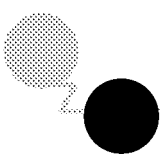 anti-IL6R / anti-IL6R / anti-HSA | 20A11-9GS-ALB8-9GS-20A11 | IL6R306 |

TABLE C-28

Potency of formatted Nanobodies vs. references in TF-1 proliferation assay at 100 IU/mL IL-6

| Compound | IC50 (nM) | Stdev (nM) | Repeats |
|---|---|---|---|
| 20A11 | 0.283 | 0.256 | 3 |
| IL6R304 | 0.715 | 0.390 | 2 |
| IL6R305 | 0.098 | 0.046 | 4 |
| IL6R306 | 0.341 | 0.162 | 3 |
| reference Fab | 6.262 | 0.706 | 2 |
| reference IgG | 0.921 | 0.275 | 4 |

TABLE C-29

Potency of formatted Nanobodies in TF-1 proliferation assay at 5000 IU/mL IL-6

| Compound | IC50 (nM) |
|---|---|
| 20A11 | 15.22 |
| IL6R304 | 15.48 |
| IL6R305 | 5.49 |
| IL6R306 | 23.19 |
| Reference IgG | 144.5 |

TABLE C-30

IC50 values (nM) of formatted Nanobodies for neutralization of IL-6 binding to sIL-6R in human plasma

| Compound | IC50 at normal IL-6 | IC50 at high IL-6 | Ratio (high/low) |
|---|---|---|---|
| reference IgG | 0.258 | 1.69 | 6.54 |
| IL6R20A11 | 0.198 | 0.356 | 1.80 |

TABLE C-30-continued

IC50 values (nM) of formatted Nanobodies for neutralization of IL-6 binding to sIL-6R in human plasma

| Compound | IC50 at normal IL-6 | IC50 at high IL-6 | Ratio (high/low) |
|---|---|---|---|
| IL6R304 | 0.229 | 0.634 | 2.77 |
| IL6R305 | 0.137 | 0.335 | 2.44 |
| IL6R306 | 0.412 | 2.39 | 5.80 |

TABLE C-31

EC50 values (nM) for binding of the formatted affinity matured Nanobodies to CHO 4D5 (4PL)

| Compound | EC50 (nM) |
|---|---|
| IL6R20A11 | 1.396 |
| IL6R304 | 1.939 |
| IL6R305 | 0.8984 |
| IL6R306 | 6.154 |

TABLE C-32

EC50 values (nM) for binding of the formatted affinity matured Nanobodies to PBL from 2 donors

| Compound | L1 | L2 | M1 | M2 | G1 | G2 |
|---|---|---|---|---|---|---|
| IL6R20A11 | 3.65 | 2.924 | 3.621 | 4.777 | 2.415 | 5.614 |
| IL6R304 | 9.273 | 20.68 | 8.241 | 14.17 | 5.985 | 17.32 |
| IL6R305 | 4.282 | 25.79 | 2.906 | 4.262 | 2.434 | 4.927 |
| IL6R306 | 60 | 49.59 | 49.38 | 59.34 | 53.99 | 77.68 |

L: lymphocytes, M: monocytes; G: granulocytes

TABLE C-33

Kinetic parameters for binding of formatted affinity matured Nanobodies to human and cyno serum albumin

| Nanobody | Human serum albumin | | | Cyno serum albumin | | |
|---|---|---|---|---|---|---|
| | $k_a$ (M$^{-1}$s$^{-1}$) | $k_d$ (s$^{-1}$) | $K_D$ (nM) | $k_a$ (M$^{-1}$s$^{-1}$) | $k_d$ (s$^{-1}$) | $K_D$ (nM) |
| ALB11 | 5.45E+05 | 1.68E−03 | 3.08 | 5.11E+05 | 1.53E−06 | 2.99 |
| IL6R304 | 2.15E+05 | 4.75E−03 | 22.1 | 1.95E+05 | 4.56E−03 | 23.4 |
| IL6R305 | 2.01E+05 | 4.07E−03 | 20.3 | 2.03E+05 | 3.87E−03 | 19.1 |
| IL6R306 | 2.25E+05 | 3.83E−03 | 17.1 | 2.12E+05 | 3.70E−03 | 17.4 |

TABLE C-34

Kinetic parameters for binding of the formatted affinity matured Nanobodies to human and cyno IL-6R

| Nanobody | Human IL-6R | | | Cyno IL-6R | | |
|---|---|---|---|---|---|---|
| | $k_a$ (M$^{-1}$s$^{-1}$) | $k_d$ (s$^{-1}$) | $K_D$ (pM) | $k_a$ (M$^{-1}$s$^{-1}$) | $k_d$ (s$^{-1}$) | $K_D$ (pM) |
| IL6R300 | 1E+06 | ND | ND | 1E+06 | ND | ND |
| IL6R304 | 7E+05 | ≤1E−05 * | ≤14 | 8E+05 | 2E−05 | 25 |

* Detection limit of the instrument

TABLE C-35

Comparison of IC50 values (nM) for neutralization of binding of hIL-6 to plasma sIL-6R in cyno and human plasma

| Test items | IC50 in human | IC50 in cyno | Ratio (human/cyno) |
|---|---|---|---|
| reference IgG | 0.258 | 0.166 | 1.55 |
| IL6R20A11 | 0.198 | 0.117 | 1.69 |
| IL6R304 | 0.229 | 0.137 | 1.67 |
| IL6R305 | 0.137 | 0.0791 | 1.73 |
| IL6R306 | 0.412 | 0.321 | 1.29 |

TABLE C-36

Dose groups for in vivo PK/PD analysis of IL6R304 and IL6R305

| Group | Test item | Nanobody dose (mg/kg b.w., i.v.) | IL-6 dose (μg/kg b.w., s.c.) | N and sex of animals | Reference no. |
|---|---|---|---|---|---|
| 6 | IL6R304 | 0.4 | 5 μg/kg once daily for 7 days, starting 24 hours post Nanobody administration | 2 m, 1 f | 11, 12, 13 |
| 7 | | 2 | | 1 m, 2 f | 14, 15, 16 |
| 8 | | 10 | | 1 m, 1 f | 17, 18 |
| 9 | IL6R305 | 0.4 | | 1 m, 2 f | 19, 20, 21 |
| 10 | | 2 | | 2 m, 1 f | 22, 23, 24 |
| 11 | | 10 | | 1 m, 1 f | 25, 26 |
| 12 | Negative control | 0 | | 2 m, 1 f | 27, 28, 29 |
| 13 | Positive control | 5 mg/kg reference IgG | | 1 m, 2 f | 30, 31, 32 |

TABLE C-37

Sampling times for PK analysis

| Group | Sampling times per animal | Number of samples |
|---|---|---|
| Groups 6-13 | Day 0: pre injection of Nanobody, and 5 min, 30 min, 3 h, and 8 h post Nanobody injection<br>Days 1, 2, 3, 4, 5, 6, 7: pre injection of IL-6<br>Days 8, 14, 21 and 29 | 352 |

TABLE C-38

Basic PK parameters of IL6R304 after a single i.v. bolus administration at 0.4 mg/kg in cynomolgus monkey
IL6R304: IV 0.4 mg/kg

| Parameter | Unit | 11m | 12m | 13f | Mean | CV % |
|---|---|---|---|---|---|---|
| Vss | mL/kg | 45.1 | 44.6 | 38.8 | 42.8 | 8 |
| CL | mL/day/kg | 24.8 | 28.2 | 21.5 | 24.8 | 14 |
| MRT | day | 1.81 | 1.58 | 1.80 | 1.73 | 8 |
| $t_{1/2}$ λz1 | day | 1.92 | 1.54 | 1.72 | 1.73 | 11 |
| λz1 Lower | day | 1 | 1 | 1 | 1.00 | 0 |
| λz1 Upper | day | 4 | 4 | 5 | 4.33 | 13 |
| $R^2$ $t_{1/2}$ λz1 | | 0.998 | 0.997 | 0.999 | 0.998 | 0 |
| $t_{1/2}$ λz2 | day | 0.566 | 0.504 | 0.521 | 0.530 | 6 |
| λz2 Lower | day | 5 | 4 | 5 | 4.67 | 12 |
| λz2 Upper | day | 7 | 6 | 7 | 6.67 | 9 |
| $R^2$ $t_{1/2}$ λz2 | | 0.967 | 1.00 | 0.938 | 0.968 | 3 |
| AUClast | day*μg/mL | 16.0 | 14.1 | 18.6 | 16.2 | 14 |
| AUCextrap | % | 0.372 | 0.365 | 0.325 | 0.354 | 7 |
| AUCinf | day*μg/mL | 16.1 | 14.2 | 18.6 | 16.3 | 14 |
| AUCinf/D | day*kg/mL | 0.040 | 0.036 | 0.047 | 0.041 | 14 |

TABLE C-39

Basic PK parameters of IL6R304 after a single i.v. bolus administration at 2 mg/kg in cynomolgus monkey. The terminal parameters for some of the animals were calculated with two data-points only ($R^2$ is 1 by default)

IL6R304: IV 2 mg/kg

| Parameter | Unit | 14m | 15f | 16f | Mean | CV % |
|---|---|---|---|---|---|---|
| Vss | mL/kg | 56.0 | 55.9 | 49.3 | 53.7 | 7 |
| CL | mL/day/kg | 9.99 | 11.0 | 10.1 | 10.4 | 6 |
| MRT | day | 5.60 | 5.06 | 4.86 | 5.17 | 7 |
| $t_{1/2}\,\lambda z1$ | day | 5.79 | 4.34 | 4.87 | 5.00 | 15 |
| $\lambda z1$ Lower | day | 2 | 2 | 2 | 2 | 0 |
| $\lambda z1$ Upper | day | 14 | 14 | 14 | 14 | 0 |
| $R^2\,t_{1/2}\,\lambda z1$ | | 0.994 | 0.979 | 0.991 | 0.988 | 1 |
| $t_{1/2}\,\lambda z2$ | day | 1.51 | 1.52 | 1.30 | 1.44 | 9 |
| $\lambda z2$ Lower | day | 14 | 14 | 14 | 14 | 0 |
| $\lambda z2$ Upper | day | 21 | 21 | 21 | 21 | 0 |
| $R^2\,t_{1/2}\,\lambda z2$ | | 1.00 | 1.00 | 1.00 | 1.00 | 0 |
| $t_{1/2}\,\lambda z3$ | day | 5.61 | 5.95 | — | 5.78 | 4 |
| $\lambda z3$ Lower | day | 21 | 21 | — | 21 | 0 |
| $\lambda z3$ Upper | day | 29 | 29 | — | 29 | 0 |
| $R^2\,t_{1/2}\,\lambda z3$ | | 1.00 | 1.00 | 1.00 | 1.00 | 0 |
| AUClast | day*µg/mL | 200 | 181 | 197 | 192 | 5 |
| AUCextrap | % | 0.295 | 0.247 | 0.090 | 0.211 | 51 |
| AUCinf | day*µg/mL | 200 | 181 | 197 | 193 | 5 |
| AUCinf/D | day*kg/mL | 0.100 | 0.091 | 0.099 | 0.096 | 5 |

TABLE C-40

Basic PK parameters of IL6R304 after a single i.v. bolus administration at 10 mg/kg in cynomolgus monkey IL6R304: IV 10 mg/kg

| Parameter | Unit | 17m | 18f | Mean | CV % |
|---|---|---|---|---|---|
| Vss | mL/kg | 76.5 | 88.8 | 82.7 | 10 |
| CL | mL/day/kg | 7.66 | 10.35 | 9.00 | 21 |
| MRT | day | 10.0 | 8.57 | 9.29 | 11 |
| $t_{1/2}\,\lambda z1$ | day | 7.15 | 6.08 | 6.61 | 11 |
| $\lambda z1$ Lower | day | 1 | 1 | 1 | 0 |
| $\lambda z1$ Upper | day | 29 | 29 | 29 | 0 |
| $R^2\,t_{1/2}\,\lambda z1$ | | 0.990 | 0.990 | 0.990 | 0 |
| AUClast | day*µg/mL | 1230 | 932 | 1081 | 19 |
| AUCextrap | % | 5.79 | 3.50 | 4.64 | 35 |
| AUCinf | day*µg/mL | 1306 | 966 | 1136 | 21 |
| AUCinf/D | day*kg/mL | 0.131 | 0.097 | 0.114 | 21 |

TABLE C-41

Basic PK parameters of IL6R305 after a single i.v. bolus administration at 0.4 mg/kg in cynomolgus monkey. The terminal parameters for some of the animals were calculated with two data-points only ($R^2$ is 1 by default)

IL6R305: IV 0.4 mg/kg

| Parameter | Unit | 19m | 20f | 21f | Mean | CV % |
|---|---|---|---|---|---|---|
| Vss | mL/kg | 59.2 | 72.5 | 63.9 | 65.2 | 10 |
| CL | mL/day/kg | 33.5 | 38.0 | 36.0 | 35.8 | 6 |
| MRT | day | 1.77 | 1.91 | 1.77 | 1.82 | 4 |
| $t_{1/2}\,\lambda z1$ | day | 1.79 | 1.25 | 1.89 | 1.64 | 21 |
| $\lambda z1$ Lower | day | 1 | 1 | 1 | 1 | 0 |
| $\lambda z1$ Upper | day | 5 | 5 | 4 | 4.67 | 12 |
| $R^2\,t_{1/2}\,\lambda z1$ | | 0.997 | 0.981 | 0.997 | 0.992 | 1 |
| $t_{1/2}\,\lambda z2$ | day | 0.446 | — | 0.495 | 0.470 | 7 |
| $\lambda z2$ Lower | day | 5 | — | 5 | 5 | 0 |
| $\lambda z2$ Upper | day | 6 | — | 6 | 6 | 0 |
| $R^2\,t_{1/2}\,\lambda z2$ | | 1.00 | — | 1.00 | 1.00 | 0 |
| AUClast | day*µg/mL | 11.84 | 9.84 | 11.02 | 10.9 | 9 |
| AUCextrap | % | 0.765 | 6.58 | 0.855 | 2.73 | 122 |
| AUCinf | day*µg/mL | 11.9 | 10.5 | 11.1 | 11.2 | 6 |
| AUCinf/D | day*kg/mL | 0.030 | 0.026 | 0.028 | 0.028 | 6 |

TABLE C-42

Basic PK parameters of IL6R305 after a single i.v. bolus administration at 2 mg/kg in cynomolgus monkey. The terminal parameters for some of the animals were calculated with two data-points only ($R^2$ is 1 by default)

IL6R305: IV 2 mg/kg

| Parameter | Unit | 22m | 23m | 24f | Mean | CV % |
|---|---|---|---|---|---|---|
| Vss | mL/kg | 27.5 | 28.0 | 30.4 | 28.6 | 5 |
| CL | mL/day/kg | 5.81 | 5.30 | 6.68 | 5.93 | 12 |
| MRT | day | 4.73 | 5.28 | 4.55 | 4.85 | 8 |
| $t_{1/2}\,\lambda z1$ | day | 4.26 | 4.56 | 4.04 | 4.29 | 6 |
| $\lambda z1$ Lower | day | 2 | 2 | 2 | 2 | 0 |
| $\lambda z1$ Upper | day | 14 | 14 | 14 | 14 | 0 |
| $R^2\,t_{1/2}\,\lambda z1$ | | 0.985 | 0.954 | 0.986 | 0.975 | 2 |
| $t_{1/2}\,\lambda z2$ | day | 1.33 | 2.34 | 1.16 | 1.61 | 40 |
| $\lambda z2$ Lower | day | 14 | 14 | 14 | 14 | 0 |
| $\lambda z2$ Upper | day | 21 | 21 | 21 | 21 | 0 |
| $R^2\,t_{1/2}\,\lambda z2$ | | 1 | 1 | 1 | 1 | 0 |
| AUClast | day*µg/mL | 344 | 374 | 299 | 339 | 11 |
| AUCextrap | % | 0.089 | 0.791 | 0.041 | 0.307 | 137 |
| AUCinf | day*µg/mL | 344 | 377 | 299 | 340 | 11 |
| AUCinf/D | day*kg/mL | 0.172 | 0.189 | 0.150 | 0.170 | 11 |

TABLE C-43

Basic PK parameters of IL6R305 after a single i.v. bolus administration at 10 mg/kg in cynomolgus monkey. The terminal parameters for some of the animals were calculated with two data-points only ($R^2$ is 1 by default)

| | | IL6R305: IV 10 mg/kg | | | |
|---|---|---|---|---|---|
| Parameter | Unit | 25m | 26f | Mean | CV |
| Vss | mL/kg | 38.3 | 59.2 | 48.7 | 30 |
| CL | mL/day/kg | 6.91 | 8.60 | 7.76 | 15 |
| MRT | day | 5.54 | 6.88 | 6.21 | 15 |
| $t_{1/2}$ λz1 | day | 5.63 | 9.10 | 7.37 | 33 |
| λz1 Lower | day | 2 | 2 | 2 | 0 |
| λz1 Upper | day | 14 | 14 | 14 | 0 |
| $R^2 t_{1/2}$ λz1 | | 0.941 | 0.968 | 0.955 | 2 |
| $t_{1/2}$ λz2 | day | 1.26 | 1.16 | 1.21 | 6 |
| λz2 Lower | day | 21 | 21 | 21 | 0 |
| λz2 Upper | day | 29 | 29 | 29 | 0 |
| $R^2 t_{1/2}$ λz2 | | 1.00 | 1.00 | 1.00 | 0 |
| AUClast | day*µg/mL | 1447 | 1162 | 1305 | 15 |
| AUCextrap | % | 0.008 | 0.009 | 0.008 | 11 |
| AUCinf | day*µg/mL | 1447 | 1162 | 1305 | 15 |
| AUCinf/D | day*kg/mL | 0.145 | 0.116 | 0.130 | 15 |

TABLE C-44

Summary of the anti-IL6R304 and anti-IL6R305 antibody appearance to full Nanobody

| IL6R304 | Cyno | ADA positive* | IL6R305 | Cyno | ADA |
|---|---|---|---|---|---|
| 0.4 mg/kg | 11m | >7 days | 0.4 mg/kg | 19m | >7 days |
| | 12m | >7 days | | 20f | >7 days |
| | 13f | >7 days | | 21f | >7 days |
| 2 mg/kg | 14m | >7 days | 2 mg/kg | 22m | >14 days |
| | 15f | >14 days | | 23m | No ADA detected |
| | 16f | No results due to high predose values | | 24f | >14 days |
| 10 mg/kg | 17m | >14 days | 10 mg/kg | 25m | >14 days |
| | 18f | >14 days | | 26f | >14 days |

*>7 days: TD 7 Negative, ≥TD 14 Positive; >14 days: TD 14 Negative, ≥TD 21 Positive

TABLE C-45

Pharmacodynamic parameters of IL6R304 in the cynomolgus monkey

| Parameter | Estimate | % CV |
|---|---|---|
| $K_{in}$ (ng/mL/h) | 2.40 | 7.37 |
| $R_0$ (ng/mL) | 21.4 | 5.23 |
| $I_{max}$ (%) | 0.970 | 0.34 |
| $IC_{50}$ (µg/mL) | 0.146 | 15.8 |
| $IC_{50}$ (nM) | 5.23 | |
| n | 1.43 | 15.3 |

TABLE C-46

Summary of mean (±SD) key PK-parameters of IL6R304 in the cynomolgus monkey after a single i.v. bolus at 1, 5, 10, 25 or 100 mg/kg

| | | 1 mg/kg | | | 5 mg/kg | | | 10 mg/kg | | | 25 mg/kg | | | 100 mg/kg | | |
|---|---|---|---|---|---|---|---|---|---|---|---|---|---|---|---|---|
| Parameter | Unit | n | Mean | SD | n | Mean | SD | n | Mean | SD | n | Mean | SD | n | Mean | SD |
| $C_0$ | µg/mL | 3 | 26.2 | 3.8 | 3 | 108.7 | 24.0 | 3 | 196.5 | 30.8 | 3 | 562.3 | 66.4 | 1 | 2840.5 | — |
| $AUC_{inf}$ | µg·h/mL | $2^a$ | 2015 | 190 | $2^b$ | 12338 | 768 | 2 | 25983 | 440 | 3 | 89526 | 28466 | 1 | 540612 | — |
| $t_{1/2}$ | d | $2^a$ | 1.81 | 0.00 | $2^b$ | 5.01 | 0.76 | 2 | 6.37 | 0.19 | 3 | 6.24 | 0.76 | 1 | 8.9 | — |
| CL | mL/h/kg | $2^a$ | 0.50 | 0.04 | $2^b$ | 0.41 | 0.02 | 2 | 0.39 | 0.01 | 3 | 0.30 | 0.11 | 1 | 0.18 | — |
| Vz | mL/kg | $2^a$ | 46.5 | 3.0 | $2^b$ | 67.3 | 18.5 | 2 | 82.3 | 1.7 | 3 | 72.6 | 18.1 | 1 | 57.6 | — |
| DN $AUC_{inf}$ | µg·h/mL | $2^a$ | 2015 | — | $2^b$ | 2468 | — | 2 | 2598 | — | 3 | 3581 | — | 1 | 5406 | — |

DN: Dose-normalized to 1 mg/kg

[a] Animal 3 excluded from descriptive statistics as no target mediated clearance was observed: $t_{1/2}$ = 4.3 days

[b] Animal 6 excluded from descriptive statistics as target mediated clearance was observed: $t_{1/2}$ = 2.2 days

TABLE C-47

Pharmacokinetic parameters of IL6R304 in cynomolgus monkey.

| Parameter | Estimate | % CV |
|---|---|---|
| $V_c$ (mL/kg) | 45.6 | 5.23 |
| $V_d$ (mL/kg) | 14.8 | 15.2 |
| $V_s$ (mL/kg) | 24.9 | 16.1 |
| $V_{dss}$ (mL/kg) | 85.3 | |
| $CL_{NON-IL6R}$ (mL/h/kg) | 0.237 | 3.39 |
| $CL_d$ (mL/h/kg) | 0.0475 | 29.9 |
| $CL_s$ (mL/h/kg) | 2.86 | 40.4 |
| $V_{max}$ (µg/h/kg) | 1.971 | 11.2 |
| $K_m$ (µg/mL) | 0.714 | 30.4 |
| $CL_{IL6R}$ (mL/h/kg) | 2.76 | |

The invention claimed is:

1. An isolated polypeptide that specifically binds IL-6R, comprising or consisting essentially of SEQ ID NO: 66.

2. A polypeptide construct that comprises, or consists essentially of, one or more polypeptides according to claim 1, and that further comprises one or more additional single variable domains, groups, residues, moieties or binding units, optionally linked via one or more linkers.

3. The polypeptide construct according to claim 2, which is a multivalent construct.

4. The polypeptide construct according to claim 2, wherein the one or more additional single variable domains are chosen from the group consisting of VHHs, humanized VHHs and camelized VHs.

5. The polypeptide construct according to claim 2, wherein the one or more additional single variable domains, groups, residues, moieties or binding units are linked via one or more linkers or spacers.

6. The polypeptide construct according to claim 5, wherein the linker is selected from the group consisting of SEQ ID NOs: 101-105.

7. The polypeptide construct according to claim 2, wherein the one or more additional single variable domains, groups, residues, moieties or binding units provide the polypeptide construct with increased half-life and wherein the one or more additional single variable domains, groups, residues, moieties or binding units are chosen from the group consisting of VHHs, humanized VHHs and camelized VHs that can bind to serum albumin, human serum albumin, a serum immunoglobulin, or IgG.

8. The polypeptide construct according to claim 7, wherein the one or more additional single variable domains are selected from the group consisting of SEQ ID NOs: 97-99.

9. The polypeptide construct according to claim 2, selected from the group consisting of SEQ ID NOs 70-72.

10. The polypeptide construct according to claim 9, which is SEQ ID NO: 70.

11. The polypeptide construct according to claim 2, which is a bivalent or trivalent construct.

12. A composition comprising at least one polypeptide according to claim 1.

13. A composition comprising at least one polypeptide construct according to claim 2.

14. The composition according to claim 13, wherein the polypeptide construct is selected from SEQ ID NOs: 70-72.

15. The composition according to claim 12, which is a pharmaceutical composition.

16. The composition according to claim 13, which is a pharmaceutical composition.

17. The composition according to claim 14, which is a pharmaceutical composition.

18. A composition comprising at least one polypeptide construct according to claim 10.

19. The composition according to claim 18, which is a pharmaceutical composition.

* * * * *